US011560589B2

(12) United States Patent
Heron et al.

(10) Patent No.: US 11,560,589 B2
(45) Date of Patent: Jan. 24, 2023

(54) ENZYME STALLING METHOD

(71) Applicant: Oxford Nanopore Technologies PLC, Oxford (GB)

(72) Inventors: Andrew John Heron, Oxford (GB); David Antoni Alves, Oxford (GB); James Anthony Clarke, Oxford (GB); Marion Louise Crawford, Oxford (GB); Daniel Ryan Garalde, Oxford (GB); Graham Hall, Oxford (GB); Daniel John Turner, Oxford (GB); James White, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 146 days.

(21) Appl. No.: 16/243,357

(22) Filed: Jan. 9, 2019

(65) Prior Publication Data

US 2019/0211390 A1 Jul. 11, 2019

Related U.S. Application Data

(63) Continuation of application No. 14/773,164, filed as application No. PCT/GB2014/050175 on Jan. 22, 2014, now Pat. No. 10,221,450.

(60) Provisional application No. 61/774,694, filed on Mar. 8, 2013.

(30) Foreign Application Priority Data

Aug. 16, 2013 (GB) .................................... 1314695
Oct. 18, 2013 (GB) .................................... 1318464
Oct. 18, 2013 (GB) .................................... 1318465

(51) Int. Cl.
*C12Q 1/6869* (2018.01)
*C12Q 1/6827* (2018.01)
*C12N 9/14* (2006.01)
*C12N 13/00* (2006.01)

(52) U.S. Cl.
CPC ............. *C12Q 1/6869* (2013.01); *C12N 9/14* (2013.01); *C12N 13/00* (2013.01); *C12Q 1/6827* (2013.01); *C12Y 306/04012* (2013.01)

(58) Field of Classification Search
CPC ................................ C12Q 1/6869; C12N 9/34
See application file for complete search history.

(56) References Cited

U.S. PATENT DOCUMENTS 5,215,899 A 6/1993 Dattagupta
5,424,413 A 6/1995 Hogan et al.
5,561,043 A 10/1996 Cantor et al.
5,576,204 A 11/1996 Blanco et al.
5,714,320 A 2/1998 Kool
5,777,078 A 7/1998 Bayley et al.
5,795,782 A 8/1998 Church et al.
5,817,771 A 10/1998 Bayley et al.
5,866,328 A 2/1999 Bensimon et al.
5,866,336 A 2/1999 Nazarenko et al.
5,985,834 A 11/1999 Engel et al.
6,015,714 A 1/2000 Baldarelli et al.
6,087,099 A 7/2000 Gupte et al.
6,114,121 A 9/2000 Fujiwara et al.
6,123,819 A 9/2000 Peeters
6,127,166 A 10/2000 Bayley et al.
6,150,112 A 11/2000 Weissman et al.
6,251,610 B1 6/2001 Gupte et al.
6,274,320 B1 8/2001 Rothberg et al.
6,362,002 B1 3/2002 Denison et al.
6,403,319 B1 6/2002 Lizardi et al.
6,426,231 B1 7/2002 Bayley et al.
6,451,563 B1 9/2002 Wittig et al.
6,451,593 B1 9/2002 Wittig et al.
6,465,193 B2 10/2002 Akeson et al.
6,498,023 B1 12/2002 Abarzua
6,627,067 B1 9/2003 Branton et al.
6,709,861 B2 3/2004 Mead et al.
6,787,308 B2 9/2004 Balasubramanian et al.
6,824,659 B2 11/2004 Bayley et al.
6,863,833 B1 3/2005 Bloom et al.
6,916,665 B2 7/2005 Bayley et al.
6,927,070 B1 8/2005 Bayley et al.
7,087,729 B1 8/2006 Prive
7,189,503 B2 3/2007 Akeson et al.
7,238,485 B2 7/2007 Akeson et al.
7,361,466 B2 4/2008 Korlach et al.
7,507,575 B2 3/2009 Bedingham et al.
7,700,281 B2 4/2010 Kubu et al.
7,745,116 B2 6/2010 Williams
(Continued)

FOREIGN PATENT DOCUMENTS

CN 101495656 7/2009
CN 102245760 11/2011
DE 112016000293 T5 9/2017
EP 2194123 B1 8/2012
EP 2682460 A1 1/2014
EP 3470529 A1 4/2019
GB 2130219 5/1984
GB 2237390 5/1991
GB 2453377 4/2009
GB 1314695.6 8/2013
(Continued)

OTHER PUBLICATIONS

Matson et al, The Gene 4 Protein of Bacteriophage T, 1983, The Journal of Biological Chemistry, 258, 14017-14024. (Year: 1983).*
Manosas et al, Magnetic Tweezers for the Study of DNA Tracking Motors, 2010, Methods in Enzymology, 475, 298-314. (Year: 2010).*
(Continued)

*Primary Examiner* — Narayan K Bhat
(74) *Attorney, Agent, or Firm* — Wolf, Greenfield & Sacks, P.C.

(57) ABSTRACT

The invention relates to new methods of moving helicases past spacers on polynucleotides and controlling the loading of helicases on polynucleotides. The invention also relates to new methods of characterising target polynucleotides using helicases.

21 Claims, 22 Drawing Sheets

Specification includes a Sequence Listing.

(56) References Cited

U.S. PATENT DOCUMENTS 8,105,846 B2 1/2012 Bayley et al.
8,143,030 B2 3/2012 Maxham et al.
8,153,375 B2 4/2012 Travers et al.
8,343,746 B2 1/2013 Rank et al.
8,383,369 B2 2/2013 Maxham et al.
8,628,940 B2 1/2014 Sorenson et al.
8,652,779 B2 2/2014 Turner et al.
8,785,211 B2 7/2014 Bayley et al.
8,822,160 B2 9/2014 Bayley et al.
8,889,348 B2 11/2014 Ju
9,057,102 B2 6/2015 Turner et al.
9,116,118 B2 8/2015 Turner et al.
9,145,623 B2 9/2015 Kavanagh et al.
9,150,918 B2 10/2015 Turner et al.
9,542,527 B2 1/2017 Travers et al.
9,546,400 B2 1/2017 Turner et al.
9,551,023 B2 1/2017 Turner et al.
9,556,480 B2 1/2017 Turner et al.
9,582,640 B2 2/2017 Travers et al.
9,600,626 B2 3/2017 Travers et al.
9,670,526 B2 6/2017 Kokoris et al.
9,678,056 B2 6/2017 Turner et al.
9,738,929 B2 8/2017 Turner et al.
9,957,560 B2 5/2018 Brown et al.
10,131,944 B2 11/2018 Bernick et al.
10,221,450 B2 3/2019 Heron et al.
10,227,632 B2 3/2019 Jarvius
10,385,389 B2 8/2019 Heron et al.
10,501,767 B2 12/2019 Stoddart et al.
10,570,440 B2 2/2020 White et al.
10,597,713 B2 3/2020 Brown et al.
10,669,578 B2 6/2020 Clarke et al.
10,851,409 B2 12/2020 Brown et al.
11,155,860 B2 10/2021 White et al.
11,168,363 B2 11/2021 Brown et al.
11,186,857 B2 11/2021 Stoddart et al.
11,261,487 B2 3/2022 Brown et al.
11,352,664 B2 6/2022 Mckeown
11,390,904 B2 7/2022 White
2001/0039039 A1 11/2001 Weissman et al.
2001/0044137 A1 11/2001 Heyman et al.
2002/0028458 A1 3/2002 Lexow
2002/0094526 A1 7/2002 Bayley et al.
2002/0098530 A1 7/2002 Pfeifer et al.
2002/0132350 A1 9/2002 Suzuki et al.
2002/0142331 A1 10/2002 Fu et al.
2002/0177701 A1 11/2002 Weissman et al.
2002/0197614 A1 12/2002 Weir et al.
2002/0197618 A1 12/2002 Sampson
2003/0044816 A1 3/2003 Denison et al.
2003/0059778 A1 3/2003 Berlin et al.
2003/0087232 A1 5/2003 Christians et al.
2003/0099951 A1 5/2003 Akeson et al.
2003/0108902 A1 6/2003 Abarzua
2003/0118595 A1 6/2003 Niemeyer et al.
2003/0165936 A1 9/2003 Rabbani et al.
2003/0166137 A1 9/2003 Zuker et al.
2003/0211502 A1 11/2003 Sauer et al.
2003/0215881 A1 11/2003 Bayley et al.
2004/0055901 A1 3/2004 Petersen et al.
2004/0209299 A1 10/2004 Pinter et al.
2004/0214177 A1 10/2004 Bension
2004/0229315 A1 11/2004 Lee et al.
2005/0042633 A1 2/2005 Williams
2005/0053961 A1 3/2005 Akeson et al.
2005/0142559 A1 6/2005 Makrigiorgos
2005/0221316 A1 10/2005 Pedersen et al.
2005/0227239 A1 10/2005 Joyce
2005/0260655 A1 11/2005 Liu et al.
2006/0063171 A1 3/2006 Akeson et al.
2006/0086626 A1 4/2006 Joyce
2006/0141516 A1 6/2006 Kobold et al.
2006/0147935 A1 7/2006 Linnarsson
2006/0292611 A1 12/2006 Berka et al.
2007/0015182 A1 1/2007 Abarzua
2007/0020640 A1 1/2007 McCloskey
2007/0031857 A1 2/2007 Makarov et al.
2007/0122885 A1 5/2007 Reeves et al.
2007/0224613 A1 9/2007 Strathmann
2007/0269825 A1 11/2007 Wang et al.
2007/0287151 A1 12/2007 Linnarsson
2008/0108082 A1 5/2008 Rank et al.
2008/0166724 A1 7/2008 Gerber et al.
2008/0206252 A1 8/2008 Pennica et al.
2008/0311582 A1 12/2008 Bayley et al.
2009/0098612 A1 4/2009 Rhee et al.
2009/0111115 A1 4/2009 Drmanac et al.
2009/0191598 A1 7/2009 Ruan et al.
2009/0256116 A1 10/2009 Shumaker-Parry et al.
2009/0269771 A1 10/2009 Schroeder
2009/0280538 A1 11/2009 Patel et al.
2009/0298075 A1 12/2009 Travers et al.
2010/0003560 A1 1/2010 Shibata
2010/0035254 A1 2/2010 Williams
2010/0035260 A1 2/2010 Olasagasti et al.
2010/0075309 A1 3/2010 Maxham et al.
2010/0075327 A1* 3/2010 Maxham ............ G01N 21/6452 435/6.1
2010/0075328 A1 3/2010 Bjornson et al.
2010/0092960 A1 4/2010 Fehr
2010/0120098 A1 5/2010 Grunenwald et al.
2010/0121582 A1 5/2010 Pan et al.
2010/0221212 A1 9/2010 Stagliano et al.
2010/0221716 A1 9/2010 Flusberg et al.
2010/0276588 A1 11/2010 Syms
2010/0331194 A1 12/2010 Turner et al.
2011/0019186 A1 1/2011 Himmelhaus et al.
2011/0124518 A1 5/2011 Cantor
2011/0136676 A1 6/2011 Greene
2011/0214991 A1 9/2011 Kim et al.
2011/0224106 A1 9/2011 Eshoo et al.
2011/0281768 A1 11/2011 Travers et al.
2011/0287435 A1 11/2011 Grunenwald et al.
2011/0311965 A1 12/2011 Maglia et al.
2012/0010085 A1 1/2012 Rava et al.
2012/0015821 A1 1/2012 Raymond
2012/0058468 A1 3/2012 Mckeown
2012/0100530 A1 4/2012 Moysey et al.
2012/0107802 A1 5/2012 Stoddart et al.
2012/0196279 A1* 8/2012 Underwood ............ C12P 19/34 435/6.1
2012/0244525 A1 9/2012 Hendrickson
2013/0017978 A1 1/2013 Kavanagh et al.
2013/0078624 A1 3/2013 Holmes et al.
2013/0143802 A1 6/2013 Chilkoti
2013/0195908 A1 8/2013 Leonetti et al.
2013/0203123 A1 8/2013 Nelson et al.
2013/0327644 A1 12/2013 Turner et al.
2014/0134618 A1 5/2014 Kokoris et al.
2014/0134629 A1 5/2014 Turner et al.
2014/0186823 A1 7/2014 Clarke et al.
2014/0194324 A1 7/2014 Gormley et al.
2014/0206842 A1 7/2014 Majeed et al.
2014/0262784 A1 9/2014 Clarke et al.
2014/0296089 A1 10/2014 Holmes et al.
2014/0308661 A1 10/2014 Holmes et al.
2015/0008126 A1 1/2015 Maglia et al.
2015/0045257 A1 2/2015 Kavanagh et al.
2015/0152492 A1 6/2015 Brown et al.
2015/0167075 A1 6/2015 Turner et al.
2015/0175663 A1 6/2015 Yokoi et al.
2015/0191709 A1 7/2015 Heron et al.
2015/0197796 A1 7/2015 White et al.
2015/0218629 A1 8/2015 Heron et al.
2015/0265994 A1 9/2015 Hyde et al.
2015/0285781 A1 10/2015 Heron et al.
2015/0307934 A1 10/2015 Turner et al.
2016/0010147 A1 1/2016 Heron et al.
2016/0010148 A1 1/2016 Turner et al.
2016/0011169 A1 1/2016 Turner et al.
2016/0194677 A1 7/2016 Stoddart et al.
2016/0257942 A1 9/2016 Bruce et al.
2016/0281159 A1 9/2016 Brown et al.
2016/0362739 A1 12/2016 Brown et al.

(56) References Cited

U.S. PATENT DOCUMENTS

| | | | |
|---|---|---|---|
| 2017/0002406 | A1 | 1/2017 | Bowen et al. |
| 2017/0067101 | A1 | 3/2017 | Clarke et al. |
| 2017/0240955 | A1 | 8/2017 | White |
| 2017/0314062 | A1 | 11/2017 | Kokoris et al. |
| 2017/0321266 | A1 | 11/2017 | Mckeown |
| 2018/0030506 | A1 | 2/2018 | Fujioka |
| 2018/0051277 | A1 | 2/2018 | Godfrey et al. |
| 2018/0291440 | A1 | 10/2018 | Mckeown |
| 2018/0291441 | A1 | 10/2018 | Brown et al. |
| 2019/0194722 | A1 | 6/2019 | Stoddart et al. |
| 2019/0376132 | A1 | 12/2019 | Mckeown |
| 2020/0002761 | A1 | 1/2020 | Mckeown |
| 2020/0024655 | A1 | 1/2020 | Brown et al. |
| 2020/0032248 | A1 | 1/2020 | White et al. |
| 2020/0087724 | A1 | 3/2020 | Heron et al. |
| 2020/0109396 | A1 | 4/2020 | Tsai et al. |
| 2020/0131549 | A1 | 4/2020 | Stoddart et al. |
| 2020/0239950 | A1 | 7/2020 | Brown et al. |
| 2020/0291452 | A1 | 9/2020 | White |
| 2020/0318179 | A1 | 10/2020 | Clarke et al. |
| 2022/0127669 | A1 | 4/2022 | Brown et al. |
| 2022/0145383 | A1 | 5/2022 | White et al. |
| 2022/0186274 | A1 | 6/2022 | Stoddart et al. |

FOREIGN PATENT DOCUMENTS

| | | | |
|---|---|---|---|
| JP | H10-146190 | | 6/1998 |
| JP | H11-137260 | | 5/1999 |
| JP | 2005-253427 | | 9/2005 |
| JP | 2012-506704 | A | 3/2012 |
| WO | WO 94/23065 | | 10/1994 |
| WO | WO 99/05167 | | 2/1999 |
| WO | WO 2000/28312 | | 5/2000 |
| WO | WO 2001/40516 | | 6/2001 |
| WO | WO 2001/42782 | | 6/2001 |
| WO | WO 2001/59453 | | 8/2001 |
| WO | WO 2002/42496 | | 5/2002 |
| WO | WO 2003/095669 | | 11/2003 |
| WO | WO 2005/056750 | | 6/2005 |
| WO | WO 2005/068656 | A1 | 7/2005 |
| WO | WO 2005/118877 | | 12/2005 |
| WO | WO 2005/124888 | | 12/2005 |
| WO | WO 2006/020775 | | 2/2006 |
| WO | WO 2006/028508 | | 3/2006 |
| WO | WO 2006/100484 | | 9/2006 |
| WO | WO 2007/057668 | | 5/2007 |
| WO | WO 2007/075987 | | 7/2007 |
| WO | WO 2007/084103 | | 7/2007 |
| WO | WO 2007/114693 | A2 | 10/2007 |
| WO | WO 2007/146158 | | 12/2007 |
| WO | WO 2008/045575 | | 4/2008 |
| WO | WO 2008/083554 | | 7/2008 |
| WO | WO 2008/102120 | | 8/2008 |
| WO | WO 2008/102121 | | 8/2008 |
| WO | WO 2008/124107 | | 10/2008 |
| WO | WO 2009/020682 | A2 | 2/2009 |
| WO | WO 2009/035647 | | 3/2009 |
| WO | WO 2009/044170 | A1 | 4/2009 |
| WO | WO 2009/077734 | A2 | 6/2009 |
| WO | WO 2009/120372 | A2 | 10/2009 |
| WO | WO 2009/120374 | A2 | 10/2009 |
| WO | WO 2010/004265 | | 1/2010 |
| WO | WO 2010/004273 | | 1/2010 |
| WO | WO 2010/030683 | A1 | 3/2010 |
| WO | WO 2010/034018 | | 3/2010 |
| WO | WO 2010/048605 | A1 | 4/2010 |
| WO | WO 2010/051773 | | 5/2010 |
| WO | WO 2010/086602 | A1 | 8/2010 |
| WO | WO 2010/086603 | | 8/2010 |
| WO | WO 2010/086622 | | 8/2010 |
| WO | WO 2010/094040 | | 8/2010 |
| WO | WO 2010/109107 | A1 | 9/2010 |
| WO | WO 2010/109197 | | 9/2010 |
| WO | WO 2010/122293 | | 10/2010 |
| WO | WO 2010/146349 | A1 | 12/2010 |
| WO | WO 2011/067559 | | 6/2011 |
| WO | WO 2012/005857 | A1 | 1/2012 |
| WO | WO 2012/033524 | A2 | 3/2012 |
| WO | WO 2012/061832 | | 5/2012 |
| WO | WO 2012/083249 | A2 | 6/2012 |
| WO | WO 2012/098561 | A2 | 7/2012 |
| WO | WO 2012/098562 | A2 | 7/2012 |
| WO | WO 2012/103545 | A1 | 8/2012 |
| WO | WO 2012/107778 | A2 | 8/2012 |
| WO | WO 2012/164270 | A1 | 12/2012 |
| WO | WO 2013/014451 | A1 | 1/2013 |
| WO | WO 2013/041878 | A1 | 3/2013 |
| WO | WO 2013/057495 | A2 | 4/2013 |
| WO | WO 2013/083983 | A1 | 6/2013 |
| WO | WO 2013/098561 | A1 | 7/2013 |
| WO | WO 2013/098562 | A2 | 7/2013 |
| WO | WO 2013/109970 | A1 | 7/2013 |
| WO | WO 2013/131962 | A1 | 9/2013 |
| WO | WO 2013/153359 | A1 | 10/2013 |
| WO | WO 2013/185137 | A1 | 12/2013 |
| WO | WO 2014/013259 | A1 | 1/2014 |
| WO | WO 2014/013260 | A1 | 1/2014 |
| WO | WO 2014/013262 | A1 | 1/2014 |
| WO | WO 2014/064443 | A2 | 5/2014 |
| WO | WO 2014/064444 | A1 | 5/2014 |
| WO | WO 2014/108810 | A2 | 7/2014 |
| WO | WO 2014/135838 | A1 | 9/2014 |
| WO | WO 2014/142850 | A1 | 9/2014 |
| WO | WO 2014/153408 | | 9/2014 |
| WO | WO 2014/187924 | A1 | 11/2014 |
| WO | WO 2015/022544 | A1 | 2/2015 |
| WO | WO 2015/031909 | A1 | 3/2015 |
| WO | WO 2015/055981 | A2 | 4/2015 |
| WO | WO 2015/056028 | A1 | 4/2015 |
| WO | WO 2015/110777 | A1 | 7/2015 |
| WO | WO 2015/110813 | A1 | 7/2015 |
| WO | WO 2015/150786 | A1 | 10/2015 |
| WO | WO 2015/189636 | A1 | 12/2015 |
| WO | WO 2015/200609 | A1 | 12/2015 |
| WO | WO 2016/003814 | A1 | 1/2016 |
| WO | WO 2016/022557 | A1 | 2/2016 |
| WO | WO 2016/028887 | A1 | 2/2016 |
| WO | WO 2016/034591 | A2 | 3/2016 |
| WO | WO 2016/055777 | A2 | 4/2016 |
| WO | WO 2016/059363 | A1 | 4/2016 |
| WO | WO 2017/215500 | A1 | 12/2017 |

OTHER PUBLICATIONS

Akeson et al., Microsecond time-scale discrimination among polycytidylic acid, polyadenylic acid, and polyuridylic acid as homopolymers or as segments within single RNA molecules. Biophys J. Dec. 1999;77(6):3227-33.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Amblard et al., Cu(I)-catalyzed Huisgen azide-alkyne 1,3-dipolar cycloaddition reaction in nucleoside, nucleotide, and oligonucleotide chemistry. Chem Rev. Sep. 2009;109(9):4207-20. doi: 10.1021/cr9001462.

Ashkenasy et al., Recognizing a single base in an individual DNA strand: a step toward DNA sequencing in nanopores. Angew Chem Int Ed Engl. Feb. 18, 2005;44(9):1401-4.

Ashkenasy et al., Single Nucleobase Sensitivity of a-Hemolysin (a-HL) Transmembrane Protein Pore: Toward Single DNA Sequencing. ACS National Meeting. 2005;45(13), Abstract No. 74.

Astier et al., Stochastic detection of motor protein-RNA complexes by single-channel current recording. Chemphyschem. Oct. 22, 2007;8(15):2189-94.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

(56) References Cited

OTHER PUBLICATIONS

Avrameas, Coupling of enzymes to proteins with glutaraldehyde. Use of the conjugates for the detection of antigens and antibodies. Immunochemistry. Jan. 1969;6(1):43-52.
Bayley et al., Stochastic sensors inspired by biology. Nature. Sep. 13, 2001;413(6852):226-30.
Bayley, Sequencing single molecules of DNA. Curr Opin Chem Biol. Dec. 2006;10(6):628-37. Epub Nov. 20, 2006.
Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.
Berger et al., Universal bases for hybridization, replication and chain termination. Nucleic Acids Res. Aug. 1, 2000;28(15):2911-4.
Bowie et al., Deciphering the message in protein sequences: tolerance to amino acid substitutions. Science. Mar. 16, 1990;247(4948):1306-10.
Braha et al., Carriers versus adapters in stochastic sensing. Chemphyschem. May 2005;6(5):889-92.
Braha et al., Designed protein pores as components for biosensors. Chem Biol. Jul. 1997;4(7):497-505.
Branton et al., The potential and challenges of nanopore sequencing. Nat Biotechnol. Oct. 2008;26(10):1146-53. doi:10.1038/nbt.1495.
Braslavsky et al., Sequence information can be obtained from single DNA molecules. Proc Natl Acad Sci USA. Apr. 1, 2003;100(7):3960-4. Epub Mar. 21, 2003.
Budanova et al., Heptakis(6-amino-6-deoxy)-beta-cyclodextrin as a chiral selector for the separation of anionic analyte enantiomers by capillary electrophoresis. Electrophoresis. Aug. 2004;25(16):2795-800.
Burgess et al., Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Busam, Structure of *Escherichia coli* exonuclease I in complex with thymidine 5'-monophosphate. Acta Crystallogr D Biol Crystallogr. Feb. 2008;64(Pt 2):206-10. doi: 10.1107/S090744490706012X. Epub Jan. 16, 2008.
Butler et al., Determination of RNA orientation during translocation through a biological nanopore. Biophys J. Jan. 1, 2006;90(1):190-9. Epub Oct. 7, 2005.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Case 1:17-cv-00275-LPS Document 18. Notice of subsequent events relating to Oxford's motion to dismiss (D.I. 9). Oct. 18, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Techologies, Inc.'s Motion to Dismiss and Request for Scheduling Conference. Nov. 30, 2017.
Case 1:17-cv-01353-RGA Document 10. Oxford's opening brief in support of its motion to partially dismiss Pacbio's complaint for patent infringement. Nov. 16, 2017.
Chan, Advances in sequencing technology. Mutat Res. Jun. 3, 2005;573(1-2):13-40.
Cheley et al., A functional protein pore with a "retro" transmembrane domain. Protein Sci. Jun. 1999;8(6):1257-67.
Cheley et al., A genetically encoded pore for the stochastic detection of a protein kinase. Chembiochem. Dec. 2006;7(12):1923-7.
Cheley et al., Spontaneous oligomerization of a staphylococcal alpha-hemolysin conformationally constrained by removal of residues that form the transmembrane beta-barrel. Protein Eng. Dec. 1997;10(12):1433-43.
Cheley et al., Stochastic sensing of nanomolar inositol 1,4,5-trisphosphate with an engineered pore. Chem Biol. Jul. 2002;9(7):829-38.
Chen et al., Atomic Layer Deposition to Fine-Tune the Surface Properties and Diameters of Fabricated Nanopores. Nano Lett. Jun. 25, 2004;4(7):1333-1337.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Comai et al., Protein engineering modulates the transport properties and ion selectivity of the pores formed by staphylococcal gamma-haemolysins in lipid membranes. Mol Microbiol. Jun. 2002;44(5):1251-67.
Comer et al., Microscopic mechanics of hairpin DNA translocation through synthetic nanopores. Biophys J. Jan. 2009;96(2):593-608. doi: 10.1016/j.bpj.2008.09.023.
Cudic et al., Binding of Nucleotides in Water by Phenathridinium Bis(intercaland) Receptor Molecules. J. Chem. Soc., Chem. Commun., pp. 1073-1075 (1995).
Dapprich, Single-molecule DNA digestion by lambda-exonuclease. Cytometry. Jul. 1, 1999;36(3):163-8.
Deamer et al., Characterization of nucleic acids by nanopore analysis. Acc Chem Res. Oct. 2002;35(10):817-25.
Deamer et al., Nanopores and nucleic acids: prospects for ultrarapid sequencing. Trends Biotechnol. Apr. 2000;18(4):147-51.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Devereux et al., A comprehensive set of sequence analysis programs for the VAX. Nucleic Acids Res. Jan. 11, 1984;12(1 Pt 1):387-95.
Dorre et al., Techniques for single molecule sequencing. Bioimaging, vol. 5:139-152 (1997).
Eid et al., Real-time DNA sequencing from single polymerase molecules. Science. Jan. 2, 2009;323(5910):133-8. doi:10.1126/science.1162986. Epub Nov. 20, 2008.
Eliseev et al., Aminocyclodextrins as Selective Hosts with Several Binding Sites for Nucleotides. Angew. Chem. Int. Ed. Engl., vol. 32(9):1331-1333 (1993).
Eliseev et al., Molecular Recognition of Nucleotides, Nucleosides, and Sugars by Aminocyclodextrins. J. Am. Chem. Soc., vol. 116:6081-6088 (1994).
El-Sagheer et al., Synthesis and polymerase chain reaction amplification of DNA strands containing an unnatural triazole linkage. J Am Chem Soc. Mar. 25, 2009;131(11):3958-64. doi: 10.1021/ja8065896.
Erie et al., A dumbbell-shaped, double-hairpin structure of DNA: a thermodynamic investigation. Biochemistry. Nov. 3, 1987;26(22):7150-9.
Flomenbom et al., Single stranded DNA translocation through a nanopore: a master equation approach. Phys Rev E Stat Nonlin Soft Matter Phys. Oct. 2003;68(4 Pt 1):041910. Epub Oct. 14, 2003.
Flusberg et al., Direct detection of DNA methylation during single-molecule, real-time sequencing. Nat Methods. Jun. 2010;7(6):461-5. doi: 10.1038/nmeth.1459. Epub May 9, 2010.
Genschel et al., Interaction of *E. coli* single-stranded DNA binding protein (SSB) with exonuclease I. The carboxy-terminus of SSB is the recognition site for the nuclease. Biol Chem. Mar. 2000;381(3):183-92.

(56) References Cited

OTHER PUBLICATIONS

Gershow et al., Recapturing and trapping single molecules with a solid-state nanopore. Nat Nanotechnol. Dec. 2007;2(12):775-9. doi:10.1038/nnano.2007.381. Epub Dec. 2, 2007.
Ghosal, Electrokinetic-flow-induced viscous drag on a tethered DNA inside a nanopore. Phys Rev E Stat Nonlin Soft Matter Phys. Dec. 2007;76(6 Pt 1):061916. Epub Dec. 26, 2007.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
Gu et al., Capture of a single molecule in a nanocavity. Science. Jan. 26, 2001;291(5504):636-40.
Gu et al., Electroosmotic enhancement of the binding of a neutral molecule to a transmembrane pore. Proc Natl Acad Sci U S A. Dec. 23, 2003;100(26):15498-503. Epub Dec. 15, 2003.
Gu et al., Prolonged residence time of a noncovalent molecular adapter, beta-cyclodextrin, within the lumen of mutant alpha-hemolysin pores. J Gen Physiol. Nov. 2001;118(5):481-94.
Gu et al., Reversal of charge selectivity in transmembrane protein pores by using noncovalent molecular adapters. Proc Natl Acad Sci U S A. Apr. 11, 2000;97(8):3959-64.
Gu et al., Single molecule sensing by nanopores and nanopore devices. Analyst. Mar. 2010;135(3):441-51. doi: 10.1039/b907735a. Epub Dec. 22, 2009.
Gu et al., Stochastic sensing of organic analytes by a pore-forming protein containing a molecular adapter. Nature. Apr. 22, 1999;398(6729):686-90.
Guan et al., Stochastic sensing of TNT with a genetically engineered pore. Chembiochem. Oct. 2005;6(10):1875-81.
Han et al., Characterization and optimization of an entropic trap for DNA separation. Anal Chem. Jan. 15, 2002;74(2):394-401.
Han et al., RecJ exonuclease: substrates, products and interaction with SSB. Nucleic Acids Res. Feb. 18, 2006;34(4):1084-91. Print 2006.
Hein et al., Click chemistry, a powerful tool for pharmaceutical sciences. Pharm Res. Oct. 2008;25(10):2216-30. doi: 10.1007/s11095-008-9616-1. Epub May 29, 2008.
Henrickson et al., Driven DNA transport into an asymmetric nanometer-scale pore. Phys Rev Lett. Oct. 2, 2000;85(14):3057-60.
Heredia et al., In vitro double transposition for DNA identification. Anal Biochem. Apr. 1, 2010;399(1):78-83. doi:10.1016/j.ab.2009.11.030. Epub Nov. 26, 2009.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., DNA Duplex Formation of Individual DNA Strands within a Single Protein Pore. Biophysical Journal, vol. 82{ 1, pt. 2):508a, No. 2482-Plat (2002).
Howorka et al., Improved protocol for high-throughput cysteine scanning mutagenesis. Biotechniques. Nov. 1998;25(5):764-6, 768, 770 passim.
Howorka et al., Kinetics of duplex formation for individual DNA strands within a single protein nanopore. Proc Natl Acad Sci U S A. Nov. 6, 2001;98(23):12996-3001. Epub Oct. 23, 2001.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Hu et al., Theory of DNA translocation through narrow ion channels and nanopores with charged walls. Phys Rev E Stat Nonlin Soft Matter Phys. Sep. 2008;78(3 Pt 1):032901. Epub Sep. 10, 2008.
Hwang et al., Electrical behavior of droplet interface bilayer networks: experimental analysis and modeling. J Am Chem Soc. Sep. 26, 2007;129(38):11854-64. Epub Sep. 1, 2007.
Jayasinghe et al., The leukocidin pore: evidence for an octamer with four LukF subunits and four LukS subunits alternating around a central axis. Protein Sci. Oct. 2005;14(10):2550-61.
Jung et al., The internal cavity of the staphylococcal alpha-hemolysin pore accommodates approximately 175 exogenous amino acid residues. Biochemistry. Jun. 28, 2005;44(25):8919-29.
Kalisch et al., Covalently linked sequencing primer linkers (splinkers) for sequence analysis of restriction fragments. Gene. 1986;44(2-3):263-70.
Kanan et al., Reaction discovery enabled by DNA-templated synthesis and in vitro selection. Nature. Sep. 30, 2004;431(7008):545-9.
Kang et al., Single protein pores containing molecular adapters at high temperatures. Angew Chem Int Ed Engl. Feb. 25, 2005;44(10):1495-9.
Kasianowicz et al., Characterization of individual polynucleotide molecules using a membrane channel. Proc Natl Acad Sci U S A. Nov. 26, 1996;93(24):13770-3.
Keyser, Controlling molecular transport through nanopores. J R Soc Interface. Oct. 7, 2011;8(63):1369-78. doi: 10.1098/rsif.2011.0222. Epub Jun. 29, 2011.
Khulbe et al., DNA translocation through a-hemolysin nanopores with potential application to macromolecular data storage. Journal Applied Physics, vol. 97(104317):1-7 (2005).
Kocalka et al., Rapid and efficient DNA strand cross-linking by click chemistry. Chembiochem. May 23, 2008;9(8):1280-5. doi:10.1002/cbic.200800006.
Kolb et al., Click Chemistry: Diverse Chemical Function from a Few Good Reactions. Angew Chem Int Ed Engl. Jun. 1, 2001;40(11):2004-2021.
Kovall et al., Toroidal structure of lambda-exonuclease. Science. Sep. 19, 1997;277(5333):1824-7.
Langecker et al., Synthetic lipid membrane channels formed by designed DNA nanostructures. Science. Nov. 16, 2012;338(6109):932-6. doi: 10.1126/science.1225624.
Lazar et al., Transforming growth factor alpha: mutation of aspartic acid 47 and leucine 48 results in different biological activities. Mol Cell Biol. Mar. 1988;8(3):1247-52.
Li et al., DNA molecules and configurations in a solid-state nanopore microscope. Nat Mater. Sep. 2003;2(9):611-5. Epub Aug. 24, 2003.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Lovett et al., Identification and purification of a single-stranded-DNA-specific exonuclease encoded by the recJ gene of *Escherichia coli*. Proc Natl Acad Sci U S A. Apr. 1989;86(8):2627-31.
Lovrinovic et al., Rapid synthesis of DNA-cysteine conjugates for expressed protein ligation. Biochem Biophys Res Commun. Sep. 30, 2005;335(3):943-8.
Lu et al., Structural basis of *Escherichia coli* single-stranded DNA-binding protein stimulation of exonuclease I. Proc Natl Acad Sci U S A. Jul. 8, 2008;105(27):9169-74. doi: 10.1073/pnas.0800741105. Epub Jun. 30, 2008.
Luo et al., Influence of polymer-pore interactions on translocation. Phys Rev Lett. Oct. 5, 2007;99(14):148102. Epub Oct. 1, 2007.
Lutz et al., Efficient construction of therapeutics, bioconjugates, biomaterials and bioactive surfaces using azide-alkyne “click” chemistry. Adv Drug Deliv Rev. Jun. 10, 2008;60(9):958-70. doi: 10.1016/j.addr.2008.02.004. Epub Mar. 4, 2008.
Maglia et al., Analysis of single nucleic acid molecules with protein nanopores. Methods Enzymol. 2010;475:591-623. doi: 10.1016/S0076-6879(10)75022-9.
Maglia et al., Enhanced translocation of single DNA molecules through alpha-hemolysin nanopores by manipulation of internal charge. Proc Natl Acad Sci U S A. Dec. 16, 2008;105(50):19720-5. doi:10.1073/pnas.0808296105. Epub Dec. 5, 2008.

(56) References Cited

OTHER PUBLICATIONS

Martin et al., Nanoscale protein pores modified with PAMAM dendrimers. J Am Chem Soc. Aug. 8, 2007;129(31):9640-9. Epub Jul. 18, 2007.

Martînez et al., The mRNA cap structure stimulates rate of poly(A) removal and amplifies processivity of degradation. J Biol Chem. Jul. 27, 2001;276(30):27923-9. Epub May 18, 2001.

Marziali et al., New DNA sequencing methods. Annu Rev Biomed Eng. 2001;3:195-223.

Mathé et al., Orientation discrimination of single-stranded DNA inside the alpha-hemolysin membrane channel. Proc Natl Acad Sci U S A. Aug. 30, 2005;102(35):12377-82. Epub Aug. 19, 2005.

Matsuura et al., Real-time observation of a single DNA digestion by lambda exonuclease under a fluorescence microscope field. Nucleic Acids Res. Aug. 15, 2001;29(16):E79.

Meller et al., Rapid nanopore discrimination between single polynucleotide molecules. Proc Natl Acad Sci U S A. Feb. 1, 2000;97(3):1079-84.

Meller et al., Single molecule measurements of DNA transport through a nanopore. Electrophoresis. Aug. 2002;23(16):2583-91.

Meller, Dynamics of polynucleotide transport through nanometre-scale pores. Journal Physics: Condensed Matter, vol. 15:R581-R607 (2003).

Merzlyak et al., Conductance and ion selectivity of a mesoscopic protein nanopore probed with cysteine scanning mutagenesis. Biophys J. Nov. 2005;89(5):3059-70. Epub Aug. 5, 2005.

Miles et al., Single molecule sensing with solid-state nanopores: novel materials, methods, and applications. Chem Soc Rev. Jan. 7, 2013;42(1):15-28. doi: 10.1039/c2cs35286a. Epub Sep. 19, 2012.

Mitchell et al., Chemical tags facilitate the sensing of individual DNA strands with nanopores. Angew Chem Int Ed Engl. 2008;47(30):5565-8. doi:10.1002/anie.200800183.

Mohammad et al., Controlling a single protein in a nanopore through electrostatic traps. J Am Chem Soc. Mar. 26, 2008;130(12):4081-8. doi: 10.1021/ja710787a. Epub Mar. 6, 2008.

Mol et al., Structure and function of the multifunctional DNA-repair enzyme exonuclease III. Nature. Mar. 23, 1995;374(6520):381-6.

Montal et al., Formation of bimolecular membranes from lipid monolayers and a study of their electrical properties. Proc Natl Acad Sci U S A. Dec. 1972;69(12):3561-6.

Movileanu et al., Detecting protein analytes that modulate transmembrane movement of a polymer chain within a single protein pore. Nat Biotechnol. Oct. 2000;18(10):1091-5.

Movileanu et al., Location of a constriction in the lumen of a transmembrane pore by targeted covalent attachment of polymer molecules. J Gen Physiol. Mar. 2001;117(3):239-52.

Muller et al., DNA-directed assembly of artificial multienzyme complexes. Biochem Biophys Res Commun. Dec. 5, 2008;377(1):62-7. doi:10.1016/j.bbrc.2008.09.078. Epub Sep. 25, 2008.

Nakane et al., A nanosensor for transmembrane capture and identification of single nucleic Acid molecules. Biophys J. Jul. 2004;87(1):615-21. Erratum in: Biophys J. Nov. 2004;87(5):3618.

Nakane et al., Nanopore sensors for nucleic acid analysis. J. Phys.: Condens. Matter, vol. 15: R 1365-R1393 (2003).

Niemeyer et al., DNA-directed assembly of bienzymic complexes from in vivo biotinylated NAD(P)H:FMN oxidoreductase and luciferase. Chembiochem. Mar. 1, 2002;3(2-3):242-5.

Nikolov et al., Behavior of giant vesicles with anchored DNA molecules. Biophys J. Jun. 15, 2007;92(12):4356-68. Epub Mar. 23, 2007.

Nwe et al., Growing applications of "click chemistry" for bioconjugation in contemporary biomedical research. Cancer Biother Radiopharm. Jun. 2009;24(3):289-302. doi: 10.1089/cbr.2008.0626.

Paner et al., Studies of DNA dumbbells. III. Theoretical analysis of optical melting curves of dumbbells with a 16 base-pair duplex stem and Tn end loops (n = 2, 3, 4, 6, 8, 10, 14). Biopolymers. Jul. 1992;32(7):881-92.

Paner et al., Studies of DNA dumbbells. VI. Analysis of optical melting curves of dumbbells with a sixteen-base pair duplex stem and end-loops of variable size and sequence. Biopolymers. Dec. 1996;39(6):779-93.

Phoenix et al., OmpF-Lpp signal sequence mutants with varying charge hydrophobicity ratios provide evidence for a phosphatidylglycerol-signal sequence interaction during protein translocation across the *Escherichia coli* inner membrane. J Biol Chem. Aug. 15, 1993;268(23):17069-73.

Purnell et al., Nucleotide identification and orientation discrimination of DNA homopolymers immobilized in a protein nanopore. Nano Lett. Sep. 2008;8(9):3029-34. doi: 10.1021/n1802312f. Epub Aug. 13, 2008.

Sanchez-Quesada et al., Cyclic Peptides as Molecular Adapters for a Pore-Forming Protein. Journal American Chemical Society, vol. 122(48):11757-11766 (2000).

Sanchez-Quesada et al., Single DNA rotaxanes of a transmembrane pore protein. Angew Chem Int Ed Engl. Jun. 7, 2004;43(23):3063-7.

Sanderson, Personal genomes: Standard and pores. Nature. Nov. 6, 2008;456(7218):23-5. doi: 10.1038/456023a.

Sauer-Budge et al., Unzipping kinetics of double-stranded DNA in a nanopore. Phys Rev Lett. Jun. 13, 2003;90(23):238101. Epub Jun. 9, 2003.

Schneider et al., DNA sequencing with nanopores. Nat Biotechnol. Apr. 10, 2012;30(4):326-8. doi: 10.1038/nbt.2181.

Seeman, Nucleic acid junctions and lattices. J Theor Biol. Nov. 21, 1982;99(2):237-47.

Seo et al., Click chemistry to construct fluorescent oligonucleotides for DNA sequencing. J Org Chem. Jan. 24, 2003;68(2):609-12.

Seol et al., Stretching of homopolymeric RNA reveals single-stranded helices and basestacking. Phys Rev Lett. Apr. 13, 2007;98(15):158103. Epub Apr. 12, 2007.

Shank et al., Redesigning channel-forming peptides: amino acid substitutions that enhance rates of supramolecular self-assembly and raise ion transport activity. Biophys J. Mar. 15, 2006;90(6):2138-50. Epub Dec. 30, 2005.

Shin et al., Kinetics of a reversible covalent-bond-forming reaction observed at the single-molecule level. Angew Chem Int Ed Engl. Oct. 4, 2002;41(19):3707-9; 3523.

Smeets et al., Salt dependence of ion transport and DNA translocation through solid-state nanopores. Nano Lett. Jan. 2006;6(1):89-95.

Song et al., Structure of staphylococcal alpha-hemolysin, a heptameric transmembrane pore. Science. Dec. 13, 1996;274(5294):1859-66.

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Sutherland et al., An analysis of mismatched duplex DNA unzipping through a bacterial nanopore. Biochem Cell Biol. Jun. 2004;82(3):407-12.

Tadey et al., Capillary electrophoretic separation of nucleotide isomers via complexation with cyclodextrin and borate. J Chromatogr B Biomed Appl. Jul. 15, 1994;657(2):365-72.

Thomas et al., Processivity of DNA exonucleases. J Biol Chem. Jan. 25, 1978;253(2):424-9.

Tohda et al., "Channel Mimetic Sensing Membranes for Nucleotides Based on Multitopic Hydrogen Bonding," Israel Journal of Chemistry, vol. 37:267-275 (1997).

Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.

Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.

Tung et al., Preparation and applications of peptide-oligonucleotide conjugates. Bioconjug Chem. Sep.-Oct. 2000;11(5):605-18.

(56) References Cited

OTHER PUBLICATIONS

United States District Court for the District of Delaware Order. *Pacific Biosciences of California, Inc.* v. *Oxford Nanopore Technolgoies, Inc.* Civil Action No. 17-275-RGA. Nov. 9, 2017.
Van De Goor, Nanopore Detection: Threading DNA Through a Tiny Hole. PharmaGenomics, vol. 4 (3):28-30 (2004).
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Venkatesan et al., Nanopore sensors for nucleic acid analysis. Nat Nanotechnol. Sep. 18, 2011;6(10):615-24. doi: 10.1038/nnano.2011.129.
Walker et al., Key residues for membrane binding, oligomerization, and pore forming activity of staphylococcal alpha-hemolysin identified by cysteine scanning mutagenesis and targeted chemical modification. J Biol Chem. Sep. 29, 1995;270(39):23065-71.
Wang et al., Bioconjugation by copper(I)-catalyzed azide-alkyne [3 + 2] cycloaddition. J Am Chem Soc. Mar. 19, 2003;125(11):3192-3.
Wang et al., Nanopores with a spark for single-molecule detection. Nat Biotechnol. Jul. 2001;19(7):622-3.
Wanunu et al., Discrimination of methylcytosine from hydroxymethylcytosine in DNA molecules. J Am Chem Soc. Jan. 26, 2011;133(3):486-92. doi:10.1021/ja107836t. Epub Dec. 14, 2010.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wemmer et al., Preparation and melting of single strand circular DNA loops. Nucleic Acids Res. Dec. 9, 1985;13(23):8611-21.
Winters-Hilt et al., Highly accurate classification of Watson-Crick basepairs on termini of single DNA molecules. Biophys J. Feb. 2003;84(2 Pt 1):967-76.
Wolfe et al., Catalyzing the translocation of polypeptides through attractive interactions. J Am Chem Soc. Nov. 14, 2007;129(45):14034-41. Epub Oct. 19, 2007.
Wong et al., Polymer capture by electro-osmotic flow of oppositely charged nanopores. J Chem Phys. Apr. 28, 2007;126(16):164903.
Wu et al., Protein nanopores with covalently attached molecular adapters. J Am Chem Soc. Dec. 26, 2007;129(51):16142-8. Epub Nov. 30, 2007.
Xie et al., Single-molecule observation of the catalytic subunit of cAMP-dependent protein kinase binding to an inhibitor peptide. Chem Biol. Jan. 2005;12(1):109-20.
Yamagata et al., Overexpression, purification and characterization of RecJ protein from Thermus thermophilus HB8 and its core domain. Nucleic Acids Res. Nov. 15, 2001;29(22):4617-24.
Cheng, et al., Functional characterization of the multidomain F plasmid Tral relaxase-helicase. J Biol Chem. Apr. 8, 2011;286(14):12670-82. doi: 10.1074/jbc.M110.207563. Epub Feb. 2, 2011.
Colas et al., Microscopical investigations of nisin-loaded nanoliposomes prepared by Mozafari method and their bacterial targeting. Micron. 2007;38(8):841-7. Epub Jul. 3, 2007.
Fairman-Williams et al., SF1 and SF2 helicases: family matters. Curr Opin Struct Biol. Jun. 2010;20(3):313-24. doi: 10.1016/j.sbi.2010.03.011. Epub Apr. 22, 2010.
Faller et al., The structure of a mycobacterial outer-membrane channel. Science. Feb. 20, 2004;303(5661):1189-92. doi: 10.1126/science.1094114.
Gacillàn-Barcia et al., The diversity of conjugative relaxases and its application in plasmid classification. FEMS Microbiol Rev. May 2009;33(3):657-87.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al., The carboxyl-terminal domain of bacteriophage T7 single-stranded DNA-binding protein modulates DNA binding and interaction with T7 DNA polymerase. J Biol Chem. Aug. 8, 2003;278(32):29538-45. doi: 10.1074/jbc.M304318200. Epub May 24, 2003.
He et al., The T4 Phage SF1B Helicase Dda is Structurally Optimized to Perform DNA Strand Separation. Structure. Jul. 3, 2012; 20(7): 1189-1200. EPub May 31, 2012. doi: 10.1016/j.str.2012.04.013.
Heron et al., Simultaneous measurement of ionic current and fluorescence from single protein pores. J Am Chem Soc. Feb. 11, 2009;131(5):1652-3. doi: 10.1021/ja808128s.
Hobbs et al., SSB protein limits RecOR binding onto single-stranded DNA. J Biol Chem. Apr. 13, 2007;282(15):11058-67. Epub Feb. 1, 2007.
Hollis et al., Structure of the gene 2.5 protein, a single-stranded DNA binding protein encoded by bacteriophage T7. Proc Natl Acad Sci U S A. Aug. 14, 2001;98(17):9557-62. doi: 10.1073/pnas.171317698. Epub Jul. 31, 2001.
Hyland et al., The DNA binding domain of the gene 2.5 single-stranded DNA-binding protein of bacteriophage T7. J Biol Chem. Feb. 28, 2003;278(9):7247-56. doi: 10.1074/jbc.M210605200. Epub Dec. 20, 2002.
Ivanov et al., DNA tunneling detector embedded in a nanopore. Nano Lett. Jan. 12, 2011;11(1):279-85. doi: 10.1021/n1103873a. Epub Dec. 6, 2010.
Kozarewa et al., 96-plex molecular barcoding for the Illumina Genome Analyzer. Methods Mol Biol. 2011;733:279-98. doi: 10.1007/978-1-61779-089-8_20.
Kozlov et al., Regulation of Single-stranded DNA Binding by the C Termini of *Esherichia coli* Single-stranded DNA-binding (SBB) Protein. J. Biol. Chem. May 28, 2010;285(22):17246-52.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Lee et al., Importance of the conserved CA dinucleotide at Mu termini. J Mol Biol. Nov. 30, 2001;314(3):433-44.
Liang, Structure of outer membrane protein G by solution NMR spectroscopy. Proc Natl Acad Sci U S A. Oct. 9, 2007;104(41):16140-5. doi: 10.1073/pnas.0705466104. Epub Oct. 2, 2007.
Liu et al., Adding new chemistries to the genetic code. Annu Rev Biochem. 2010;79:413-44. doi: 10.1146/annurev.biochem.052308.105824.
Liu et al., Structure of the DNA repair helicase XPD. Cell. May 30, 2008;133(5):801-12. doi: 10.1016/j.cell.2008.04.029.
Locher et al., Transmembrane signaling across the ligand-gated FhuA receptor: crystal structures of free and ferrichrome-bound states reveal allosteric changes. Cell. Dec. 11, 1998;95(6):771-8. doi: 10.1016/s0092-8674(00)81700-6.
Lohman et al., Non-hexameric DNA helicases and translocases: mechanisms and regulation. Nat Rev Mol Cell Biol. May 2008;9(5):391-401. doi: 10.1038/nrm2394.
Lu et al., Peptide inhibitors identify roles for SSB C-terminal residues in SSB/Exonuclease I complex formation. Biochemistry. Jul. 28, 2009;48(29): 6764-6771. doi: 10.1021/bi900361r. Author Manuscript.
Ma et al., Bright functional rotaxanes. Chem Soc Rev. Jan. 2010;39(1):70-80. doi: 10.1039/b901710k. Epub Jul. 21, 2009.
Miner et al., Molecular barcodes detect redundancy and contamination in hairpin-bisulfite PCR. Nucleic Acids Res. 2004; 32(17): e135. EPub Sep. 30, 2004. doi: 10.1093/nar/gnh132.
North et al., Host factors that promote transpososome disassembly and the PriA-PriC pathway for restart primosome assembly. Mol Microbiol. Jun. 2005;56(6):1601-16.
O'Shea et al., X-ray structure of the GCN4 leucine zipper, a two-stranded, parallel coiled coil. Science. Oct. 25, 1991;254(5031):539-44.
Pfeiffer et al., Bivalent cholesterol-based coupling of oligonucletides to lipid membrane assemblies. J Am Chem Soc. Aug. 25, 2004;126(33):10224-5.

(56) References Cited

OTHER PUBLICATIONS

Remaut et al., Protein-protein interaction through beta-strand addition. Trends Biochem Sci. Aug. 2006;31(8):436-44. Epub Jul. 7, 2006.
Rezende et al., Essential amino acid residues in the single-stranded DNA-binding protein of bacteriophage T7. Identification of the dimer interface. J Biol Chem. Dec. 27, 2002;277(52):50643-53. doi: 10.1074/jbc.M207359200. Epub Oct. 12, 2002.
Saariaho et al., Characteristics of MuA transposase-catalyzed processing of model transposon end DNA hairpin substrates. Nucleic Acids Res. Jun. 6, 2006;34(10):3139-49. Print 2006.
Satapathy et al., ATPase activity of RecD is essential for growth of the Antarctic Pseudomonas syringae Lz4W at low temperature. FEBS J. Apr. 2008;275(8):1835-51. doi: 10.1111/j.1742-4658.2008.06342.X. Epub Mar. 9, 2008.
Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.
Soni et al., Synchronous optical and electrical detection of biomolecules traversing through solid-state nanopores. Rev Sci Instrum. Jan. 2010;81(1):014301. doi: 10.1063/1.3277116.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
Van Heel et al., Single-particle electron cryo-microscopy: towards atomic resolution. Q Rev Biophys. Nov. 2000;33(4):307-69.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Yamashita et al., Crystal structures of the OmpF porin: function in a colicin translocon. EMBO J. Aug. 6, 2008;27(15):2171-80. doi: 10.1038/emboj.2008.137. Epub Jul. 17, 2008.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Apr. 2011;6(4): 253-260. EPub Feb. 20, 2011. doi: 10.1038/nnano.2011.12.
[No Author Listed], Multiplex sequencing. https://www.illumina.com/science/technology/next-generation-sequencing/multiplex-sequencing.html. Printed on Nov. 4, 2021. 1 page.
[No Author Listed], Single-molecule real-time sequencing. Wikipedia entry/ Sep. 19, 2021. Retrieved from https://en.wikipedia.org/w/index.php?title+Singlemolecule_real-time_sequencing&oldid=1045146197. Printed on Nov. 4, 2021. 10 pages.
Dong et al., Amplified detection of nucleic acid by G-quadruplex based hybridization chain reaction. Biosens Bioelectron. Oct.-Dec. 2012;38(1):258-63. doi: 10.1016/j.bios.2012.05.042. Epub Jun. 8, 2012.
Gill et al., Nucleic acid isothermal amplification technologies: a review. Nucleosides Nucleotides Nucleic Acids. Mar. 2008;27(3):224-43. doi: 10.1080/15257770701845204.
Kahvejian et al., Making single-molecule sequencing a reality. American Laboratory. Jan. 1, 2008;40(20):48-53. www.americanlaboratory.com/913-Technical-Articles/780-Making-Single-Molecule-Sequencing-a-Reality/. Last accessed Dec. 10, 2021.
Kuipers, Random mutagenesis by using mixtures of dNTP and diTP in PCR. Methods Mol Biol. 1996;57:351-6. doi: 10.1385/0-89603-332-5:351.
Pettersson et al., Generations of sequencing technologies. Genomics. Feb. 2009;93(2):105-11. doi: 10.1016/j.ygeno.2008.10.003. Epub Nov. 21, 2008.
Shendure et al., Overview of DNA sequencing strategies. Curr Protoc Mol Biol. Jan. 2008;Chapter 7:Unit 7.1. doi: 10.1002/0471142727.mb0701s81.
Spee et al., Efficient random mutagenesis method with adjustable mutation frequency by use of PCR and diTP. Nucleic Acids Res. Feb. 11, 1993;21(3):777-8. doi: 10.1093/nar/21.3.777.
Wang et al., A simple and reproducible method for directed evolution: combination of random mutation with diTP and DNA fragmentation with endonuclease V. Mol Biotechnol. Jan. 2013;53(1):49-54. doi: 10.1007/s12033-012-9516-9.
United Kingdom Search Report for Application No. GB1907244.6 dated Feb. 18, 2020.
International Search Report and Written Opinion for Application No. PCT/GB2015/050140, dated May 8, 2015.
International Preliminary Report on Patentability for Application No. PCT/GB2015/050140, dated Aug. 4, 2016.
International Search Report and Written Opinion for Application No. PCT/GB2020/051260 dated Jul. 10, 2020.
International Preliminary Report on Patentability for Application No. PCT/GB2020/051260 dated Dec. 2, 2021.
[No Author Listed] Nextera™ DNA Sample Preparation Kits (Illumina) Oct. 2011. (2 pages).
[No Author Listed] Oxford Nanopore ""Product"" brochure (2020) https://nanoporetech.com/sites/default/files/s3/literature/product-brochure.Pdf (36 pages).
Ahern, Biochemical, reagents kits offer scientists good return on investment. The Scientist. Jul. 24, 1995;9(15):20.
Burton et al., ClpX-mediated remodeling of mu transpososomes: selective unfolding of subunits destabilizes the entire complex. Mol Cell. Aug. 2001;8(2):449-54. doi: 10.1016/s1097-2765(01)00307-0.
Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.
De Vlaminck et al., Mechanism of homology recognition in DNA recombination from dual-molecule experiments. Mol Cell. Jun. 8, 2012;46(5):616-24. doi: 10.1016/j.molcel.2012.03.029. Epub May 3, 2012.
Eoff et al., Chemically modified DNA substrates implicate the importance of electrostatic interactions for DNA unwinding by Dda helicase. Biochemistry. Jan. 18, 2005;44(2):666-74.
Goryshin et al., Tn5 in vitro transposition. J Biol Chem. Mar. 27, 1998;273(13):7367-74. doi: 10.1074/jbc.273.13.7367.
Haque et al., DNA-associated click chemistry. Science China Chemistry. Feb. 2014;57(2):215-231. doi:10.1007/s11426-013-5035-1.
Higgins et al., DNA-joining enzymes: a review. Methods Enzymol. 1979;68:50-71. doi: 10.1016/0076-6879(79)68006-0.
Jain et al., The Oxford Nanopore MinION: delivery of nanopore sequencing to the genomics community. Genome Biol. Nov. 25, 2016;17(1):239. doi: 10.1186/s13059-016-1103-0. Erratum in: Genome Biol. Dec. 13, 2016;17 (1):256.
Kanaan et al., UPF1-like helicase grip on nucleic acids dictates processivity. Nat Commun. Sep. 14, 2018;9(1):3752. doi: 10.1038/s41467-018-06313-y.
Klenchin et al., Phosphate coordination and movement of DNA in the Tn5 synaptic complex: role of the (R)YREK motif. Nucleic Acids Res. Oct. 2008;36(18):5855-62. doi: 10.1093/nar/gkn577. Epub Sep. 12, 2008.
Le et al., Thermostable DNA ligase-mediated PCR production of circular plasmid (PPCP) and its application in directed evolution via in situ error-prone PCR. DNA Res. Aug. 2013;20(4):375-82. doi: 10.1093/dnares/dst016. Epub Apr. 30, 2013.
Li et al., ChIA-PET tool for comprehensive chromatin interaction analysis with paired-end tag sequencing. Genome Biol. 2010;11(2):R22. doi: 10.1186/GB-2010-11-2-r22. Epub Feb. 25, 2010.
Lovett, The DNA Exonucleases of *Escherichia coli*. EcoSal Plus. Dec. 2011;4(2):10.1128/ecosalplus.4.4.7. doi: 10.1128/ecosalplus.4.4.7. Author Manuscript, 45 pages.
Maine et al., Inhibition of the DNA unwinding and ATP hydrolysis activities of the bacteriophage T4 DDA helicase by a sequence specific DNA-protein complex. Biochem Biophys Res Commun. Feb. 15, 1994;198(3):1070-7. doi: 10.1006/bbrc.1994.1152.
Manosas et al., Magnetic tweezers for the study of DNA tracking motors. Methods Enzymol. 2010;475:297-320. doi: 10.1016/S0076-6879(10)75013-8.
Matson et al., The gene 4 protein of bacteriophage T7. Characterization of helicase activity. J Biol Chem. Nov. 25, 1983;258(22):14017-24.

(56) References Cited

OTHER PUBLICATIONS

Montal et al., Formation of bimolecular membranes from lipid monolayers and a study of their electrical properties. Proc Natl Acad Sci U S A. Dec. 1972;69(12):3561-6. doi: 10.1073/pnas.69.12.3561.

Reznikoff, Tn5 as a model for understanding DNA transposition. Mol Microbiol. Mar. 2003;47(5):1199-206. doi: 10.1046/j.1365-2958.2003.03382.x.

Rhee et al., Comprehensive genome-wide protein-DNA interactions detected at single-nucleotide resolution. Cell. Dec. 9, 2011;147(6):1408-19. doi: 10.1016/j.cell.2011.013.

Saariaho et al., Characteristics of MuA transposase-catalyzed processing of model transposon end DNA hairpin substrates. Nucleic Acids Res. Jun. 6, 2006;34(10):3139-49.

Shelbourne et al., Fast copper-free click DNA ligation by the ring-strain promoted alkyne-azide cycloaddition reaction. Chem Commun (Camb). Jun. 14, 2011;47(22):6257-9. doi: 10.1039/c1cc10743g. Epub May 6, 2011.

Sternberg et al., DNA interrogation by the CRISPR RNA-guided endonuclease Cas9. Nature. Mar. 6, 2014;507(7490):62-7. doi: 10.1038/nature13011. Epub Jan. 29, 2014. Author Manuscript, 16 pages.

Tackett et al., Unwinding of unnatural substrates by a DNA helicase. Biochemistry. Jan. 16, 2001;40(2):543-8.

Tuteja et al., Helicases as molecular motors: An insight. Physica A. Dec. 1, 2006;372(1):70-83. doi: 10.1016/j.physa.2006.05.014. Epub Jun. 5, 2006.

Wang et al., Measuring and modeling the kinetics of individual DNA-DNA polymerase complexes on a nanopore. ACS Nano. May 28, 2013;7(5):3876-86. doi: 10.1021/nn401180j. Epub Apr. 16, 2013.

Wiedmann et al., Ligase chain reaction (LCR)—overview and applications. PCR Methods Appl. Feb. 1994;3(4):S51-64. doi: 10.1101/gr.3.4.s51.

Wilkinson et al., Bacterial DNA ligases. Mol Microbiol. Jun. 2001;40(6):1241-8. doi: 10.1046/j.1365-2958.2001,02479.x.

Wu et al., Sequence-specific capture of protein-DNA complexes for mass spectrometric protein identification. PLoS One. 2011;6(10):e26217. doi: 10.1371/journal.pone.0026217. Epub Oct. 20, 2011.

Yen et al., SWR-C and INO80 chromatin remodelers recognize nucleosome-free regions near +1 nucleosomes. Cell. Sep. 12, 2013;154(6):1246-56. doi: 10.1016/j.cell.2013.08.043.

* cited by examiner

A

B

ENZYME STALLING METHOD

RELATED APPLICATIONS

This Application is a continuation under 35 U.S.C. § 120 of U.S. application Ser. No. 14/773,164, filed Sep. 4, 2015, entitled "ENZYME STALLING METHOD", which is a national stage filing under 35 U.S.C. § 371 of International Patent Application Serial No. PCT/GB2014/050175, filed Jan. 22, 2014, entitled "ENZYME STALLING METHOD", which claims the benefit under 35 U.S.C. § 119(e) of U.S. Application Ser. No. 61/774,694, filed Mar. 8, 2013, entitled "ENZYME STALLING METHOD". Foreign priority benefits are claimed under 35 U.S.C. § 119(a)-(d) or 35 U.S.C. § 365(b) of British application number 1318464.3, filed Oct. 18, 2013, British application number 1318465.0, filed Oct. 18, 2013, and British application number 1314695.6, filed Aug. 16, 2013. The entire contents of each of the foregoing applications are incorporated herein by reference.

FIELD OF THE INVENTION

The invention relates to new methods of moving helicases past spacers on polynucleotides and controlling the loading of helicases on polynucleotides. The invention also relates to new methods of characterising target polynucleotides using helicases.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the "strand sequencing" method, a single polynucleotide strand is passed through the pore and the identities of the nucleotides are derived. Strand sequencing can involve the use of a nucleotide handling protein, such as a helicase, to control the movement of the polynucleotide through the pore.

SUMMARY OF THE INVENTION

Spacers in polynucleotides are typically capable of stalling helicases, i.e. preventing helicases from moving further along the polynucleotides past the spacers. The inventors have surprisingly demonstrated that it is possible to move one or more stalled helicases past a spacer in a polynucleotide by contacting the helicase and polynucleotide with a transmembrane pore and applying a potential. Since the helicase is typically too large to fit through the pore, the force of the polynucleotide moving through the pore along the potential moves the helicase past the spacer. This has important applications for controlling the movement of polynucleotides and characterising, such as sequencing, polynucleotides. The inventors have also surprisingly demonstrated that it is possible to control the loading of one or more helicases on a polynucleotide using one or more spacers.

The invention therefore provides a method of moving one or more stalled helicases past one or more spacers in a target polynucleotide, comprising contacting (a) the one or more stalled helicases and the target polynucleotide with a transmembrane pore and (b) applying a potential across the pore and thereby moving the one or more helicases past the one or more spacers on the target polynucleotide.

The invention also provides:

a method of controlling the movement of a target polynucleotide through a transmembrane pore, comprising (a) providing the target polynucleotide with one or more spacers; (b) contacting the target polynucleotide with one or more helicases such that the one or more helicases stall at the one or more spacers; (c) contacting the target polynucleotide and the one or more stalled helicases with the pore; and (d) applying a potential across the pore such that the one or more helicases move past the one or more spacers and control the movement of the target polynucleotide through the pore;

a method of characterising a target polynucleotide, comprising (a) carrying out the method of controlling the movement of a target polynucleotide through a transmembrane pore of the invention; and (b) taking one or more measurements as the polynucleotide moves with respect to the pore wherein the measurements are indicative of one or more characteristics of the polynucleotide and thereby characterising the target polynucleotide;

a method of controlling the loading of one or more helicases on a target polynucleotide, comprising (a) providing the polynucleotide with one or more spacers; and (b) contacting the polynucleotide provided in (a) with the one or more helicases such that the one or more helicases bind to the polynucleotide and stall at each spacer;

an adaptor for controlling the movement of a target polynucleotide, wherein the adaptor comprises (a) (L-S-D)n or (D-S-L)n in the 5' to 3' direction, wherein L is a single stranded polynucleotide or a non-hybridised polynucleotide, S is a spacer and D is a double stranded polynucleotide and wherein n is a whole number and (b) one or more helicases stalled on each adaptor; and a kit for controlling the movement of a target polynucleotide, wherein the kit comprises (a) one or more spacers, (b) one or more helicases and (c) a transmembrane pore.

G1G2))) controls the translocation of the Lambda DNA construct (0.2 nM as described and illustrated in FIG. 1) through a nanopore (MS(B1-G75S/G77S/L88N/Q126R)8 MspA (MspA-B2C) (SEQ ID NO: 2 with mutations 075S/G77S/L88N/Q126R)).

Figure 2:
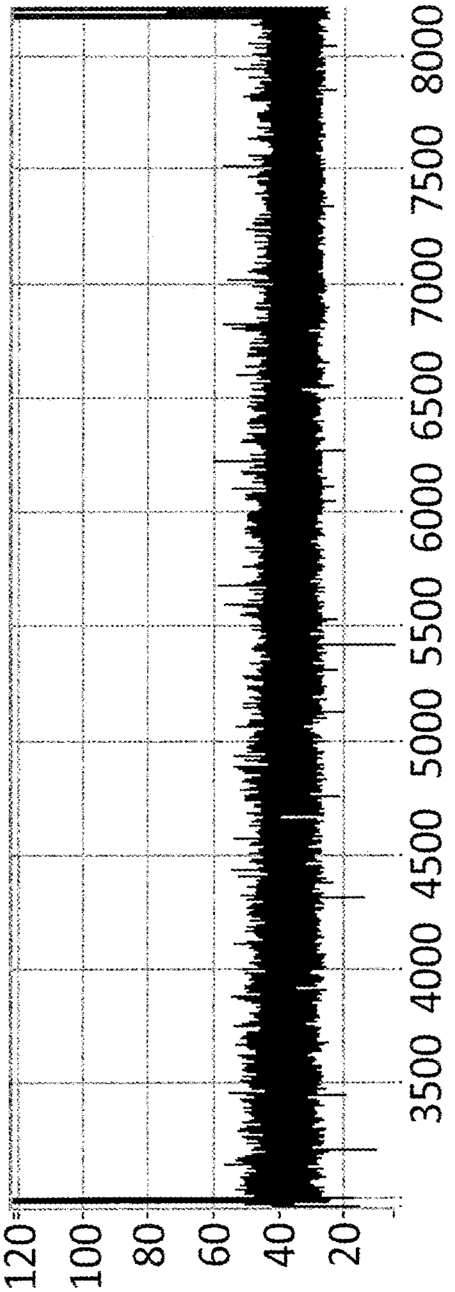
FIG. 2 shows an example current trace (y-axis label=Current (pA, 20 to 120), x-axis label=Time (s, 3500 to 8000)) of when a helicase (T4 Dda-E94C/A360C (SEQ ID NO: 8 with mutations E94C/A360C and then (ΔM1)
Figure 3:
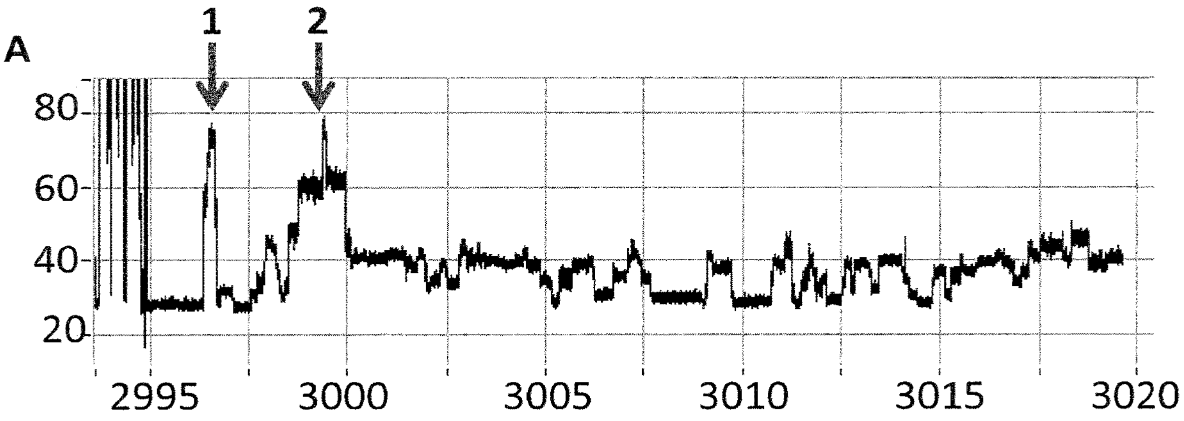
Figure 3:
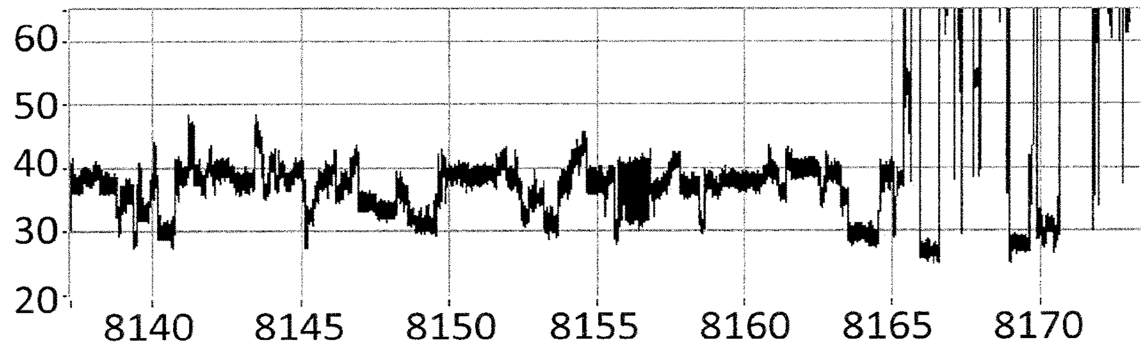

FIG. 3 shows zoomed in regions of the helicase-controlled DNA movement shown in the current trace in FIG. 2 (y-axis label=Current (pA, upper trace 20 to 80, lower trace 20 to 60), x-axis label=Time (s, upper trace 2995 to 3020, lower trace 8140 to 8170) for both the upper and lower traces). A) shows the beginning of the helicase-controlled DNA movement and B) shows the end of the helicase controlled DNA movement. The arrow labelled 1 corresponds to when the first four iSpC3 spacers (which is used to stall the movement of the enzyme prior to capture by the nanopore) moves through the nanopore. The arrow labelled 2 corresponds to a second group of four iSpC3 spacers moving through the nanopore.

Figure 4:
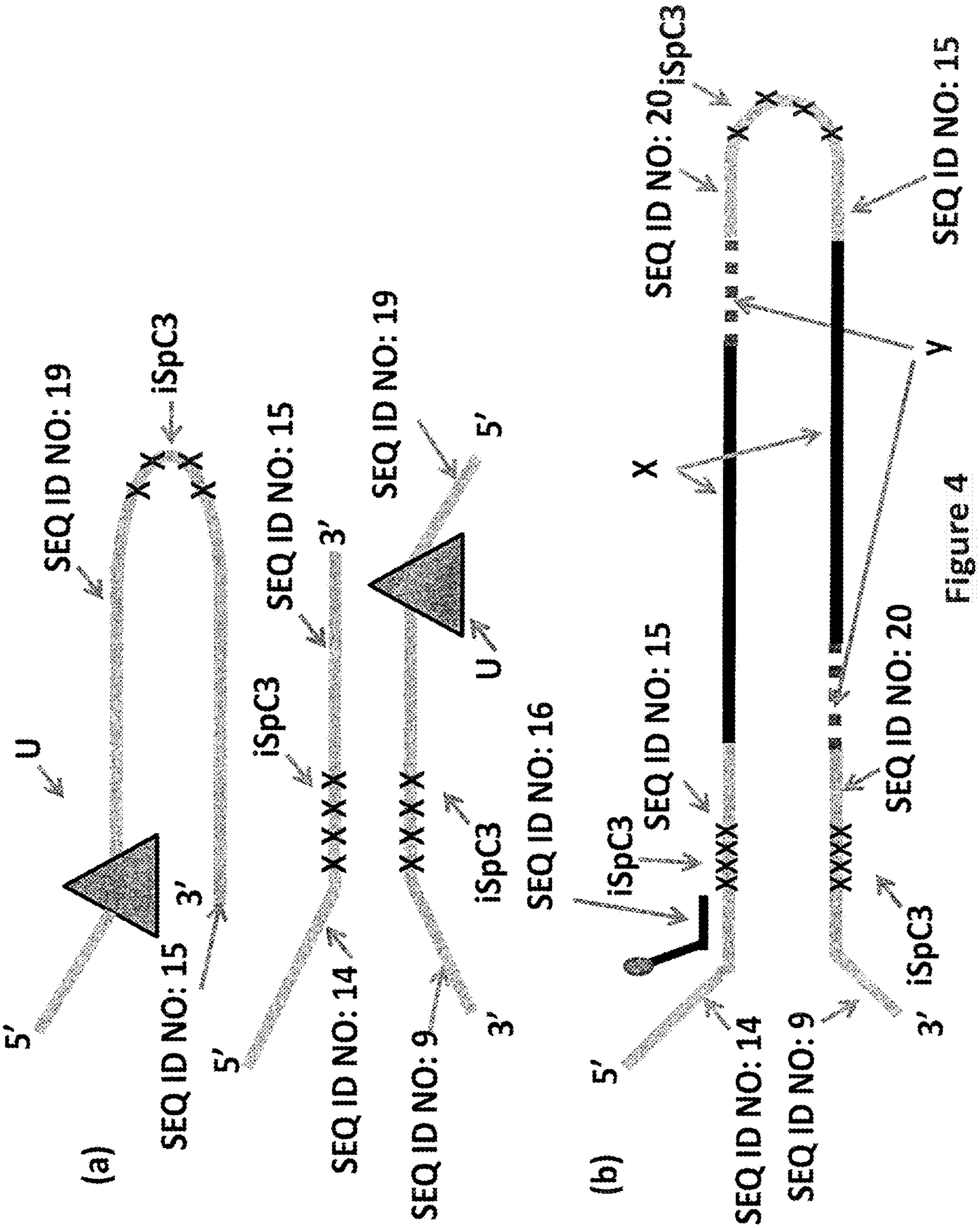

FIG. 4(*a*) shows the hairpin and Y-shaped MuA substrate designs used in Example 2. The dUMP in SEQ ID NO: 19 is highlighted as a triangle and the iSpC3 spacers are shown as x's. FIG. 4(*b*) shows the Lambda DNA construct produced during the sample preparation procedure detailed in Example 2. The 5-10 kB fragment of Lambda DNA is labelled X, the fragment of DNA filled in by the polymerase and joined to the rest of the construct by the ligase is labelled y (and is shown as a dotted line) and the iSpC3 spacers are shown as x's. A tether sequence (SEQ ID NO: 16) is hybridised to the DNA construct as shown. Attached t the 3' end of SEQ ID NO: 16 is six iSp18 spacers attached to two thymine residues and a 3' cholesterol TEG (shown as a grey circle).

Figure 5:
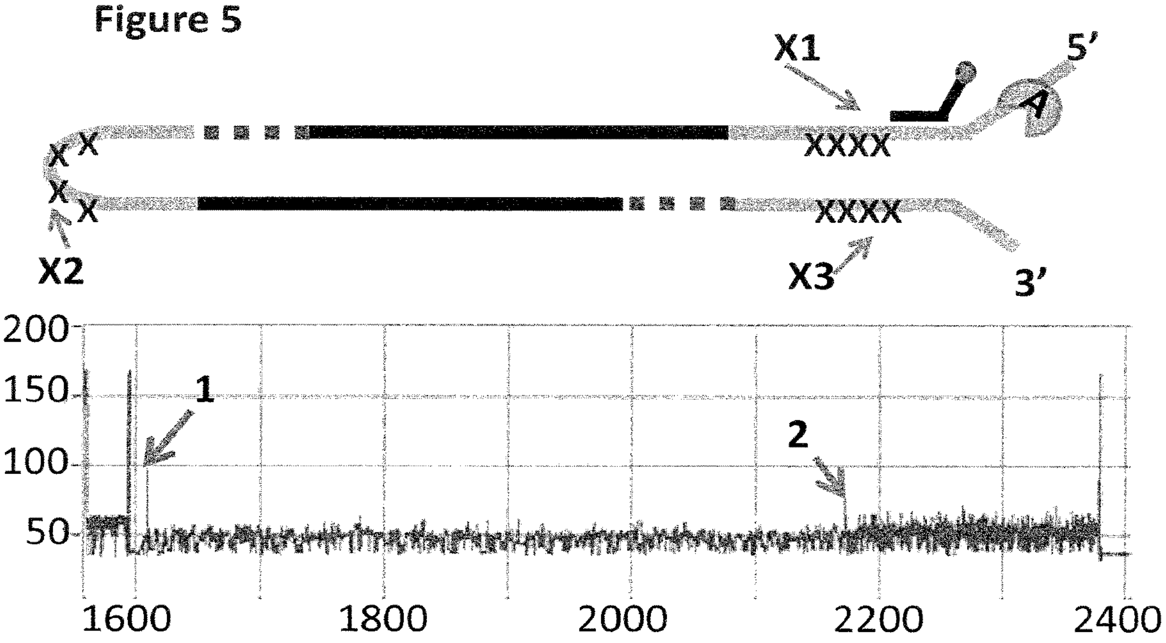
Figure 5:
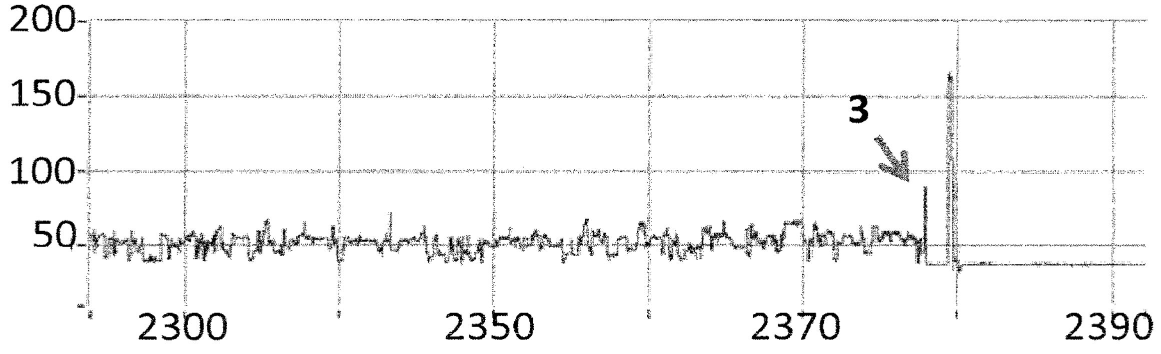

FIG. 5 shows example current traces (y-axis label=Current (pA), x-axis label=Time (s) for both upper and lower traces) of when a helicase (Trwc Cba (SEQ ID NO: 9) controls the translocation of the Lambda DNA construct (shown in FIG. 4*b*) through a nanopore (MS(B1-G75S/G77S/L88N/Q126R)8 MspA (SEQ ID NO: 2 with mutations G75S/G77S/L88N/Q126R)). The upper trace shows helicase controlled DNA movement of the entire lambda DNA construct through the nanopore, the first iSpC3 spacer labelled X1 produces the spike in current labelled 1 and the second iSpC3 spacers labelled X2 produces the spike in current labelled 2. The lower trace shows a zoomed in region of the end of the helicase controlled DNA movement through the nanopore, the third iSpcC3 spacer labelled X3 produces the spike in current labelled 3.

Figure 6:
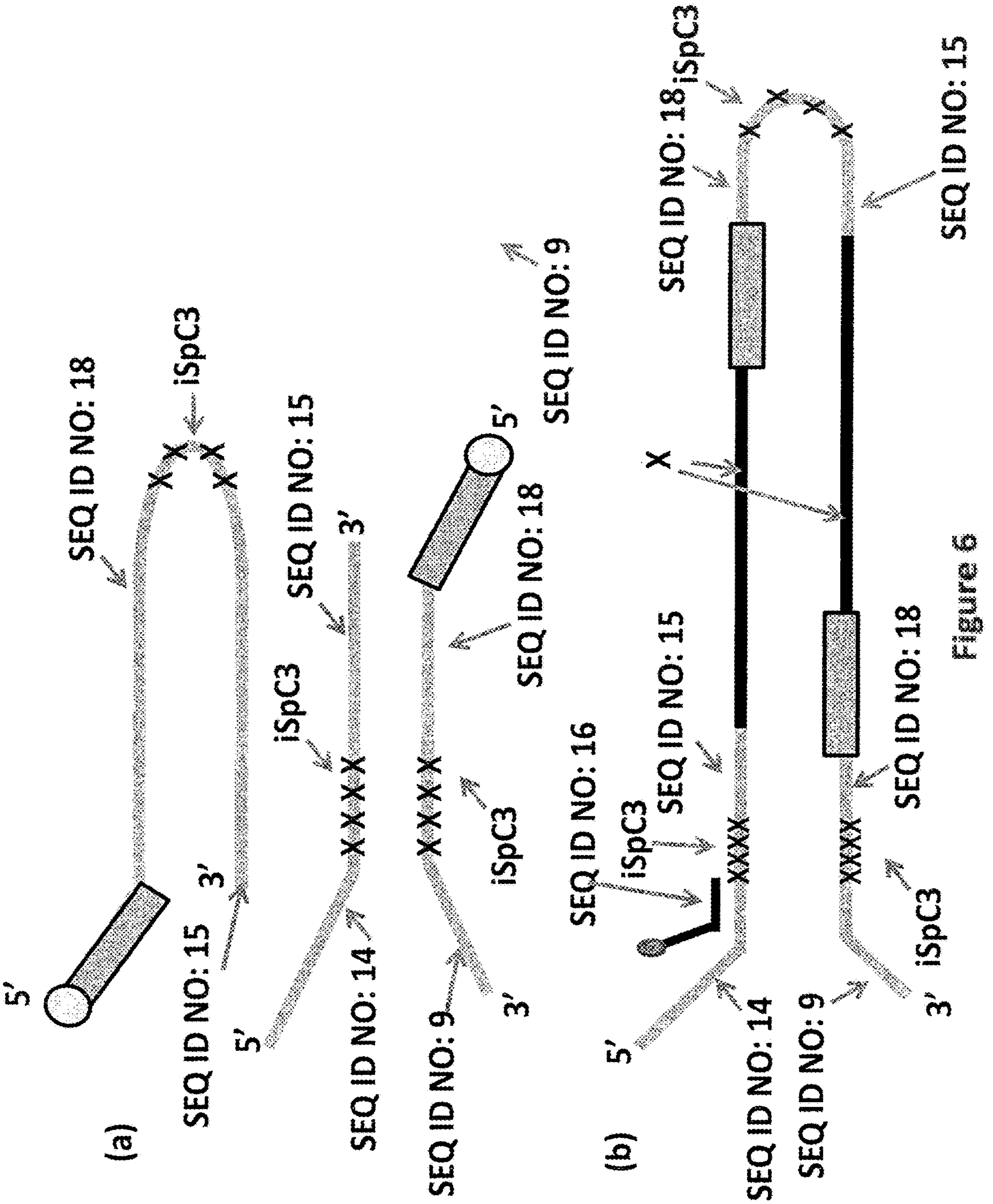

FIG. 6(*a*) shows the hairpin and Y-shaped MuA substrates designs used in Example 3. The 5' phosphate is labelled as a circle, the inosines in SEQ ID NO: 18 are highlighted as a rectangle and the iSpC3 spacers are shown as x's. FIG. 6(*b*) shows the Lambda DNA construct produced during the sample preparation procedure detailed in Example 3. The 5-10 kB fragment of Lambda DNA is labelled X, the inosines which have now been attached to x are labelled as a rectangle and the iSpC3 spacers are shown as x's. A tether sequence (SEQ ID NO: 16) is hybridised to the DNA construct as shown. Attached t the 3' end of SEQ ID NO: 16 is six iSp18 spacers attached to two thymine residues and a 3' cholesterol TEG (shown as a grey circle).

Figure 7:
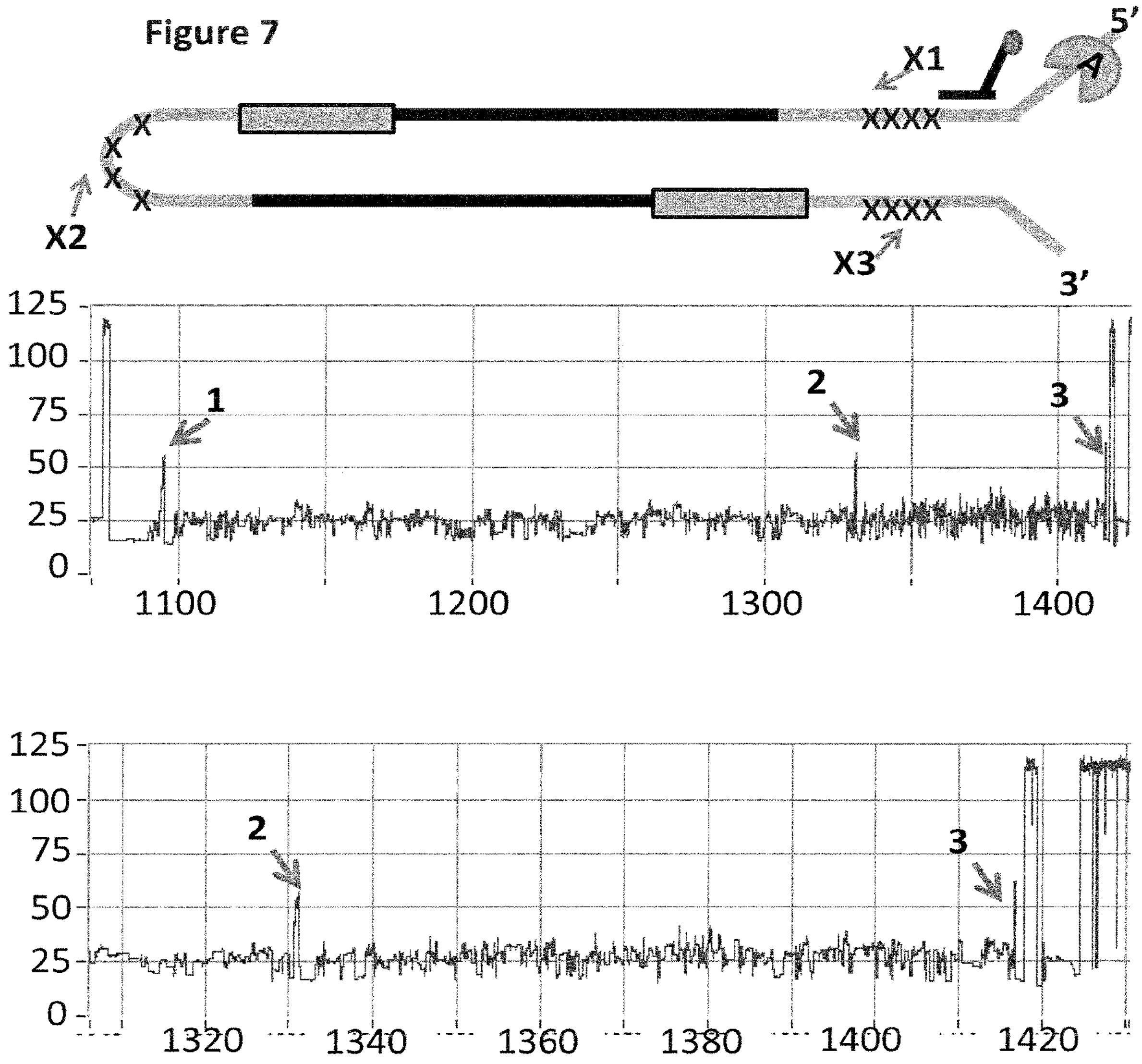

FIG. 7 shows example current traces (y-axis label=Current (pA), x-axis label=Time (s) for both upper and lower traces) of when a helicase (Trwc Cba (SEQ ID NO: 17) controls the translocation of the Lambda DNA construct (shown in FIG. 6*b*) through a nanopore (MS(B1-G75S/G77S/L88N/Q126R)8 MspA (SEQ ID NO: 2 with mutations G75S/G77S/L88N/Q126R)). The upper trace shows helicase controlled DNA movement of the entire lambda DNA construct through the nanopore, the first iSpC3 spacer labelled X1 produces the spike in current labelled 1, the second iSpC3 spacer labelled X2 produces the spike in current labelled 2 and the third iSpC3 spacer labelled X3 produces the spike in current labelled 3. The lower trace shows a zoomed in region of the second half of the helicase controlled DNA movement through the nanopore, the second iSpC3 spacer labelled X2 produces the spike in current labelled 2 and the third iSpC3 spacer labelled X3 produces the spike in current labelled 3.

Figure 8:
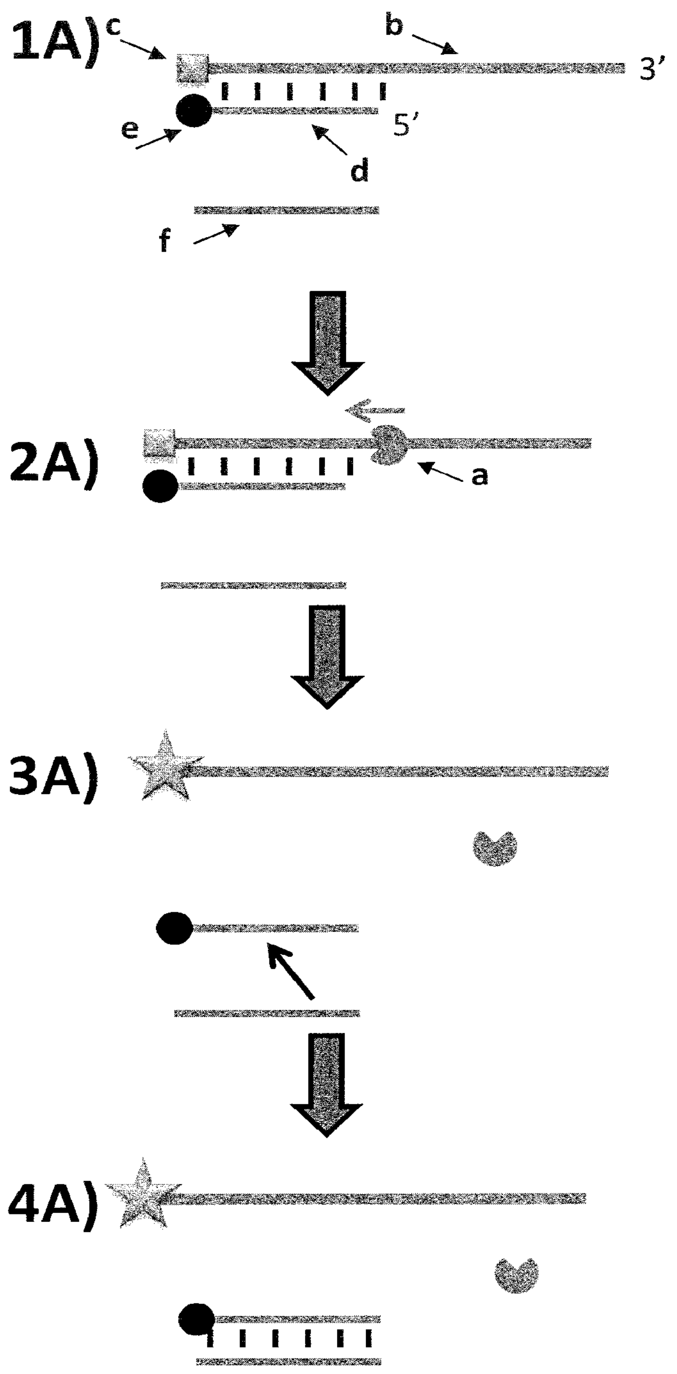

FIG. 8 Fluorescence assay for testing enzyme activity. A custom fluorescent substrate was used to assay the ability of the helicase (labelled a) to displace hybridised dsDNA. 1) The fluorescent substrate strand (48.75 nM final, SEQ ID NO: 25 and 26) has a 3' ssDNA overhang (20 bases), and a 40 base section of hybridised dsDNA. The upper strand (b) has a carboxyfluorescein base (c) at the 5' end of SEQ ID NO: 25, and the hybridised complement (d) has a black-hole quencher (BHQ-1) base (e) at the 3' end of SEQ ID NO: 26. When hybridised, the fluorescence from the fluorescein is quenched by the local BHQ-1, and the substrate is essentially non-fluorescent. 0.975 μM of a capture strand (f, SEQ ID NO: 27) that is part-complementary to the lower strand of the fluorescent substrate is included in the assay. 2) In the presence of ATP (0.975 mM) and $MgCl_2$ (10 mM), helicase Hel308 Mbu (12 nM, SEQ ID NO: 28) binds to the 3' overhang of the fluorescent substrate, moves along the upper strand, and displaces the complementary strand (d) as shown. 3) Once the complementary strand with BHQ-1 is fully displaced the fluorescein on the major strand fluoresces (shown as a star shape). 4) The displaced lower strand (d) preferentially anneals to an excess of capture strand (f) to prevent re-annealing of initial substrate and loss of fluorescence.

Figure 9:
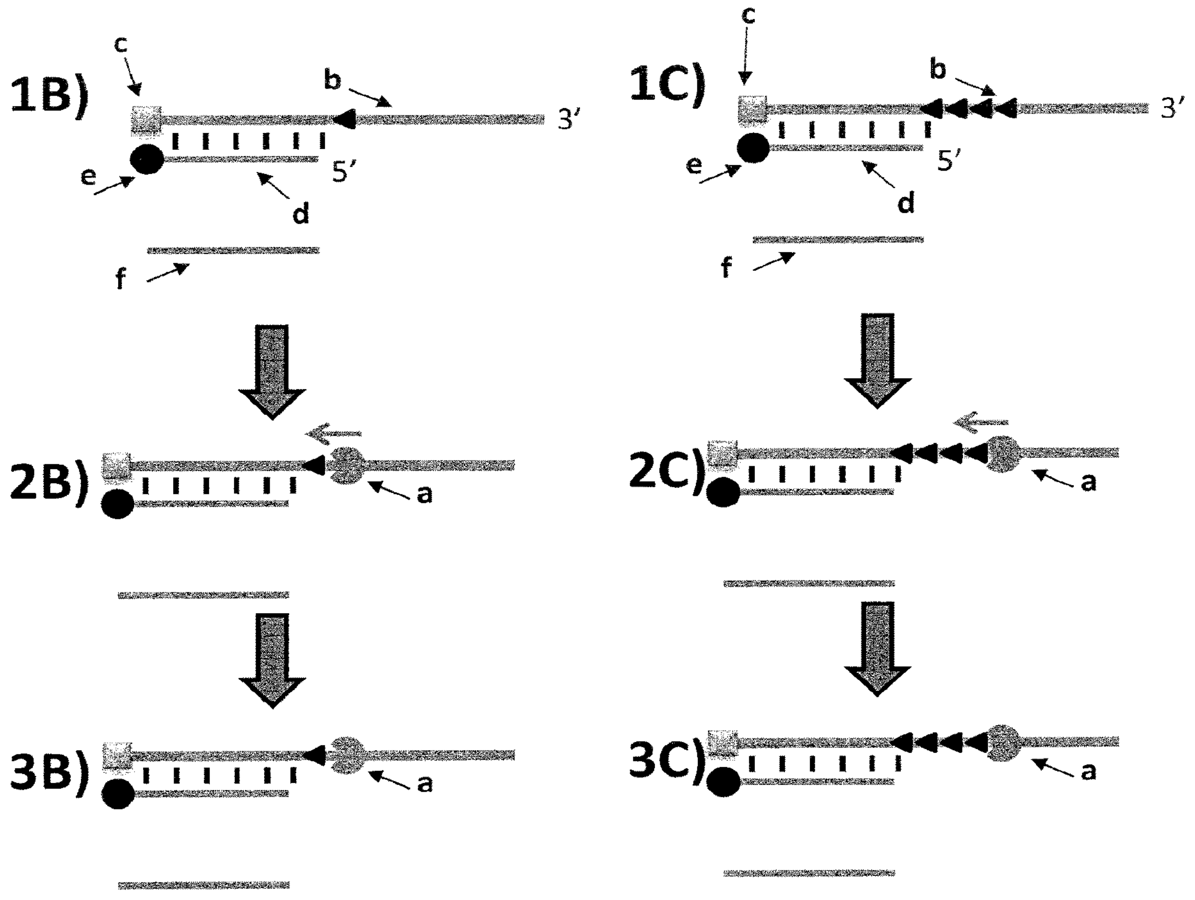

FIG. 9 Fluorescence assay for testing enzyme activity. Two possible fluorescent substrates were used to assay the ability of the helicase (labelled a) to displace hybridised dsDNA, these are shown in FIG. 9(*a*) (labelled 1C-3C) has four Sp9 spacers (shown as a black triangle) connecting the 3' end of SEQ ID NO: 27 to the 3' end of SEQ ID NO: 29 and (b) (labelled 1B-3B) has one Sp9 spacer (shown as a black triangle) connecting the 3' end of SEQ ID NO: 27 to the 3' end of SEQ ID NO: 29. The fluorescent substrate strand (48.75 nM final either a) or b) described previously) has a 3' ssDNA overhang (20 bases), and a 40 base section of hybridised dsDNA. The upper strand (b) has a carboxyfluorescein base (c) at the 5' end of SEQ ID NO: 27, and the hybridised complement (d) has a black-hole quencher (BHQ-1) base (e) at the 3' end of SEQ ID NO: 26. When hybridised, the fluorescence from the fluorescein is quenched by the local BHQ-1, and the substrate is essentially non-fluorescent. 1 μM of a capture strand (f, SEQ ID NO: 27) that is part-complementary to the lower strand of the fluorescent substrate is included in the assay. 2 a and b) In the presence of ATP (0.975 mM) and $MgCl_2$ (10 mM), helicase Hel308 Mbu (SEQ ID NO: 28) binds to the 3' overhang of the fluorescent substrate, moves along the upper strand up to the Sp9 group(s). The sp9 group (1 in B and 4 in C) stops the helicase from moving past it and the helicase does not displace the complementary strand (SEQ ID NO: 26). Therefore, the fluorescein and black hole quencher remain in close proximity to each other and fluorescence is not observed.

Figure 10:
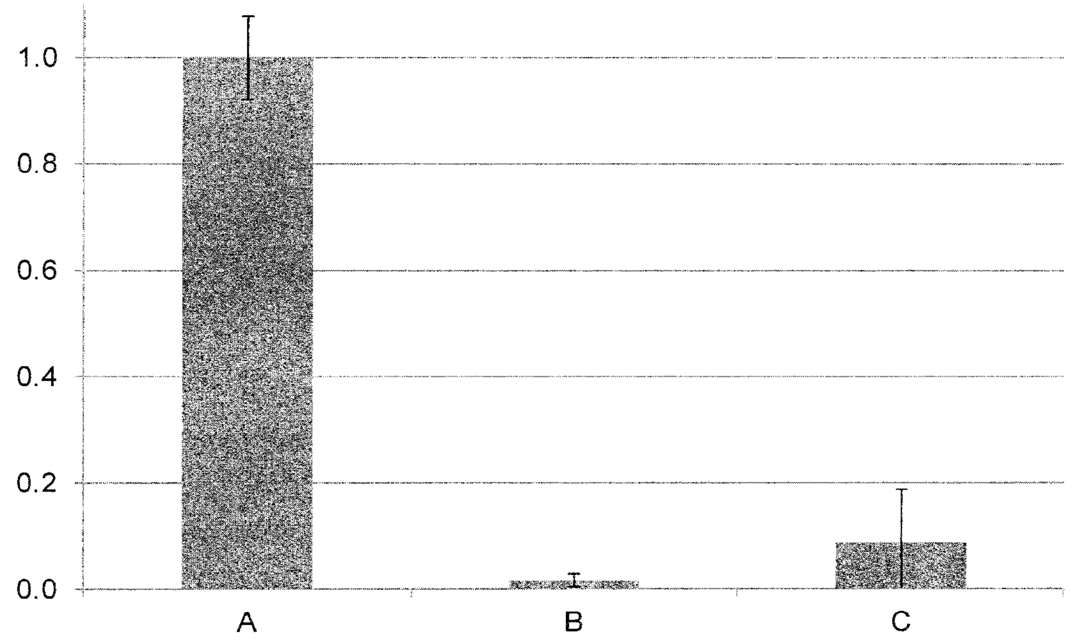

FIG. 10 Graph (y-axis=Relative dsDNA turnover, x-axis=fluorescent substrate) of the relative dsDNA turnover rate in buffer solutions (100 mM HEPES pH8, 0.975 mM ATP, 10 mM $MgCl_2$, 1 mg/mL BSA, 48.75 nM fluorescent substrate DNA (A=SEQ ID NOs: 25 and 26, B=SEQ ID NO: 27 attached at its 3' end by one Sp9 spacers to the 5' end of SEQ ID NO: 29 and hybridised to SEQ ID NO: 26, C=SEQ ID NO: 27 attached at its 3' end by four Sp9 spacers to the 5' end of SEQ ID NO: 29 and hybridised to SEQ ID NO: 26), 0.975 μM capture DNA (SEQ ID NO: 27)) for the Hel308 Mbu helicase (labeled A, SEQ ID NO: 28) at 400 mM of KCl.

Figure 11:
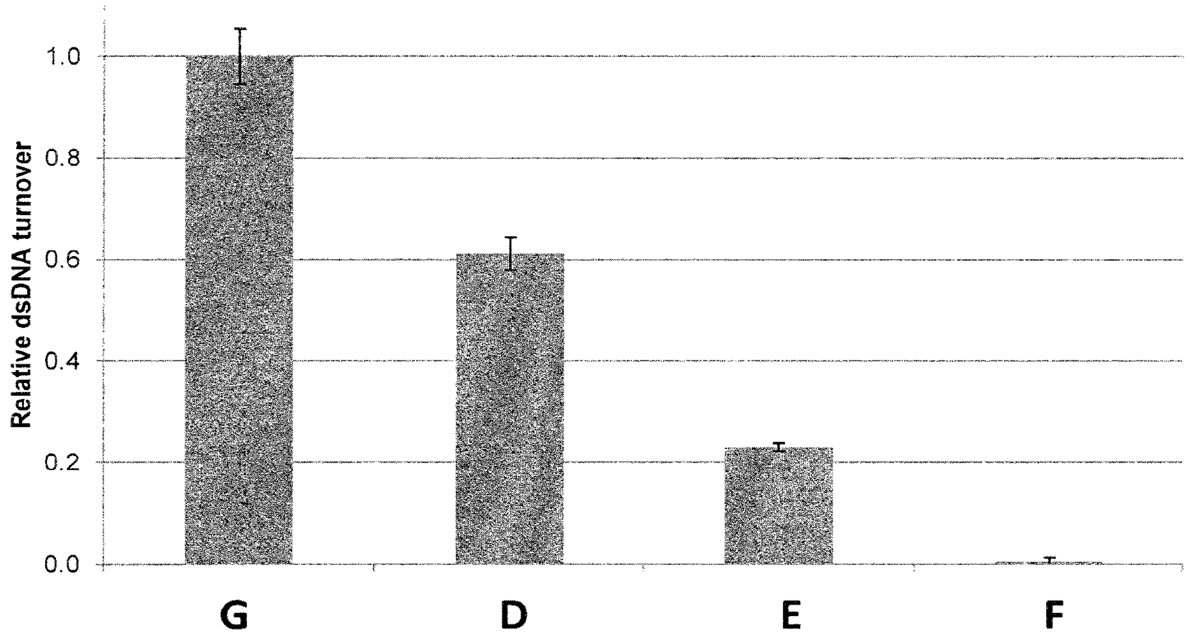

FIG. 11 Graph (y-axis=Relative dsDNA turnover, x-axis=fluorescent substrate) of the relative dsDNA turnover rate in buffer solutions (100 mM HEPES pH8, 0.975 mM ATP, 10 mM $MgCl_2$, 1 mg/mL BSA, 48.75 nM fluorescent substrate DNA (D=SEQ ID NOs: 32 and 26, E=SEQ ID NO: 27 attached at its 3' end by one idSp groups to the 5' end of SEQ ID NO: 30 and hybridised to SEQ ID NO: 26, F=SEQ ID NO: 27 attached at its 3' end by four idSp groups to the 5' end of SEQ ID NO: 31 and hybridised to SEQ ID NO: 26 and G=SEQ ID NO: 33 hybridised to SEQ ID NO: 26), 0.975 μM capture DNA (SEQ ID NO: 27)) for the Hel308 Mbu helicase (labeled A, SEQ ID NO: 28) at 400 mM of KCl.

Figure 12:
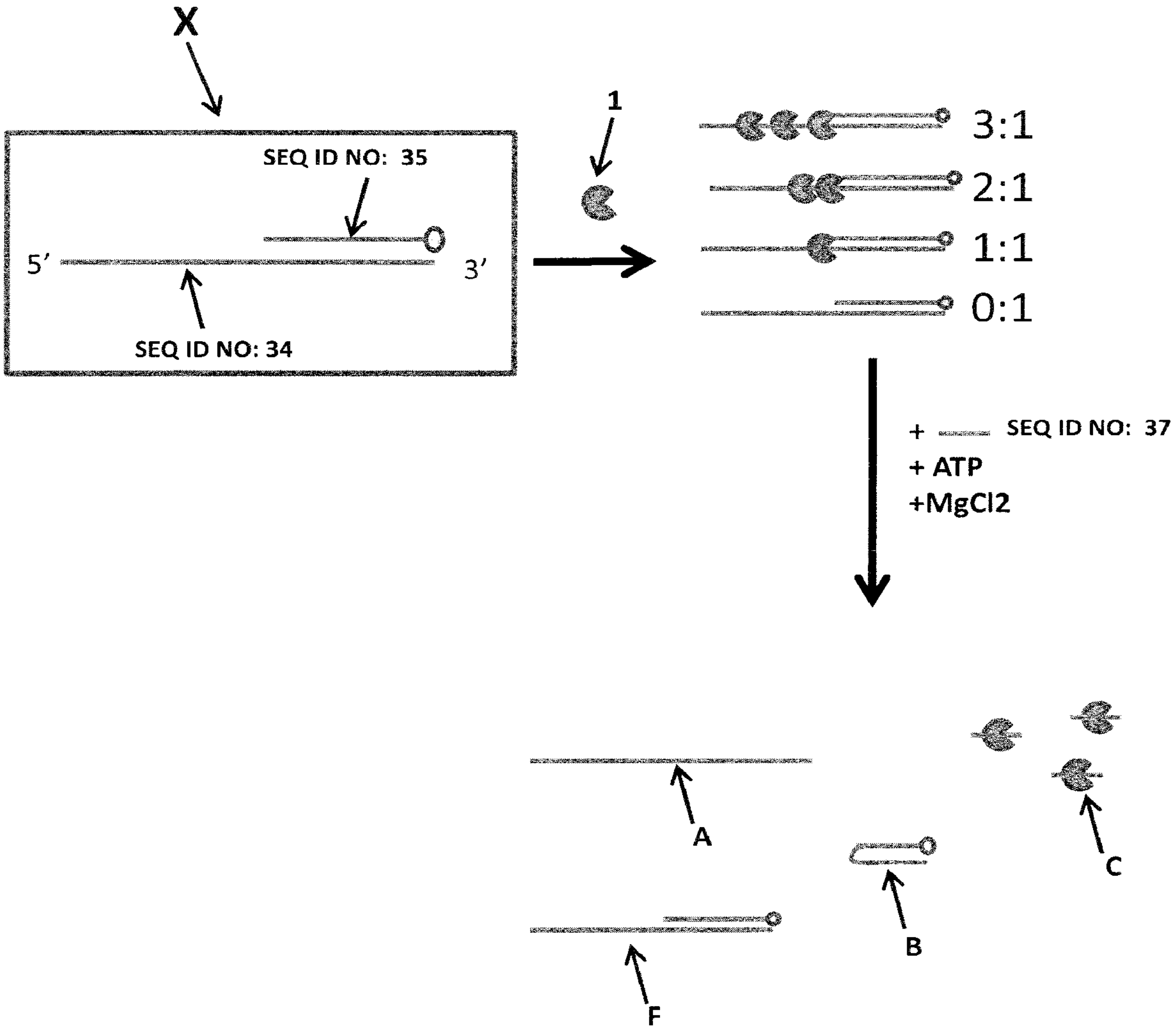

FIG. 12 shows the experimental steps for the control strand which does not contain iSpC3 or iSp18 spacers which stall the helicase (labelled 1). The control strand (SEQ ID NO: 34) contains no spacers or blocking groups and is hybridised to a shorter complementary strand of DNA (SEQ ID NO: 35, which has a carboxyfluorescein attached to its 5' end, shown as a grey circle). This produces a partially double stranded construct which has a 50 nucleotide overhang. The construct (SEQ ID NO: 34 hybridised to SEQ ID NO: 35) is pro incubated with T4 Dda-E94C/A360C to allow the enzyme to bind to the overhang. Owing to the length of the overhang more than one enzyme can bind to it as shown. The enzyme is then provided with the necessary components to promote helicase movement (ATP and MgCl2). Additional capture strand (SEQ ID NO: 37) is also added with the ATP and MgCl2. The helicase then translocates along the control strand, displacing the shorter complementary strand, leaving the control strand with no helicase or complementary strand bound (labelled A). The complementary strand then forms a hairpin so that it cannot re-anneal to the control strand (labelled B). Helicase which is free in solution or has moved along the control DNA and fallen off at the end is then bound by the excess of capture strand (SEQ ID NO: 37, complex labelled C) as shown. Any DNA which does not bind a helicase remains intact (remains as species F). The sample mixture is then run on a gel and the separate species identified by the bands they produce on the gel.

Figure 13:
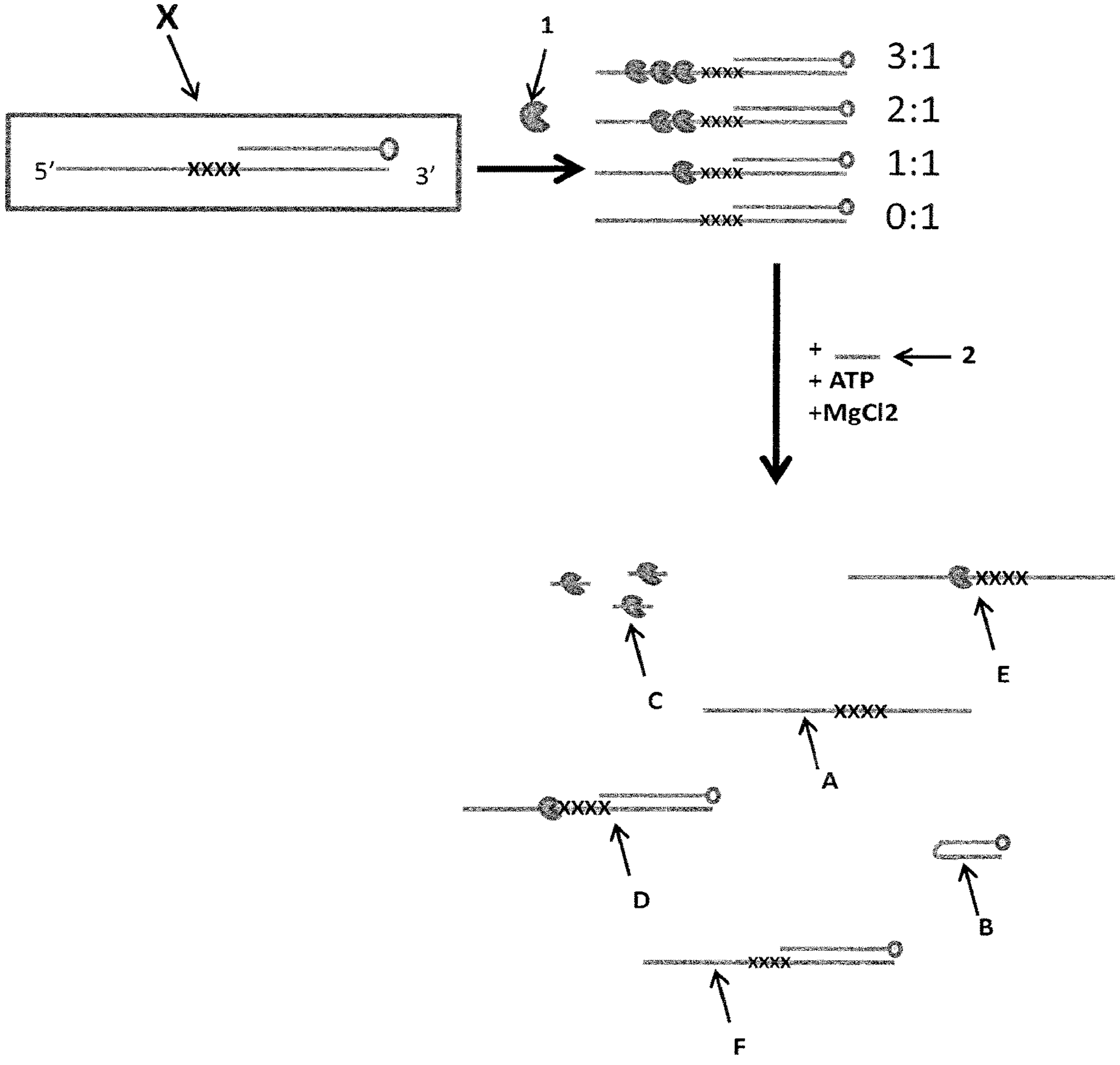

FIG. 13 shows the experimental steps for a strand which contains iSpC3 or iSp18 spacers (shown as X's in the figure) in order to stall the helicase (labelled 1). The same procedure was carried out as shown in FIG. 12, the enzyme was pre-incubated with the DNA construct (the shorter complementary strand has a carboxyfluorescein attached to its 5' end). The spacer groups are located in front of the double stranded region and the helicase is capable of binding to the DNA as shown. Upon the addition of ATP, MgCl2 and capture DNA (labelled 2) the helicase is then provided with the necessary components to promote helicase movement. If the spacers are capable of stalling the helicase then it will remain bound to the DNA construct which still contains the short complementary strand (labelled D). If the spacers are not capable of stalling the helicase then it will move past the spacer and displace the complementary strand (labelled B) leaving species A with no helicase bound. The free enzyme will then bind to the excess capture strand (labelled C) and the displaced complementary strand will form a hairpin (labelled B). If the spacers are able to stall one helicase but not two helicases then the first helicase will be pushed past the spacers by the helicase behind and will displace the complementary stand. However, the second helicase will not be able to move past the spacers resulting in the complex labelled E. Any DNA which does not bind a helicase remains intact with no helicase bound (species F) The sample mixture is then run on a gel and the separate species identified by the bands they produce on the gel.

Figure 14:
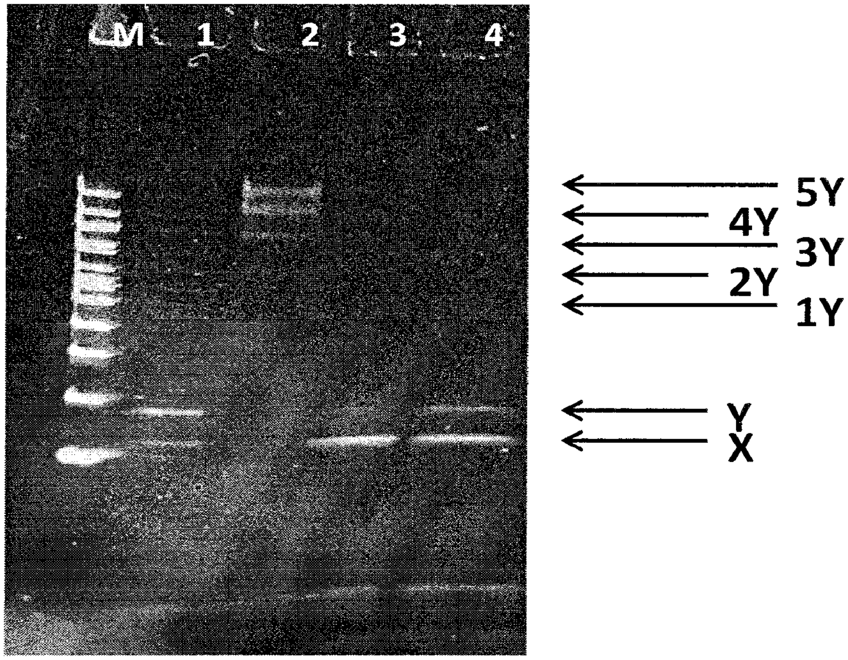

FIG. 14 shows the gel assay which was run for the control strand (1 in table 11). The lane labelled M shows a DNA ladder for reference (bands correspond from lowest mass (bottom of the gel) to highest mass (top of the gel) 200 bp (base pairs), 300 bp, 400 bp, 500/517 bp, 600 bp, 700 bp, 800 bp, 900 bp, 1000 bp, 1200 bp and 1517 bp). Lane 1 contains annealed DNA only (SEQ ID NO: 34 hybridised to SEQ ID NO: 35). Lane 2 contains the helicase (T4 Dda-E94C/A360C) pre-bound to control strand (no fuel added). Lane 3 shows the control strand after fuel (ATP and MgCl2) has been added in buffer 1. Lane 4 shows the control strand after fuel (ATP and MgCl2) has been added in buffer 2. Band X corresponds to SEQ ID NO: 34 only and band Y corresponds to SEQ ID NO: 34 hybridised to SEQ ID NO: 35. The region labelled 1Y corresponds to one helicase bound to SEQ ID NO: 34 hybridised to SEQ ID NO: 35. The region labelled 2Y corresponds to two helicases bound to SEQ ID NO: 34 hybridised to SEQ ID NO: 35. The region labelled 3Y corresponds to three helicases bound to SEQ ID NO: 34 hybridised to SEQ ID NO: 35. The region labelled 4Y corresponds to four helicases bound to SEQ ID NO: 34 hybridised to SEQ ID NO: 35. The region labelled 5Y corresponds to five helicases bound to SEQ ID NO: 34 hybridised to SEQ ID NO: 35.

Figure 15:
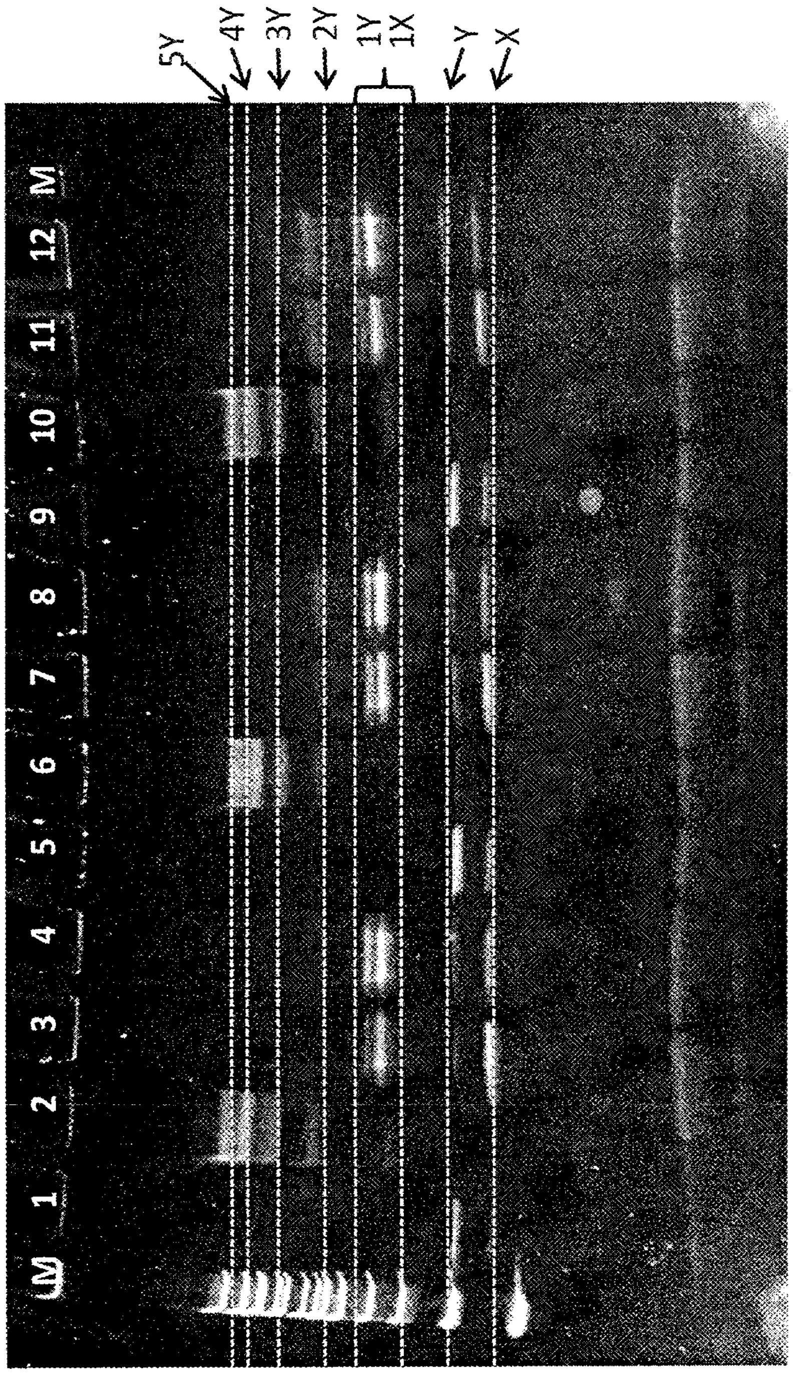

FIG. 15 shows the gel assay which was run for the DNA constructs containing 3 (7 in table 11, corresponding lanes=1-4), 4 (8 in table 11, corresponding lanes=5-8) and 5 iSp18 spacers (9 in table 11, corresponding lanes=9-12) at the junction between ssDNA and dsDNA. The lanes labelled M show a DNA ladder for reference (bands correspond from lowest mass (bottom of the gel) to highest mass (top of the gel) 200 bp (base pairs), 300 bp, 400 bp, 500/517 bp, 600 bp, 700 bp, 800 bp, 900 bp, 1000 bp, 1200 bp and 1517 bp). Lane 1 contains annealed DNA only (SEQ ID NO: 9 attached at its 3' end to three iSp18 spacers which are attached to the 5' end of SEQ ID NO: 36 hybridised to SEQ ID NO: 35). Lane 2 contains the helicase (T4 Dda-E94C/A360C) pre-bound to the DNA construct with no fuel added (SEQ ID NO: 9 attached at its 3' end to three iSp18 spacers which are attached to the 5' end of SEQ ID NO: 36 hybridised to SEQ ID NO: 35). Lane 3 shows the DNA construct (SEQ ID NO: 9 attached at its 3' end to three iSp18 spacers which are attached to the 5' end of SEQ ID NO: 36 hybridised to SEQ ID NO: 35) after fuel (ATP and MgCl2) has been added in buffer 1. Lane 4 shows the DNA construct (SEQ ID NO: 9 attached at its 3' end to three iSp18 spacers which are attached to the 5' end of SEQ ID NO: 36 hybridised to SEQ ID NO: 35) after fuel (ATP and MgCl2) has been added in buffer 2. Lane 5 contains annealed DNA only (SEQ ID NO: 9 attached at its 3' end to four iSp18 spacers which are attached to the 5' end of SEQ ID NO: 36 hybridised to SEQ ID NO: 35). Lane 6 contains the helicase (T4 Dda-E94C/A360C) pre-bound to the DNA construct with no fuel added (SEQ ID NO: 9 attached at its 3' end to four iSp18 spacers which are attached to the 5' end of SEQ ID NO: 36 hybridised to SEQ ID NO: 35). Lane 7 shows the DNA construct (SEQ ID NO: 9 attached at its 3' end to four iSp18 spacers which are attached to the 5' end of SEQ ID NO: 36 hybridised to SEQ ID NO: 35) after fuel (ATP and MgCl2) has been added in buffer 1. Lane 8 shows the DNA construct (SEQ ID NO: 9 attached at its 3' end to four iSp18 spacers which are attached to the 5' end of SEQ ID NO: 36 hybridised to SEQ ID NO: 35) after fuel (ATP and MgCl2) has been added in buffer 2. Lane 9 contains annealed DNA only (SEQ ID NO: 9 attached at its 3' end to five iSp18 spacers which are attached to the 5' end of SEQ ID NO: 36 hybridised to SEQ ID NO: 35). Lane 10 contains the helicase (T4 Dda-E94C/A360C) pre-bound to the DNA construct with no fuel added (SEQ ID NO: 9 attached at its 3' end to five iSp18 spacers which are attached to the 5' end of SEQ ID NO: 36 hybridised to SEQ ID NO: 35). Lane 11 shows the DNA construct (SEQ ID NO: 9 attached at its 3' end to five iSp18 spacers which are attached to the 5' end of SEQ ID NO: 36 hybridised to SEQ ID NO: 35) after fuel (ATP and MgCl2) has been added in buffer 1. Lane 12 shows the DNA construct (SEQ ID NO: 9 attached at its 3' end to five iSp18 spacers which are attached to the 5' end of SEQ ID NO: 36 hybridised to SEQ ID NO: 35) after fuel (ATP and MgCl2) has been added in buffer 2. Band X corresponds to ssDNA construct only (e.g. SEQ ID NO: 9 attached at its 3' end to three four or five iSp18 spacers which are attached to the 5' end of SEQ ID NO: 36) only and Band Y corresponds to the dsDNA construct only (SEQ ID NO: 9 attached at its 3' end to three, four or five iSp18 spacers which are attached to the 5' end of SEQ ID NO: 36 hybridised to SEQ ID NO: 35). The region labelled 1X corresponds to one helicase bound to SEQ ID NO: 9 attached at its 3' end to three, four or five iSp18 spacers which are attached to SEQ ID NO: 36. The region labelled 1Y corresponds to one helicase bound to SEQ ID NO: 9 attached at its 3' end to three, four or five iSp18 spacers which are attached to SEQ ID NO: 36 hybridised to SEQ ID NO: 35. The region labelled 2Y corresponds to two helicases bound to SEQ ID NO: 9 attached at its 3' end to three, four or five iSp18 spacers which are attached to SEQ ID NO: 36 hybridised to SEQ ID NO: 35. The region labelled 3Y corresponds to three helicases bound to SEQ ID NO: 9 attached at its 3' end to three, four or five iSp18 spacers which are attached to SEQ ID) NO: 36 hybridised to SEQ ID NO: 35. The region labelled 4Y corresponds to four helicases bound to SEQ ID NO: 9 attached at its 3' end to three, four or five iSp18 spacers which are attached to SEQ ID NO: 36 hybridised to SEQ ID NO: 35. The region labelled 5Y corresponds to five helicases bound to SEQ ID NO: 9 attached at its 3' end to three, four or five iSp18 spacers which are attached to SEQ ID NO: 36 hybridised to SEQ ID NO: 35.

Figure 16:
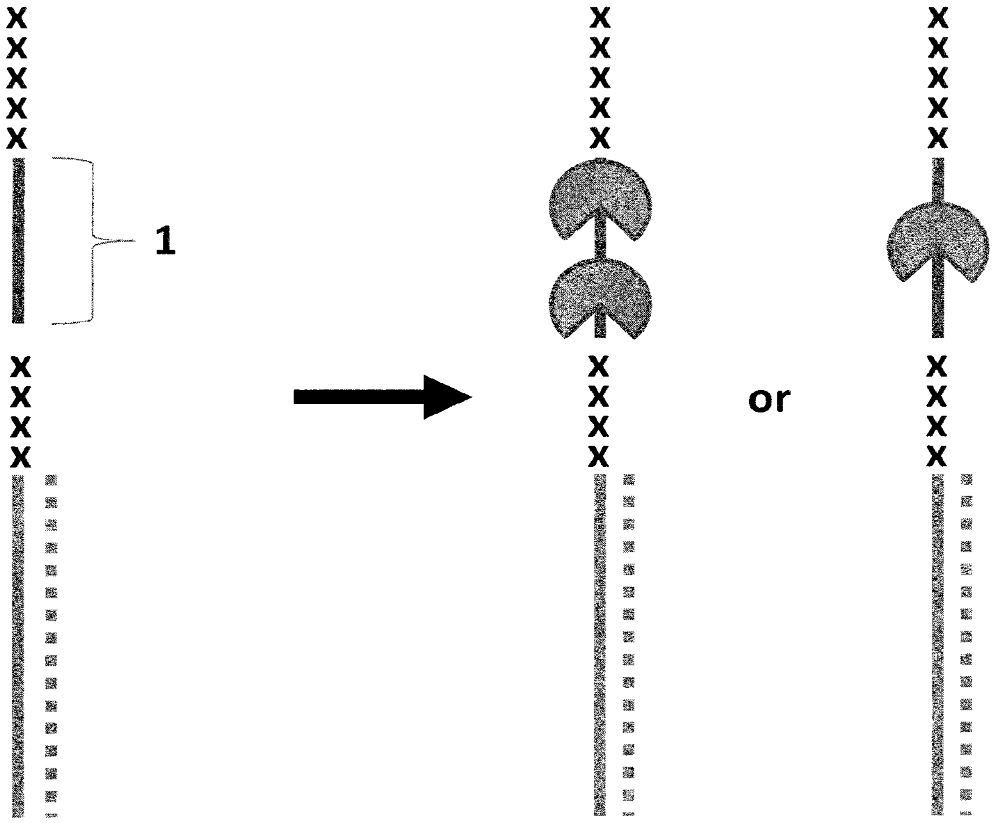

FIG. 16 shows the standard DNA construct used in Example 9. The x's represent spacer groups onto which the helicase cannot bind. The length of the region labelled 1 can be altered in order to control the number of helicases which can bind to that region. The figure shows, as an example, the binding of one or two helicases in region 1.

Figure 17:
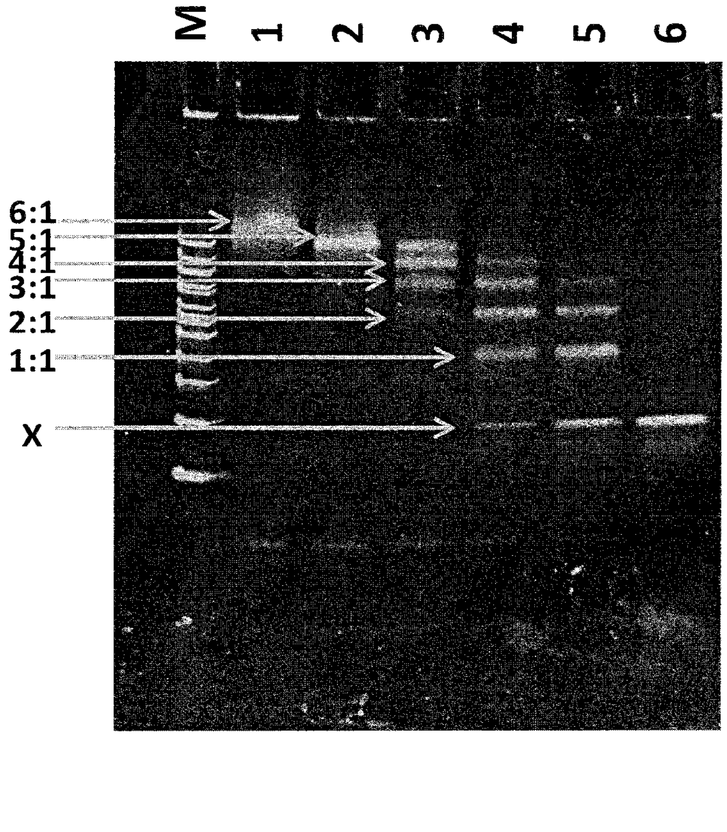

FIG. 17 shows an example gel assay of the DNA construct labelled 3 in Table 12 (Five iSpC3 spacers attached to the 5' end of SEQ ID NO: 9, which is attached at its 3' end to four iSpC3 spacers which are attached to the 5' end of SEQ ID NO: 36 which is hybridised to SEQ ID NO: 35). The lane labelled M shows a DNA ladder for reference (bands correspond from lowest mass (bottom of the gel) to highest mass (top of the gel) 200 bp (base pairs), 300 bp, 400 bp, 500/517 bp, 600 bp, 700 bp, 800 bp, 900 bp, 1000 bp, 1200 bp and 1517 bp). Lanes 1-6 correspond to different concentrations of T4 Dda-E94C/A360C−1=5000 nM, 2=2500 nM, 3=1250 nM, 4=625 nM, 5=312.5 nM and 6=0 nM). The band observed at level X corresponds to the unbound dsDNA construct. The numbers on the left-hand side of the gel relate to the number of enzymes bound to the DNA. For this DNA construct it was possible to bind up to 6 helicases at the highest concentration of enzyme added. The numbers shown at the top of the gel correspond to the concentration of T4 Dda-E94C/A360C) added.

Figure 18:
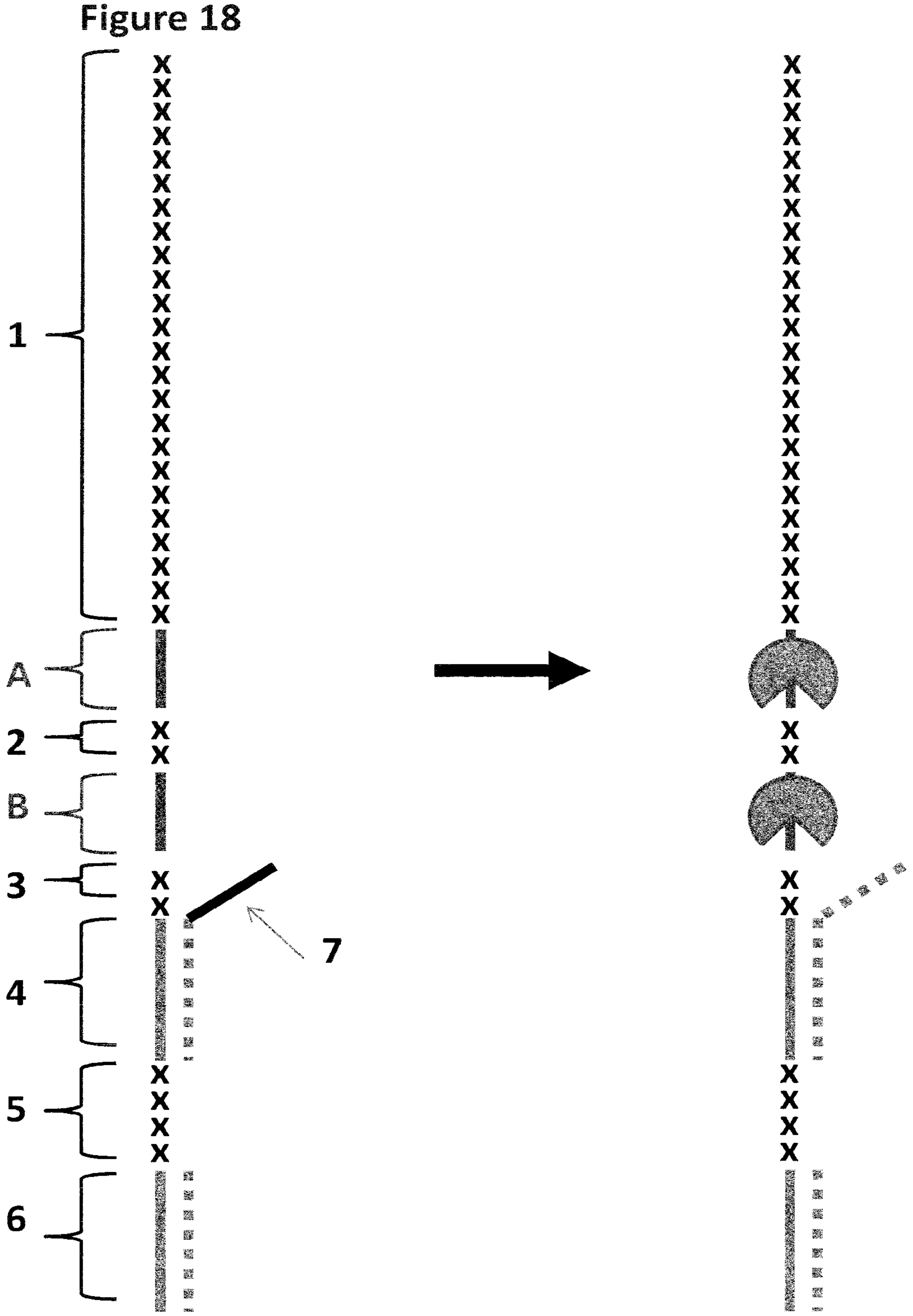

FIG. 18 shows the DNA construct used in example 9. Regions labelled A and B are short strands of DNA (SEQ ID NO: 37) which have been designed so that one helicase can bind to each region (as shown on the right-hand side). Region 1 corresponds to 25 SpC3 spacers, region 2 corresponds to two iSp18 spacers, region 3 corresponds to two iSp18 spacers, region 4 is a section of DNA (SEQ ID NO: 10) which hybridises to another strand of DNA which may or may not be made up of forked DNA (e.g. SEQ ID NO: 42=non-forked (missing fragment labelled 7) and SEQ ID NO: 12 attached to six iSp18 spacers (shown as fragment labelled 7)=forked), region 5 corresponds to four 5-nitroindoles and region 6 corresponds to another region of DNA (SEQ ID NO: 41) which is hybridised to its complement (SEQ ID NO: 43).

Figure 19:
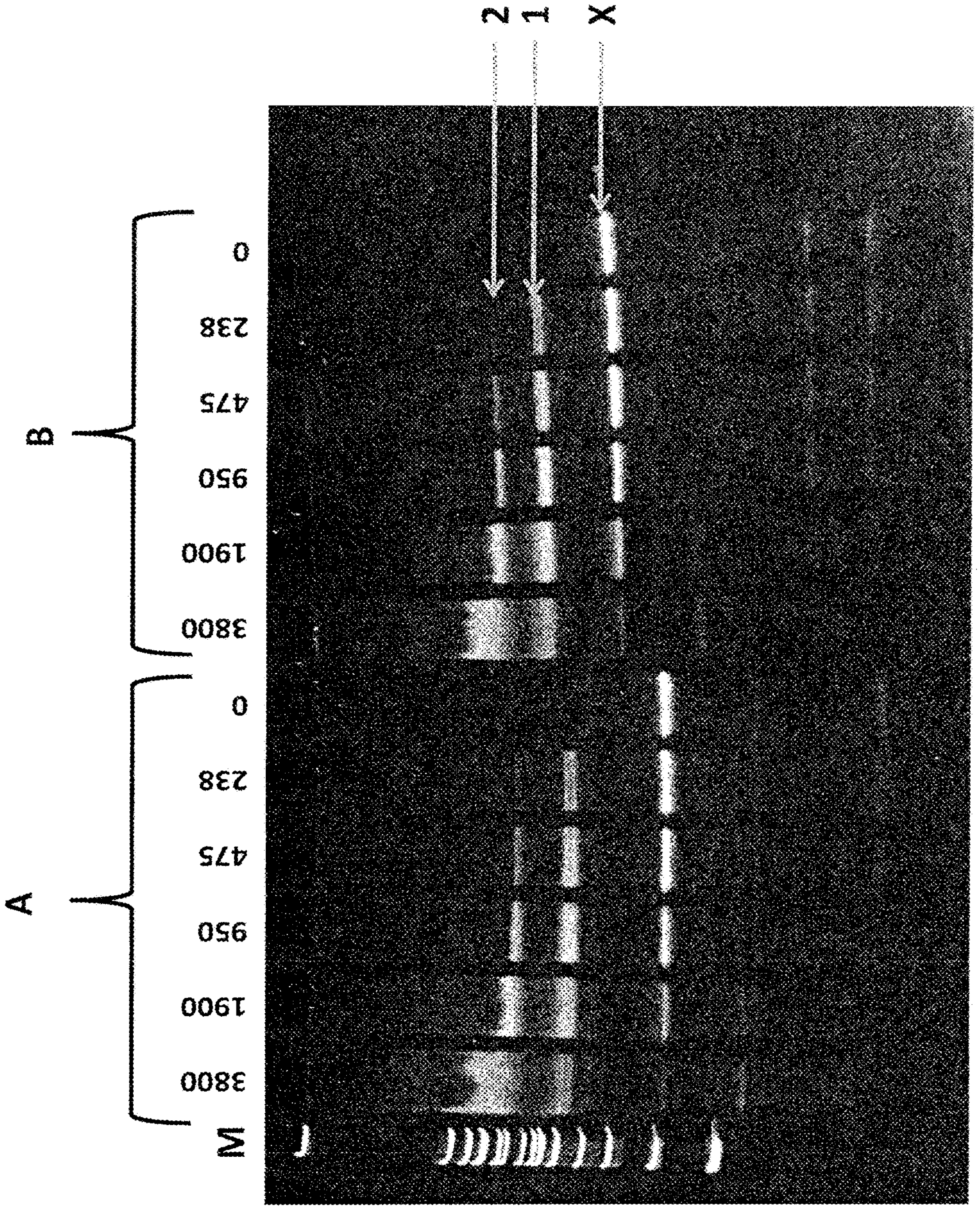

FIG. 19 shows a gel assay of the DNA construct described and shown in FIG. 18. The band observed at level X corresponds to the unbound dsDNA construct. The lane labelled M shows a DNA ladder for reference (bands correspond from lowest mass (bottom of the gel) to highest mass (top of the gel) 200 bp (base pairs), 300 bp, 400 bp, 500/517 bp, 600 bp, 700 bp, 800 bp, 900 bp, 1000 bp, 1200 bp and 1517 bp). The numbers on the left-hand side of the gel relate to the number of enzymes bound to the DNA. For this DNA construct it was possible to observe binding of two helicases (one at region A and the second at region B as shown in FIG. 18) from a concentration of 475 nM enzyme and above. The numbers shown at the top of the gel correspond to the concentration of T4 Dda-E94C/A360C) added.

Figure 20:
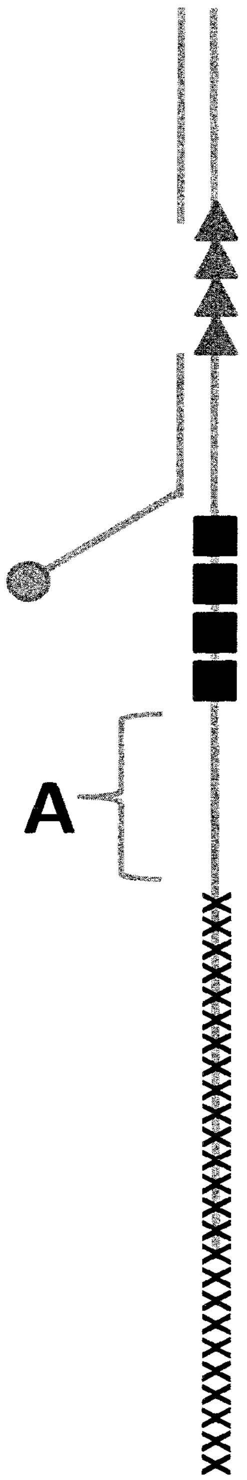

FIG. 20 shows the DNA construct used in Example 10 (referred to as DNA construct X1). There are 25 SpC3 spacers (shown as x's) attached to the 5' end of SEQ ID NO: 38 which is attached at its 3' end to 4 iSp18 spacers (shown as black squares). The four iSp18 spacers are attached to the 5' end of SEQ ID NO: 10 which is attached at its 3' end to four 5-nitroindoles (shown as grey triangles). The four nitroindoles are then attached to the 5' end of SEQ ID NO: 41. The complementary DNA strand which hybridises to SEQ ID NO: 41 is SEQ ID NO: 43. The complementary DNA strand which hybridises to SEQ ID NO: 10 is SEQ ID NO: 12 (attached to SEQ ID NO: 12's 3' end is six iSp18 spacers attached to two thymine residues and a 3' cholesterol TEG (shown as a grey circle)). The region labelled A corresponds to the region of the construct where T4 Dda-E94C/A360C is able to bind.

Figure 21:
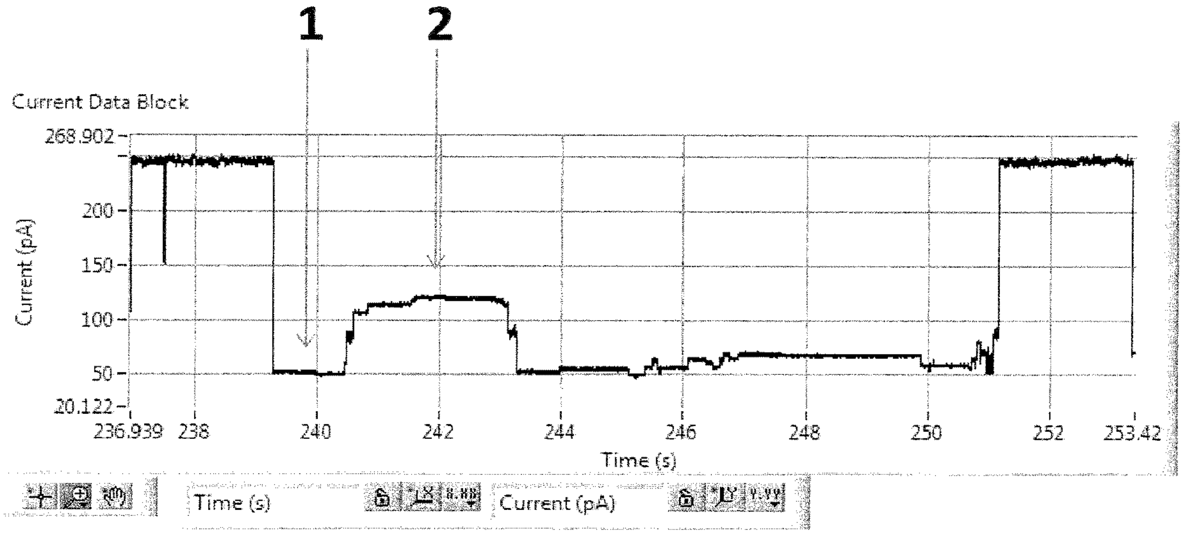

FIG. 21 shows an example current trace (y-axis label=Current (pA, 50 to 250), x-axis label=Time (s, 238 to 252)) of when a helicase (T4 Dda-E94C/A360C) controls the translocation of the DNA construct (0.1 nM, see FIG. 20 description) through a nanopore (MspA-B2C). The region labelled 1 shows the helicase controlled translocation of the polyT region (SEQ ID NO: 38, that the enzyme bound onto) through the nanopore. The region labelled 2 corresponds to the helicase controlled translocation of the iSp18 spacers through the nanopore.

Figure 22:
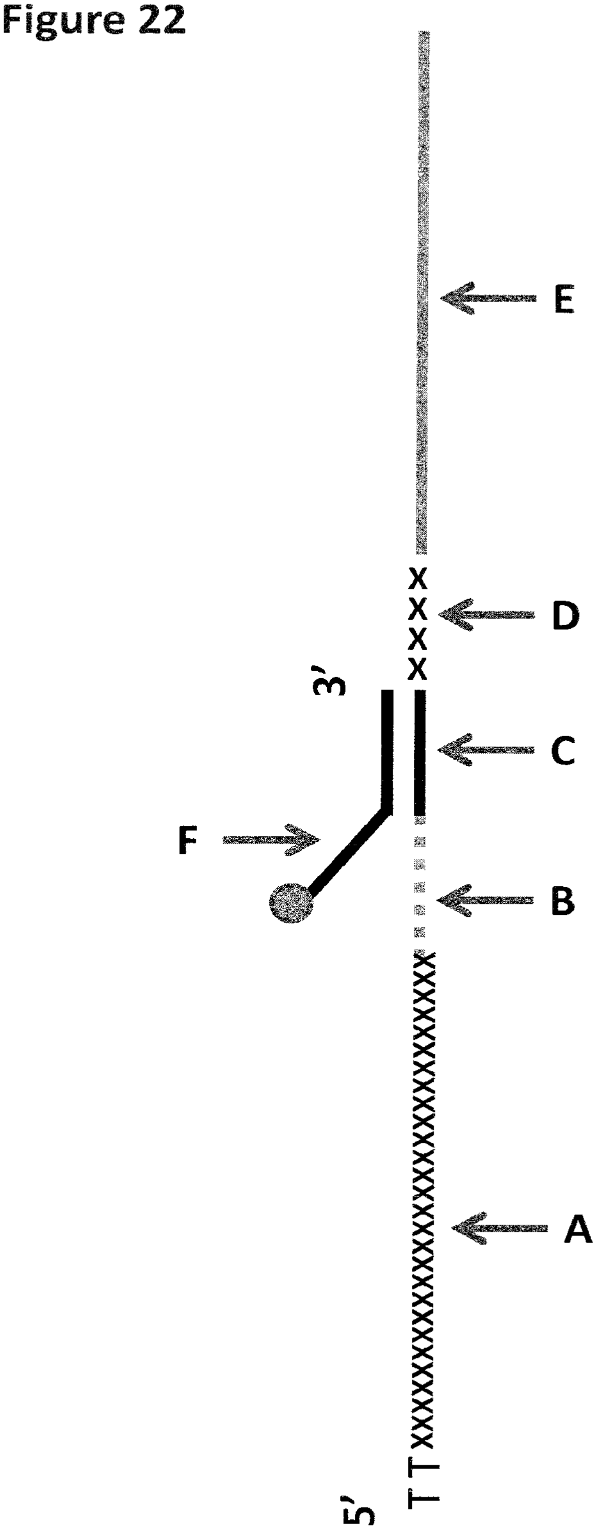

FIG. 22 shows a diagram of the DNA construct used in Example 4. Two thymines are attached at the 3' end to 28 iSpC3 spacers (labelled A). The 28 iSpC3 spacers are attached at the other end to the 5' end of SEQ ID NO: 23 (sequence corresponds to region B=polyT section and region C=sequence complementary to the tether sequence (SEQ ID NO: 12)). The 3' end of SEQ ID NO: 23 is attached to four iSpC3 spacers (labelled D). The other end of the 4 iSpC3 spacers is attached to the 5' end of SEQ ID NO: 24. The tether sequence (SEQ ID NO: 12) is attached at its 3' end to six iSp18 spacers attached to two thymine residues and a 3' cholesterol TEG.

DESCRIPTION OF THE SEQUENCE LISTING

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the amino acid sequence of the helicase Dda 1993 from Enterobactcria phage T4.

SEQ ID NO: 9 shows a polynucleotide sequence used in Example 1, 2, 3, 7 and 8.

SEQ ID NO: 10 shows a polynucleotide sequence used in Example 1 and 9.

SEQ ID NO: 11 shows a polynucleotide sequence used in Example 1. SEQ ID NO: 11 is attached by its 5' end to three iSpC3 spacers which are attached to the 3' end of SEQ ID NO: 10.

SEQ ID NO: 12 shows a polynucleotide sequence used in Examples 1 and 9. In Example 1 SEQ ID NO: 12 is attached at its 3' end to six iSp18 spacers attached to two thymine residues and a 3' cholesterol TEG. In Example 9 SEQ ID NO: 12 is attached at its 3' end to six iSp18 spacers only.

SEQ ID NO: 13 shows the polynucleotide sequence of the Entcrobacteria phage λ. The sequence contains an additional 12 base overhang attached at the 5' end of the sense strand. The sequence shown here is that of the sense strand only.

SEQ ID NO: 14 shows a polynucleotide sequence used in Examples 2 and 3. SEQ ID NO: 14 is attached at its 3' end to the 5' end of SEQ ID NO: 15 by four iSpC3 spacer units.

SEQ ID NO: 15 shows a polynucleotide sequence used in Examples 2 and 3. SEQ ID NO: 15 is attached at its 5' end to the 3' end of SEQ ID NO: 14 by four iSpC3 spacer units.

SEQ ID NO: 16 shows a polynucleotide sequence used in Example 2 and 3 which at the 3' end of the sequence has six iSp18 spacers attached to two thymine residues and a 3' cholesterol TEG.

SEQ ID NO: 17 shows the amino acid sequence of the Trwc Cba helicase.

SEQ ID NO: 18 shows a polynucleotide sequence used in Example 3. SEQ ID NO: 18 is attached at its 3' end to the 5' end of SEQ ID NO: 9 by four iSpC3 spacer units. This sequence has a phosphate attached to its 5' end and 5 deoxyinosines at positions 1 to 5.

SEQ ID NO: 19 shows a polynucleotide sequence used in Example 2.

SEQ ID NO: 20 shows a polynucleotide sequence used in Example 2.

SEQ ID NOs: 21 and 22 are placeholders to maintain the numbering of the following sequences.

SEQ ID NO: 23 shows the polynucleotide sequence used in Example 4. Attached to the 5' end of this sequence is 28 iSpC3 spacers units the last of which has an additional two T's attached to the 5' end of the spacer group. Attached to the 3' end of this sequence is four iSpC3 spacer units which are attached to the 5' end of SEQ ID NO: 24.

SEQ ID NO: 24 shows the polynucleotide sequence used in Example 9. Attached to the 5' end of this sequence is four iSpC3 spacer units, the last of which is attached to SEQ ID NO: 23. Attached to the 5' end of SEQ ID NO: 23 is 28 iSpC3 spacer units the last of which has an additional two T's attached to the 5' end of the spacer group.

SEQ ID NO: 25 shows a polynuclcotide sequence used in Example 5. It has a carboxyfluorescein (FAM) base at its 5' end.

SEQ ID NO: 26 shows a polynucleotide sequence used in Example 5 and 6. It has a black-hole quencher (BHQ-1) base at its 3' end.

SEQ ID NO: 27 shows a polynucleotide sequence used in Examples 5 and 6.

SEQ ID NO: 28 shows the amino acid sequence of Hel308 Mbu.

SEQ ID NO: 29 shows a polynucleotide sequence used in Example 5. This sequence is connected to SEQ ID NO: 27 at its 5' end by either one or four iSp9 spacer groups.

SEQ ID NO: 30 shows a polynucleotide sequence used in Example 6. This sequence is connected to SEQ ID NO: 27 at its 5' end by one idSp group.

SEQ ID NO: 31 shows a polynucleotide sequence used in Example 6. This sequence is connected to SEQ ID NO: 27 at its 5' end by four idSp groups.

SEQ ID NO: 32 shows a polynucleotide sequence used in Example 6. It has a carboxyfluorescein (FAM) base at its 5' end.

SEQ ID NO: 33 shows a polynucleotide sequence used in Example 6. It has a carboxyfluorescein (FAM) base at its 5' end.

SEQ ID NO: 34 shows a polynucleotide sequence used in Example 7.

SEQ ID NO: 35 shows a polynucleotide sequence used in Example 7 and 8. It has a carboxyfluorescein (FAM) base at its 5' end.

SEQ ID NO: 36 shows a polynucleotide sequence used in Example 7 and 8.

SEQ ID NO: 37 shows a polynucleotide sequence used in Example 7, 8 and 9.

SEQ ID NO: 38 shows a polynucleotide sequence used in Example 8 and 10.

SEQ ID NO: 39 shows a polynucleotide sequence used in Example 8.

SEQ ID NO: 40 shows a polynucleotide sequence used in Example 8.

SEQ ID NO: 41 shows a polynucleotide sequence used in Example 9.

SEQ ID NO: 42 shows a polynuclcotide sequence used in Example 9.

SEQ ID NO: 43 shows a polynucleotide sequence used in Example 9.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms “a”, “an”, and “the” include plural referents unless the content clearly dictates otherwise. Thus, for example, reference to “a polynucleotide” includes two or more polynuclcotides, reference to “a spacer” includes two or more spacers, reference to “a helicase” includes two or more helicases, reference to “a transmembrane pore” includes two or more pores, and the like.

All publications, patents and patent applications cited herein, whether supra or infra, are hereby incorporated by reference in their entirety.

Methods of Moving Helicases Past Spacers

The invention provides a method of moving one or more stalled helicases past one or more spacers in a target polynucleotide. A helicase is stalled if it has stopped moving along the polynucleotide. Each spacer typically stalls the one or more helicases. Methods for determining whether or not one or more helicases are stalled are discussed below. The one or more helicases may be stalled before a spacer. The one or more helicases may be stalled by a spacer. The one or more helicases may be stalled on a spacer. The invention concerns moving the one or more stalled helicases past, i.e. beyond, the one or more spacers.

The one or more stalled helicases and the target polynucleotide are contacted with a transmembrane pore and a potential is applied. As described in more detail below, the target polynucleotide moves through the pore with the field resulting from the applied potential. The one or more helicases are typically too large to move through the pore. When a part of the target polynucleotide enters the pore and moves through the pore along the field resulting from the applied potential, the one or more helicases are moved past the spacer by the pore as the target polynucleotide moves through the pore. This is because the target polynucleotide (including the one or more spacers) moves through the pore and the one or more helicases remain on top of the pore.

This allows the position of the one or more helicases on the target polynucleotide to be controlled. Before the one or more stalled helicases and the target polynucleotide are contacted with a transmembrane pore and the potential is applied, the one or more helicases remain in the position where they are stalled. Even in the presence of the necessary components to facilitate helicase movement (e.g. ATP and $Mg^{2+}$), the one or more helicases will not move past a spacer on the target polynucleotide and will not move along the portion of the target polynucleotide on other side of the spacer until they are in the presence of the transmembrane pore and the applied potential.

The one or more helicases will also remain in the position where they are stalled in the presence of the transmembrane pore, but in the absence of the applied potential. In this instance, the application of a potential moves the one or more helicases past a spacer. The application of a potential can therefore be used to instigate the movement of the one or more helicases past a spacer and along the portion of the target polynucleotide on other side of the spacer. For instance, an increase in voltage may be used to move the one or more helicases past the spacer.

The invention also provides a method of controlling the movement of a target polynucleotide through a transmembrane pore. The target polynucleotide is provided with one or more spacers. The target polynucleotide is contacted with one or more helicases and the one or more helicases stall at the one or more spacers. This ensures that the one or more helicases remain at one or more specific positions on the polynucleotide. This is discussed in more detail below. The target polynucleotide and the one or more stalled helicases are contacted with a transmembrane pore. Once a potential is applied, the one or more helicases move past the one or more spacers and along the portion of the polynucleotide on other side of the spacer(s). This allows the one or more helicases to control the movement of the polynucleotide through the pore. The potential is also typically used to thread the polunucleotide into the pore.

Helicases can control the movement of polynucleotides in at least two active modes of operation (when the helicase is provided with all the necessary components to facilitate movement, e.g. ATP and $Mg^{2+}$) and one inactive mode of operation (when the helicase is not provided with the necessary components to facilitate movement). When provided with all the necessary components to facilitate movement, the helicase moves along the polynucleotide in a 5' to 3' or a 3' to 5' direction (depending on the helicase), but the orientation of the polynucleotide in the pore (which is dependent on which end of the polynucleotide is captured by the pore) means that the helicase can be used to either move the polynucleotide out of the pore against the applied field or move the polynucleotide into the pore with the applied field. When the end of the polynucleotide towards which the helicase moves is captured by the pore, the helicase works against the direction of the field resulting from the applied potential and pulls the threaded polynucleotide out of the pore and into the cis chamber. However, when the end away from which the helicase moves is captured in the pore, the helicase works with the direction of the field resulting from the applied potential and pushes the threaded polynucleotide into the pore and into the trans chamber.

When the helicase is not provided with the necessary components to facilitate movement it can bind to the polynucleotide and act as a brake slowing the movement of the polynucleotide when it is pulled into the pore by the field resulting from the applied potential. In the inactive mode, it does not matter which end of the polynucleotide is captured, it is the applied field which pulls the polynucleotide into the pore towards the trans side with the helicase acting as a brake. When in the inactive mode, the movement control of the polynucleotide by the helicase can be described in a number of ways including ratcheting, sliding and braking.

In the method of the invention, the one or more helicases preferably control the movement of the target polynucleotide through the pore with the field resulting from the applied potential. In one preferred embodiment, the one or more helicases are used in the active mode and the end away from which the one or more helicases move is captured by the pore such that the one or more helicases work with the field resulting from the applied potential and push the polynucleotide through the pore. If the one or more helicases move in the 5' to 3' direction, the 5' end of the target polynucleotide is preferably captured by the pore. In such embodiments, the one or more helicases are moved past the one or more spacers in the 5' to 3' direction. If the one or more helicases move in the 3' to 5' direction, the 3' end of the target polynucleotide is preferably captured by the pore. In such embodiments, the one or more helicases are moved past the one or more spacers in the 3' to 5' direction.

In another preferred embodiment, the one or more helicases are used in the inactive mode such that the applied field pulls the target polynucleotide through the pore and the one or more helicases act as a brake. In the method of the invention, the one or more helicases preferably slow or brake the movement of the target polynucleotide through the pore with the field resulting from the applied potential. In either case, the one or more helicases are typically too large to move through the pore and the pore pushes the one or more helicases past the one or more spacers on the polynucleotide as the polynucleotide moves through the pore with the field resulting from the applied potential.

The method of controlling the movement of a target polynucleotide through a transmembrane pore can be helpful during characterisation of the polynucleotide using the pore, for instance during strand sequencing. The invention also provides a method of characterising a target polynucleotide. The target polynucleotide is provided with one or more spacers. The target polynucleotide is contacted with one or more helicases and the one or more helicases stall at the one or more spacers. This ensures that the one or more helicases remain at one or more specific positions on the polynucleotide. This is discussed in more detail below. The target polynucleotide and the one or more stalled helicases are contacted with a transmembrane pore. Once a potential is applied, the one or more helicases move past the one or more spacers and along the portion of the polynucleotide on other side of the spacer(s). This allows the one or more helicases to control the movement of the polynucleotide through the pore. The method also comprises taking one or more measurements as the polynucleotide moves with respect to the pore. The measurements are indicative of one or more characteristics of the polynucleotide.

The ability to stall one or more helicases on the target polynucleotide and move the one or more helicases past the one or more spacers using a transmembrane pore and an applied potential is advantageous because it allows effective chareterisation, such as sequencing, of the target polynucleotide. For instance, the one or more helicases can be stalled towards one end of the target polynucleotide in a leader sequence which is designed to be captured by the pore and does not need to be characterised (as described below). The stalling of the one or more helicases in the leader sequence means that the one or more helicases do not move away from the leader sequence along the part of the polynucleotide to be characterised until it/they are contacted with the pore and a potential is applied. Once the one or more helicases and the polynucleotide are contacted with the pore and a potential is applied, the leader sequence is typically captured by the pore and moves through the pore. This movement moves the one or more helicases past the spacer(s) and along the part of polynucleotide to be characterised (as described above). The one or more helicases may then control the movement of the part of the polynucleotide to be characterised.

If the one or more helicases are not stalled in the leader sequence, it/they would move along the polynucleotide away from the leader sequence and along the part of the polynucleotide to be characterised. When the one or more helicases and the polynucleotide are contacted with the pore and a potential is applied under these circumstances, the leader sequence and some, if not all, of the polynucleotide to be characterised will move in an uncontrolled manner through the pore along the field resulting from the applied potential. Only once the one or more helicases come into contact with the pore will it/they begin to control the movement of the part of the polynucleotide to be characterised as discussed above. Any part of the polynucleotide which moves through the pore in an uncontrolled manner cannot be characterised as described below. If the one or more helicases move away from the leader sequence and along most of the rest of the target polynucleotide little, if any, of the polynucleotide will be characterised.

The use of one or more spacers in accordance with the invention also allows the number and position of the one or more helicases on the target polynucleotide to be controlled as discussed in more detail below. For instance, a specific number of helicases may be stalled at specific positions on adaptors which may be ligated to the target polynucleotide before characterisation. Such adaptors are provided by the invention and may be provided in a kit for characterisation. The use of one or more spacers ensures that the helicases remain where they supposed to be until the characterisation is begun, even if the adaptor and/or target polynucleotide before characterisation are in the presence of the components necessary to facilitate helicase movement (e.g. ATP and $Mg^{2+}$).

Polynucleotide

A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below.

A nucleotide typically contains a nucleobase, a sugar and at least one phosphate group. The nucleobase and sugar form a nucleoside.

The nucleobese is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The nucleotide in the polynucleotide is typically a ribonucleotide or deoxyribonucleotide. The polynucleotide may comprise the following nucleosides: adenosine, uridine, guanosine and cytidine. The nuclcotide is preferably a deoxyribonucleotide. The polynucleotide preferably comprises the following nucleosides: deoxyadenosine (dA), deoxyuridine (dU) and/or thymidine (dT), deoxyguanosine (dG) and deoxycytidine (dC).

The nucleotide typically contains a monophosphate, diphosphate or triphosphate. Phosphates may be attached on the 5' or 3' side of a nucleotide.

Suitable nucleotides include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dUMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP. The nucleotides are most preferably selected from dAMP, dTMP, dGMP, dCMP and dUMP. The polynucleotide preferably comprises the following nucleotides: dAMP, dUMP and/or dTMP, dGMP and dCMP.

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide can be a nucleic acid. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic nucleic acid (RNA) or deoxyribonucleic acid (DNA).

The polynucleotide preferably does not comprise any abasic nucleotides (i.e. nucleotides which lack a nucleobase), except in the one or more spacers. The polynucleotide preferably does not comprise any C3 spacers (i.e. nucleotide which lack a nucleobase and a sugar), except in the one or more spacers.

The polynucleotide may be any length. For example, the polynucleotide can be at least 10, at least 50, at least 100, at least 150, at least 200, at least 250, at least 300, at least 400 or at least 500 nucleotides in length. The polynucleotide can be 1000 or more nucleotides, 5000 or more nucleotides in length or 100000 or more nucleotides in length.

The helicase may move along the whole or only part of the target polynucleotide in the method of the invention. The whole or only part of the target polynucleotide may be characterised using the method of the invention.

The target polynucleotide may be single stranded. At least a portion of the target polynucleotide is preferably double stranded. Helicases typically bind to single stranded polynucleotides. If at least a portion of the target polynucleotide is double stranded, the target polynucleotide preferably comprises a single stranded region or a non-hybridised region. The one or more helicases are capable of binding to the single stranded region or one strand of the non-hybridised region. The target polynucleotide preferably comprises one or more single stranded regions or one or more non-hybridised regions.

The one or more spacers are preferably included in the single stranded region or the non-hybridised region of the target polynucleotide. The target polynucleotide may comprise more than one single stranded region or more than one non-hybridised region. The target polynucleotide may comprise a single stranded region or a non-hybridised region within its sequence and/or at one or both ends. The one or more spacers may be included in the double stranded region of the target polynucleotide.

If the one or more helicases used in the method move in the 5' to 3' direction, the target polynucleotide preferably comprises a single stranded region or a non-hybridised region at its 5' end. If the one or more helicases used in the method move in the 3' to 5' direction, the target polynucleotide preferably comprises a single stranded region or a non-hybridised region at its 3' end. If the one or more helicases are used in the inactive mode (i.e. as a brake), it does not matter where the single stranded region or the non-hybridised region is located.

The single stranded region preferably comprises a leader sequence which preferentially threads into the pore. The leader sequence facilitates the method of the invention. The leader sequence is designed to preferentially thread into the transmembrane pore and thereby facilitate the movement of target polynucleotide through the pore. The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

If at least a portion of the target polynucleotide is double stranded, the two strands of the double stranded portion are preferably linked using a bridging moiety, such as a hairpin. This facilitates characterisation method of the invention. Linking the two strands of the target polynuclcotide by a bridging moiety allows both strands of the polynucleotide to be characterised, such as sequenced, by the transmembrane pore. The two strands dchybridise as the polynucleotide moves though the pore as a single stranded polynucleotide. This method is advantageous because it doubles the amount of information obtained from a single double stranded target polynucleotide. Moreover, because the sequence in the complementary 'anti-sense' strand is necessarily orthogonal to the sequence of the 'sense' strand, the information from the two strands can be combined informatically. Thus, this mechanism provides an orthogonal proof-reading capability that provides higher confidence observations.

Any of the embodiments disclosed in International Application No. PCT/GB2012/051786 (published as WO 2013/014451) may be used. The bridging moiety typically covalently links the two strands of the polynucleotide. The bridging moiety can be anything that is capable of linking the two strands of the target polynucleotide, provided that the bridging moiety does not interfere with movement of the polynucleotide through the transmembrane pore. Suitable bridging moieties include, but are not limited to a polymeric linker, a chemical linker, a polynucleotide or a polypeptide. Preferably, the bridging moiety comprises DNA, RNA, modified DNA (such as abasic DNA), RNA, PNA, LNA or polyctheylone glycol (PEG). The bridging moiety is more preferably DNA or RNA. The bridging moiety may comprise the one or more spacers.

The bridging moiety is most preferably a hairpin loop. The hairpin loop may be formed from any of the polynucleotides disclosed above. The hairpin loop or the loop of the hairpin loop is typically from about 4 to about 100 nucleotides in length, preferably from about 4 to about 8 nucleotides in length.

The bridging moiety is linked to the two strands of the target polynucleotide by any suitable means known in the art. The bridging moiety may be synthesized separately and chemically attached or enzymatically ligated to the target polynucleotide. Alternatively, the bridging moiety may be generated in the processing of the target polynucleotide.

The bridging moiety is linked to the target polynucleotide at or near one end of the target polynucleotide. The bridging moiety is preferably linked to the target polynucleotide within 10 nucleotides of the end of the polynucleotide.

The one or more spacers are preferably positioned such that it/they stall(s) the one or more helicases and prevents it/them from moving along the target polynucleotide to be controlled or characterised. For instance, the one or more spacers are preferably located between a leader sequence and the target polynucleotide to be controlled or characterised, for instance within a leader sequence at one end of the polynucleotide. The leaders sequence typically enters the pore with the field resulting from the applied potential and the one or more helicases are moved past the one or more spacers as the polynucleotide moves through the pore. The one or more helicases may then control the movement of the remainder of the target polynucleotide through the pore and facilitate its characterisation.

In the most preferred embodiment, the target polynucleotide comprises a double stranded portion which is linked at one end by a bridging moiety, such as a hairpin loop, and a single stranded portion at the at the other end from the bridging moiety which comprises a leader sequence. The one or more spacers may be present in the leader sequence and/or the bridging moiety.

The target polynucleotide is present in any suitable sample. The invention is typically carried out on a sample that is known to contain or suspected to contain the target polynucleotide. The invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, quinoa, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Spacer(s)

The one or more spacers are included in the target polynucleotide. The one or more spacers are preferably part of the target polynucleotide, for instance it/they interrupt(s) the polynucleotide sequence. The one or more spacers are preferably not part of one or more blocking molecules, such as speed bumps, hybridised to the target polynucleotide.

There may be any number of spacers in the target polynucleotide, such as 1, 2, 3, 4, 5, 6, 7, 8, 9, 10 or more spacers. There are preferably two, four or six spacers in the target polynucleotide. There may be spacer in different regions of the target polynucleotide, such as a spacer in the leader sequence and a spacer in the hairpin loop.

The one or more spacers each provides an energy barrier which the one or more helicases cannot overcome even in the active mode. The one or more spacers may stall the one or more more helicases by by reducing the traction of the helicase (for instance by removing the bases from the nucleotides in the target polynucleotide) or physically blocking movement of the one or more helicases (for instance using a bulky chemical group).

The one or more spacers may comprise any molecule or combination of molecules that stalls the one or more helicases. The one or more spacers may comprise any molecule or combination of molecules that prevents the one or more helicases from moving along the target polynucleotide. It is straightforward to determine whether or not the one or more helicases are stalled at one or more spacers in the absence of a transmembrane pore and an applied potential. For instance, this can be assayed as shown in the Examples, for instance the ability of a helicase to mve past a spacer and displace a complementary strand of DNA can be measured by PAGE.

The one or more spacers typically comprise a linear molecule, such as a polymer. The one or more spacers typically have a different structure from the target polynucleotide. For instance, if the target polynucleotide is DNA, the one or more spacers are typically not DNA. In particular, if the target polynucleotide is deoxyribonucleic acid (DNA) or ribonucleic acid (RNA), the one or more spacers preferably comprise peptide nucleic acid (PNA), glycerol nucleic acid (GNA), threose nucleic acid (TNA), locked nucleic acid (LNA) or a synthetic polymer with nucleotide side chains.

The one or more spacers preferably comprises one or more nitroindoles, such as one or more 5-nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more iSpC3 groups (i.e. nucleotides which lack sugar and a base), one or more photo-cleavable (PC) groups, one or more hexandiol groups, one or more spacer 9 (iSp9) groups, one or more spacer 18 (iSp18) groups, a polymer or one or more thiol connections. The one or more spacers may comprise any combination of these groups. Many of these groups are commercially available from IDT® (Integrated DNA Technologies®).

The one or more spacers may contain any number of these groups. For instance, for 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, the one or more spacers preferably comprise 2, 3, 4, 5, 6, 7, 8, 9, 10, 11, 12 or more. The one or more spacers preferably comprise 2, 3, 4, 5, 6, 7, 8 or more iSp9 groups. The one or more spacers preferably comprise 2, 3, 4, 5 or 6 or more iSp18 groups. The most preferred spacer is four iSp18 groups.

The polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The one or more spacers preferably comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into target polynucleotides by removing the nucleobases from one or more adjacent nucleotides. For instance, polunucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polunucleotides may be modified to include uracil and the nucleobases removed with Uracil-DNA Glycosylase (UDG). In one embodiment, the one or more spacers do not comprise any abasic nuclcotides.

The one or more helicases may be stalled by (i.e. before) or on each linear molecule spacers. If linear molecule spacers are used, the target polynucleotide is preferably provided with a double stranded region of polynucleotide adjacent to the end of each spacer past which the one or more helicases are to be moved. The double stranded region typically helps to stall the one or more helicases on the adjacent spacer. The presence of the double stranded region(s) is particularly preferred if the method is carried out at at a salt concentration of about 100 mM or lower. Each double stranded region is typically at least 10, such as at least 12, nucleotides in length. If the target polynucleotide used in the invention is single stranded, a double stranded region may formed by hybridising a shorter polynucleotide to a region adjacent to a spacer. The shorter polynucleotide is typically formed from the same nucleotides as the target polynucleotide, but may be formed from different nucleotides. For instance, the shorter polynucleotide may be formed from LNA.

If linear molecule spacers are used, the target polynucleotide is preferably provided with a blocking molecule at end of each spacer opposite to end past which the one or more helicases are to be moved. This can help to ensure that the one or more helicases remain stalled on each spacer. It may also help retain the one or more helicases on the target polynucleotide in the case that it/they diffuse(s) off in solution. The blocking molecule may be any of the chemical groups discussed below which physically cause the one or more helicases to stall. The blocking molecule may be a double stranded region of ploynucleotide.

The one or more spacers preferably comprise one or more chemical groups which physically cause the one or more helicases to stall. The one or more chemical groups are preferably one or more pendant chemical groups. The one or more chemical groups may be attached to one or more nucleobases in the target polynucleotide. The one or more chemical groups may be attached to the target polynucleotide backbone. Any number of these chemical groups may be present, such as 2, 3, 4, 5, 6, 7, 8, 9, 10, 11, 12 or more. Suitable groups include, but are not limited to, fluorophores, streptavidin and/or biotin, cholesterol, methylene blue, dinitrophenols (DNPs), digoxigenin and/or anti-digoxigenin and dibenzylcyclooctyne groups.

Different spacers in the target polynucleotide may comprise different stalling molecules. For instance, one spacer may comprise one of the linear molecules discussed above and another spacer may comprise one or more chemical groups which physically cause the one or more helicases to stall. A spacer may comprise any of the linear molecules discussed above and one or more chemical groups which physically cause the one or more helicases to stall, such as one or more abasics and a fluorophore.

Suitable spacers can be designed depending on the type of target polynucleotide and the conditions under which the method of the invention is carried out. Most helicases bind and move along DNA and so may be stalled using anything that is not DNA. Suitable molecules are discussed above.

The method of the invention is preferably carried out in the presence of free nucleotides and/or the presence of a helicase cofactor. This is discussed in more detail below. In the absence of the transmembrane pore and an applied potential, the one or more spacers are preferably capable of stalling the one or more helicases in the presence of free nucleotides and/or the presence of a helicase cofactor.

If the method of the invention is carried out in the presence of free nucleotides and a helicase cofactor as discussed below (such that the one of more helicases are in the active mode), one or more longer spacers are typically used to ensure that the one or more helicases are stalled on the target polynucleotide before they are contacted with the transmembrane pore and a potential is applied. One or more shorter spacers may be used in the absence of free nucleotides and a helicase cofactor (such that the one or more helicases are in the inactive mode).

The salt concentration also affects the ability of the one or more spacers to stall the one or more helicases. In the absence of the transmembrane pore and an applied potential, the one or more spacers are preferably capable of stalling the one or more helicases at a salt concentration of about 100 mM or lower. The higher the salt concentration used in the method of the invention, the shorter the one or more spacers that are typically used and vice versa.

Preferred combinations of features are shown in Table 1 below.

| Target polynucleotide | Spacer composition* | Spacer length (i.e. number of *) | Salt [ ] | Free nucleotides? | Helicase cofactor? |
|---|---|---|---|---|---|
| DNA | iSpC3 | 4 | 1M | Yes | Yes |
| DNA | iSp18 | 4 | 100-1000 mM | Yes | Yes |
| DNA | iSp18 | 6 | <100-1000 mM | Yes | Yes |
| DNA | iSp18 | 2 | 1M | Yes | Yes |
| DNA | iSpC3 | 12 | <100-1000 mM | Yes | Yes |
| DNA | iSpC3 | 20 | <100-1000 mM | Yes | Yes |
| DNA | iSp9 | 6 | 100-1000 mM | Yes | Yes |
| DNA | idSp | 4 | 1M | Yes | Yes |

As discussed in more detail below, the method may concern moving two or more helicases past a spacer. In such instances, the length of the spacer is typically increased to prevent the trailing helicase from pushing the leading helicase past the spacer in the absence of the pore and applied potential. If the method concerns moving two or more helicases past one or more spacers, the spacer lengths discussed above may be increased at least 1.5 fold, such 2 fold, 2.5 fold or 3 fold. For instance, if the method concerns moving two or more helicases past one or more spacers, the spacer lengths in the third column of Table 1 above may be increased 1.5 fold, 2 fold, 2.5 fold or 3 fold.

The two or more helicases may also be separated such that each has its own one or more spacers. This is discussed in more detail below.

Helicase(s)

Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925; PCT/GB2013/051924 and PCT/GB2013/051928; and in UK Application No. 1318464.3 filed on 18 Oct. 2013).

The helicase preferably comprises the sequence shown in SEQ ID NO: 17 (Trwe Cba) or as variant thereof, the sequence shown in SEQ ID NO: 28 (Hel308 Mbu) or a variant thereof or the sequence shown in SEQ ID NO: 8 (Dda) or a variant thereof. Variants may differ from the native sequences in any of the ways discussed below for transmembrane pores. A preferred variant of SEQ ID NO: 8 comprises E94C/A360C and then ($\Delta$M1)G1G2 (i.e. deletion of M1 and then addition G1 and G2).

Any number of helicases may be moved past the one or more spacers in accordance with the invention. For instance, 1, 2, 3, 4, 5, 6, 7, 8, 9, 10 or more helicases may be moved past the one or more spacer. In some embodiments, different numbers of helicases may be moved past each spacer. For instance, if two helicases are stalled using two separate spacers, one helicase (the first helicase) may be moved past the first spacer, but two helicases (the first and second helicases) may be moved past the second spacer.

The method of the invention preferably comprises moving two or more, such as three or more or four or more, stalled helicases past one or more spacers. The two or more helicases are typically the same helicases. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925; PCT/GB2013/051924 and PCT/GB2013/051928; and in UK Application No. 1318464.3 filed on 18 Oct. 2013.

Conditions and Transmembrane Pores

The method comprises applying a potential across the pore. The applied potential may be a voltage potential. The method may comprise applying a voltage potential across the pore. The method may comprise increasing the voltage applied across the pore. In this embodiment, the initial voltage potential is typically not sufficient to move the one or more helicases past the one or more spacer and the increased voltage potential is typically sufficient to move the one or more helicases past the one or more spacers. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5. In some instances, the current passing through the pore as the target polynucleotide moves with respect to the pore is used to determine the sequence of the target polynucleotide. This is strand sequencing.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores, polynucleotide pores and solid state pores.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer.

The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Examples. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The target polynucleotide is preferably coupled to the membrane. This may be done using any known method. If the membrane is an amphiphilic layer, such as a lipid bilayer (as discussed in detail above), the target polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The target polynucleotide may be coupled directly to the membrane. It may be coupled to the membrane using any of the ways disclosed in International Application Number No. PCT/GB2012/051191 (published as WO 2012/164270). The target polynucleotide is preferably coupled to the membrane via a linker. Preferred linkers include, but are not limited to, polymers, such as polynucleotides, polyethylene glycols (PEGs) and polypeptides. If a target polynucleotide is coupled directly to the membrane, then some data will be lost as the characterising run cannot continue to the end of the polynucleotide due to the distance between the membrane and the pore and/or helicase. If a linker is used, then the target polynucleotide can be processed to completion. If a linker is used, the linker may be attached to the target polynucleotide at any position. The linker is typically attached to the target polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the membrane and the pore and/or helicase. If the coupling is transient, then when the coupled end randomly becomes free of the membrane, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 2 below.

TABLE 2

| Attachment group | Type of coupling | Reference |
|---|---|---|
| Thiol | Stable | Yoshina-lshii, C. and S. G. Boxer (2003). "Arrays of mobile tethered vesicles on supported lipid bilayers." J Am Chem Soc 125(13): 3696-7. |
| Biotin | Stable | Nikolov, V., R. Lipowsky, et al. (2007). "Behavior of giant vesicles with anchored DNA molecules." Biophys J 92(12): 4356-68 |
| Cholesterol | Transient | Pfeiffer, I. and F. Hook (2004). "Bivalent cholesterol-based coupling of oligonucletides to lipid membrane assemblies." J Am Chem Soc 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." Langmuir 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the membrane. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tehen, et al. (1988). "Nonradioactive labeling of synthetic oligonucleotide probes with terminal deoxynucleotidyl transferase." *Anal Biochem* 169(2): 376-82).

Alternatively, the reactive group could be considered to be a short region in the polynucleotide to one already coupled to the membrane, so that attachment can be achieved via hybridisation. The region could be part of the polynucleotide or ligated to it. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5).

Most preferably, the polynucleotide is coupled to the membrane using a cholesterol-tagged polynucleotide which hybridises to the polynucleotide.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore allows a polynucleotide or nucleic acid, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, lysening, outer membrane porin F (OmpF), outer membrane porin G (OmpG), outer membrane phospholipase A and *Netsseria* autotransporter lipoprotein (NalP). α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Map comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%0, for example at least 85%, 90% or 95%, amino acid identity over a stretch of 100 or more, for example 125, 150, 175 or 200 or more, contiguous amino acids ("hard homology").

Standard methods in the mt may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, 149H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-(B1)8 and is called MS-(B2)8. The pore used in the invention is preferably MS-(B2)8. The further preferred variant comprises the mutations G75S/G77S/L88N/Q126R. The variant of SEQ ID NO: 2 has the mutations G75S/G77S/L88N/Q126R in addition to all the mutations of MS-(B1)8 and is called MS-(B2C)8. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 3 below. Where amino acids have similar polarity, this can also be determined by reference to the hydropathy scale for amino acid side chains in Table 4.

TABLE 3

Chemical properties of amino acids

| | | | |
|---|---|---|---|
| Ala | aliphatic, hydrophobic, neutral | Met | hydrophobic, neutral |
| Cys | polar, hydrophobic, neutral | Ash | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 4

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form 1-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a his tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the helicase. The variant preferably comprises one or more reactive cysteine residues that facilitate attachment to the helicasc. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

The helicase may be covalently attached to the pore. The helicase is preferably not covalently attached to the pore.

Any of the proteins described herein may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the helicase or pore. An example of this would be to react a gel-shift reagent to a cysteine engineered on the outside of the pore. This has been demonstrated as a method for separating hemolysin hetero-oligomers (Chem Biol. 1997 July; 4 (7):497-505).

The target polynucleotide, helicase or pore may be labelled with a revealing label. The revealing label may be any suitable label which can be detected. Suitable labels include, but are not limited to, fluorescent molecules, radioisotopes, e.g. $^{125}I$, $^{35}S$, enzymes, antibodies, antigens, polynucleotides and ligands such as biotin.

Proteins may be made synthetically or by recombinant means. For example, proteins may be synthesized by in vitro translation and transcription (IVTT). The amino acid sequence of the protein may be modified to include non-naturally occurring amino acids or to increase the stability of the protein. When a protein is produced by synthetic means, such amino acids may be introduced during production. Proteins may also be altered following either synthetic or recombinant production.

Proteins may also be produced using D-amino acids. For instance, the pore or helciase may comprise a mixture of L-amino acids and D-amino acids. This is conventional in the art for producing such proteins or peptides.

The proteins used in the invention may also contain other non-specific modifications as long as they do not interfere with the proteins' function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Polynucleotide sequences encoding a protein may be derived and replicated using standard methods in the art. Polynucleotide sequences encoding a protein may be expressed in a bacterial host cell using standard techniques in the art. The protein may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The gene encoding the sequence of interest may be amplified using PCR involving specific primers. The amplified sequences may then be incorporated into a recombinant replicable vector such as a cloning vector. The vector may be used to replicate the polynucleotide in a compatible host cell. Thus polynucleotide sequences may be made by introducing a polynucleotide encoding the sequence of interest into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into a suitable expression vector. In an expression vector, the polynucleotide sequence is typically operably linked to a control sequence which is capable of providing for the expression of the coding sequence by the host cell. Such expression vectors can be used to express a construct.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide may be introduced into the vector.

The expression vector may then be introduced into a suitable host cell. Thus, a construct can be produced by inserting a polynucleotide sequence encoding a construct into an expression vector, introducing the vector into a compatible bacterial host cell, and growing the host cell under conditions which bring about expression of the polynuclcotide sequence.

The vectors may be for example, plasmid, virus or phage vectors provided with an origin of replication, optionally a promoter for the expression of the said polynucleotide sequence and optionally a regulator of the promoter. The vectors may contain one or more selectable marker genes, for example an ampicillin resistance gene. Promoters and other expression regulation signals may be selected to be compatible with the host cell for which the expression vector is designed. A T7, trc, lac, ara or $\lambda_L$ promoter is typically used.

The host cell typically expresses the construct at a high level. Host cells transformed with a polynucleotide sequence will be chosen to be compatible with the expression vector used to transform the cell. The host cell is typically bacterial and preferably *E. coli*. Any cell with a λ DE3 lysogen, for example Rosetta2(DE3)pLys, C41 (DE3), BL21 (DE3), JM109 (DE3), B834 (DE3), TUNER, Origami and Origami B, can express a vector comprising the T7 promoter.

Proteins may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured for example by determining the number of interactions between the target polynucleotide and the pore or the duration of interaction between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunnelling measurements (Ivanov AP et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1): 014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Examples. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. Hel308, XPD, RecD, TraI and Dda helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports helicase function, such as about 37° C.

The method may be carried out in the presence of free nucleotides or free nucleotide analogues and/or a helicase cofactor that facilitates the action of the helicase. The method may also be carried out in the absence of free nucleotides or free nucleotide analogues and in the absence of a helicase cofactor. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The helicase cofactor is a factor that allows the helicase or construct to function. The helicase cofactor is preferably a divalent metal cation. The divalent metal cation is preferably $Mg^{2+}$, $Mn^{2+}$, $Ca^{2+}$ or $Co^{2+}$. The helicase cofactor is most preferably $Mg^{2+}$.

Methods of Controlling the Loading of One or More Helicases on a Target Polynucleotide The invention also provides a method of controlling the loading of one or more helicases on a target polynucleotide. The method comprises providing the target polynucleotide with one or more spacers. The method preferably comprises modifying the target polynucleotide so that it comprises one or more spacers. All of the spacer embodiments discussed above equally apply to this method.

The method also comprises contacting the target polynucleotide with the one or more helicases such that the one or more helicases bind to the target polynucleotide and one or more helicases stall at each spacer. The stalling of helicases at spacers may be assayed as discussed above.

The target polynucleotide may comprise any number of spacers as discussed above. The target polynucleotide preferably comprises two or more spacers, such as 3, 4, 5, 6, 7, 8, 9, 10 or more spacers. Any number of helicases may be stalled at each spacer as discussed above. In this way, it is possible to control where and how many helicases are loaded on the target polynucleotide and thereby facilitate characterisation of the target polynucleotide. The one or more helicases may be moved past the one or more spacers using any of the methods discussed above.

The target polynucleotide is preferably provided with one or more spacers S and one or more single stranded regions or one or more non-hybridised regions L (L is for loading site). The length of each region L depends on the number of helicases that should bind to each L and be stalled at each spacer S. The one or more spacers S and one or more regions L may be adjacent to (i.e. next to) one another or may be separated by part of the target polynucleotide. Each spacer is typically located at or near the end of each region L towards which the helicase moves. For instance, if the helicase is a 5' to 3' helicase, each spacer is typically located at or near the 3' end of each region, i.e 5'-L-S-3'. If the helicase is a 3' to 5' helicase, each spacer is typically located at or near the 5' end of each region, i.e 5'-S-L-3'.

The target polynucleotide is preferably provided with (L-S)n or (S-L)n in the 5' to 3' direction, wherein L is a single stranded polynucleotide or a non-hybridised polynucleotide, S is a spacer and n is a whole number, such as 1, 2, 3, 4, 5, 6, 7, 8, 9, 10 or more. n is preferably 1, 2, 3 or 4. The 5' to 3' direction refers to the target polynucleotide.

The target polynucleotide is preferably provided with one or more single stranded regions or one or more non-hybridised regions L each of which has a spacer S at or near either end, i.e. provided with (S-L-S)n.

In a preferred embodiment, the spacer is adjacent to a double stranded region D as discussed above, i.e. 5'-L-S-D-3' for 5' to 3' helicases or helicases used in the inactive mode or 5'-D-S-L-3' for 3' to 5' helicases or helicases used in the inactive mode. The target polynucleotide is preferably provided with (L-S-D)n or (D-S-L)n in the 5' to 3' direction, wherein L is a single stranded polynucleotide or a non-hybridised polynucleotide, S is a spacer, D is a double stranded polynucleotide and n is a whole number, such as 1, 2, 3, 4, 5, 6, 7, 8, 9, 10 or more. n is preferably 1, 2, 3 or 4. L may be the same type of polynucleotide as D or may be a different type of polynucleotide from D. L and/or D may be the same type of polynucleotide as the target polynucleotide or may be a different type of polynucleotide from the target polynucleotide.

In a preferred embodiment, a blocking molecule B is provided at the end of each spacer opposite to the end past which the one or more helicases are to be moved, i.e. 5'-B-L-S-3' for 5' to 3' helicases or helicases used in the inactive mode or 5'-S-L-B-3' for 3' to 5' helicases. The target polynucleotide is preferably provided with (B-L-S)n or (S-L-B)n in the 5' to 3' direction, wherein L is a single stranded polynucleotide or a non-hybridised polynucleotide, S is a spacer, B is blocking molecule and n is a whole number, such as 1, 2, 3, 4, 5, 6, 7, 8, 9, 10 or more. n is preferably 1, 2, 3 or 4.

In the most preferred embodiment, the target polynucleotide is provided with both D and B, i.e 5'-B-L-S-D-3' for 5' to 3' helicases or helicases used in the inactive mode or 5'-D-S-L-B-3' for 3' to 5' helicases. The target polynucleotide is most preferably provided with (B-L-S-D)n or (D-S-L-B)n in the 5' to 3' direction, wherein L is a single stranded polynucleotide or a non-hybridised polynucleotide, S is a spacer, B is blocking molecule, D is a double stranded polynucleotide and n is a whole number, such as 1, 2, 3, 4, 5, 6, 7, 8, 9, 10 or more. n is preferably 1, 2, 3 or 4.

The target polynucleotide may be provided with any number of these spacer-containing units. For instance, the target polynucleotide may be provided with (5'-L-S-3')n, (5'-S-L-3')n, (S-L-S)n, (5'-L-S-D-3')n, (5'-D-S-L-3')n, (5'-B-L-S-3')n, (5'-S-L-B-3')n, (5'-B-L-S-D-3')n or (5'-D-S-L-B-3')n, where n is 2 or more, such as such as 3, 4, 5, 6, 7, 8, 9, 10 or more. Such embodiments allow multiple helicases to be stalled on the target polynucleotide.

The target polynucleotide may be provided with all of the embodiments discussed above with reference to L, S, D and B by ligating an adaptor of the invention to the target polynucleotide.

In a preferred embodiment, the target polynucleotide is contacted with the one or more helicases such that one helicase (i.e. only one helicase) stalls at each spacer. This can be achieved by providing the target polynucleotide with one or more spacers S and one or more single stranded regions or one or more non-hybridised regions $L^1$ each of which is only long enough for one helicase to bind. The target polynucleotide is preferably provided with ($L^1$-S)n or (S-$L^1$)n in the 5' to 3' direction, wherein $L^1$ is a single stranded polynucleotide or a non-hybridised polynucleotide which is only long enough for one helicase to bind, S is a spacer and n is a whole number, such as 1, 2, 3, 4, 5, 6, 7, 8, 9, 10 or more. n is preferably 1, 2, 3 or 4.

The length of region $L^1$ depends on the footprint of the helicase and can be calculated in a straightforward manner. Region $L^1$ may be part of the target polynucleotide or may be added to the target polynucleotide, for instance as part of an adaptor of the invention. Region $L^1$ is typically 8, 9, 10, 12, 13, 14 or 15 nucleotides in length. The one or more spacers S and one or more $L^1$ regions may be adjacent to (i.e. next to) one another or may be separated by part of the target polynucleotide. Each spacer S is typically located at or near the end of each region $L^1$ towards which the helicase moves. For instance, if the helicase is a 5' to 3' helicase, each spacer S is typically located at or near the 3' end of each region $L^1$, i.e 5'-$L^1$-S-3'. If the helicase is a 3' to 5' helicase, each spacer S is typically located at or near the 5' end of each region $L^1$, i.e 5'-S-$L^1$-3'. The target polynucleotide is preferably provided with one or more single stranded regions or one or more non-hybridised regions $L^1$ each of which is only long enough for one helicase to bind and each of which has a spacer S at or near either end, i.e. (S-$L^1$-S)n.

The target polynucleotide may be provided with (5'-$L^1$-S-3')n, (5'-S-$L^1$-3')n, (S-$L^1$-S)n, (5'-$L^1$-S-D-3')n, (5'-D-S-$L^1$-3')n, (5'-B-$L^1$-S-3')n, (5'-S-$L^1$-B-3')n, (5'-B-$L^1$-S- D-3')n or (5'-D-S-$L^1$-B-3')n, where n is a whole number, such as 1, 2, 3, 4, 5, 6, 7, 8, 9, 10 or more. n is preferably 1, 2, 3 or 4. Such embodiments allow n helicases to be stalled on the target polynucleotide. One helicase is stalled by each spacer.

In another preferred embodiment, the target polynucleotide is contacted with the one or more helicases such that two helicases (i.e. only two helicases) stall at each spacer. This can be achieved by providing the target polynucleotide with one or more spacers S and one or more single stranded regions or one or more non-hybridised regions $L^2$ each of which is only long enough for two helicases to bind. The target polynucleotide is preferably provided with ($L^2$-S)n or (S-$L^2$)n in the 5' to 3' direction, wherein L is a single stranded polynucleotide or a non-hybridised polynucleotide which is only long enough for two helicases to bind, S is a spacer and n is a whole number, such as 1, 2, 3, 4, 5, 6, 7, 8, 9, 10 or more. n is preferably 1, 2, 3 or 4.

The length of region $L^2$ depends on the footprint of the helicases and can be calculated in a straightforward manner. Region $L^2$ may be part of the target polynucleotide or may be added to the target polynucleotide, for instance as part of an adaptor of the invention. Region $L^2$ is typically 16, 17, 18, 19, 20, 21 or 22 nucleotides in length. The one or more spacers S and one or more regions $L^2$ may be adjacent to (i.e. next to) one another or may be separated by part of the polynucleotide. Each spacer is typically located at or near the end of each region towards which the helicase moves. For instance, if the helicase is a 5' to 3' helicase, each spacer is typically located at or near the 3' end of each region. The polynucleotide is preferably provided with one or more single stranded regions or one or more non-hydrisied regions $L^2$ each of which is only long enough for two helicases to bind and each of which has a spacer S at or near either end, i.e. (S-$L^2$-S)n.

The target polynucleotide may be provided with (5'-$L^2$-S-3')n, (5'-S-$L^2$-3')n, (S-$L^2$-S)n, (5'-$L^2$-S-D-3')n, (5'-D-S-$L^2$-3')n, (5'-B-$L^2$-S-3')n, (5'-S-$L^2$-B-3')n, (5'-B-$L^2$-S- D-3')n or (5'-D-S-$L^2$-B-3')n, where n is a whole number, such as 1, 2, 3, 4, 5, 6, 7, 8, 9, 10 or more. n is preferably 1, 2, 3 or 4. Such embodiments allow 2n helicases to be stalled on the target polynucleotide. Two helicases are stalled by each spacer.

The two helicases stalled at each spacer are preferably different from one another. This can be controlled in several ways. For instance, two different helicases may be attached to one another, such as covalently attached to one another, and then stalled at each spacer. Suitable constructs are discussed above. Alternatively, blocking polynucleotides may be used to ensure that different helicases are stalled by each spacer. If the method comprises providing the polynucleotide with one or more spacers S and one or more single stranded regions or one or more non-hydrisied regions $L^2$ each of which is only long enough for two helicases to bind, the method preferably comprises hybridising a blocking polynucleotide to part of each region $L^2$ so that the remaining (i.e. non-blocked) part of each region is only long enough to bind one helicase. Blocking polynucleotides are typically 2, 3, 4, 5, 6, 7 or 8 nucleotides in length. The blocking polynucleotide prevents two helicases from binding to the same region at the same time. The polynucleotide comprising the blocking polynucleotides is preferably contacted with one or more helicases such that one helicase binds to the remaining (i.e. non-blocked) part of each region $L^2$. Each helicase may then be used to remove each blocking polynucleotide. The one or more bound helicases are preferably provided with free nucleotides and a helicase cofactor such that they remove each blocking polynucleotide and stall at each spacer S. The polynucleotide produced in in this way is then preferably contacted with one or more helicases which are different from the helicases used earlier in the method such that one different helicase binds to each region and is stalled by the spacer and the other stalled helicase.

The method preferably comprises (a) providing the target polynucleotide with ($L^2$-S)n or (S-$L^2$)n in the 5' to 3' direction, wherein L is a single stranded polynucleotide or a non-hybridised polynucleotide which is only long enough for two helicases to bind, S is a spacer and n is a whole number, such as 1, 2, 3, 4, 5, 6, 7, 8, 9, 10 or more; (b) hybridising a blocking polynucleotide to part of each region $L^2$ so that the remaining part of each region $L^2$ is only long enough to bind one helicase; (c) contacting the target polynucleotide produced in (b) with one or more helicases such that one helicase binds to the remaining part of each region $L^2$; (d) providing the one or more bound helicases in (c) with free nucleotides and a helicase cofactor such that they remove each blocking polynucleotide and stall at each spacer S; and (e) contacting the target polynucleotide produced in (d) with one or more helicases which are different from those used in (c) such that one different helicase binds to each region $L^2$ and is stalled by each spacer and each helicase stalled in (d). n is preferably 1, 2, 3 or 4. Other arrangements of S and $L^2$, such (S-$L^2$-S)n, (5'-$L^2$-S-D-3')n, (5'-D-S-$L^2$-3')n, (5'-B-$L^2$-S-3')n, (5'-S-$L^2$-B-3')n, (5'-B-$L^2$-S-D-3')n and (5'-D-S-$L^2$-B-3')n as discussed above, may also be used in this embodiment.

As discussed above, the length of a spacer may be used to control the number of helicases that are stalled and/or the number of helicases which may be moved past the spacer. Longer spacers may be used to stall more helicases. Trains of two or more helicases, such as 3, 4 or 5 helicases, may also move past longer spacers because trailing helicases may push leading helicases past the spacer. The embodiments with reference to $L^1$ and $L^2$ above can be modified such that 3, 4 or 5 helicases are stalled at each spacer. For instance, the polynucleotide may be provided with one or more spacers S and one or more single stranded regions or one or more non-hybridised regions each of which is only long enough for three (L3), four ($L^4$) or five ($L^5$) helicases to bind.

Adaptor

The invention also provides an adaptor for controlling the movement of a target polynucleotide. The adaptor is preferably for characterising a target polynucleotide. The adaptor comprises (a) (L-S-D)n or (D-S-L)n in the 5' to 3' direction, wherein L is a single stranded polynucleotide or a non-hybridised polynucleotide, S is a spacer and D is a double stranded polynucleotide and wherein n is a whole number, such as 1, 2, 3, 4, 5, 6, 7, 8, 9, 10 or more, and (b) one or more helicases stalled on each adaptor. n is preferably 1, 2, 3 or 4. The 5' to 3' direction refers to the direction of the L and D polynucleotides in the adaptor.

The one or more helicases may be stalled before the spacer S, by the spacer S or on the spacer S.

The adaptor may be ligated to a target polynucleotide such that the target polynucleotide may be used in any of the method discussed above.

L may be $L^1$ or $L^2$ as discussed above. An adaptor may comprise a combination of $L^1$ and $L^2$.

All of the spacer embodiments discussed above equally apply to this method.

Any of the embodiments discussed above with reference to L, S and D equally apply to the adaptors of the invention. The adaptor may comprise (5'-$L^1$-S-D-3')n, (5'-D-S-$L^1$-3')n, (5'-B-$L^1$-S-D-3')n or (5'-D-S-$L^1$-B-3')n, (5'-$L^2$-S-D-3')n, (5'-D-S-$L^2$-3')n, (5'-B-$L^2$-S-D-3')n or (5'-D-S-$L^2$-B-3')n in the 5' to 3' direction, where n is a whole number, such as 1, 2, 3, 4, 5, 6, 7, 8, 9, 10 or more. n is preferably 1, 2, 3 or 4. $L^1$ or $L^2$ may be replaced with $L^3$, $L^4$ or $L^5$.

Most preferably n is 1 and one or two helicases are stalled one the adaptor.

Kit

The invention also provides a kit for controlling the movement of a target polynucleotide. The kit is preferably for characterising a target polynucleotide. The kit comprises (a) one or more spacers, (b) one or more helicases and (c) a transmembrane pore. All of the spacer embodiments discussed above with reference to the methods of the invention equally apply to the kits of the invention. For instance, the one or more spacers may be part of a polynucleotide adaptor, preferably a single stranded polynucleotide adaptor, which may be ligated to to the target polynucleotide and which comprises a leader sequence which preferentially threads into the pore. The kit may comprise any of the helicases and pores discussed above.

The one or more spacers and the one or more helicases may be part of an adaptor of the invention.

The kit may further comprise the components of a membrane, such as the phospholipids needed to form an amphiphilic layer, such as a lipid bilayer.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise the components necessary to facilitate helicase movement (e.g. ATP and $Mg^{2+}$). The following Examples illustrate the invention.

EXAMPLES

Example 1

This example describes how a T4 Dda-E94C/A360C (SEQ ID NO: 8 with mutations E94C/A360C and then (ΔM1)G1G2) helicase can control the movement of intact DNA strands through a single MspA nanopore (MS(B1-G75S/G77S/L88N/Q126R)8 (MspA-B2C) (SEQ ID NO: 2 with mutations G75S/G77S/L88N/Q126R). The iSpC3 spacers in the lambda DNA construct (SEQ ID NO: 9 attached by its 3' end to four iSpC3 spacers which are attached to the 5' end of SEQ ID NO: 10 which is attached to three iSpC3 spacers which are attached to the 3' end to SEQ ID NO: 11, the SEQ ID NO: 10 region of this construct is hybridised to SEQ ID NO: 12 (which has attached to its 3' end, six iSp18 spacers attached to two thymine residues and a 3' cholesterol TEG)) are used to stall the enzyme until the construct is captured by the nanopore. Upon capture the force of the applied potential moves the enzyme T4 Dda-E94C/A360C past the stalling spacer and allows enzyme controlled DNA movement of the lambda construct through the nanopore.

Materials and Methods

Prior to setting up the experiment, the Lambda DNA construct (SEQ ID NO: 9 attached by its 3' end to four iSpC3 spacers which are attached to the 5' end of SEQ ID NO: 10 which is attached at its 3' end to SEQ ID NO: 11, the SEQ ID NO: 10 region of this construct is hybridised to SEQ ID NO: 12 (which has a 3' cholesterol tether)) and T4 Dda-E94C/A360C were pre-incubated together for 15 minutes at 23° C. in buffer (20 mM CAPS, pH 10.0, 500 mM NaCl, 5% Glycerol, 2 mM DTT).

Electrical measurements were acquired at 20° C. (by placing the experimental system on a cooler plate) from single MspA nanopores (MspA-B2C) inserted in block co-polymer in buffer (600 mM KCl, 25 mM potassium phosphate, 75 mM Potassium Ferrocyanide (II), 25 mM Potassium ferricyanide (III), pH 8). After achieving a single pore inserted in the block co-polymer, then buffer (1 mL, 600 mM KCl, 25 mM potassium phosphate, 75 mM Potassium Ferrocyanide (II), 25 mM Potassium ferricyanide (III), pH 8) was flowed through the system to remove any excess MspA nanopores (MspA-B2C) and finally experimental buffer was flowed into the system (2 mL 960 mM KCl, 25 mM potassium phosphate, 3 mM Potassium Ferrocyanide (II), 1 mM Potassium ferricyanide (III), pH 8). $MgCl_2$ (10 mM final concentration) and ATP (1 mM final concentration) were mixed together with buffer (960 mM KCl, 25 mM potassium phosphate, 3 mM Potassium Ferrocyanide (II), 1 mM Potassium ferricyanide (III), pH 8) and then added to the Lambda DNA construct (0.2 nM final concentration), T4 Dda-E94C/A360C (10 nM final concentration) buffer (20 mM CAPS, pH 10.0, 500 mM NaCl, 5% Glycerol, 2 mM DTT) pre-mix. The pre-mix was then added to the single nanopore experimental system. Experiments were carried out for four hours following a potential flip process (+100 mV for 2 s, then 0 V for 2 s, then −120 mV for 14500 s applied at the cis side) and helicase-controlled DNA movement was monitored.

Results and Discussion

Figure 1:
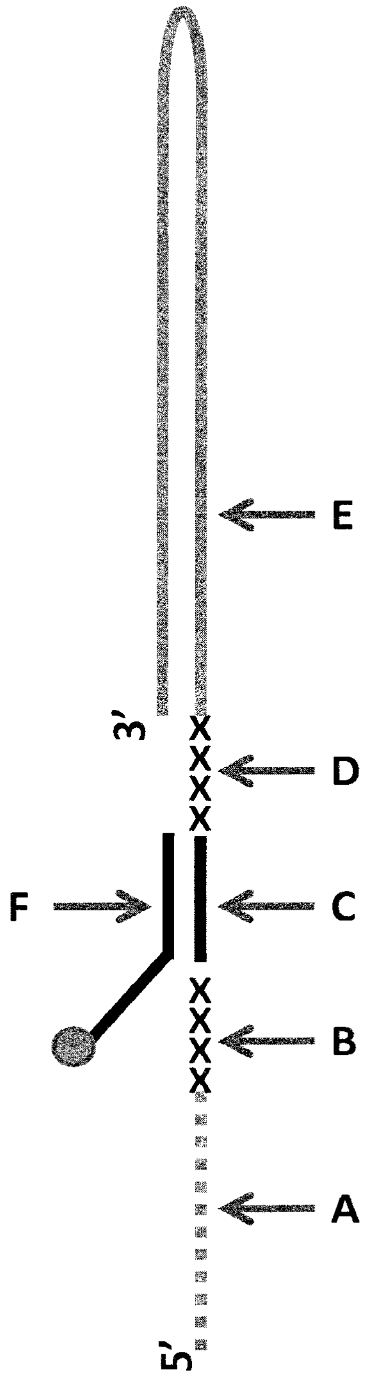
FIG. 1 shows a diagram of the lambda DNA construct used in Example 1. SEQ ID NO: 9 (labelled A) is attached at its 3' end to four iSpC3 spacers (labelled B). The four iSpC3 spacers are attached to the 5' end of SEQ ID NO: 10 (labelled C). SEQ ID NO: 10 is attached to four iSpC3 spacers (labelled D) which are attached to SEQ ID NO: 11 (labelled E) at its 5' end. SEQ ID NO: 10 is hybridised to SEQ ID NO: 12 (labelled F, which has a 3' cholesterol tether).

The DNA construct is shown in FIG. 1. The T4 Dda-E94C/A360C is able to bind on to the region of the construct labelled A (SEQ ID NO: 9) when pre-incubated with the DNA construct. However, the enzyme is not able to motor past the stalling groups when in free solution (labelled B and D in FIG. 1). Therefore, the enzyme is stalled at the iSpC3 spacers (labelled B in FIG. 1) until the DNA construct is captured by the nanopore. Once captured by the nanopore, the force of the applied potential moves the enzyme T4 Dda-E94C/A360C past the stalling spacer and allows enzyme controlled DNA movement of the lambda construct through the nanopore. An example of a helicase-controlled DNA movement is shown in FIG. 2. The helicase-controlled DNA movement was 5170 seconds long and corresponds to the translocation of approximately 30 kB of the lambda construct through the nanopore. FIG. 3 shows zoomed in regions of the beginning (a) and end (b) of the helicase-controlled DNA movement, 1 and 2 show when the iSpC3 spacers translocate through the nanopore under control of the helicase.

Example 2

The DNA construct used in this example was produced by fragmentation of Lambda DNA into ~5-10 kB fragments using MuA. The fragments which were produced by the sample prep were then passed through a nanopore, with their movement controlled by a helicase enzyme. The helicase was moved past the dsDNA region (where the tether hybridises to the construct) and the spacers by the force of the applied potential across the nanopore. The observance of characteristic blocks produced by the helicase controlled movement of the markers through the nanopore showed the sample preparation procedure had been successful and that the enzyme had been stalled as shown in FIG. 4(*b*). This meant that the enzyme had a defined start point and was unable to move past the dsDNA region (where the tether hybridises to the construct) and spacers until captured by the nanopore.

Materials and Methods 2.1 Anneal of DNA Strands to Form Y-Shaped and Hairpin MuA Substrates The Y-shaped and hairpin MuA substrates were prepared as shown in Table 5 below. The sample mixtures which contained the DNA to form the Y-shaped and hairpin MuA substrates were then heated to 95° C. for 2 minutes and then cooled to 16° C. at a rate of 2° C. per minute. This allowed SEQ ID NOs: 14 and 15 (where SEQ ID NO: 14 is attached at its 3' end to the 5' end of SEQ ID NO: 15 by four iSpC3 spacer units) to anneal to SEQ ID NO: 19 and 9 (where SEQ ID NO: 19 is attached at its 3' end to the 5' end of SEQ ID NO: 9 by four iSpC3 spacer units) to form the Y-shaped MuA substrate and for SEQ ID NO: 19 and 20 (where SEQ ID NO: 19 is attached at its 3' end to the 5' end of SEQ ID NO: 15 by four iSpC3 spacer units) to form a hairpin loop MuA substrate. The DNA substrate designs of the two MuA substrates formed are shown in FIG. 4(*a*).

TABLE 5

| Reagent | Y-shaped | Hairpin | Final Concentrations |
|---|---|---|---|
| Water | 12 uL | 14 uL | |
| 0.5M NaCl | 2 uL | 2 uL | 50 mM |
| 0.1M Tris pH 7.5 | 2 uL | 2 uL | 10 mM |
| SEQ ID NO: 14 and 15 (where SEQ ID NO: 14 is attached at its 3' end to the 5' end of SEQ ID NO: 15 by four iSpC3 spacer units) (100 uM) | 2 uL | | 10 uM |
| SEQ ID NO: 19 and 9 (where SEQ ID NO: 19 is attached at its 3' end to the 5' end of SEQ ID NO: 9 by four iSpC3 spacer units) (100 uM) | 2 uL | | 10 uM |
| SEQ ID NO: 19 and 20 (where SEQ ID NO: 19 is attached at its 3' end to the 5' end of SEQ ID NO: 15 by four iSpC3 spacer units) (100 uM) | | 2 uL | 10 uM |
| Total | 20 uL | 20 uL | |

2.2 Fragmentation of the DNA Template Using the MuA Transposase

Double-stranded Lambda DNA (SEQ ID NO: 13 corresponds to the sequence of the sense strand) was fragmented into approximately 5-10 kB length strands using a MuA transposase. The MuA transposase inserted the MuA substrates (the Y-shaped and the hairpin MuA substrates) which were annealed in section 3.1. The sample was prepared as shown in Table 6 below. The sample was then incubated at 30° C. for 1 hour and heat inactivated at 75° C. for 10 minutes. The sample was then further purified using a QIAquick™ PCR Purification kit (Qiagen) and eluted in 26 μL.

TABLE 6

| Reagent | Sample Volume 1 | Final Concentrations |
|---|---|---|
| Water | 17.7 uL | |
| Lambda DNA (90 ng/uL) (SEQ ID NO: 13 shows the sense strand sequence only) | 22.3 uL | 2 μg |
| Y-shaped MuA substrate (1 uM) | 8 uL | 100 nM |
| Hairpin MuA substrate (1 uM) | 8 uL | 100 nM |
| 5x Buffer (125 mM Tris (pH 8.0), 50 mM $MgCl_2$, 550 mM NaCl, 0.25% Triton X-100 and 50% Glycerol) | 16 uL | 1x |
| MuA (4 uM, Thermo, catalogue No. F-750C) | 8 uL | 400 nM |
| Total | 80 uL | |

2.3 USER Digest of Fragmented Lambda DNA with Inserted MuA Substrates

Purified sample volume 1 from step 3.2 was then treated with USER™ digest in order to remove the dUMP from SEQ ID NOs: 19. See Table 7 below for appropriate volumes and concentrations. The sample was then incubated at 37° C. for 30 minutes before it was cooled in an ice block.

TABLE 7

| Reagent | Sample Volume 2 | Final Concentrations |
|---|---|---|
| Sample Volume 1 | 26 uL | 8 pmol of U |
| 10x DNA ligase buffer | 3 uL | 1x |
| USER (1 U/uL) | 1 uL | 1 U |
| Total | 30 uL | |

2.4 Repair of Single-Stranded Gap in the Double-Stranded Lambda DNA Construct Fragments Sample Volume 2 produced after treatment with USER™ was then treated with DNA polymerase and ligase in order to close the single-stranded gap. Sample volume 3 (see table 8 below for appropriate volumes and concentrations) was incubated for 30 minutes at 16° C. and then EDTA (0.5 M, 10 μL) was added to sample volume 3. A QIAquick™ PCR Purification kit was then used to purify each sample, which was eluted in 50 μL of water. An aliquot of the purified sample (1 μL) was run on an Agilent 12000 chip to quantify the sample and Tris-HCl and NaCl (pH 7.5) until were added to the rest of the sample until the concentrations were 10 mM and 50 mM respectively. Finally, SEQ ID NO: 16 (3' end of the sequence has six iSp18 spacers attached to two thymine residues and a 3' cholesterol TEG, 0.5 μM) was annealed to the purified sample.

TABLE 8

| Reagent | Sample Volume 3 | Final Concentrations |
|---|---|---|
| Water | 6.2 uL | |
| Sample Volume 2 | 30 uL | |

TABLE 8-continued

| Reagent | Sample Volume 3 | Final Concentrations |
|---|---|---|
| 10x DNA ligase buffer | 1 uL | 1x |
| dNTPs (10 mM) | 0.8 uL | 200 uM |
| T4 DNAP exo(□) (Lucigen) | 1 uL | |
| Ligase (NEB; M0202M) | 1 uL | 1x |
| Total | 40 uL | |

2.5 Electrophysiology Experiment Showing Helicase Controlled DNA Movement of the Purified and Fragmented Lambda DNA Construct Prior to setting up the experiment, the Lambda DNA construct (0.2 nM, 5-10 kB fragments of Lambda DNA which have had the Y-shaped MuA substrates and the hairpin MuA substrates attached to either end of the fragments by the MuA transposase (see FIG. 4(*b*) for an example construct)) and Trwc Cba (SEQ ID NO: 9, 1 μM) were pre-incubated together for 1 hour in buffer (50 mM CAPS, pH 10.0 (pH altered to pH 10.0 by addition of NaOH), 100 mM NaCl).

Electrical measurements were acquired from single MspA nanopores (MapA-B2C) inserted in block co-polymer in buffer (600 mM KCl, 25 mM KH2PO4, 75 mM Potassium Ferrocyanide (II), 25 mM Potassium ferricyanide (III), pH 8). After achieving a single pore in the bilayer, then buffer (1 mL, 600 mM KCl, 25 mM KH2PO4, 75 mM Potassium Ferrocyanide (II), 25 mM Potassium ferricyanide (III), pH 8) was flowed through the system to remove any excess MspA nanopores (MspA-B2C) and the experimental system was placed on a cooler plate set to 8° C. which gave a system temperature of ~15° C. $MgCl_2$ (10 mM) and dTTP (5 mM) were mixed together with buffer (600 mM KCl, 25 mM KH2PO4, 75 mM Potassium Ferrocyanide (II), 25 mM Potassium ferricyanide (III), pH 8) and then added to the Lambda DNA construct (0.2 nM), Trwc Cba (SEQ ID NO: 9, 1 μM) buffer (50 mM CAPS, pH 10.0 (pH altered to pH 10.0 by addition of NaOH), 100 mM NaCl) pre-mix. The pre-mix was then added to the single nanopore experimental system. Experiments were carried out for two hours following a potential flip process (+120 mV for 30 mins, then −100 mV for 2 seconds and then 0 mV for 2 seconds) and helicase-controlled DNA movement was monitored.

2.6 Results and Discussion

Helicase controlled DNA movement was observed for the Lambda DNA construct, an example of a helicase-controlled DNA movement is shown in FIG. 5. The iSpC3 spacers present in the Lambda DNA construct produced a characteristic block level highlighted by the numbers 1, 2 and 3 in FIG. 5. The Y-shaped MuA substrate has four iSpC3 spacers in either strand and the hairpin MuA substrate also has four iSpC3 spacers, each iSpC3 spacer allows more current to flow as that region of the Lambda DNA construct translocates through the nanopore. If the sample preparation has occurred successfully then the iSpC3 spacer events will be observed at the beginning of the Lambda DNA construct, in the middle (marking the transition between sense and antisense sequences) and at the end. FIG. 5 clearly shows three instances of increased current flow which correspond to the iSpC3 spacer regions. Therefore, the sample preparation procedure effectively introduced MuA substrates into the Lambda DNA to produce the Lambda DNA constructs shown in FIG. 4(*b*). Upon capture of the DNA by the nanopore, the enzyme (labelled A) is moved past the dsDNA region (where the tether hybridises to the construct) and the spacers by the force of the applied potential across the nanopore.

Example 3

The DNA construct used in this example was produced by fragmentation of Lambda DNA into ~5-10 kB fragments using MuA. This example is similar to the one described in Example 2, however, the sample preparation procedure is different (steps 2.3 and 2.4 as described above are not required) as the transposase sequences contain inosines in this example. The enzyme was moved past the dsDNA region and the spacers by the force of the applied potential across the nanopore.

Materials and Methods 3.1 Anneal of DNA Strands to Form Y-Shaped and Hairpin MuA Substrates The Y-shaped 2 and hairpin 2 MuA substrates were prepared as described in Example 2.1 above. Volumes, concentrations and sequences that were used in this example are detailed in table 9 below. The DNA substrate designs of the two constructs formed are shown in FIG. 6(*a*).

TABLE 9

| Reagent | Y-shaped 2 | Hairpin 2 | Final Concentrations |
|---|---|---|---|
| Water | 12 uL | 14 uL | |
| 0.5M NaCl | 2 uL | 2 uL | 50 mM |
| 0.1M Tris pH 7.5 | 2 uL | 2 uL | 10 mM |
| SEQ ID NO: 14 and 15 (where SEQ ID NO: 14 is attached at its 3' end to the 5' end of SEQ ID NO: 15 by four iSpC3 spacer units) (100 uM) | 2 uL | | 10 uM |
| SEQ ID NO: 18 and 9 (where SEQ ID NO: 18 is attached at its 3' end to the 5' end of SEQ ID NO: 9 by four iSpC3 spacer units) (100 uM) | 2 uL | | 10 uM |
| SEQ ID NO: 18 and 15 (where SEQ ID NO: 18 is attached at its 3' end to the 5' end of SEQ ID NO: 15 by four iSpC3 pacer units) (100 uM) | | 2 uL | 10 uM |
| Total | 20 uL | 20 uL | |

3.2 Fragmentation of the DNA Template Using the MuA Transposase

Double-stranded Lambda DNA (SEQ ID NO: 13 shows the sequence of the sense strand only) was fragmented into approximately 5-10 kB length strands using a MuA transposase. The MuA transposase inserted the MuA substrates (the Y-shaped 2 and the hairpin 2 MuA substrates) which were annealed in section 3.1. The sample was prepared by an analogous procedure as that described in Section 2.2 and table 6 above except the MuA substrates used were the Y-shaped 2 and the hairpin 2 MuA substrates. In this case the purified sample X was eluted in a volume of 20 μL.

3.3 Nick Repair in the Double-Stranded Lambda DNA Construct Fragments

Once the Y-shaped 2 and the hairpin 2 MuA substrates have been inserted into the fragmented Lambda DNA it is necessary to repair the nick in the strand and join the inosines to the Lambda DNA fragment to produce a complete double-stranded Lambda DNA fragment. One reaction was assembled on ice as described in Table 10 below. The sample was incubated at 16° C. for 60 mins before EDTA (10 μL, 0.5 M) was added to the sample. The resultant sample mixture was purified using a QiaQuick™ purify and was eluted in 50 μL of water. An aliquot of the purified sample (1 μL) was run on an Agilent 12000 chip to quantify the sample and Tris-HCl and NaCl (pH 7.5) were added to the rest of the sample until the concentrations were 10 mM and 50 mM respectively. Finally, SEQ ID NO: 16 (3' end of the sequence has six iSp18 spacers attached to two thymine residues and a 3' cholesterol TEG, 0.5 μM) was annealed to the purified Lambda DNA construct.

TABLE 10

| Reagent | Sample Z | Final Concentrations |
|---|---|---|
| Sample X | 16 uL | |
| 2x DNA ligase buffer | 20 uL | 1x |
| Ligase (NEB; M0202M) | 4 uL | |
| Total | 40 uL | |

3.4 Electrophysiology Experiment Showing Helicase Controlled DNA Movement of the Purified and Fragmented Lambda DNA Construct Prior to setting up the experiment, the Lambda DNA construct (0.2 nM, 5-10 kB fragments of Lambda DNA which have had the Y-shaped 2 and the hairpin 2 MuA substrates attached to either end of the fragments by the MuA transposase (see FIG. 6(*b*) for an example construct)) and Trwc Cba (SEQ ID NO: 17, 1 μM) were pro-incubated together for 1 hour in buffer (50 mM CAPS, pH 10.0 (pH altered to pH 10.0 by addition of NaOH), 100 mM NaCl).

Electrical measurements were acquired from single MspA nanopores (MspA-B2C) inserted in block co-polymer in buffer (600 mM KCl, 25 mM KH2PO4, 75 mM Potassium Ferrocyanide (II), 25 mM Potassium ferricyanide (III), pH 8). After achieving a single pore in the bilayer, then buffer (3 mL, 600 mM KCl, 25 mM KH2PO4, 75 mM Potassium Ferrocyanide (II), 25 mM Potassium ferricyanide (III), pH 8) was flowed through the system to remove any excess MspA nanopores (MspA-B2C) and the experimental system was placed on a cooler plate set to 8° C. which gave a system temperature of ~15° C. $MgCl_2$ (10 mM) and dTTP (5 mM) were mixed together with buffer (600 mM KCl, 25 mM KH2PO4, 75 mM Potassium Ferrocyanide (II), 25 mM Potassium ferricyanide (III), pH 8) and then added to the Lambda DNA construct (0.2 nM), Trwc Cba (SEQ ID NO: 17, 1 μM) buffer (50 mM CAPS, pH 10.0 (pH altered to pH 10.0 by addition of NaOH), 100 mM NaCl) pre-mix. The pre-mix was then added to the single nanopore experimental system. Experiments were carried out for two hours following a potential flip process (+120 mV for 30 mins, then −100 mV for 2 seconds and then 0 mV for 2 seconds) and helicase-controlled DNA movement was monitored.

3.5 Results and Discussion

Helicase controlled DNA movement was observed for the Lambda DNA construct, an example of a helicase-controlled DNA movement is shown in FIG. 7. The iSpC3 spacers present in the Lambda DNA construct produced a characteristic block level highlighted by numbers 1-3 in FIG. 7. The Y-shaped 2 MuA substrate has four iSpC3 spacers in either strand and the hairpin 2 MuA substrate also has four iSpC3 spacers, each iSpC3 spacer allows more current to flow as that region of the Lambda DNA construct translocates through the nanopore. If the sample preparation occurred successfully then the iSpC3 spacer events will be observed at the beginning of the Lambda DNA construct, in the middle (making the transition between the sense and antisense sequences) and at the end. FIG. 7 clearly shows three instances of increased current flow which correspond to the iSpC3 spacer regions. Therefore, the sample preparation procedure effectively introduced MuA substrates into the Lambda DNA to produce the Lambda DNA constructs shown in FIG. 6(*b*). Upon capture of the DNA by the nanopore, the enzyme (labelled A) is past the dsDNA region (where the tether hybridises to the construct) and the spacers by the force of the applied potential across the nanopore. Owing to the use of the inosines in the Y-shaped 2 and the hairpin 2 MuA substrates, the steps in the sample preparation procedure were reduced as once the MuA substrates had been inserted all that was necessary was to close the nicks in the double-stranded DNA constructs.

Example 4

This Example compares the ability of a TrwC Cba monomer (SEQ ID NO: 17), to control the movement of intact DNA strands (attached to the 5' end of SEQ ID NO: 23 is 28 iSpC3 spacers units the last of which has an additional two T's attached to the 5' end of the spacer group, attached to the 3' end of SEQ ID NO: 23 is a further four iSpC3 spacers which are attached to the 5' end of SEQ ID NO: 24, where SEQ ID NO: 12 is hybridised to a region of SEQ ID NO: 23) through a nanopore, to that of the TrwC Cba Q276C-3.4 kDa dimer (where each monomer unit comprises SEQ ID NO: 17 with the mutation Q276C, with one monomer unit being linked to the other via position 276 of each monomer unit using a 3.4 kDa PEG linker). The DNA construct used in this example is shown in FIG. 22 (the helicase is capable of binding to the region labelled B). When the DNA construct is captured by the nanopore, the applied potential across the nanopore moves the enzyme past the dsDNA region (where the tether hybridises to the construct) and spacers and helicase controlled DNA movement is observed.

Upon comparison of the helicase controlled movement of the monomer with the dimer, it was observed that the dimer resulted in a greater percentage of long dwell helicase-controlled DNA movement (a long dwell movement is a helicase-controlled DNA movement which is more than three standard deviations away from the mean of the major population of helicase-controlled DNA movements) than the monomer.

Materials and Methods

Prior to setting up the experiment, the DNA (1 nM, attached to the 5' end of SEQ ID NO: 23 is 28 iSpC3 spacers units the last of which has an additional two T's attached to the 5' end of the spacer group, attached to the 3' end of SEQ ID NO: 23 is a further four iSpC3 spacers which are attached to the 5' end of SEQ ID NO: 24, where SEQ ID NO: 12 is hybridised to a region of SEQ ID NO: 23) and the enzyme (either a TrwC Cba monomer (1 nM, SEQ ID NO: 17) or TrwC Cba Q276C-3.4 kDa dimer (0.3 nM, where each monomer unit comprises SEQ ID NO: 17 with the mutation Q276C, with one monomer unit being linked to the other via position 276 of each monomer unit using a 3.4 kDa PEG linker)) were pre-incubated together for >16 hours.

Electrical measurements were acquired from single MspA nanopores MS(G75S/G77S/L88N/Q126R)8 MspA (SEQ ID NO: 2 with the mutations G75S/G77S/L88N/Q126R) inserted in block copolymer in buffer (625 mM KCl, 100 mM Hepes, 75 mM Potassium Ferrocyanide (II), 25 mM Potassium ferricyanide (III), pH 8). $MgCl_2$ (10 mM) and dTTP (5 mM) were mixed together with buffer (625 mM KCl, 100 mM Hepes, 75 mM Potassium Ferrocyanide (II), 25 mM Potassium ferricyanide (III), pH 8) and then added to the DNA (construct described previously), enzyme pre-mix (either a TrwC Cba monomer (1 nM, SEQ ID NO: 17) or TrwC Cba Q276C-3.4 kDa dimer (I nM, where each monomer unit comprises SEQ ID NO: 17 with the mutation Q276C, with one monomer unit being linked to the other via position 276 of each monomer unit using a 3.4 kDa PEG linker)). After achieving a single pore in the bilayer, the pre-mix was added to the single nanopore experimental system. Experiments were carried out at a constant potential of +120 mV and helicase-controlled DNA movement was monitored.

Results and Discussion

Helicase controlled DNA movement was observed for the helicase TrwC Cba monomer (SEQ ID NO: 17) and TrwC Cba Q276C-3.4 kDa dimer (where each monomer unit comprises SEQ ID NO: 17 with the mutation Q276C, with one monomer unit being linked to the other via position 276 of each monomer unit using a 3.4 kDa PEG linker). Upon capture of the DNA construct by the nanopore the helicase was moved past the dsDNA region (where the tether hybridises to the construct) and the spacers and helicase controlled movement was observed.

Of the helicase-controlled DNA movements observed there is a major population which accounts for around 95% of movements detected, however, there is a small percentage of movements which are significantly longer in dwell time (more than three standard deviations away from the mean of the major population of helicase-controlled DNA movements). These longer movements allow improved data analysis. When the TrwC Cba Q276C-3.4 kDa dimer (1 nM) was used to control DNA movement then a much higher percentage (20% for the TrwC Cba Q276C-3.4 kDa dimer in comparison to and 5% for the TrwC Cba monomer) of these longer dwell time movements (more than three standard deviations away from the mean of the major population of helicase-controlled DNA movements) was observed. The use of the dimer helicase provides an advantage over the monomer as it allows improved data analysis in the nanopore sequencing system.

Example 5

This Example illustrates that Sp9 spacer units can be used to stall the movement of Hel308 Mbu (SEQ ID NO: 28) (when provided with both ATP and MgCl2) in a fluorescence based assay for testing enzyme activity.

Materials and Methods

Three different custom fluorescent substrates (A=(control strands containing no spacers) SEQ ID NOs: 25 and 26, B=(strand containing a single Sp9 spacer) SEQ ID NO: 27 attached at its 3' end by one Sp9 spacers to the 5' end of SEQ ID NO: 29 and hybridised to SEQ ID NO: 26, C=(strand containing four Sp9) SEQ ID NO: 27 attached at its 3' end by four Sp9 spacers to the 5' end of SEQ ID NO: 29 and hybridised to SEQ ID NO: 26) were used to assay the ability of Hel308 Mbu (SEQ ID NO: 28) to displace hybridised dsDNA. FAM labelled DNA (for fluorescent substrate A=SEQ ID NO: 25, B=SEQ ID NO: 27 attached by its 3' end to one sp9 spacer which is attached to the 3' end of SEQ ID NO: 29, C=SEQ ID NO: 27 attached by its 3' end to four sp9 spacers which are attached to the 3' end of SEQ ID NO: 29) is annealed to the partially complementary strand which has a black-hole quencher attached to its 3' end (SEQ ID NO: 26) in a one to one ratio (1 uM of each strand) in 400 mM KCl, 100 mM HEPES pH8, 10 mM $MgCl_2$, 1 mg/ml BSA.

The strands were annealed at room temperature for 30 minutes. The annealed DNA (A=SEQ ID NOs: 25 and 26, B=SEQ ID NO: 27 attached at its 3' end by one Sp9 spacers to the 5' end of SEQ ID NO: 29 and hybridised to SEQ ID NO: 26, C=SEQ ID NO: 27 attached at its 3' end by four Sp9 spacers to the 5' end of SEQ ID NO: 29 and hybridised to SEQ ID NO: 26) was diluted to 50 nM in 400 mM KCl, 100 mM HEPES pH8, 10 mM $MgCl_2$, 1 mg/ml BSA, 1 mM ATP (1 uM capture DNA (SEQ ID NO: 27 also present). A sample of Hel308 Mbu (SEQ ID NO: 28) was diluted to 475 nM in 400 mM KCl, 100 mM HEPES pH8, 10 mM MgCl2, 1 mg/ml BSA. Hel308 Mbu (12 nM) was then assayed (as described below and shown in FIGS. 8 and 9) against 48.75 nM annealed DNA in 400 mM KCl, 100 mM HEPES pH8, 10 mM $MgCl_2$, 1 mg/ml BSA, 0.975 mM ATP (0.975 uM capture DNA also present).

The control strand A is shown in FIG. 8, where in 1A) the fluorescent substrate strand (48.75 nM final) has a 3' ssDNA overhang, and a 40 base section of hybridised dsDNA. The upper strand, containing the 3' ssDNA overhang, has a carboxyfluorescein base attached to the 5' end of SEQ ID NO: 25, and the hybrised complement has a black-hole quencher (BHQ-1) base attached to the 3' end of SEQ ID NO: 26. When hybridised the fluorescence from the fluorescein is quenched by the local BHQ-1, and the substrate is essentially non-fluorescent. 1 μM of a capture strand (SEQ ID NO: 27) that is part-complementary to the lower strand of the fluorescent substrate is included in the assay. As shown in 2A), in the presence of ATP (0.975 mM) and $MgCl_2$ (10 mM), helicase (12 nM) added to the substrate binds to the 3' tail of the fluorescent substrate, moves along the upper strand, and displaces the complementary strand. As shown in 3A), once the complementary strand with BHQ-1 is fully displaced the fluorescein on the major strand fluoresces. As shown in 4A), the displaced strand preferentially anneals to an excess of capture strand to prevent re-annealing of initial substrate and loss of fluorescence. FIG. 9 shows the steps of the assay for strands B (1B-3B) and C (1C-3C), for these strands the Sp9 spacers stall the helicase and prevent it from separating the strand with the fluorescein attached from the strand with the black hole quencher attached.

Results and Discussion

The graph in FIG. 10 shows the initial rate of activity in buffer solution (100 mM Hepes pH8.0, 0.975 mM ATP, 10 mM $MgCl_2$, 1 mg/ml BSA, 48.75 nM fluorescent substrate DNA (substrates A, B and C as discussed above), 0.975 μM capture DNA (SEQ ID NO: 27)) for the Hel308 Mbu (labeled A in FIGS. 8 and 9; SEQ ID NO: 28) at 400 mM of KCl. At the salt concentration investigated the Hel308 Mbu (SEQ ID NO: 28) exhibited dsDNA turnover of the control strand A. However, FIG. 10 clearly indicates that for both constructs which have Sp9 spacers in the sequence (B (one Sp9 spacer) and C (four Sp9 spacers)) the dsDNA turnover was abolished. This indicates that in the presence of ATP and MgCl2 the Sp9 spacers stall the Hel308 Mbu enzyme in free solution.

Example 6

This Example illustrates that idSp groups can be used to stall the movement of Hel308 Mbu (SEQ ID NO: 28) (when provided with both ATP and MgCl2) in a fluorescence based assay for testing enzyme activity.

Materials and Methods

Four different custom fluorescent substrates (D=(control strand containing no spacers) SEQ ID NOs: 32 and 26, E=(strand containing a single idSp spacer) SEQ ID NO: 27 attached at its 3' end by one idSp group to the 5' end of SEQ ID NO: 30 and hybridised to SEQ ID NO: 26, F=(strand containing four idSp) SEQ ID NO: 27 attached at its 3' end by four idSp groups to the 5' end of SEQ ID NO: 31 and hybridised to SEQ ID NO: 26 and G=(second control strand containing no spacers) SEQ ID NOs: 33 and 26) were used to assay the ability of Hel308 Mbu (SEQ ID NO: 28) to displace hybridised dsDNA. FAM labelled DNA (for fluorescent substrate D=SEQ ID NO: 32, E=SEQ ID NO: 27 attached by its 3' end to one idSp group which is attached to the 3' end of SEQ ID NO: 30, F=SEQ ID NO: 27 attached by its 3' end to four idSp groups which are attached to the 3' end of SEQ ID NO: 31 and G=SEQ ID NO: 33) is annealed to the partially complementary strand which has a black-hole quencher attached to its 3' end (SEQ ID NO: 26) in a 1 to 1.2 ratio (1:1.2 μM) in 400 mM KCl, 100 mM HEPES pH8, 10 mM $MgCl_2$, 1 mg/ml BSA. The strands were annealed at room temperature for 15 minutes. The annealed DNA (D=SEQ ID NOs: 32 and 26, E=SEQ ID NO: 27 attached at its 3' end by one idSp group to the 5' end of SEQ ID NO: 30 and hybridised to SEQ ID NO: 26, F=SEQ ID NO: 27 attached at its 3' end by four idSp groups to the 5' end of SEQ ID NO: 31 and hybridised to SEQ ID NO: 26 and G=SEQ ID NOs: 33 and 26) was diluted to 50 nM in 400 mM KCl, 100 mM HEPES pH8, 10 mM $MgCl_2$, 1 mg/ml BSA, 1 mM ATP (1 uM capture DNA (SEQ ID NO: 27 also present). Hel308 Mbu (12 nM) was then assayed (as described previously in Example 5 (except the DNA constructs are different and contain idSp groups instead of Sp9 spacers) and shown in FIGS. 8 and 9 (again where the Sp9 groups in these figures are replaced with idSp groups)) against 48.75 nM annealed DNA in 400 mM KCl, 100 mM HEPES pH8, 10 mM $MgCl_2$, 1 mg/ml BSA, 0.975 mM ATP (0.975 uM capture DNA also present).

Results and Discussion

The graph in FIG. 11 shows the initial rate of activity in buffer solution (100 mM Hepes pH 8.0, 0.975 mM ATP, 10 mM $MgCl_2$, 1 mg/ml BSA, 48.75 nM fluorescent substrate DNA (substrates D, E, F and G as discussed above), 0.975 μM capture DNA (SEQ ID NO: 27)) for the Hel308 Mbu (labelled A in FIGS. 8 and 9; SEQ ID NO: 28) at 400 mM of KCl. At the salt concentration investigated the Hel308 Mbu (SEQ ID NO: 28) exhibited dsDNA turnover of the control strands D and G. However, FIG. 11 clearly indicates that for the construct which has four idSp spacers in the sequence (F) the dsDNA turnover was abolished. This indicates that in the presence of ATP and MgCl2 the four idSp groups stall the Hel308 Mbu enzyme in free solution.

Example 7

This Example illustrates a gel based assay that was used to measure the ability of iSpC3 spacers and iSp18 spacers to stall the movement of T4 Dda-E94C/A360C.

Materials and Methods

The annealed DNA complexes (sequences tested are shown in table 11 below) were mixed in a ratio of (1:1, v/v) with T4 Dda-E94C/A360C in 25 mM phosphate pH 8.0, 200 mM KCl giving final concentrations of T4 Dda-E94C/A360C (2000 nM) and DNA (100 nM). The helicase was allowed to bind to the DNA for 2 hours at ambient temperature. Capture strand (SEQ ID NO: 37, 20 μM) was added to each sample to bind any unbound enzyme and the samples incubated at ambient temperature for 30 mins. Buffer was added to the samples (DNA construct from table 11=50 nM, capture DNA (SEQ ID NO: 37)=10 μM and T4

Dda-E94C/A360C=1000 nM) and they were incubated at ambient temperature for one hour (either Buffer 1=25 mM phosphate pII 8.0, 200 mM KCl, 20 mM MgCl2, 10 mM ATP or Buffer 2=25 mM phosphate pH 8.0, 1 M KCl, 25 mM potassium ferricyanide(III), 75 mM potassium ferrocyanide, 20 mM MgCl2, 10 mM ATP). Loading buffer (25 mM Phosphate pH8.0, 151.5 mM KCl, 25% Glycerol, 125 mM EDTA) is added to each sample to quench the helicase activity. The samples were loaded onto 4-20% TBE gel and the gel run at 160 V for 1.5 hours. The Gel was then stained with SYBR gold in order to observe the DNA bands.

TABLE 11

| DNA construct Number | DNA sequences which make up the construct |
|---|---|
| 1 (positive control, no spacers) | SEQ ID NO: 34 hybridised to SEQ ID NO: 35 |
| 2 (4 × iSpC3 spacers) | SEQ ID NO: 9 attached at its 3' end to four iSpC3 spacers which are attached to the 5' end of SEQ ID NO: 36 hybridised to SEQ ID NO: 35 |
| 3 (8 × iSpC3 spacers) | SEQ ID NO: 9 attached at its 3' end to eight iSpC3 spacers which are attached to the 5' end of SEQ ID NO: 36 hybridised to SEQ ID NO: 35 |
| 4 (12 × iSpC3 spacers) | SEQ ID NO: 9 attached at its 3' end to twelve iSpC3 spacers which are attached to the 5' end of SEQ ID NO: 36 hybridised to SEQ ID NO: 35 |
| 5 (1 × iSp18 spacer) | SEQ ID NO: 9 attached at its 3' end to one iSp18 spacer which are attached to the 5' end of SEQ ID NO: 36 hybridised to SEQ ID NO: 35 |
| 6 (2 × iSp18 Spacer) | SEQ ID NO: 9 attached at its 3' end to two iSp18 spacers which are attached to the 5' end of SEQ ID NO: 36 hybridised to SEQ ID NO: 35 |
| 7 (3 × iSp18 spacer) | SEQ ID NO: 9 attached at its 3' end to three iSp18 spacers which are attached to the 5' end of SEQ ID NO: 36 hybridised to SEQ ID NO: 35 |
| 8 (4 × iSp18 spacer) | SEQ ID NO: 9 attached at its 3' end to four iSp18 spacers which are attached to the 5' end of SEQ ID NO: 36 hybridised to SEQ ID NO: 35 |
| 9 (5 × iSp18 spacer) | SEQ ID NO: 9 attached at its 3' end to five iSp18 spacers which are attached to the 5' end of SEQ ID NO: 36 hybridised to SEQ ID NO: 35 |

Results and Discussion

FIG. 12 show the gel of the positive control experiment where the DNA construct contains no spacers to stall the helicase (T4 Dda-E94C/A360C). Lane 2 of FIG. 14 shows that the up to 5 helicase enzymes can bind onto the single-stranded section of SEQ ID NO: 34. Upon the addition of ATP and MgCl2, the higher bands corresponding to the dsDNA construct bound to multiple enzymes disappears and band corresponding to the ssDNA construct (labelled X and corresponding to SEQ ID NO: 34 only) increases in intensity. This indicates that when the helicase is provided with fuel it moves along the DNA and displaces the hybridised complementary strand (SEQ ID NO: 35).

FIG. 15 shows an example of a gel showing the enzyme activity experiment for DNA constructs 7-9 of table 11 (e.g. DNA which has three, four or five iSp18 spacers just before the ssDNA/dsDNA junction). Lanes 1-4 correspond to three iSp18 spacers, lanes 5-7 correspond to four iSp18 spacers and lanes 9-12 correspond to five iSp18 spacers. Lanes 2, 6 and 10 show that, similarly to the control, up to five helicase enzymes can bind onto the single-stranded section of the DNA constructs 7-9 in table 11. Upon the addition of ATP and MgCl2 the helicases will be provided with the necessary components in order to move along the DNA strand. Lanes 3-4, 7-8 and 11-12 show the various DNA constructs under two different buffer conditions (buffer 1 and 2) after the addition of ATP and MgCl2. Two bands are clearly visible at the region labelled 1Y and 1X. 1Y corresponds to the dsDNA construct with one helicase stalled and bound. This shows that three, four and five iSP18 spacers are able to stall the helicase under the conditions tested. 1X corresponds to the ssDNA construct with one helicase stalled and bound. This band has resulted from multiple helicases binding to the DNA construct and the helicases pushing the front helicase past the stalling groups, thus displacing the short complementary strand (SEQ ID NO: 35). However, this band still has one helicase bound as a single helicase cannot move past the iSp18 spacers (e.g. species E in FIG. 13 results). In the case of 4 and 5 iSp18 spacers being used to stall the helicase there are faint bands at level 2Y. This shows that under the conditions tested, when 4/5 iSp18 spacers are used it is possible to stall the movement of up to two helicases.

Of the other spacer combinations investigated (entries 2-6 of table 11) in at least one of the buffer conditions tested both iSpC3 and iSp18 spacers were capable of stalling one helicase. Of the two buffer conditions tested, generally more efficient stalling was observed for buffer 2 than buffer 1. The greater the number of spacers included the more efficient the stalling of the helicases under the conditions tested.

Example 8

This Example investigates the number of bases needed to control the binding of only one or two T4 Dda-E94C/A360C helicases in a particular region.

Materials and Methods

DNA constructs (1 μM or 100 nM final concentration) detailed below in Table 12 were incubated in appropriate buffer with serially diluted T4 Dda-E94C/A360C. The samples were then loaded on 4-20% TBE gels and run at 160 V for 90 minutes. The gels containing entries 1-6 were then stained using SYBR. FIG. 16 shows the type of DNA construct used in this experiment. The length of the region labelled 1 is varied from 2 to 50 to optimise conditions so that it is possible to control the number of T4 Dda-E94C/A360C helicases which can bind to the DNA.

TABLE 12

| Entry | DNA Construct | Buffer | Incubation Conditions | Concentrations of T4 Dda - E94C/A360C |
|---|---|---|---|---|
| 1 | 1 µM, Five iSpC3 spacers attached to the 5' end of SEQ ID NO: 37, which is attached at its 3' end to four iSpC3 spacers which are attached to the 5' end of SEQ ID NO: 36 which is hybridised to SEQ ID NO: 35. | 25 mM phosphate, 151.5 mM KCl pH 8.0 | overnight at room temperature | 5000 nM, 2500 nM, 1250 nM, 625 nM, 312.5 nM, 0M |
| 2 | 1 µM, Five iSpC3 spacers attached to the 5' end of SEQ ID NO: 38, which is attached at its 3' end to four iSpC3 spacers which are attached to the 5' end of SEQ ID NO: 36 which is hybridised to SEQ ID NO: 35. | 25 mM phosphate, 151.5 mM KCl pH 8.0 | overnight at room temperature | 5000 nM, 2500 nM, 1250 nM, 625 nM, 312.5 nM, 0M |
| 3 | 1 µM, Five iSpC3 spacers attached to the 5' end of SEQ ID NO: 9, which is attached at its 3' end to four iSpC3 spacers which are attached to the 5' end of SEQ ID NO: 36 which is hybridised to SEQ ID NO: 35. | 25 mM phosphate, 151.5 mM KCl pH8.0 | overnight at room temperature | 5000 nM, 2500 nM, 1250 nM, 625 nM, 312.5 nM, 0M |
| 4 | 1 µM, Five iSpC3 spacers attached to the 5' end of two thymines, which are attached at the 3' end to four iSpC3 spacers which are attached to the 5' end of SEQ ID NO: 36 which is hybridised to SEQ ID NO: 35. | 25 mM phosphate, 151.5 mM KCl pH 8.0 | 1.5 hours at room temperature | 3750 nM, 1875 nM, 938 nM, 469 nM, 235 nM, 0M |
| 5 | 1 µM, Five iSpC3 spacers attached to the 5' end of four thymines, which are attached at the 3' end to four iSpC3 spacers which are attached to the 5' end of SEQ ID NO: 36 which is hybridised to SEQ ID NO: 35. | 25 mM phosphate, 151.5 mM KCl pH 8.0 | 1.5 hours at room temperature | 3750 nM, 1875 nM, 938 nM, 469 nM, 235 nM, 0M |
| 6 | 1 µM, Five iSpC3 spacers attached to the 5' end of eight thymines, which are attached at the 3' end to four iSpC3 spacers which are attached to the 5' end of SEQ ID NO: 36 which is hybridised to SEQ ID NO: 35. | 25 mM phosphate, 151.5 mM KCl pH 8.0 | 1.5 hours at room temperature | 3750 nM, 1875 nM, 938 nM, 469 nM, 235 nM, 0M |
| 7 | 100 nM, Five iSpC3 spacers attached to the 5' end of SEQ ID NO: 39, which is attached at its 3' end to four iSp18 spacers which are attached to the 5' end of SEQ ID NO: 36 which is hybridised to SEQ ID NO: 35. | 25 mM phosphate, 151.5 mM KCl pH8.0 | Overnight at room temperature | 2700 nM, 1350 nM, 675 nM, 337.5 nM, 169 nM, 0M |
| 8 | 100 nM, Five iSpC3 spacers attached to the 5' end of SEQ ID NO: 40, which is attached at its 3' end to four iSp18 spacers which are attached to the 5' end of SEQ ID NO: 36 which is hybridised to SEQ ID NO: 35. | 25 mM phosphate, 151.5 mM KCl pH 8.0 | Overnight at room temperature | 2700 nM, 1350 nM, 675 nM, 338 nM, 169 nM, 0M |

Results and Discussion

Each of the DNA constructs listed in Table 12 were investigated to determine how many enzymes can bind to region 1 (shown in FIG. 16) which has been varied from 2 bases to 50 bases. For each of the DNA constructs tested only a single band for unbound DNA was observed when no helicase was added. Under the conditions investigated, construct 4 (which has a binding region of 2 thymine bases) and construct 5 (which has a binding region of 4 thymine bases) were not observed to allow any helicases to bind at any concentration (see table 14). Construct 6 (which has a binding region of 8 thymine bases see table 14) and construct 1 (which had a binding region of 10 thymine bases) was observed to bind one helicase only (see table 13). Construct 2 which has a binding region of 20 thymine bases allowed two enzymes to bind at the higher concentrations tested and construct 3 which has a binding region of 50 thymine bases allowed up to 6 enzymes to bind at the highest concentrations tested (see FIG. 17 for the gel showing this experiment see table 13). Constructs 1-6 used iSpC3 spacers to prevent binding of the helicase at the junction of the ssDNA/dsDNA region. Constructs 7 and 8 used iSp18 spacers to prevent binding of the helicase at the junction of the ssDNA/dsDNA region. Construct 7 (which has a binding region of 16 thymines) and construct 8 (which has a binding region of 18 thymines) both allowed up to two helicases to bind under the conditions tested (see table 15). Therefore, binding regions greater than 8 thymine bases long allow at least one enzyme to bind to the DNA constructs.

TABLE 13

| DNA Construct | Concentration of T4 Dda - E94C/A360C | | | | |
|---|---|---|---|---|---|
| Entry No | 5000 | 2500 | 1250 | 625 | 312.5 |
| 1 | One enzyme bound only | One enzyme bound only | One enzyme bound only | One enzyme bound only. Faint band for unbound DNA. | One enzyme bound only. Unbound DNA |
| 2 | Two enzymes bound. | Two enzymes bound. | Two enzymes bound. | Two enzymes bound. One enzyme bound. | One enzyme bound only. Unbound DNA |
| 3 (shown in FIG. 17) | Six enzymes bound (lane 1 FIG. 17). | Five enzymes bound (lane 2 FIG. 17). | Faint band for two enzymes bound. Three enzymes bound. Four enzymes bound, Five enzymes bound (lane 3 FIG. 17). | One enzyme bound. Two enzymes bound. Three enzymes bound. Faint band for four enzymes bound (lane 4 FIG. 17). | One enzyme bound. Two enzymes bound. Faint band for three enzymes bound (lane 5 FIG. 17). |

TABLE 14

| DNA Construct | Concentration of T4 Dda - E94C/A360C | | | | |
|---|---|---|---|---|---|
| Entry No | 3750 | 1875 | 938 | 469 | 235 |
| 4 | Unbound DNA only. | Unbound DNA only. | Unbound DNA only. | Unbound DNA only. | Unbound DNA only. |
| 5 | Unbound DNA only. | Unbound DNA only. | Unbound DNA only. | Unbound DNA only. | Unbound DNA only. |
| 6 | One enzyme bound. Faint band for unbound DNA | One enzyme bound. Unbound DNA | Faint band for one enzyme bound. Unbound DNA | Faint band for one enzyme bound. Unbound DNA | Unbound DNA only. |

TABLE 15

| DNA Construct | Concentration of T4 Dda - E94C/A360C | | | | |
|---|---|---|---|---|---|
| Entry No | 2700 | 1350 | 675 | 338 | 169 |
| 7 | Two enzymes bound. | Two enzymes bound. One enzyme bound. Faint band for unbound DNA | Faint band for two enzymes bound. One enzyme bound. Faint band for unbound DNA | One enzyme bound. Unbound DNA. | Faint band for one enzyme bound. Unbound DNA |
| 8 | Two enzymes bound. | Two enzymes bound. Faint band for one enzyme bound. | Faint band for two enzymes bound. One enzyme bound. Unbound DNA | Faint band for one enzyme bound. Unbound DNA | Unbound DNA only. |

Example 9

This Example investigates the concentration of T4 Dda-E94C/A360C helicase which when added to the DNA construct X (described and shown in FIG. 18) results in the binding of two helicases.

Materials and Methods

Two DNA constructs were tested one which has a complementary strand of DNA which is not forked (SEQ ID NO: 42 is hybridised to the DNA construct shown in FIG. 18) and one which is forked (SEQ ID NO: 12 (which has 6 iSp18 spacers attached to the 3' end) is hybridised to the DNA construct shown in FIG. 18). The DNA strands shown in Table 16 were annealed at 1 μM in 25 mM phosphate pH 8.0, 1515.5 mM KCl (a 10% excess of complementary strands SEQ ID NO: 43 (in entries 9 and 10 below) and SEQ ID NO: 12 (entry 10 below) or SEQ ID NO: 42 (entry 9 below) was used).

TABLE 16

| DNA Construct Entry No: | DNA Strands Annealed |
|---|---|
| 9 | 25 SpC3 spacers are attached to the 5' end of SEQ ID NO: 37 which is attached at its 3' end to two iSp18 spacers. The iSp18 spacers are attached to another DNA fragment of SEQ ID NO: 37 which again is attached at its 3' end to the another two iSp18 spacers. The second instance of iSp18 spacers is attached to the 5' end of SEQ ID NO: 10 which is attached its 3' end to four nitroindoles. The four nitroindoles are then attached to the 5' end of SEQ ID NO: 41. SEQ ID NO: 41 is hybridised to the complementary strand SEQ ID NO: 43. SEQ ID NO: 10 is hybridised to the non-forked complementary strand SEQ ID NO: 42. |
| 10 | 25 SpC3 spacers are attached to the 5' end of SEQ ID NO: 37 which is attached at its 3' end to two iSp18 spacers. The iSp18 spacers are attached to another DNA fragment of SEQ ID NO: 37 which again is attached at its 3' end to the another two iSp18 spacers. The second instance of iSp18 spacers is attached to the 5' end of SEQ ID NO: 10 which is attached its 3' end to four nitroindoles. The four nitroindoles are then attached to the 5' end of SEQ ID NO: 41. SEQ ID NO: 41 is hybridised to the complementary strand SEQ ID NO: 43. SEQ ID NO: 10 is hybridised to the forked complementary strand SEQ ID NO: 12 which has 6 iSp18 spacers attached at its 3' end. |

T4 Dda-E94C/A360C was buffer exchanged into 25 mM phosphate pH 8.0, 151.5 mM KCl and serially diluted. The helicase and DNA were then mixed (1:1, v/v) with the DNA construct samples 9 and 10 described above (final concentration DNA=100 nM, helicase concentrations investigated=3800 nM, 1900 nM, 950 nM, 475 nM, 238 nM, 0 nM). The DNA and enzyme volumes were then incubated at ambient temperature for 1.5 hours. Dye free loading buffer (5×, 7.5 μL) was added to each sample (30 μL). Each sample (37.5 μL) was then loaded onto 4-20% TBE gel and run at 160 V for 90 minutes. The gel was then stained using SYBR.

Results and Discussion

The two DNA constructs listed in Table 16 were investigated to determine what concentration of T4 Dda-E94C/A360C helicase is required in order to promote binding of two helicases. For each of the DNA constructs tested only a single band for unbound DNA was observed when no helicase was added. Under the conditions investigated, both constructs 9 (non-forked construct) and 10 (forked) observed binding of one helicase from 238 nM helicase and two enzymes from 475 nM and higher. As the concentration of enzyme was increased the band corresponding to two enzymes bound increased in intensity. The design of the DNA construct shown in FIG. 18 allows the binding of only two enzymes at concentrations as high as 3800 nM. Therefore, the spacers investigated do not allow the helicase to bind to them when the constructs are pre-incubated.

Example 10

This Example shows how the T4 Dda-E94C/A360C is stalled by four iSp18 spacers in free solution until the construct (DNA construct X1) is captured by the nanopore. Upon capture the force of the applied potential moves the enzyme T4 Dda-E94C/A360C past the stalling spacer and allows enzyme controlled DNA movement of the lambda construct through the nanopore.

Materials and Methods

Prior to setting up the experiment, the DNA construct X1 (0.13 μL, 100 nM) and T4 Dda-E94C/A360C (15.6 μL, 250 nM) were pre-incubated together for 1 hour at room temperature in buffer (50 mM potassium phosphate, 253 mM KCl, pH 8.0).

Electrical measurements were acquired at 30° C. (by placing the experimental system on a cooler plate) from single MspA nanopores (MspA-B2C) inserted in block co-polymer in buffer (600 mM KCl, 25 mM potassium phosphate, 75 mM Potassium Ferrocyanide (11), 25 mM Potassium ferricyanide (III), pH 8). After achieving a single pore inserted in the block co-polymer, then buffer (1 mL, 600 mM KCl, 25 mM potassium phosphate, 75 mM Potassium Ferrocyanide (II), 25 mM Potassium ferricyanide (III), pH 8) was flowed through the system to remove any excess MspA nanopores (MspA-B2C). Potassium ferricyanide (III) (200 μM final concentration) was added to the DNA (0.1 nM final concentration) enzyme (3 nM final concentration) pre-mix and left to incubate for one minute before $MgCl_2$ (10 mM final concentration) and ATP (1 mM final concentration) were mixed together with buffer (1260 μL, 600 mM KCl, 25 mM potassium phosphate, 75 mM Potassium Ferrocyanide (II), 25 mM Potassium ferricyanide (III), pH 8). This experimental mix was then added to the single nanopore experimental system. Experiments were carried out for six hours following a potential flip process (+180 mV for 2 s, then 0 V for 2 s, then −120 mV for 3600 s (×6 repeats) applied at the cis side) and helicase-controlled DNA movement was monitored.

Results and Discussion

The DNA construct is shown in FIG. 20. The T4 Dda-E94C/A360C is able to bind on to the region of the construct labelled A (SEQ ID NO: 9) when pre-incubated with the DNA construct. However, the enzyme is not able to motor past the stalling groups (four iSp18 spacers) when in free solution (labelled as black boxes). Therefore, the enzyme is stalled at the iSp18 spacers (labelled B in FIG. 1) until the DNA construct is captured by the nanopore. Once captured by the nanopore, the force of the applied potential moves the enzyme T4 Dda-E94C/A360C past the stalling spacer (four iSp18 spacers) and allows enzyme controlled DNA movement of the DNA construct X1 construct through the nanopore. An example of a helicase-controlled DNA movement is shown in FIG. 21. The section labelled 1 showed when the pT region of SEQ ID NO 38 translocated through the nanopore under control of the helicase. The section labelled 2 showed when the iSp18 spacer translocated through the nanopore under the control of the helicase. The helicase was observed to have a defined start point (resulting from the stalling of the helicase by the iSp18 spacers) as the helicase events observed showed the pT region and the iSp18 signal at the beginning of the helicase controlled DNA movements.

The invention claimed is:

1. A single molecule sequencing method for characterising a template deoxyribonucleic acid (DNA) strand comprising:

(a) incubating the template DNA strand and a nucleotide handling protein bound thereto, with all components necessary to facilitate movement of the nucleotide handling protein along the template DNA strand, for a period of time wherein the movement of the nucleotide handling protein along the template DNA strand is not detected, wherein all components necessary to facilitate movement comprise dTTP; and (b) initiating detection of the movement of the nucleotide handling protein along the template DNA strand; and (c) determining one or more characteristics of a portion of the template DNA strand based on the detection of the movement of the nucleotide handling protein along the template DNA strand.

2. The method according to claim 1, further comprising the step of fragmenting the template DNA strand prior to incubating step (a).

3. The method according to claim 1, wherein the template DNA strand is provided as a fragmented strand.

4. The method according to claim 1, wherein the template DNA strand is a fragment of 5 to 10 kb.

5. The method according to claim 1, further comprising the step of ligating a single stranded DNA adaptor to the template DNA strand prior to incubating step (a).

6. The method according to claim 1, further comprising the step of ligating a hairpin adaptor to the template DNA strand prior to incubating step (a).

7. The method according to claim 1, further comprising the step of ligating a single stranded DNA adaptor to the template DNA strand and then further loading the nucleotide handling protein at a loading site of the adaptor, prior to incubating step (a).

8. The method according to claim 1, further comprising the step of ligating a hairpin adaptor to the template DNA strand and then further loading the nucleotide handling protein at a loading site of the hairpin adaptor, prior to incubating step (a).

9. The method according to claim 1, further comprising the step of ligating a single stranded DNA adaptor to the template DNA strand, wherein the nucleotide handling protein is already bound to the adaptor at a loading site of the adaptor, prior to incubating step (a).

10. The method according to claim 1, further comprising the step of ligating a hairpin adaptor to the template DNA strand, wherein the nucleotide handling protein is already bound to the hairpin adaptor at a loading site of the adaptor, prior to incubating step (a).

11. The method according to claim 1, further comprising the step of fragmenting the template DNA and ligating a single stranded DNA adaptor to the template DNA strand prior to incubating step (a).

12. The method according to claim 1, further comprising the step of fragmenting the template polynucleotide, ligating a single stranded DNA adaptor to the template DNA strand and then loading the nucleotide handling protein at a loading site of the adaptor prior to incubating step (a).

13. The method according to claim 1, further comprising the step of fragmenting the template DNA and ligating a single stranded DNA adaptor to the template DNA strand prior to incubating step (a), wherein the nucleotide handling protein is already bound to the loading site of the adaptor.

14. The method according to claim 1, further comprising the step of fragmenting the template DNA and ligating a hairpin adaptor to the template DNA strand and then loading the nucleotide handling protein at a loading site of the hairpin adaptor prior to incubating step (a).

15. The method according to claim 1, further comprising the step of fragmenting the template DNA and ligating a hairpin adaptor to the template DNA strand prior to incubating step (a), wherein the nucleotide handling protein is already bound to the loading site of the hairpin adaptor.

16. The method according to claim 1, wherein the template DNA is ligated to a single stranded DNA adaptor comprising a pre-bound nucleotide handling protein.

17. The method according to claim 1, wherein the template DNA is ligated to a hairpin adaptor comprising a pre-bound nucleotide handling protein.

18. The method according to claim 1, wherein the template DNA is coupled to a surface.

19. The method according to claim 1, wherein the components necessary to facilitate movement of the nucleotide handling protein along the template DNA strand comprise $Mg^{2+}$ and dTTP.

20. The method according to claim 1, wherein detection of the movement of the nucleotide handling protein along the template DNA strand comprises detection of electrical and/or optical signals.

21. The method according to claim 1, wherein the one or more characteristics are selected from the group consisting of: (i) the length of the template DNA strand, (ii) the identity of the template DNA strand, (iii) the sequence of the template DNA strand, (iv) the secondary structure of the template DNA strand and (v) whether or not the template DNA strand is modified.

* * * * *

SEQUENCE LISTING

<160> NUMBER OF SEQ ID NOS: 43

<210> SEQ ID NO 1
<211> LENGTH: 558
<212> TYPE: DNA
<213> ORGANISM: Artificial Sequence
<220> FEATURE:
<223> OTHER INFORMATION: Polynucleotide sequence encoding the MS-B1 mutant MspA monomer

<400> SEQUENCE: 1
atgggtctgg ataatgaact gagcctggtg gacggtcaag atcgtaccct gacggtgcaa 60
caatgggata cctttctgaa tggcgttttt ccgctggatc gtaatcgcct gacccgtgaa 120
tggtttcatt ccggtcgcgc aaaatatatc gtcgcaggcc cgggtgctga cgaattcgaa 180
ggcacgctgg aactgggtta tcagattggc tttccgtggt cactgggcgt tggtatcaac 240
ttctcgtaca ccacgccgaa tattctgatc aacaatggta acattaccgc accgccgttt 300
ggcctgaaca gcgtgattac gccgaacctg tttccgggtg ttagcatctc tgcccgtctg 360
ggcaatggtc cgggcattca agaagtggca acctttagtg tgcgcgtttc cggcgctaaa 420
ggcggtgtcg cggtgtctaa cgcccacggt accgttacgg gcgcggccgg cggtgtcctg 480
ctgcgtccgt tcgcgcgcct gattgcctct accggcgaca gcgttacgac ctatggcgaa 540
ccgtggaata tgaactaa 558

<210> SEQ ID NO 2
<211> LENGTH: 184
<212> TYPE: PRT
<213> ORGANISM: Artificial Sequence
<220> FEATURE:
<223> OTHER INFORMATION: Amino acid sequence of the mature form of the MS-B1 mutant of the MspA monomer

<400> SEQUENCE: 2

Gly Leu Asp Asn Glu Leu Ser Leu Val Asp Gly Gln Asp Arg Thr Leu
1 5 10 15

Thr Val Gln Gln Trp Asp Thr Phe Leu Asn Gly Val Phe Pro Leu Asp
20 25 30

Arg Asn Arg Leu Thr Arg Glu Trp Phe His Ser Gly Arg Ala Lys Tyr
35 40 45

Ile Val Ala Gly Pro Gly Ala Asp Glu Phe Glu Gly Thr Leu Glu Leu
50 55 60

Gly Tyr Gln Ile Gly Phe Pro Trp Ser Leu Gly Val Gly Ile Asn Phe
65 70 75 80

Ser Tyr Thr Thr Pro Asn Ile Leu Ile Asn Asn Gly Asn Ile Thr Ala
85 90 95

Pro Pro Phe Gly Leu Asn Ser Val Ile Thr Pro Asn Leu Phe Pro Gly
100 105 110

Val Ser Ile Ser Ala Arg Leu Gly Asn Gly Pro Gly Ile Gln Glu Val
115 120 125

Ala Thr Phe Ser Val Arg Val Ser Gly Ala Lys Gly Gly Val Ala Val
130 135 140

Ser Asn Ala His Gly Thr Val Thr Gly Ala Ala Gly Gly Val Leu Leu
145 150 155 160

Arg Pro Phe Ala Arg Leu Ile Ala Ser Thr Gly Asp Ser Val Thr Thr
165 170 175

Tyr Gly Glu Pro Trp Asn Met Asn
180

-continued

<210> SEQ ID NO 3
<211> LENGTH: 885
<212> TYPE: DNA
<213> ORGANISM: Artificial Sequence
<220> FEATURE:
<223> OTHER INFORMATION: Polynucleotide sequence encoding one monomer of
alpha-hemolysin-E111N/K147N

<400> SEQUENCE: 3

```
atggcagatt ctgatattaa tattaaaacc ggtactacag atattggaag caatactaca     60

gtaaaaacag gtgatttagt cacttatgat aaagaaaatg gcatgcacaa aaaagtattt    120

tatagtttta tcgatgataa aaatcacaat aaaaaactgc tagttattag aacaaaaggt    180

accattgctg gtcaatatag agtttatagc gaagaaggtg ctaacaaaag tggtttagcc    240

tggccttcag cctttaaggt acagttgcaa ctacctgata atgaagtagc tcaaatatct    300

gattactatc caagaaattc gattgataca aaaaactata tgagtacttt aacttatgga    360

ttcaacggta atgttactgg tgatgataca ggaaaaattg gcggccttat tggtgcaaat    420

gtttcgattg gtcatacact gaactatgtt caacctgatt tcaaaacaat tttagagagc    480

ccaactgata aaaaagtagg ctggaaagtg atatttaaca atatggtgaa tcaaaattgg    540

ggaccatacg atcgagattc ttggaacccg gtatatggca atcaactttt catgaaaact    600

agaaatggtt ctatgaaagc agcagataac ttccttgatc ctaacaaagc aagttctcta    660

ttatcttcag ggttttcacc agacttcgct acagttatta ctatggatag aaaagcatcc    720

aaacaacaaa caaatataga tgtaatatac gaacgagttc gtgatgatta ccaattgcat    780

tggacttcaa caaattggaa aggtaccaat actaaagata aatggacaga tcgttcttca    840

gaaagatata aaatcgattg ggaaaaagaa gaaatgacaa attaa                    885
```

<210> SEQ ID NO 4
<211> LENGTH: 293
<212> TYPE: PRT
<213> ORGANISM: Artificial Sequence
<220> FEATURE:
<223> OTHER INFORMATION: Amino acid sequence of one monomer of
alpha-HL-NN

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140
```

```
Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290


<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 6
<211> LENGTH: 184
<212> TYPE: PRT
```

-continued

<213> ORGANISM: Mycobacterium smegmatis

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr

```
                165                 170                 175

Gly Glu Pro Trp Asn Met Asn
            180


<210> SEQ ID NO 8
<211> LENGTH: 439
<212> TYPE: PRT
<213> ORGANISM: Enterobacteria phage T4

<400> SEQUENCE: 8

Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
    50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
        115                 120                 125

Leu Ser Thr Ile Pro Pro Trp Cys Thr Ile Ile Gly Ile Gly Asp Asn
    130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350
```

```
Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435


<210> SEQ ID NO 9
<211> LENGTH: 50
<212> TYPE: DNA
<213> ORGANISM: Artificial Sequence
<220> FEATURE:
<223> OTHER INFORMATION: Polynucleotide sequence used in Example 1, 2,
      3, 7 and 8

<400> SEQUENCE: 9

tttttttttt tttttttttt tttttttttt tttttttttt tttttttttt                50


<210> SEQ ID NO 10
<211> LENGTH: 27
<212> TYPE: DNA
<213> ORGANISM: Artificial Sequence
<220> FEATURE:
<223> OTHER INFORMATION: Polynucleotide sequence used in Example 1 and 9

<400> SEQUENCE: 10

ggttgtttct gttggtgctg atattgc                                         27


<210> SEQ ID NO 11
<211> LENGTH: 97138
<212> TYPE: DNA
<213> ORGANISM: Artificial Sequence
<220> FEATURE:
<223> OTHER INFORMATION: Polynucleotide sequence used in Example 1

<400> SEQUENCE: 11

gctccactaa agggccgatt gacgggcggc gacctcgcgg gttttcgcta tttatgaaaa     60

ttttccggtt taaggcgttt ccgttcttct tcgtcataac ttaatgtttt tatttaaaat    120

accctctgaa aagaaaggaa acgacaggtg ctgaaagcga ggctttttgg cctctgtcgt    180

ttcctttctc tgtttttgtc cgtggaatga acaatggaag tcaacaaaaa gcagctggct    240

gacattttcg gtgcgagtat ccgtaccatt cagaactggc aggaacaggg aatgcccgtt    300

ctgcgaggcg gtggcaaggg taatgaggtg ctttatgact ctgccgccgt cataaaatgg    360

tatgccgaaa gggatgctga aattgagaac gaaaagctgc gccgggaggt tgaagaactg    420

cggcaggcca gcgaggcaga tctccagcca ggaactattg agtacgaacg ccatcgactt    480

acgcgtgcgc aggccgacgc acaggaactg aagaatgcca gagactccgc tgaagtggtg    540

gaaaccgcat tctgtacttt cgtgctgtcg cggatcgcag gtgaaattgc cagtattctc    600

gacgggctcc ccctgtcggt gcagcggcgt tttccggaac tggaaaaccg acatgttgat    660

ttcctgaaac gggatatcat caaagccatg aacaaagcag ccgcgctgga tgaactgata    720

ccggggttgc tgagtgaata tatcgaacag tcaggttaac aggctgcggc attttgtccg    780
```

-continued

```
cgccgggctt cgctcactgt tcaggccgga gccacagacc gccgttgaat gggcggatgc    840
taattactat ctcccgaaag aatccgcata ccaggaaggg cgctgggaaa cactgccctt    900
tcagcgggcc atcatgaatg cgatgggcag cgactacatc cgtgaggtga atgtggtgaa    960
gtctgcccgt gtcggttatt ccaaaatgct gctgggtgtt tatgcctact ttatagagca   1020
taagcagcgc aacaccctta tctggttgcc gacggatggt gatgccgaga actttatgaa   1080
aacccacgtt gagccgacta ttcgtgatat tccgtcgctg ctggcgctgg ccccgtggta   1140
tggcaaaaag caccgggata acacgctcac catgaagcgt ttcactaatg ggcgtggctt   1200
ctggtgcctg ggcggtaaag cggcaaaaaa ctaccgtgaa aagtcggtgg atgtggcggg   1260
ttatgatgaa cttgctgctt ttgatgatga tattgaacag gaaggctctc cgacgttcct   1320
gggtgacaag cgtattgaag gctcggtctg gccaaagtcc atccgtggct ccacgccaaa   1380
agtgagaggc acctgtcaga ttgagcgtgc agccagtgaa tccccgcatt ttatgcgttt   1440
tcatgttgcc tgcccgcatt gcggggagga gcagtatctt aaatttggcg acaaagagac   1500
gccgtttggc ctcaaatgga cgccggatga cccctccagc gtgtttttatc tctgcgagca   1560
taatgcctgc gtcatccgcc agcaggagct ggactttact gatgcccgtt atatctgcga   1620
aaagaccggg atctggaccc gtgatggcat tctctggttt tcgtcatccg gtgaagagat   1680
tgagccacct gacagtgtga cctttcacat ctggacagcg tacagcccgt tcaccacctg   1740
ggtgcagatt gtcaaagact ggatgaaaac gaaaggggat acgggaaaac gtaaaacctt   1800
cgtaaacacc acgctcggtg agacgtggga ggcgaaaatt ggcgaacgtc cggatgctga   1860
agtgatggca gagcggaaag agcattattc agcgcccgtt cctgaccgtg tggcttacct   1920
gaccgccggt atcgactccc agctggaccg ctacgaaatg cgcgtatggg gatgggggcc   1980
gggtgaggaa agctggctga ttgaccggca gattattatg ggccgccacg acgatgaaca   2040
gacgctgctg cgtgtggatg aggccatcaa taaaacctat acccgccgga atggtgcaga   2100
aatgtcgata tcccgtatct gctgggatac tggcgggatt gacccgacca ttgtgtatga   2160
acgctcgaaa aaacatgggc tgttccgggt gatccccatt aaaggggcat ccgtctacgg   2220
aaagccggtg gccagcatgc cacgtaagcg aaacaaaaac ggggtttacc ttaccgaaat   2280
cggtacggat accgcgaaag agcagattta taaccgcttc acactgacgc cggaaggggga   2340
tgaaccgctt cccggtgccg ttcacttccc gaataacccg gatatttttg atctgaccga   2400
agcgcagcag ctgactgctg aagagcaggt cgaaaaatgg gtggatggca ggaaaaaaat   2460
actgtgggac agcaaaaagc gacgcaatga ggcactcgac tgcttcgttt atgcgctggc   2520
ggcgctgcgc atcagtattt cccgctggca gctggatctc agtgcgctgc tggcgagcct   2580
gcaggaagag gatggtgcag caaccaacaa gaaaacactg gcagattacg cccgtgcctt   2640
atccggagag gatgaatgac gcgacaggaa gaacttgccg ctgcccgtgc ggcactgcat   2700
gacctgatga caggtaaacg ggtggcaaca gtacagaaag acggacgaag ggtggagttt   2760
acggccactt ccgtgtctga cctgaaaaaa tatattgcag agctggaagt gcagaccggc   2820
atgacacagc gacgcagggg acctgcagga ttttatgtat gaaaacgccc accattccca   2880
cccttctggg gccggacggc atgacatcgc tgcgcgaata tgccggttat cacggcggtg   2940
gcagcggatt tggagggcag ttgcggtcgt ggaacccacc gagtgaaagt gtggatgcag   3000
ccctgttgcc caactttacc cgtggcaatg cccgcgcaga cgatctggta cgcaataacg   3060
gctatgccgc caacgccatc cagctgcatc aggatcatat cgtcgggtct tttttccggc   3120
tcagtcatcg cccaagctgg cgctatctgg gcatcgggga ggaagaagcc cgtgcctttt   3180
```

-continued

```
cccgcgaggt tgaagcggca tggaaagagt ttgccgagga tgactgctgc tgcattgacg   3240
ttgagcgaaa acgcacgttt accatgatga ttcgggaagg tgtggccatg cacgccttta   3300
acggtgaact gttcgttcag gccacctggg ataccagttc gtcgcggctt ttccggacac   3360
agttccggat ggtcagcccg aagcgcatca gcaacccgaa caataccggc gacagccgga   3420
actgccgtgc cggtgtgcag attaatgaca gcggtgcggc gctgggatat tacgtcagcg   3480
aggacgggta tcctggctgg atgccgcaga aatggacatg gataccccgt gagttacccg   3540
gcgggcgcgc ctcgttcatt cacgtttttg aacccgtgga ggacgggcag actcgcggtg   3600
caaatgtgtt ttacagcgtg atggagcaga tgaagatgct cgacacgctg cagaacacgc   3660
agctgcagag cgccattgtg aaggcgatgt atgccgccac cattgagagt gagctggata   3720
cgcagtcagc gatggatttt attctgggcg cgaacagtca ggagcagcgg gaaaggctga   3780
ccggctggat tggtgaaatt gccgcgtatt acgccgcagc gccggtccgg ctgggaggcg   3840
caaaagtacc gcacctgatg ccgggtgact cactgaacct gcagacggct caggatacgg   3900
ataacggcta ctccgtgttt gagcagtcac tgctgcggta tatcgctgcc gggctgggtg   3960
tctcgtatga gcagctttcc cggaattacg cccagatgag ctactccacg gcacgggcca   4020
gtgcgaacga gtcgtgggcg tactttatgg ggcggcgaaa attcgtcgca tcccgtcagg   4080
cgagccagat gtttctgtgc tggctggaag aggccatcgt tcgccgcgtg gtgacgttac   4140
cttcaaaagc gcgcttcagt tttcaggaag cccgcagtgc ctgggggaac tgcgactgga   4200
taggctccgg tcgtatggcc atcgatggtc tgaaagaagt tcaggaagcg gtgatgctga   4260
tagaagccgg actgagtacc tacgagaaag agtgcgcaaa acgcggtgac gactatcagg   4320
aaatttttgc ccagcaggtc cgtgaaacga tggagcgccg tgcagccggt cttaaaccgc   4380
ccgcctgggc ggctgcagca tttgaatccg ggctgcgaca atcaacagag gaggagaaga   4440
gtgacagcag agctgcgtaa tctcccgcat attgccagca tggcctttaa tgagccgctg   4500
atgcttgaac ccgcctatgc gcgggttttc ttttgtgcgc ttgcaggcca gcttgggatc   4560
agcagcctga cggatgcggt gtccggcgac agcctgactg cccaggaggc actcgcgacg   4620
ctggcattat ccggtgatga tgacggacca cgacaggccc gcagttatca ggtcatgaac   4680
ggcatcgccg tgctgccggt gtccggcacg ctggtcagcc ggacgcgggc gctgcagccg   4740
tactcgggga tgaccggtta caacggcatt atcgcccgtc tgcaacaggc tgccagcgat   4800
ccgatggtgg acggcattct gctcgatatg gacacgcccg gcgggatggt ggcgggggca   4860
tttgactgcg ctgacatcat cgcccgtgtg cgtgacataa aaccggtatg ggcgcttgcc   4920
aacgacatga actgcagtgc aggtcagttg cttgccagtg ccgcctcccg gcgtctggtc   4980
acgcagaccg cccggacagg ctccatcggc gtcatgatgg ctcacagtaa ttacggtgct   5040
gcgctggaga aacagggtgt ggaaatcacg ctgatttaca gcggcagcca taaggtggat   5100
ggcaacccct acagccatct tccggatgac gtccgggaga cactgcagtc ccggatggac   5160
gcaacccgcc agatgtttgc gcagaaggtg tcggcatata ccggcctgtc cgtgcaggtt   5220
gtgctggata ccgaggctgc agtgtacagc ggtcaggagg ccattgatgc cggactggct   5280
gatgaacttg ttaacagcac cgatgcgatc accgtcatgc gtgatgcact ggatgcacgt   5340
aaatcccgtc tctcaggagg gcgaatgacc aaagagactc aatcaacaac tgtttcagcc   5400
actgcttcgc aggctgacgt tactgacgtg gtgccagcga cggagggcga gaacgccagc   5460
gcggcgcagc cggacgtgaa cgcgcagatc accgcagcgg ttgcggcaga aaacagccgc   5520
```

-continued

```
attatgggga tcctcaactg tgaggaggct cacggacgcg aagaacaggc acgcgtgctg   5580
gcagaaaccc ccggtatgac cgtgaaaacg gcccgccgca ttctggccgc agcaccacag   5640
agtgcacagg cgcgcagtga cactgcgctg gatcgtctga tgcagggggc accggcaccg   5700
ctggctgcag gtaacccggc atctgatgcc gttaacgatt tgctgaacac accagtgtaa   5760
gggatgttta tgacgagcaa agaaaccttt acccattacc agccgcaggg caacagtgac   5820
ccggctcata ccgcaaccgc gcccggcgga ttgagtgcga aagcgcctgc aatgaccccg   5880
ctgatgctgg acacctccag ccgtaagctg gttgcgtggg atggcaccac cgacggtgct   5940
gccgttggca ttcttgcggt tgctgctgac cagaccagca ccacgctgac gttctacaag   6000
tccggcacgt tccgttatga ggatgtgctc tggccggagg ctgccagcga cgagacgaaa   6060
aaacggaccg cgtttgccgg aacggcaatc agcatcgttt aactttaccc ttcatcacta   6120
aaggccgcct gtgcggcttt ttttacggga tttttttatg tcgatgtaca caaccgccca   6180
actgctggcg gcaaatgagc agaaatttaa gtttgatccg ctgtttctgc gtctcttttt   6240
ccgtgagagc tatcccttca ccacggagaa agtctatctc tcacaaattc cgggactggt   6300
aaacatggcg ctgtacgttt cgccgattgt ttccggtgag gttatccgtt cccgtggcgg   6360
ctccacctct gaatttacgc cgggatatgt caagccgaag catgaagtga atccgcagat   6420
gaccctgcgt cgcctgccgg atgaagatcc gcagaatctg gcggacccgg cttaccgccg   6480
ccgtcgcatc atcatgcaga acatgcgtga cgaagagctg gccattgctc aggtcgaaga   6540
gatgcaggca gtttctgccg tgcttaaggg caaatacacc atgaccggtg aagccttcga   6600
tccggttgag gtggatatgg gccgcagtga ggagaataac atcacgcagt ccggcggcac   6660
ggagtggagc aagcgtgaca agtccacgta tgacccgacc gacgatatcg aagcctacgc   6720
gctgaacgcc agcggtgtgg tgaatatcat cgtgttcgat ccgaaaggct gggcgctgtt   6780
ccgttccttc aaagccgtca aggagaagct ggatacccgt cgtggctcta attccgagct   6840
ggagacagcg gtgaaagacc tgggcaaagc ggtgtcctat aaggggatgt atggcgatgt   6900
ggccatcgtc gtgtattccg gacagtacgt ggaaaacggc gtcaaaaaga acttcctgcc   6960
ggacaacacg atggtgctgg ggaacactca ggcacgcggt ctgcgcacct atggctgcat   7020
tcaggatgcg gacgcacagc gcgaaggcat taacgcctct gcccgttacc cgaaaaactg   7080
ggtgaccacc ggcgatccgg cgcgtgagtt caccatgatt cagtcagcac cgctgatgct   7140
gctggctgac cctgatgagt tcgtgtccgt acaactggcg taatcatggc ccttcggggc   7200
cattgtttct ctgtggagga gtccatgacg aaagatgaac tgattgcccg tctccgctcg   7260
ctgggtgaac aactgaaccg tgatgtcagc ctgacgggga cgaaagaaga actggcgctc   7320
cgtgtggcag agctgaaaga ggagcttgat gacacggatg aaactgccgg tcaggacacc   7380
cctctcagcc gggaaaatgt gctgaccgga catgaaaatg aggtgggatc agcgcagccg   7440
gataccgtga ttctggatac gtctgaactg gtcacggtcg tggcactggt gaagctgcat   7500
actgatgcac ttcacgccac gcgggatgaa cctgtggcat ttgtgctgcc gggaacggcg   7560
tttcgtgtct ctgccggtgt ggcagccgaa atgacagagc gcggcctggc cagaatgcaa   7620
taacgggagg cgctgtggct gatttcgata acctgttcga tgctgccatt gcccgcgccg   7680
atgaaacgat acgcgggtac atgggaacgt cagccaccat tacatccggt gagcagtcag   7740
gtgcggtgat acgtggtgtt tttgatgacc ctgaaaatat cagctatgcc ggacagggcg   7800
tgcgcgttga aggctccagc ccgtccctgt ttgtccggac tgatgaggtg cggcagctgc   7860
ggcgtggaga cacgctgacc atcggtgagg aaaatttctg ggtagatcgg gtttcgccgg   7920
```

-continued atgatggcgg aagttgtcat ctctggcttg gacggggcgt accgcctgcc gttaaccgtc 7980
gccgctgaaa gggggatgta tggccataaa aggtcttgag caggccgttg aaaacctcag 8040
ccgtatcagc aaaacggcgg tgcctggtgc cgccgcaatg gccattaacc gcgttgcttc 8100
atccgcgata tcgcagtcgg cgtcacaggt tgcccgtgag acaaaggtac gccggaaact 8160
ggtaaaggaa agggccaggc tgaaaagggc cacggtcaaa aatccgcagg ccagaatcaa 8220
agttaaccgg ggggatttgc ccgtaatcaa gctgggtaat gcgcgggttg tcctttcgcg 8280
ccgcaggcgt cgtaaaaagg ggcagcgttc atccctgaaa ggtggcggca gcgtgcttgt 8340
ggtgggtaac cgtcgtattc ccggcgcgtt tattcagcaa ctgaaaaatg gccggtggca 8400
tgtcatgcag cgtgtggctg ggaaaaaccg ttaccccatt gatgtggtga aaatcccgat 8460
ggcggtgccg ctgaccacgg cgtttaaaca aaatattgag cggatacggc gtgaacgtct 8520
tccgaaagag ctgggctatg cgctgcagca tcaactgagg atggtaataa agcgatgaaa 8580
catactgaac tccgtgcagc cgtactggat gcactggaga agcatgacac cggggcgacg 8640
ttttttgatg gtcgccccgc tgtttttgat gaggcggatt ttccggcagt tgccgtttat 8700
ctcaccggcg ctgaatacac gggcgaagag ctggacagcg atacctggca ggcggagctg 8760
catatcgaag ttttcctgcc tgctcaggtg ccggattcag agctggatgc gtggatggag 8820
tcccggattt atccggtgat gagcgatatc ccggcactgt cagatttgat caccagtatg 8880
gtggccagcg gctatgacta ccggcgcgac gatgatgcgg gcttgtggag ttcagccgat 8940
ctgacttatg tcattaccta tgaaatgtga ggacgctatg cctgtaccaa atcctacaat 9000
gccggtgaaa ggtgccggga ccaccctgtg ggtttataag gggagcggtg acccttacgc 9060
gaatccgctt tcagacgttg actggtcgcg tctggcaaaa gttaaagacc tgacgcccgg 9120
cgaactgacc gctgagtcct atgacgacag ctatctcgat gatgaagatg cagactggac 9180
tgcgaccggg caggggcaga aatctgccgg agataccagc ttcacgctgg cgtggatgcc 9240
cggagagcag gggcagcagg cgctgctggc gtggtttaat gaaggcgata cccgtgccta 9300
taaaatccgc ttcccgaacg gcacggtcga tgtgttccgt ggctgggtca gcagtatcgg 9360
taaggcggtg acggcgaagg aagtgatcac ccgcacggtg aaagtcacca atgtgggacg 9420
tccgtcgatg gcagaagatc gcagcacggt aacagcggca accggcatga ccgtgacgcc 9480
tgccagcacc tcggtggtga aagggcagag caccacgctg accgtggcct tccagccgga 9540
gggcgtaacc gacaagagct ttcgtgcggt gtctgcggat aaaacaaaag ccaccgtgtc 9600
ggtcagtggt atgaccatca ccgtgaacgg cgttgctgca ggcaaggtca acattccggt 9660
tgtatccggt aatggtgagt ttgctgcggt tgcagaaatt accgtcaccg ccagttaatc 9720
cggagagtca gcgatgttcc tgaaaaccga atcatttgaa cataacggtg tgaccgtcac 9780
gctttctgaa ctgtcagccc tgcagcgcat tgagcatctc gccctgatga aacggcaggc 9840
agaacaggcg gagtcagaca gcaaccggaa gtttactgtg gaagacgcca tcagaaccgg 9900
cgcgtttctg gtggcgatgt ccctgtggca taaccatccg cagaagacgc agatgccgtc 9960
catgaatgaa gccgttaaac agattgagca ggaagtgctt accacctggc ccacggaggc 10020
aatttctcat gctgaaaacg tggtgtaccg gctgtctggt atgtatgagt ttgtggtgaa 10080
taatgcccct gaacagacag aggacgccgg gcccgcagag cctgtttctg cgggaaagtg 10140
ttcgacggtg agctgagttt tgccctgaaa ctggcgcgtg agatggggcg acccgactgg 10200
cgtgccatgc ttgccgggat gtcatccacg gagtatgccg actggcaccg cttttacagt 10260

-continued

```
acccattatt ttcatgatgt tctgctggat atgcactttt ccgggctgac gtacaccgtg  10320
ctcagcctgt ttttcagcga tccggatatg catccgctgg atttcagtct gctgaaccgg  10380
cgcgaggctg acgaagagcc tgaagatgat gtgctgatgc agaaagcggc agggcttgcc  10440
ggaggtgtcc gctttggccc ggacgggaat gaagttatcc ccgcttcccc ggatgtggcg  10500
gacatgacgg aggatgacgt aatgctgatg acagtatcag aagggatcgc aggaggagtc  10560
cggtatggct gaaccggtag gcgatctggt cgttgatttg agtctggatg cggccagatt  10620
tgacgagcag atggccagag tcaggcgtca tttttctggt acggaaagtg atgcgaaaaa  10680
aacagcggca gtcgttgaac agtcgctgag ccgacaggcg ctggctgcac agaaagcggg  10740
gatttccgtc gggcagtata aagccgccat gcgtatgctg cctgcacagt tcaccgacgt  10800
ggccacgcag cttgcaggcg ggcaaagtcc gtggctgatc ctgctgcaac aggggggggca  10860
ggtgaaggac tccttcggcg ggatgatccc catgttcagg gggcttgccg gtgcgatcac  10920
cctgccgatg gtgggggcca cctcgctggc ggtggcgacc ggtgcgctgg cgtatgcctg  10980
gtatcagggc aactcaaccc tgtccgattt caacaaaacg ctggtccttt ccggcaatca  11040
ggcgggactg acggcagatc gtatgctggt cctgtccaga gccgggcagg cggcagggct  11100
gacgtttaac cagaccagcg agtcactcag cgcactggtt aaggcggggg taagcggtga  11160
ggctcagatt gcgtccatca gccagagtgt ggcgcgtttc tcctctgcat ccggcgtgga  11220
ggtggacaag gtcgctgaag ccttcgggaa gctgaccaca gacccgacgt cggggctgac  11280
ggcgatggct cgccagttcc ataacgtgtc ggcggagcag attgcgtatg ttgctcagtt  11340
gcagcgttcc ggcgatgaag ccggggcatt gcaggcggcg aacgaggccg caacgaaagg  11400
gtttgatgac cagacccgcc gcctgaaaga gaacatgggc acgctggaga cctgggcaga  11460
caggactgcg cgggcattca aatccatgtg ggatgcggtg ctggatattg gtcgtcctga  11520
taccgcgcag gagatgctga ttaaggcaga ggctgcgtat aagaaagcag acgacatctg  11580
gaatctgcgc aaggatgatt attttgttaa cgatgaagcg cgggcgcgtt actgggatga  11640
tcgtgaaaag gcccgtcttg cgcttgaagc cgcccgaaag aaggctgagc agcagactca  11700
acaggacaaa aatgcgcagc agcagagcga taccgaagcg tcacggctga aatataccga  11760
agaggcgcag aaggcttacg aacggctgca gacgccgctg gagaaatata ccgcccgtca  11820
ggaagaactg aacaaggcac tgaaagacgg gaaaatcctg caggcggatt acaacacgct  11880
gatggcggcg gcgaaaaagg attatgaagc gacgctgaaa aagccgaaac agtccagcgt  11940
gaaggtgtct gcgggcgatc gtcaggaaga cagtgctcat gctgccctgc tgacgcttca  12000
ggcagaactc cggacgctgg agaagcatgc cggagcaaat gagaaaatca gccagcagcg  12060
ccgggatttg tggaaggcgg agagtcagtt cgcggtactg gaggaggcgg cgcaacgtcg  12120
ccagctgtct gcacaggaga aatccctgct ggcgcataaa gatgagacgc tggagtacaa  12180
acgccagctg gctgcacttg gcgacaaggt tacgtatcag gagcgcctga acgcgctggc  12240
gcagcaggcg gataaattcg cacagcagca acgggcaaaa cgggccgcca ttgatgcgaa  12300
aagccggggg ctgactgacc ggcaggcaga acgggaagcc acggaacagc gcctgaagga  12360
acagtatggc gataatccgc tggcgctgaa taacgtcatg tcagagcaga aaaagacctg  12420
ggcggctgaa gaccagcttc gcgggaactg gatggcaggc ctgaagtccg gctggagtga  12480
gtgggaagag agcgccacgg acagtatgtc gcaggtaaaa agtgcagcca cgcagacctt  12540
tgatggtatt gcacagaata tggcggcgat gctgaccggc agtgagcaga actggcgcag  12600
cttcacccgt tccgtgctgt ccatgatgac agaaattctg cttaagcagg caatggtggg  12660
```

-continued

```
gattgtcggg agtatcggca gcgccattgg cggggctgtt ggtggcggcg catccgcgtc  12720
aggcggtaca gccattcagg ccgctgcggc gaaattccat tttgcaaccg gaggatttac  12780
gggaaccggc ggcaaatatg agccagcggg gattgttcac cgtggtgagt ttgtcttcac  12840
gaaggaggca accagccgga ttggcgtggg gaatctttac cggctgatgc gcggctatgc  12900
caccggcggt tatgtcggta caccgggcag catggcagac agccggtcgc aggcgtccgg  12960
gacgtttgag cagaataacc atgtggtgat taacaacgac ggcacgaacg ggcagatagg  13020
tccggctgct ctgaaggcgg tgtatgacat ggcccgcaag ggtgcccgtg atgaaattca  13080
gacacagatg cgtgatggtg gcctgttctc cggaggtgga cgatgaagac cttccgctgg  13140
aaagtgaaac ccggtatgga tgtggcttcg gtcccttctg taagaaaggt gcgctttggt  13200
gatggctatt ctcagcgagc gcctgccggg ctgaatgcca acctgaaaac gtacagcgtg  13260
acgctttctg tcccccgtga ggaggccacg gtactggagt cgtttctgga agagcacggg  13320
ggctggaaat cctttctgtg gacgccgcct tatgagtggc ggcagataaa ggtgacctgc  13380
gcaaaatggt cgtcgcgggt cagtatgctg cgtgttgagt tcagcgcaga gtttgaacag  13440
gtggtgaact gatgcaggat atccggcagg aaacactgaa tgaatgcacc cgtgcggagc  13500
agtcggccag cgtggtgctc tgggaaatcg acctgacaga ggtcggtgga gaacgttatt  13560
ttttctgtaa tgagcagaac gaaaaaggtg agccggtcac ctggcagggg cgacagtatc  13620
agccgtatcc cattcagggg agcggttttg aactgaatgg caaaggcacc agtacgcgcc  13680
ccacgctgac ggtttctaac ctgtacggta tggtcaccgg gatggcggaa gatatgcaga  13740
gtctggtcgg cggaacggtg gtccggcgta aggtttacgc ccgttttctg gatgcggtga  13800
acttcgtcaa cggaaacagt tacgccgatc cggagcagga ggtgatcagc cgctggcgca  13860
ttgagcagtg cagcgaactg agcgcggtga gtgcctcctt tgtactgtcc acgccgacgg  13920
aaacggatgg cgctgttttt ccgggacgta tcatgctggc caacacctgc acctggacct  13980
atcgcggtga cgagtgcggt tatagcggtc cggctgtcgc ggatgaatat gaccagccaa  14040
cgtccgatat cacgaaggat aaatgcagca aatgcctgag cggttgtaag ttccgcaata  14100
acgtcggcaa ctttggcggc ttcctttcca ttaacaaact ttcgcagtaa atcccatgac  14160
acagacagaa tcagcgattc tggcgcacgc ccggcgatgt gcgccagcgg agtcgtgcgg  14220
cttcgtggta agcacgccgg agggggaaag atatttcccc tgcgtgaata tctccggtga  14280
gccggaggct atttccgtat gtcgccggaa gactggctgc aggcagaaat gcagggtgag  14340
attgtggcgc tggtccacag ccacccccggt ggtctgccct ggctgagtga ggccgaccgg  14400
cggctgcagg tgcagagtga tttgccgtgg tggctggtct gccgggggac gattcataag  14460
ttccgctgtg tgccgcatct caccgggcgg cgctttgagc acggtgtgac ggactgttac  14520
acactgttcc gggatgctta tcatctggcg gggattgaga tgccggactt tcatcgtgag  14580
gatgactggt ggcgtaacgg ccagaatctc tatctggata atctggaggc gacggggctg  14640
tatcaggtgc cgttgtcagc ggcacagccg ggcgatgtgc tgctgtgctg ttttggttca  14700
tcagtgccga atcacgccgc aatttactgc ggcgacggcg agctgctgca ccatattcct  14760
gaacaactga gcaaacgaga gaggtacacc gacaaatggc agcgacgcac acactccctc  14820
tggcgtcacc gggcatggcg cgcatctgcc tttacgggga tttacaacga tttggtcgcc  14880
gcatcgacct tcgtgtgaaa acgggggctg aagccatccg ggcactggcc acacagctcc  14940
cggcgtttcg tcagaaactg agcgacggct ggtatcaggt acggattgcc gggcgggacg  15000
```

-continued

```
tcagcacgtc cgggttaacg gcgcagttac atgagactct gcctgatggc gctgtaattc  15060
atattgttcc cagagtcgcc ggggccaagt caggtggcgt attccagatt gtcctggggg  15120
ctgccgccat tgccggatca ttctttaccg ccggagccac ccttgcagca tggggggcag  15180
ccattggggc cggtggtatg accggcatcc tgttttctct cggtgccagt atggtgctcg  15240
gtggtgtggc gcagatgctg gcaccgaaag ccagaactcc ccgtatacag acaacggata  15300
acggtaagca gaacacctat ttctcctcac tggataacat ggttgcccag ggcaatgttc  15360
tgcctgttct gtacggggaa atgcgcgtgg ggtcacgcgt ggtttctcag gagatcagca  15420
cggcagacga aggggacggt ggtcaggttg tggtgattgg tcgctgatgc aaaatgtttt  15480
atgtgaaacc gcctgcgggc ggttttgtca tttatggagc gtgaggaatg ggtaaaggaa  15540
gcagtaaggg gcataccccg cgcgaagcga aggacaacct gaagtccacg cagttgctga  15600
gtgtgatcga tgccatcagc gaagggccga ttgaaggtcc ggtggatggc ttaaaaagcg  15660
tgctgctgaa cagtacgccg gtgctggaca ctgaggggaa taccaacata tccggtgtca  15720
cggtggtgtt ccgggctggt gagcaggagc agactccgcc ggagggattt gaatcctccg  15780
gctccgagac ggtgctgggt acggaagtga aatatgacac gccgatcacc cgcaccatta  15840
cgtctgcaaa catcgaccgt ctgcgcttta ccttcggtgt acaggcactg gtggaaacca  15900
cctcaaaggg tgacaggaat ccgtcggaag tccgcctgct ggttcagata caacgtaacg  15960
gtggctgggt gacggaaaaa gacatcacca ttaagggcaa aaccacctcg cagtatctgg  16020
cctcggtggt gatgggtaac ctgccgccgc gcccgtttaa tatccggatg cgcaggatga  16080
cgccggacag caccacagac cagctgcaga acaaaacgct ctggtcgtca tacactgaaa  16140
tcatcgatgt gaaacagtgc tacccgaaca cggcactggt cggcgtgcag gtggactcgg  16200
agcagttcgg cagccagcag gtgagccgta attatcatct gcgcgggcgt attctgcagg  16260
tgccgtcgaa ctataacccg cagacgcggc aatacagcgg tatctgggac ggaacgttta  16320
aaccggcata cagcaacaac atggcctggt gtctgtggga tatgctgacc catccgcgct  16380
acggcatggg gaaacgtctt ggtgcggcgg atgtggataa atgggcgctg tatgtcatcg  16440
gccagtactg cgaccagtca gtgccggacg gctttggcgg cacggagccg cgcatcacct  16500
gtaatgcgta cctgaccaca cagcgtaagg cgtgggatgt gctcagcgat ttctgctcgg  16560
cgatgcgctg tatgccggta tggaacgggc agacgctgac gttcgtgcag gaccgaccgt  16620
cggataagac gtggacctat aaccgcagta atgtggtgat gccggatgat ggcgcgccgt  16680
tccgctacag cttcagcgcc ctgaaggacc gccataatgc cgttgaggtg aactggattg  16740
acccgaacaa cggctgggag acggcgacag agcttgttga agatacgcag gccattgccc  16800
gttacggtcg taatgttacg aagatggatg cctttggctg taccagccgg gggcaggcac  16860
accgcgccgg gctgtggctg attaaaacag aactgctgga aacgcagacc gtggatttca  16920
gcgtcggcgc agaagggctt cgccatgtac cgggcgatgt tattgaaatc tgcgatgatg  16980
actatgccgg tatcagcacc ggtggtcgtg tgctggcggt gaacagccag acccggacgc  17040
tgacgctcga ccgtgaaatc acgctgccat cctccggtac cgcgctgata agcctggttg  17100
acggaagtgg caatccggtc agcgtggagg ttcagtccgt caccgacggc gtgaaggtaa  17160
aagtgagccg tgttcctgac ggtgttgctg aatacagcgt atgggagctg aagctgccga  17220
cgctgcgcca gcgactgttc cgctgcgtga gtatccgtga gaacgacgac ggcacgtatg  17280
ccatcaccgc cgtgcagcat gtgccggaaa aagaggccat cgtggataac ggggcgcact  17340
ttgacggcga acagagtggc acggtgaatg gtgtcacgcc gccagcggtg cagcacctga  17400
```

ccgcagaagt cactgcagac agcggggaat atcaggtgct ggcgcgatgg gacacaccga 17460
aggtggtgaa gggcgtgagt ttcctgctcc gtctgaccgt aacagcggac gacggcagtg 17520
agcggctggt cagcacggcc cggacgacgg aaaccacata ccgcttcacg caactggcgc 17580
tggggaacta caggctgaca gtccgggcgg taaatgcgtg ggggcagcag ggcgatccgg 17640
cgtcggtatc gttccggatt gccgcaccgg cagcaccgtc gaggattgag ctgacgccgg 17700
gctattttca gataaccgcc acgccgcatc ttgccgttta tgacccgacg gtacagtttg 17760
agttctggtt ctcggaaaag cagattgcgg atatcagaca ggttgaaacc agcacgcgtt 17820
atcttggtac ggcgctgtac tggatagccg ccagtatcaa tatcaaaccg ggccatgatt 17880
attactttta tatccgcagt gtgaacaccg ttggcaaatc ggcattcgtg gaggccgtcg 17940
gtcgggcgag cgatgatgcg gaaggttacc tggatttttt caaaggcaag ataaccgaat 18000
cccatctcgg caaggagctg ctggaaaaag tcgagctgac ggaggataac gccagcagac 18060
tggaggagtt ttcgaaagag tggaaggatg ccagtgataa gtggaatgcc atgtgggctg 18120
tcaaaattga gcagaccaaa gacggcaaac attatgtcgc gggtattggc ctcagcatgg 18180
aggacacgga ggaaggcaaa ctgagccagt ttctggttgc cgccaatcgt atcgcattta 18240
ttgacccggc aaacgggaat gaaacgccga tgtttgtggc gcagggcaac cagatattca 18300
tgaacgacgt gttcctgaag cgcctgacgg cccccaccat taccagcggc ggcaatcctc 18360
cggccttttc cctgacaccg gacggaaagc tgaccgctaa aaatgcggat atcagtggca 18420
gtgtgaatgc gaactccggg acgctcagta atgtgacgat agctgaaaac tgtacgataa 18480
acggtacgct gagggcggaa aaaatcgtcg ggacattgt aaaggcggcg agcgcggctt 18540
ttccgcgcca gcgtgaaagc agtgtggact ggccgtcagg tacccgtact gtcaccgtga 18600
ccgatgacca tccttttgat cgccagatag tggtgcttcc gctgacgttt cgcggaagta 18660
agcgtactgt cagcggcagg acaacgtatt cgatgtgtta tctgaaagta ctgatgaacg 18720
gtgcggtgat ttatgatggc gcggcgaacg aggcggtaca ggtgttctcc cgtattgttg 18780
acatgccagc gggtcgggga aacgtgatcc tgacgttcac gcttacgtcc acacggcatt 18840
cggcagatat tccgccgtat acgtttgcca gcgatgtgca ggttatggtg attaagaaac 18900
aggcgctggg catcagcgtg gtctgagtgt gttacagagg ttcgtccggg aacgggcgtt 18960
ttattataaa acagtgagag gtgaacgatg cgtaatgtgt gtattgccgt tgctgtcttt 19020
gccgcacttg cggtgacagt cactccggcc cgtgcggaag gtggacatgg tacgtttacg 19080
gtgggctatt ttcaagtgaa accgggtaca ttgccgtcgt tgtcgggcgg ggataccggt 19140
gtgagtcatc tgaaagggat taacgtgaag taccgttatg agctgacgga cagtgtgggg 19200
gtgatggctt ccctggggtt cgccgcgtcg aaaaagagca gcacagtgat gaccggggag 19260
gatacgtttc actatgagag cctgcgtgga cgttatgtga gcgtgatggc cggaccggtt 19320
ttacaaatca gtaagcaggt cagtgcgtac gccatggccg gagtggctca cagtcggtgg 19380
tccggcagta caatggatta ccgtaagacg gaaatcactc ccgggtatat gaaagagacg 19440
accactgcca gggacgaaag tgcaatgcgg catacctcag tggcgtggag tgcaggtata 19500
cagattaatc cggcagcgtc cgtcgttgtt gatattgctt atgaaggctc cggcagtggc 19560
gactggcgta ctgacggatt catcgttggg gtcggttata aattctgatt agccaggtaa 19620
cacagtgtta tgacagcccg ccggaaccgg tgggcttttt tgtggggtga atatggcagt 19680
aaagatttca ggagtcctga aagacggcac aggaaaaccg gtacagaact gcaccattca 19740

-continued

```
gctgaaagcc agacgtaaca gcaccacggt ggtggtgaac acggtgggct cagagaatcc  19800
ggatgaagcc gggcgttaca gcatggatgt ggagtacggt cagtacagtg tcatcctgca  19860
ggttgacggt tttccaccat cgcacgccgg gaccatcacc gtgtatgaag attcacaacc  19920
ggggacgctg aatgattttc tctgtgccat gacggaggat gatgcccggc cggaggtgct  19980
gcgtcgtctt gaactgatgg tggaagaggt ggcgcgtaac gcgtccgtgg tggcacagag  20040
tacggcagac gcgaagaaat cagccggcga tgccagtgca tcagctgctc aggtcgcggc  20100
ccttgtgact gatgcaactg actcagcacg cgccgccagc acgtccgccg gacaggctgc  20160
atcgtcagct caggaagcgt cctccggcgc agaagcggca tcagcaaagg ccactgaagc  20220
ggaaaaaagt gccgcagccg cagagtcctc aaaaaacgcg gcggccacca gtgccggtgc  20280
ggcgaaaacg tcagaaacga atgctgcagc gtcacaacaa tcagccgcca cgtctgcctc  20340
caccgcggcc acgaaagcgt cagaggccgc cacttcagca cgagatgcgg tggcctcaaa  20400
agaggcagca aaatcatcag aaacgaacgc atcatcaagt gccggtcgtg cagcttcctc  20460
ggcaacggcg gcagaaaatt ctgccagggc ggcaaaaacg tccgagacga atgccaggtc  20520
atctgaaaca gcagcggaac ggagcgcctc tgccgcggca gacgcaaaaa cagcggcggc  20580
ggggagtgcg tcaacggcat ccacgaaggc gacagaggct gcgggaagtg cggtatcagc  20640
atcgcagagc aaaagtgcgg cagaagcggc ggcaatacgt gcaaaaaatt cggcaaaacg  20700
tgcagaagat atagcttcag ctgtcgcgct tgaggatgcg gacacaacga gaaaggggat  20760
agtgcagctc agcagtgcaa ccaacagcac gtctgaaacg cttgctgcaa cgccaaaggc  20820
ggttaaggtg gtaatggatg aaacgaacag aaaagcccac tggacagtcc ggcactgacc  20880
ggaacgccaa cagcaccaac cgcgctcagg ggaacaaaca atacccagat tgcgaacacc  20940
gcttttgtac tggccgcgat tgcagatgtt atcgacgcgt cacctgacgc actgaatacg  21000
ctgaatgaac tggccgcagc gctcgggaat gatccagatt ttgctaccac catgactaac  21060
gcgcttgcgg gtaaacaacc gaagaatgcg acactgacgg cgctggcagg gctttccacg  21120
gcgaaaaata aattaccgta ttttgcggaa aatgatgccg ccagcctgac tgaactgact  21180
caggttggca gggatattct ggcaaaaaat tccgttgcag atgttcttga ataccttggg  21240
gccggtgaga attcggcctt tccggcaggt gcgccgatcc cgtggccatc agatatcgtt  21300
ccgtctggct acgtcctgat gcaggggcag gcgtttgaca aatcagccta cccaaaactt  21360
gctgtcgcgt atccatcggg tgtgcttcct gatatgcgag gctggacaat caaggggaaa  21420
cccgccagcg gtcgtgctgt attgtctcag gaacaggatg gaattaagtc gcacacccac  21480
agtgccagtg catccggtac ggatttgggg acgaaaacca catcgtcgtt tgattacggg  21540
acgaaaacaa caggcagttt cgattacggc accaaatcga cgaataacac gggggctcat  21600
gctcacagtc tgagcggttc aacaggggcc gcgggtgctc atgcccacac aagtggttta  21660
aggatgaaca gttctggctg gagtcagtat ggaacagcaa ccattacagg aagtttatcc  21720
acagttaaag gaaccagcac acagggtatt gcttatttat cgaaaacgga cagtcagggc  21780
agccacagtc actcattgtc cggtacagcc gtgagtgccg gtgcacatgc gcatacagtt  21840
ggtattggtg cgcaccagca tccggttgtt atcggtgctc atgcccattc tttcagtatt  21900
ggttcacacg gacacaccat caccgttaac gctgcgggta acgcggaaaa caccgtcaaa  21960
aacattgcat ttaactatat tgtgaggctt gcataatggc attcagaatg agtgaacaac  22020
cacggaccat aaaaatttat aatctgctgg ccggaactaa tgaatttatt ggtgaaggtg  22080
acgcatatat tccgcctcat accggtctgc ctgcaaacag taccgatatt gcaccgccag  22140
```

-continued

```
atattccggc tggctttgtg gctgttttca acagtgatga ggcatcgtgg catctcgttg  22200
aagaccatcg gggtaaaacc gtctatgacg tggcttccgg cgacgcgtta tttatttctg  22260
aactcggtcc gttaccggaa aattttacct ggttatcgcc gggaggggaa tatcagaagt  22320
ggaacggcac agcctgggtg aaggatacgg aagcagaaaa actgttccgg atccgggagg  22380
cggaagaaac aaaaaaaagc ctgatgcagg tagccagtga gcatattgcg ccgcttcagg  22440
atgctgcaga tctggaaatt gcaacgaagg aagaaacctc gttgctggaa gcctggaaga  22500
agtatcgggt gttgctgaac cgtgttgata catcaactgc acctgatatt gagtggcctg  22560
ctgtccctgt tatggagtaa tcgttttgtg atatgccgca gaaacgttgt atgaaataac  22620
gttctgcggt tagttagtat attgtaaagc tgagtattgg tttatttggc gattattatc  22680
ttcaggagaa taatggaagt tctatgactc aattgttcat agtgtttaca tcaccgccaa  22740
ttgcttttaa gactgaacgc atgaaatatg gtttttcgtc atgttttgag tctgctgttg  22800
atatttctaa agtcggtttt ttttcttcgt tttctctaac tattttccat gaaatacatt  22860
tttgattatt atttgaatca attccaatta cctgaagtct ttcatctata attggcattg  22920
tatgtattgg tttattggag tagatgcttg cttttctgag ccatagctct gatatccaaa  22980
tgaagccata ggcatttgtt attttggctc tgtcagctgc ataacgccaa aaaatatatt  23040
tatctgcttg atcttcaaat gttgtattga ttaaatcaat tggatggaat tgtttatcat  23100
aaaaaattaa tgtttgaatg tgataaccgt cctttaaaaa agtcgtttct gcaagcttgg  23160
ctgtatagtc aactaactct tctgtcgaag tgatattttt aggcttatct accagtttta  23220
gacgctcttt aatatcttca ggaattattt tattgtcata ttgtatcatg ctaaatgaca  23280
atttgcttat ggagtaatct tttaatttta aataagttat tctcctggct tcatcaaata  23340
aagagtcgaa tgatgttggc gaaatcacat cgtcacccat tggattgttt atttgtatgc  23400
caagagagtt acagcagtta tacattctgc catagattat agctaaggca tgtaataatt  23460
cgtaatcttt tagcgtatta gcgacccatc gtctttctga tttaataata gatgattcag  23520
ttaaatatga aggtaatttc ttttgtgcaa gtctgactaa ctttttttata ccaatgttta  23580
acatactttc atttgtaata aactcaatgt cattttcttc aatgtaagat gaaataagag  23640
tagcctttgc ctcgctatac atttctaaat cgccttgttt ttctatcgta ttgcgagaat  23700
ttttagccca agccattaat ggatcatttt tccatttttc aataacatta ttgttatacc  23760
aaatgtcata tcctataatc tggtttttgt ttttttgaat aataaatgtt actgttcttg  23820
cggtttggag gaattgattc aaattcaagc gaaataattc agggtcaaaa tatgtatcaa  23880
tgcagcattt gagcaagtgc gataaatctt taagtcttct ttcccatggt tttttagtca  23940
taaaactctc catttgata ggttgcatgc tagatgctga tatattttag aggtgataaa  24000
attaactgct taactgtcaa tgtaatacaa gttgtttgat ctttgcaatg attcttatca  24060
gaaaccatat agtaaattag ttacacagga aatttttaat attattatta tcattcatta  24120
tgtattaaaa ttagagttgt ggcttggctc tgctaacacg ttgctcatag gagatatggt  24180
agagccgcag acacgtcgta tgcaggaacg tgctgcggct ggctggtgaa cttccgatag  24240
tgcgggtgtt gaatgatttc cagttgctac cgattttaca tattttttgc atgagagaat  24300
ttgtaccacc tcccaccgac catctatgac tgtacgccac tgtccctagg actgctatgt  24360
gccggagcgg acattacaaa cgtccttctc ggtgcatgcc actgttgcca atgacctgcc  24420
taggaattgg ttagcaagtt actaccggat tttgtaaaaa cagccctcct catataaaaa  24480
```

-continued gtattcgttc acttccgata agcgtcgtaa ttttctatct ttcatcatat tctagatccc 24540
tctgaaaaaa tcttccgagt ttgctaggca ctgatacata actcttttcc aataattggg 24600
gaagtcattc aaatctataa taggtttcag atttgcttca ataaattctg actgtagctg 24660
ctgaaacgtt gcggttgaac tatatttcct tataactttt acgaaagagt ttctttgagt 24720
aatcacttca ctcaagtgct tccctgcctc caaacgatac ctgttagcaa tatttaatag 24780
cttgaaatga tgaagagctc tgtgtttgtc ttcctgcctc cagttcgccg ggcattcaac 24840
ataaaaactg atagcacccg gagttccgga aacgaaattt gcatataccc attgctcacg 24900
aaaaaaaatg tccttgtcga tatagggatg aatcgcttgg tgtacctcat ctactgcgaa 24960
aacttgacct ttctctccca tattgcagtc gcggcacgat ggaactaaat taataggcat 25020
caccgaaaat tcaggataat gtgcaatagg aagaaaatga tctatatttt ttgtctgtcc 25080
tatatcacca caaaatggac atttttcacc tgatgaaaca agcatgtcat cgtaatatgt 25140
tctagcgggt ttgtttttat ctcggagatt attttcataa agcttttcta atttaacctt 25200
tgtcaggtta ccaactacta aggttgtagg ctcaagaggg tgtgtcctgt cgtaggtaaa 25260
taactgacct gtcgagctta atattctata ttgttgttct ttctgcaaaa aagtggggaa 25320
gtgagtaatg aaattatttc taacatttat ctgcatcata ccttccgagc atttattaag 25380
catttcgcta taagttctcg ctggaagagg tagtttttc attgtacttt accttcatct 25440
ctgttcatta tcatcgcttt taaaacggtt cgaccttcta atcctatctg accattataa 25500
ttttttagaa tggtttcata agaaagctct gaatcaacgg actgcgataa taagtggtgg 25560
tatccagaat ttgtcacttc aagtaaaaac acctcacgag ttaaaacacc taagttctca 25620
ccgaatgtct caatatccgg acggataata tttattgctt ctcttgaccg taggactttc 25680
cacatgcagg attttggaac ctcttgcagt actactgggg aatgagttgc aattattgct 25740
acaccattgc gtgcatcgag taagtcgctt aatgttcgta aaaaagcaga gagcaaaggt 25800
ggatgcagat gaacctctgg ttcatcgaat aaaactaatg acttttcgcc aacgacatct 25860
actaatcttg tgatagtaaa taaaacaatt gcatgtccag agctcattcg aagcagatat 25920
ttctggatat tgtcataaaa caatttagtg aatttatcat cgtccacttg aatctgtggt 25980
tcattacgtc ttaactcttc atatttagaa atgaggctga tgagttccat atttgaaaag 26040
ttttcatcac tacttagttt tttgatagct tcaagccaga gttgtctttt tctatctact 26100
ctcatacaac caataaatgc tgaaatgaat tctaagcgga gatcgcctag tgattttaaa 26160
ctattgctgg cagcattctt gagtccaata taaaagtatt gtgtaccttt tgctgggtca 26220
ggttgttctt taggaggagt aaaaggatca aatgcactaa acgaaactga aacaagcgat 26280
cgaaaatatc cctttgggat tcttgactcg ataagtctat tattttcaga gaaaaaatat 26340
tcattgtttt ctgggttggt gattgcacca atcattccat tcaaaattgt tgttttacca 26400
cacccattcc gcccgataaa agcatgaatg ttcgtgctgg gcatagaatt aaccgtcacc 26460
tcaaaaggta tagttaaatc actgaatccg ggagcacttt ttctattaaa tgaaaagtgg 26520
aaatctgaca attctggcaa accatttaac acacgtgcga actgtccatg aatttctgaa 26580
agagttaccc ctctaagtaa tgaggtgtta aggacgcttt cattttcaat gtcggctaat 26640
cgatttggcc atactactaa atcctgaata gctttaagaa ggttatgttt aaaaccatcg 26700
cttaatttgc tgagattaac atagtagtca atgctttcac ctaaggaaaa aaacatttca 26760
gggagttgac tgaatttttt atctattaat gaataagtgc ttacttcttc tttttgacct 26820
acaaaaccaa ttttaacatt tccgatatcg catttttcac catgctcatc aaagacagta 26880

-continued

```
agataaaaca ttgtaacaaa ggaatagtca ttccaaccat ctgctcgtag gaatgcctta  26940
tttttttcta ctgcaggaat atacccgcct ctttcaataa cactaaactc caacatatag  27000
taacccttaa ttttattaaa ataaccgcaa tttatttggc ggcaacacag gatctctctt  27060
ttaagttact ctctattaca tacgttttcc atctaaaaat tagtagtatt gaacttaacg  27120
gggcatcgta ttgtagtttt ccatatttag ctttctgctt ccttttggat aacccactgt  27180
tattcatgtt gcatggtgca ctgtttatac caacgatata gtctattaat gcatatatag  27240
tatcgccgaa cgattagctc ttcaggcttc tgaagaagcg tttcaagtac taataagccg  27300
atagatagcc acggacttcg tagccatttt tcataagtgt taacttccgc tcctcgctca  27360
taacagacat tcactacagt tatggcggaa aggtatgcat gctgggtgtg gggaagtcgt  27420
gaaagaaaag aagtcagctg cgtcgtttga catcactgct atcttcttac tggttatgca  27480
ggtcgtagtg ggtggcacac aaagctttgc actggattgc gaggctttgt gcttctctgg  27540
agtgcgacag gtttgatgac aaaaaattag cgcaagaaga caaaaatcac cttgcgctaa  27600
tgctctgtta caggtcacta ataccatcta agtagttgat tcatagtgac tgcatatgtt  27660
gtgttttaca gtattatgta gtctgttttt tatgcaaaat ctaatttaat atattgatat  27720
ttatatcatt ttacgtttct cgttcagctt ttttatacta agttggcatt ataaaaaagc  27780
attgcttatc aatttgttgc aacgaacagg tcactatcag tcaaaataaa atcattattt  27840
gatttcaatt ttgtcccact ccctgcctct gtcatcacga tactgtgatg ccatggtgtc  27900
cgacttatgc ccgagaagat gttgagcaaa cttatcgctt atctgcttct catagagtct  27960
tgcagacaaa ctgcgcaact cgtgaaaggt aggcggatcc ccttcgaagg aaagacctga  28020
tgcttttcgt gcgcgcataa aataccttga tactgtgccg gatgaaagcg gttcgcgacg  28080
agtagatgca attatggttt ctccgccaag aatctctttg catttatcaa gtgtttcctt  28140
cattgatatt ccgagagcat caatatgcaa tgctgttggg atggcaattt ttacgcctgt  28200
tttgctttgc tcgacataaa gatatccatc tacgatatca gaccacttca tttcgcataa  28260
atcaccaact cgttgcccgg taacaacagc cagttccatt gcaagtctga gccaacatgg  28320
tgatgattct gctgcttgat aaattttcag gtattcgtca gccgtaagtc ttgatctcct  28380
tacctctgat tttgctgcgc gagtggcagc gacatggttt gttgttatat ggccttcagc  28440
tattgcctct cggaatgcat cgctcagtgt tgatctgatt aacttggctg acgccgcctt  28500
gccctcgtct atgtatccat tgagcattgc cgcaatttct tttgtggtga tgtcttcaag  28560
tggagcatca ggcagacccc tccttattgc tttaattttg ctcatgtaat ttatgagtgt  28620
cttctgcttg attcctctgc tggccaggat tttttcgtag cgatcaagcc atgaatgtaa  28680
cgtaacggaa ttatcactgt tgattctcgc tgtcagaggc ttgtgtttgt gtcctgaaaa  28740
taactcaatg ttggcctgta tagcttcagt gattgcgatt cgcctgtctc tgcctaatcc  28800
aaactcttta cccgtccttg ggtccctgta gcagtaatat ccattgtttc ttatataaag  28860
gttagggggt aaatcccggc gctcatgact tcgccttctt cccatttctg atcctcttca  28920
aaaggccacc tgttactggt cgatttaagt caacctttac cgctgattcg tggaacagat  28980
actctcttcc atccttaacc ggaggtggga atatcctgca ttcccgaacc catcgacgaa  29040
ctgtttcaag gcttcttgga cgtcgctggc gtgcgttcca ctcctgaagt gtcaagtaca  29100
tcgcaaagtc tccgcaatta cacgcaagaa aaaaccgcca tcaggcggct tggtgttctt  29160
tcagttcttc aattcgaata ttggttacgt ctgcatgtgc tatctgcgcc catatcatcc  29220
```

agtggtcgta gcagtcgttg atgttctccg cttcgataac tctgttgaat ggctctccat 29280
tccattctcc tgtgactcgg aagtgcattt atcatctcca taaaacaaaa cccgccgtag 29340
cgagttcaga taaaataaat ccccgcgagt gcgaggattg ttatgtaata ttgggtttaa 29400
tcatctatat gttttgtaca gagagggcaa gtatcgtttc caccgtactc gtgataataa 29460
ttttgcacgg tatcagtcat ttctcgcaca ttgcagaatg gggatttgtc ttcattagac 29520
ttataaacct tcatggaata tttgtatgcc gactctatat ctataccttc atctacataa 29580
acaccttcgt gatgtctgca tggagacaag acaccggatc tgcacaacat tgataacgcc 29640
caatcttttt gctcagactc taactcattg atactcattt ataaactcct tgcaatgtat 29700
gtcgtttcag ctaaacggta tcagcaatgt ttatgtaaag aaacagtaag ataatactca 29760
acccgatgtt tgagtacggt catcatctga cactacagac tctggcatcg ctgtgaagac 29820
gacgcgaaat tcagcatttt cacaagcgtt atcttttaca aaaccgatct cactctcctt 29880
tgatgcgaat gccagcgtca gacatcatat gcagatactc acctgcatcc tgaacccatt 29940
gacctccaac cccgtaatag cgatgcgtaa tgatgtcgat agttactaac gggtcttgtt 30000
cgattaactg ccgcagaaac tcttccaggt caccagtgca gtgcttgata acaggagtct 30060
tcccaggatg gcgaacaaca agaaactggt ttccgtcttc acggacttcg ttgctttcca 30120
gtttagcaat acgcttactc ccatccgaga taacaccttc gtaatactca cgctgctcgt 30180
tgagttttga ttttgctgtt tcaagctcaa cacgcagttt ccctactgtt agcgcaatat 30240
cctcgttctc ctggtcgcgg cgtttgatgt attgctggtt tctttcccgt tcatccagca 30300
gttccagcac aatcgatggt gttaccaatt catggaaaag gtctgcgtca aatccccagt 30360
cgtcatgcat tgcctgctct gccgcttcac gcagtgcctg agagttaatt tcgctcactt 30420
cgaacctctc tgtttactga taagttccag atcctcctgg caacttgcac aagtccgaca 30480
accctgaacg accaggcgtc ttcgttcatc tatcggatcg ccacactcac aacaatgagt 30540
ggcagatata gcctggtggt tcaggcggcg catttttatt gctgtgttgc gctgtaattc 30600
ttctatttct gatgctgaat caatgatgtc tgccatcttt cattaatccc tgaactgttg 30660
gttaatacgc ttgagggtga atgcgaataa taaaaaagga gcctgtagct ccctgatgat 30720
tttgcttttc atgttcatcg ttccttaaag acgccgttta acatgccgat tgccaggctt 30780
aaatgagtcg gtgtgaatcc catcagcgtt accgtttcgc ggtgcttctt cagtacgcta 30840
cggcaaatgt catcgacgtt tttatccgga aactgctgtc tggctttttt tgatttcaga 30900
attagcctga cgggcaatgc tgcgaagggc gttttcctgc tgaggtgtca ttgaacaagt 30960
cccatgtcgg caagcataag cacacagaat atgaagcccg ctgccagaaa aatgcattcc 31020
gtggttgtca tacctggttt ctctcatctg cttctgcttt cgccaccatc atttccagct 31080
tttgtgaaag ggatgcggct aacgtatgaa attcttcgtc tgtttctact ggtattggca 31140
caaacctgat tccaatttga gcaaggctat gtgccatctc gatactcgtt cttaactcaa 31200
cagaagatgc tttgtgcata cagcccctcg tttattattt atctcctcag ccagccgctg 31260
tgctttcagt ggatttcgga taacagaaag gccgggaaat acccagcctc gctttgtaac 31320
ggagtagacg aaagtgattg cgcctacccg gatattatcg tgaggatgcg tcatcgccat 31380
tgctccccaa atacaaaacc aatttcagcc agtgcctcgt ccattttttc gatgaactcc 31440
ggcacgatct cgtcaaaact cgccatgtac ttttcatccc gctcaatcac gacataatgc 31500
aggccttcac gcttcatacg cgggtcatag ttggcaaagt accaggcatt ttttcgcgtc 31560
acccacatgc tgtactgcac ctgggccatg taagctgact ttatggcctc gaaaccaccg 31620
agccggaact tcatgaaatc ccgggaggta aacgggcatt tcagttcaag gccgttgccg 31680
tcactgcata aaccatcggg agagcaggcg gtacgcatac tttcgtcgcg atagatgatc 31740
ggggattcag taacattcac gccggaagtg aattcaaaca gggttctggc gtcgttctcg 31800
tactgttttc cccaggccag tgctttagcg ttaacttccg gagccacacc ggtgcaaacc 31860
tcagcaagca gggtgtggaa gtaggacatt ttcatgtcag gccacttctt tccggagcgg 31920
ggttttgcta tcacgttgtg aacttctgaa gcggtgatga cgccgagccg taatttgtgc 31980
cacgcatcat ccccctgttc gacagctctc acatcgatcc cggtacgctg caggataatg 32040
tccggtgtca tgctgccacc ttctgctctg cggctttctg tttcaggaat ccaagagctt 32100
ttactgcttc ggcctgtgtc agttctgacg atgcacgaat gtcgcggcga aatatctggg 32160
aacagagcgg caataagtcg tcatcccatg ttttatccag ggcgatcagc agagtgttaa 32220
tctcctgcat ggtttcatcg ttaaccggag tgatgtcgcg ttccggctga cgttctgcag 32280
tgtatgcagt attttcgaca atgcgctcgg cttcatcctt gtcatagata ccagcaaatc 32340
cgaaggccag acgggcacac tgaatcatgg ctttatgacg taacatccgt ttgggatgcg 32400
actgccacgg ccccgtgatt tctctgcctt cgcgagtttt gaatggttcg cggcggcatt 32460
catccatcca ttcggtaacg cagatcggat gattacggtc cttgcggtaa atccggcatg 32520
tacaggattc attgtcctgc tcaaagtcca tgccatcaaa ctgctggttt tcattgatga 32580
tgcgggacca gccatcaacg cccaccaccg gaacgatgcc attctgctta tcaggaaagg 32640
cgtaaatttc tttcgtccac ggattaaggc cgtactggtt ggcaacgatc agtaatgcga 32700
tgaactgcgc atcgctggca tcacctttaa atgccgtctg gcgaagagtg gtgatcagtt 32760
cctgtgggtc gacagaatcc atgccgacac gttcagccag cttcccagcc agcgttgcga 32820
gtgcagtact cattcgtttt atacctctga atcaatatca acctggtggt gagcaatggt 32880
ttcaaccatg taccggatgt gttctgccat gcgctcctga aactcaacat cgtcatcaaa 32940
cgcacgggta atggattttt tgctggcccc gtggcgttgc aaatgatcga tgcatagcga 33000
ttcaaacagg tgctggggca ggcctttttc catgtcgtct gccagttctg cctctttctc 33060
ttcacgggcg agctgctggt agtgacgcgc ccagctctga gcctcaagac gatcctgaat 33120
gtaataagcg ttcatggctg aactcctgaa atagctgtga aaatatcgcc cgcgaaatgc 33180
cgggctgatt aggaaaacag gaaagggggt tagtgaatgc ttttgcttga tctcagtttc 33240
agtattaata tccatttttt ataagcgtcg acggcttcac gaaacatctt ttcatcgcca 33300
ataaaagtgg cgatagtgaa tttagtctgg atagccataa gtgtttgatc cattctttgg 33360
gactcctggc tgattaagta tgtcgataag gcgtttccat ccgtcacgta atttacgggt 33420
gattcgttca agtaaagatt cggaagggca gccagcaaca ggccaccctg caatggcata 33480
ttgcatggtg tgctccttat ttatacataa cgaaaaacgc ctcgagtgaa gcgttattgg 33540
tatgcggtaa aaccgcactc aggcggcctt gatagtcata tcatctgaat caaatattcc 33600
tgatgtatcg atatcggtaa ttcttattcc ttcgctacca tccattggag gccatccttc 33660
ctgaccattt ccatcattcc agtcgaactc acacacaaca ccatatgcat ttaagtcgct 33720
tgaaattgct ataagcagag catgttgcgc cagcatgatt aatacagcat ttaatacaga 33780
gccgtgttta ttgagtcggt attcagagtc tgaccagaaa ttattaatct ggtgaagttt 33840
ttcctctgtc attacgtcat ggtcgatttc aatttctatt gatgctttcc agtcgtaatc 33900
aatgatgtat tttttgatgt ttgacatctg ttcatatcct cacagataaa aaatcgccct 33960

-continued cacactggag ggcaaagaag atttccaata atcagaacaa gtcggctcct gtttagttac 34020
gagcgacatt gctccgtgta ttcactcgtt ggaatgaata cacagtgcag tgtttattct 34080
gttatttatg ccaaaaataa aggccactat caggcagctt tgttgttctg tttaccaagt 34140
tctctggcaa tcattgccgt cgttcgtatt gcccatttat cgacatattt cccatcttcc 34200
attacaggaa acatttcttc aggcttaacc atgcattccg attgcagctt gcatccattg 34260
catcgcttga attgtccaca ccattgattt ttatcaatag tcgtagtcat acggatagtc 34320
ctggtattgt tccatcacat cctgaggatg ctcttcgaac tcttcaaatt cttcttccat 34380
atatcacctt aaatagtgga ttgcggtagt aaagattgtg cctgtctttt aaccacatca 34440
ggctcggtgg ttctcgtgta cccctacagc gagaaatcgg ataaactatt acaaccccta 34500
cagtttgatg agtatagaaa tggatccact cgttattctc ggacgagtgt tcagtaatga 34560
acctctggag agaaccatgt atatgatcgt tatctgggtt ggacttctgc ttttaagccc 34620
agataactgg cctgaatatg ttaatgagag aatcggtatt cctcatgtgt ggcatgtttt 34680
cgtctttgct cttgcatttt cgctagcaat taatgtgcat cgattatcag ctattgccag 34740
cgccagatat aagcgattta agctaagaaa acgcattaag atgcaaaacg ataaagtgcg 34800
atcagtaatt caaaacctta cagaagagca atctatggtt ttgtgcgcag cccttaatga 34860
aggcaggaag tatgtggtta catcaaaaca attcccatac attagtgagt tgattgagct 34920
tggtgtgttg aacaaaactt tttcccgatg gaatggaaag catatattat tccctattga 34980
ggatatttac tggactgaat tagttgccag ctatgatcca tataatattg agataaagcc 35040
aaggccaata tctaagtaac tagataagag gaatcgattt tcccttaatt ttctggcgtc 35100
cactgcatgt tatgccgcgt tcgccaggct tgctgtacca tgtgcgctga ttcttgcgct 35160
caatacgttg caggttgctt tcaatctgtt tgtggtattc agccagcact gtaaggtcta 35220
tcggatttag tgcgctttct actcgtgatt tcggtttgcg attcagcgag agaatagggc 35280
ggttaactgg ttttgcgctt accccaacca acaggggatt tgctgctttc cattgagcct 35340
gtttctctgc gcgacgttcg cggcggcgtg tttgtgcatc catctggatt ctcctgtcag 35400
ttagctttgg tggtgtgtgg cagttgtagt cctgaacgaa aaccccccgc gattggcaca 35460
ttggcagcta atccggaatc gcacttacgg ccaatgcttc gtttcgtatc acacacccca 35520
aagccttctg ctttgaatgc tgcccttctt cagggcttaa tttttaagag cgtcaccttc 35580
atggtggtca gtgcgtcctg ctgatgtgct cagtatcacc gccagtggta tttatgtcaa 35640
caccgccaga gataatttat caccgcagat ggttatctgt atgtttttta tatgaattta 35700
ttttttgcag gggggcattg tttggtaggt gagagatctg aattgctatg tttagtgagt 35760
tgtatctatt tatttttcaa taaatacaat tggttatgtg ttttgggggc gatcgtgagg 35820
caaagaaaac ccggcgctga ggccgggtta ttcttgttct ctggtcaaat tatatagttg 35880
gaaaacaagg atgcatatat gaatgaacga tgcagaggca atgccgatgg cgatagtggg 35940
tatcatgtag ccgcttatgc tggaaagaag caataacccg cagaaaaaca aagctccaag 36000
ctcaacaaaa ctaagggcat agacaataac taccgatgtc atatacccat actctctaat 36060
cttggccagt cggcgcgttc tgcttccgat tagaaacgtc aaggcagcaa tcaggattgc 36120
aatcatggtt cctgcatatg atgacaatgt cgccccaaga ccatctctat gagctgaaaa 36180
agaaacacca ggaatgtagt ggcggaaaag gagatagcaa atgcttacga taacgtaagg 36240
aattattact atgtaaacac caggcatgat tctgttccgc ataattactc ctgataatta 36300
atccttaact ttgcccacct gcctttttaa acattccagt atatcacttt tcattcttgc 36360

-continued gtagcaatat gccatctctt cagctatctc agcattggtg accttgttca gaggcgctga 36420
gagatggcct ttttctgata gataatgttc tgttaaaata tctccggcct catcttttgc 36480
ccgcaggcta atgtctgaaa attgaggtga cgggttaaaa ataatatcct tggcaacctt 36540
ttttatatcc cttttaaatt ttggcttaat gactatatcc aatgagtcaa aaagctcccc 36600
ttcaatatct gttgccccta agacctttaa tatatcgcca aatacaggta gcttggcttc 36660
taccttcacc gttgttcggc cgatgaaatg catatgcata acatcgtctt tggtggttcc 36720
cctcatcagt ggctctatct gaacgcgctc tccactgctt aatgacattc ctttcccgat 36780
taaaaaatct gtcagatcgg atgtggtcgg cccgaaaaca gttctggcaa aaccaatggt 36840
gtcgccttca acaaacaaaa aagatgggaa tcccaatgat tcgtcatctg cgaggctgtt 36900
cttaatatct tcaactgaag ctttagagcg atttatcttc tgaaccagac tcttgtcatt 36960
tgttttggta aagagaaaag tttttccatc gattttatga atatacaaat aattggagcc 37020
aacctgcagg tgatgattat cagccagcag agaattaagg aaaacagaca ggtttattga 37080
gcgcttatct ttccctttat ttttgctgcg gtaagtcgca taaaaaccat tcttcataat 37140
tcaatccatt tactatgtta tgttctgagg ggagtgaaaa ttcccctaat tcgatgaaga 37200
ttcttgctca attgttatca gctatgcgcc gaccagaaca ccttgccgat cagccaaacg 37260
tctcttcagg ccactgacta gcgataactt tccccacaac ggaacaactc tcattgcatg 37320
ggatcattgg gtactgtggg tttagtggtt gtaaaaacac ctgaccgcta tccctgatca 37380
gtttcttgaa ggtaaactca tcacccccaa gtctggctat gcagaaatca cctggctcaa 37440
cagcctgctc agggtcaacg agaattaaca ttccgtcagg aaagcttggc ttggagcctg 37500
ttggtgcggt catggaatta ccttcaacct caagccagaa tgcagaatca ctggcttttt 37560
tggttgtgct tacccatctc tccgcatcac ctttggtaaa ggttctaagc ttaggtgaga 37620
acatccctgc ctgaacatga gaaaaaacag ggtactcata ctcacttcta agtgacggct 37680
gcatactaac cgcttcatac atctcgtaga tttctctggc gattgaaggg ctaaattctt 37740
caacgctaac tttgagaatt tttgtaagca atgcggcgtt ataagcattt aatgcattga 37800
tgccattaaa taaagcacca acgcctgact gccccatccc catcttgtct gcgacagatt 37860
cctgggataa gccaagttca tttttctttt tttcataaat tgctttaagg cgacgtgcgt 37920
cctcaagctg ctcttgtgtt aatggtttct tttttgtgct catacgttaa atctatcacc 37980
gcaagggata aatatctaac accgtgcgtg ttgactattt tacctctggc ggtgataatg 38040
gttgcatgta ctaaggaggt tgtatggaac aacgcataac cctgaaagat tatgcaatgc 38100
gctttgggca aaccaagaca gctaaagatc tcggcgtata tcaaagcgcg atcaacaagg 38160
ccattcatgc aggccgaaag atttttttaa ctataaacgc tgatggaagc gtttatgcgg 38220
aagaggtaaa gcccttcccg agtaacaaaa aaacaacagc ataaataacc ccgctcttac 38280
acattccagc cctgaaaaag ggcatcaaat taaaccacac ctatggtgta tgcatttatt 38340
tgcatacatt caatcaattg ttatctaagg aaatacttac atatggttcg tgcaaacaaa 38400
cgcaacgagg ctctacgaat cgagagtgcg ttgcttaaca aaatcgcaat gcttggaact 38460
gagaagacag cggaagctgt gggcgttgat aagtcgcaga tcagcaggtg gaagagggac 38520
tggattccaa agttctcaat gctgcttgct gttcttgaat ggggggtcgt tgacgacgac 38580
atggctcgat tggcgcgaca agttgctgcg attctcacca ataaaaaacg cccggcggca 38640
accgagcgtt ctgaacaaat ccagatggag ttctgaggtc attactggat ctatcaacag 38700
gagtcattat gacaaataca gcaaaaatac tcaacttcgg cagaggtaac tttgccggac 38760
aggagcgtaa tgtggcagat ctcgatgatg gttacgccag actatcaaat atgctgcttg 38820
aggcttattc gggcgcagat ctgaccaagc gacagtttaa agtgctgctt gccattctgc 38880
gtaaaaccta tgggtggaat aaaccaatgg acagaatcac cgattctcaa cttagcgaga 38940
ttacaaagtt acctgtcaaa cggtgcaatg aagccaagtt agaactcgtc agaatgaata 39000
ttatcaagca gcaaggcggc atgtttggac caaataaaaa catctcagaa tggtgcatcc 39060
ctcaaaacga gggaaaatcc cctaaaacga gggataaaac atccctcaaa ttgggggatt 39120
gctatccctc aaaacagggg gacacaaaag acactattac aaaagaaaaa agaaaagatt 39180
attcgtcaga gaattctggc gaatcctctg accagccaga aaacgacctt tctgtggtga 39240
aaccggatgc tgcaattcag agcggcagca agtgggggac agcagaagac ctgaccgccg 39300
cagagtggat gtttgacatg gtgaagacta tcgcaccatc agccagaaaa ccgaattttg 39360
ctgggtgggc taacgatatc cgcctgatgc gtgaacgtga cggacgtaac caccgcgaca 39420
tgtgtgtgct gttccgctgg gcatgccagg acaacttctg gtccggtaac gtgctgagcc 39480
cggccaaact ccgcgataag tggacccaac tcgaaatcaa ccgtaacaag caacaggcag 39540
gcgtgacagc cagcaaacca aaactcgacc tgacaaacac agactggatt tacggggtgg 39600
atctatgaaa aacatcgccg cacagatggt taactttgac cgtgagcaga tgcgtcggat 39660
cgccaacaac atgccggaac agtacgacga aaagccgcag gtacagcagg tagcgcagat 39720
catcaacggt gtgttcagcc agttactggc aactttcccg gcgagcctgg ctaaccgtga 39780
ccagaacgaa gtgaacgaaa tccgtcgcca gtgggttctg gcttttcggg aaaacgggat 39840
caccacgatg gaacaggtta acgcaggaat gcgcgtagcc cgtcggcaga atcgaccatt 39900
tctgccatca cccgggcagt ttgttgcatg gtgccgggaa gaagcatccg ttaccgccgg 39960
actgccaaac gtcagcgagc tggttgatat ggtttacgag tattgccgga agcgaggcct 40020
gtatccggat gcggagtctt atccgtggaa atcaaacgcg cactactggc tggttaccaa 40080
cctgtatcag aacatgcggg ccaatgcgct tactgatgcg gaattacgcc gtaaggccgc 40140
agatgagctt gtccatatga ctgcgagaat taaccgtggt gaggcgatcc ctgaaccagt 40200
aaaacaactt cctgtcatgg gcggtagacc tctaaatcgt gcacaggctc tggcgaagat 40260
cgcagaaatc aaagctaagt tcggactgaa aggagcaagt gtatgacggg caaagaggca 40320
attattcatt acctggggac gcataatagc ttctgtgcgc cggacgttgc cgcgctaaca 40380
ggcgcaacag taaccagcat aaatcaggcc gcggctaaaa tggcacgggc aggtcttctg 40440
gttatcgaag gtaaggtctg gcgaacggtg tattaccggt ttgctaccag ggaagaacgg 40500
gaaggaaaga tgagcacgaa cctggttttt aaggagtgtc gccagagtgc cgcgatgaaa 40560
cgggtattgg cggtatatgg agttaaaaga tgaccatcta cattactgag ctaataacag 40620
gcctgctggt aatcgcaggc ctttttattt gggggagagg gaagtcatga aaaaactaac 40680
ctttgaaatt cgatctccag cacatcagca aaacgctatt cacgcagtac agcaaatcct 40740
tccagaccca accaaaccaa tcgtagtaac cattcaggaa cgcaaccgca gcttagacca 40800
aaacaggaag ctatgggcct gcttaggtga cgtctctcgt caggttgaat ggcatggtcg 40860
ctggctggat gcagaaagct ggaagtgtgt gtttaccgca gcattaaagc agcaggatgt 40920
tgttcctaac cttgccggga atggctttgt ggtaataggc cagtcaacca gcaggatgcg 40980
tgtaggcgaa tttgcggagc tattagagct tatacaggca ttcggtacag agcgtggcgt 41040
taagtggtca gacgaagcga gactggctct ggagtggaaa gcgagatggg gagacagggc 41100

-continued

```
tgcatgataa atgtcgttag tttctccggt ggcaggacgt cagcatattt gctctggcta  41160
atggagcaaa agcgacgggc aggtaaagac gtgcattacg ttttcatgga tacaggttgt  41220
gaacatccaa tgacatatcg gtttgtcagg gaagttgtga agttctggga tataccgctc  41280
accgtattgc aggttgatat caacccggag cttggacagc caaatggtta tacggtatgg  41340
gaaccaaagg atattcagac gcgaatgcct gttctgaagc catttatcga tatggtaaag  41400
aaatatggca ctccatacgt cggcggcgcg ttctgcactg acagattaaa actcgttccc  41460
ttcaccaaat actgtgatga ccatttcggg cgagggaatt acaccacgtg gattggcatc  41520
agagctgatg aaccgaagcg gctaaagcca aagcctggaa tcagatatct tgctgaactg  41580
tcagactttg agaaggaaga tatcctcgca tggtggaagc aacaaccatt cgatttgcaa  41640
ataccggaac atctcggtaa ctgcatattc tgcattaaaa aatcaacgca aaaaatcgga  41700
cttgcctgca aagatgagga gggattgcag cgtgttttta atgaggtcat cacgggatcc  41760
catgtgcgtg acggacatcg ggaaacgcca aaggagatta tgtaccgagg aagaatgtcg  41820
ctggacggta tcgcgaaaat gtattcagaa aatgattatc aagccctgta tcaggacatg  41880
gtacgagcta aaagattcga taccggctct tgttctgagt catgcgaaat atttggaggg  41940
cagcttgatt tcgacttcgg gagggaagct gcatgatgcg atgttatcgg tgcggtgaat  42000
gcaaagaaga taaccgcttc cgaccaaatc aaccttactg gaatcgatgg tgtctccggt  42060
gtgaaagaac accaacaggg gtgttaccac taccgcagga aaaggaggac gtgtggcgag  42120
acagcgacga agtatcaccg acataatctg cgaaaactgc aaataccttc caacgaaacg  42180
caccagaaat aaacccaagc caatcccaaa agaatctgac gtaaaaacct tcaactacac  42240
ggctcacctg tgggatatcc ggtggctaag acgtcgtgcg aggaaaacaa ggtgattgac  42300
caaaatcgaa gttacgaaca agaaagcgtc gagcgagctt taacgtgcgc taactgcggt  42360
cagaagctgc atgtgctgga agttcacgtg tgtgagcact gctgcgcaga actgatgagc  42420
gatccgaata gctcgatgca cgaggaagaa gatgatggct aaaccagcgc gaagacgatg  42480
taaaaacgat gaatgccggg aatggtttca ccctgcattc gctaatcagt ggtggtgctc  42540
tccagagtgt ggaaccaaga tagcactcga acgacgaagt aaagaacgcg aaaaagcgga  42600
aaaagcagca gagaagaaac gacgacgaga ggagcagaaa cagaaagata aacttaagat  42660
tcgaaaactc gccttaaagc cccgcagtta ctggattaaa caagcccaac aagccgtaaa  42720
cgccttcatc agagaaagag accgcgactt accatgtatc tcgtgcggaa cgctcacgtc  42780
tgctcagtgg gatgccggac attaccggac aactgctgcg gcacctcaac tccgatttaa  42840
tgaacgcaat attcacaagc aatgcgtggt gtgcaaccag cacaaaagcg gaaatctcgt  42900
tccgtatcgc gtcgaactga ttagccgcat cgggcaggaa gcagtagacg aaatcgaatc  42960
aaaccataac cgccatcgct ggactatcga agagtgcaag gcgatcaagg cagagtacca  43020
acagaaactc aaagacctgc gaaatagcag aagtgaggcc gcatgacgtt ctcagtaaaa  43080
accattccag acatgctcgt tgaaacatac ggaaatcaga cagaagtagc acgcagactg  43140
aaatgtagtc gcggtacggt cagaaaatac gttgatgata aagacgggaa aatgcacgcc  43200
atcgtcaacg acgttctcat ggttcatcgc ggatggagtg aaagagatgc gctattacga  43260
aaaaattgat ggcagcaaat accgaaatat ttgggtagtt ggcgatctgc acggatgcta  43320
cacgaacctg atgaacaaac tggatacgat tggattcgac aacaaaaaag acctgcttat  43380
ctcggtgggc gatttggttg atcgtggtgc agagaacgtt gaatgcctgg aattaatcac  43440
```

-continued

```
attcccctgg ttcagagctg tacgtggaaa ccatgagcaa atgatgattg atggcttatc  43500
agagcgtgga aacgttaatc actggctgct taatggcggt ggctggttct ttaatctcga  43560
ttacgacaaa gaaattctgg ctaaagctct tgcccataaa gcagatgaac ttccgttaat  43620
catcgaactg gtgagcaaag ataaaaaata tgttatctgc cacgccgatt atccctttga  43680
cgaatacgag tttggaaagc cagttgatca tcagcaggta atctggaacc gcgaacgaat  43740
cagcaactca caaaacggga tcgtgaaaga aatcaaaggc gcggacacgt tcatctttgg  43800
tcatacgcca gcagtgaaac cactcaagtt tgccaaccaa atgtatatcg ataccggcgc  43860
agtgttctgc ggaaacctaa cattgattca ggtacaggga gaaggcgcat gagactcgaa  43920
agcgtagcta aatttcattc gccaaaaagc ccgatgatga gcgactcacc acgggccacg  43980
gcttctgact ctctttccgg tactgatgtg atggctgcta tggggatggc gcaatcacaa  44040
gccggattcg gtatggctgc attctgcggt aagcacgaac tcagccagaa cgacaaacaa  44100
aaggctatca actatctgat gcaatttgca cacaaggtat cggggaaata ccgtggtgtg  44160
gcaaagcttg aaggaaatac taaggcaaag gtactgcaag tgctcgcaac attcgcttat  44220
gcggattatt gccgtagtgc cgcgacgccg gggcaagat gcagagattg ccatggtaca  44280
ggccgtgcgg ttgatattgc caaaacagag ctgtggggga gagttgtcga gaaagagtgc  44340
ggaagatgca aaggcgtcgg ctattcaagg atgccagcaa gcgcagcata tcgcgctgtg  44400
acgatgctaa tcccaaacct tacccaaccc acctggtcac gcactgttaa gccgctgtat  44460
gacgctctgg tggtgcaatg ccacaaagaa gagtcaatcg cagacaacat tttgaatgcg  44520
gtcacacgtt agcagcatga ttgccacgga tggcaacata ttaacggcat gatattgact  44580
tattgaataa aattgggtaa atttgactca acgatgggtt aattcgctcg ttgtggtagt  44640
gagatgaaaa gaggcggcgc ttactaccga ttccgcctag ttggtcactt cgacgtatcg  44700
tctggaactc caaccatcgc aggcagagag gtctgcaaaa tgcaatcccg aaacagttcg  44760
caggtaatag ttagagcctg cataacggtt tcgggatttt ttatatctgc acaacaggta  44820
agagcattga gtcgataatc gtgaagagtc ggcgagcctg gttagccagt gctctttccg  44880
ttgtgctgaa ttaagcgaat accggaagca gaaccggatc accaaatgcg tacaggcgtc  44940
atcgccgccc agcaacagca caacccaaac tgagccgtag ccactgtctg tcctgaattc  45000
attagtaata gttacgctgc ggccttttac acatgacctt cgtgaaagcg ggtggcagga  45060
ggtcgcgcta acaacctcct gccgttttgc ccgtgcatat cggtcacgaa caaatctgat  45120
tactaaacac agtagcctgg atttgttcta tcagtaatcg accttattcc taattaaata  45180
gagcaaatcc ccttattggg ggtaagacat gaagatgcca gaaaaacatg acctgttggc  45240
cgccattctc gcggcaaagg aacaaggcat cggggcaatc cttgcgtttg caatggcgta  45300
ccttcgcggc agatataatg gcggtgcgtt tacaaaaaca gtaatcgacg caacgatgtg  45360
cgccattatc gcctagttca ttcgtgacct tctcgacttc gccggactaa gtagcaatct  45420
cgcttatata acgagcgtgt ttatcggcta catcggtact gactcgattg gttcgcttat  45480
caaacgcttc gctgctaaaa aagccggagt agaagatggt agaaatcaat aatcaacgta  45540
aggcgttcct cgatatgctg gcgtggtcgg agggaactga taacggacgt cagaaaacca  45600
gaaatcatgg ttatgacgtc attgtaggcg gagagctatt tactgattac tccgatcacc  45660
ctcgcaaact tgtcacgcta aacccaaaac tcaaatcaac aggcgccgga cgctaccagc  45720
ttctttcccg ttggtgggat gcctaccgca agcagcttgg cctgaaagac ttctctccga  45780
aaagtcagga cgctgtggca ttgcagcaga ttaaggagcg tggcgcttta cctatgattg  45840
```

-continued atcgtggtga tatccgtcag gcaatcgacc gttgcagcaa tatctgggct tcactgccgg 45900
gcgctggtta tggtcagttc gagcataagg ctgacagcct gattgcaaaa ttcaaagaag 45960
cgggcggaac ggtcagagag attgatgtat gagcagagtc accgcgatta tctccgctct 46020
ggttatctgc atcatcgtct gcctgtcatg ggctgttaat cattaccgtg ataacgccat 46080
tacctacaaa gcccagcgcg acaaaaatgc cagagaactg aagctggcga acgcggcaat 46140
tactgacatg cagatgcgtc agcgtgatgt tgctgcgctc gatgcaaaat acacgaagga 46200
gttagctgat gctaaagctg aaaatgatgc tctgcgtgat gatgttgccg ctggtcgtcg 46260
tcggttgcac atcaaagcag tctgtcagtc agtgcgtgaa gccaccaccg cctccggcgt 46320
ggataatgca gcctcccccc gactggcaga caccgctgaa cgggattatt tcaccctcag 46380
agagaggctg atcactatgc aaaaacaact ggaaggaacc cagaagtata ttaatgagca 46440
gtgcagatag agttgcccat atcgatgggc aactcatgca attattgtga gcaatacaca 46500
cgcgcttcca gcggagtata aatgcctaaa gtaataaaac cgagcaatcc atttacgaat 46560
gtttgctggg tttctgtttt aacaacattt tctgcgccgc cacaaatttt ggctgcatcg 46620
acagttttct tctgcccaat tccagaaacg aagaaatgat gggtgatggt ttcctttggt 46680
gctactgctg ccggtttgtt ttgaacagta aacgtctgtt gagcacatcc tgtaataagc 46740
agggccagcg cagtagcgag tagcattttt ttcatggtgt tattcccgat gctttttgaa 46800
gttcgcagaa tcgtatgtgt agaaaattaa acaaacccta aacaatgagt tgaaatttca 46860
tattgttaat atttattaat gtatgtcagg tgcgatgaat cgtcattgta ttcccggatt 46920
aactatgtcc acagccctga cggggaactt ctctgcggga gtgtccggga ataattaaaa 46980
cgatgcacac agggtttagc gcgtacacgt attgcattat gccaacgccc cggtgctgac 47040
acggaagaaa ccggacgtta tgatttagcg tggaaagatt tgtgtagtgt tctgaatgct 47100
ctcagtaaat agtaatgaat tatcaaaggt atagtaatat cttttatgtt catggatatt 47160
tgtaacccat cggaaaactc ctgctttagc aagattttcc ctgtattgct gaaatgtgat 47220
ttctcttgat ttcaacctat cataggacgt ttctataaga tgcgtgtttc ttgagaattt 47280
aacatttaca accttttttaa gtccttttat taacacggtg ttatcgtttt ctaacacgat 47340
gtgaatatta tctgtggcta gatagtaaat ataatgtgag acgttgtgac gttttagttc 47400
agaataaaac aattcacagt ctaaatcttt tcgcacttga tcgaatattt ctttaaaaat 47460
ggcaacctga gccattggta aaaccttcca tgtgatacga gggcgcgtag tttgcattat 47520
cgtttttatc gtttcaatct ggtctgacct ccttgtgttt tgttgatgat ttatgtcaaa 47580
tattaggaat gttttcactt aatagtattg gttgcgtaac aaagtgcggt cctgctggca 47640
ttctggaggg aaatacaacc gacagatgta tgtaaggcca acgtgctcaa atcttcatac 47700
agaaagattt gaagtaatat tttaaccgct agatgaagag caagcgcatg gagcgacaaa 47760
atgaataaag aacaatctgc tgatgatccc tccgtggatc tgattcgtgt aaaaaatatg 47820
cttaatagca ccatttctat gagttaccct gatgttgtaa ttgcatgtat agaacataag 47880
gtgtctctgg aagcattcag agcaattgag gcagcgttgg tgaagcacga taataatatg 47940
aaggattatt ccctggtggt tgactgatca ccataactgc taatcattca aactatttag 48000
tctgtgacag agccaacacg cagtctgtca ctgtcaggaa agtggtaaaa ctgcaactca 48060
attactgcaa tgccctcgta attaagtgaa tttacaatat cgtcctgttc ggagggaaga 48120
acgcgggatg ttcattcttc atcactttta attgatgtat atgctctctt ttctgacgtt 48180

-continued

```
agtctccgac ggcaggcttc aatgacccag gctgagaaat tcccggaccc tttttgctca  48240
agagcgatgt taatttgttc aatcatttgg ttaggaaagc ggatgttgcg ggttgttgtt  48300
ctgcgggttc tgttcttcgt tgacatgagg ttgccccgta ttcagtgtcg ctgatttgta  48360
ttgtctgaag ttgtttttac gttaagttga tgcagatcaa ttaatacgat acctgcgtca  48420
taattgatta tttgacgtgg tttgatggcc tccacgcacg ttgtgatatg tagatgataa  48480
tcattatcac tttacgggtc ctttccggtg atccgacagg ttacggggcg gcgacctcgt  48540
tctgtttatg tttcttgttt gttagccttt tggctaacaa acaagaaaca taaacagaac  48600
gcgtaacctg tcggatcacc ggaaaggacc cgtaaagtga taatgattat catctacata  48660
tcacaacgtg cgtggaggcc atcaaaccac gtcaaataat caattatgac gcaggtatcg  48720
tattaattga tctgcatcaa cttaacgtaa aaacaacttc agacaataca aatcagcgac  48780
actgaatacg gggcaacctc atgtcaacga agaacagaac ccgcagaaca acaacccgca  48840
acatccgctt tcctaaccaa atgattgaac aaattaacat cgctcttgag caaaaagggt  48900
ccgggaattt ctcagcctgg gtcattgaag cctgccgtcg gagactaacg tcagaaaaga  48960
gagcatatac atcaattaaa agtgatgaag aatgaacatc ccgcgttctt ccctccgaac  49020
aggacgatat tgtaaattca cttaattacg agggcattgc agtaattgag ttgcagtttt  49080
accactttcc tgacagtgac agactgcgtg ttggctctgt cacagactaa atagtttgaa  49140
tgattagcag ttatggtgat cagtcaacca ccagggaata atccttcata ttattatcgt  49200
gcttcaccaa cgctgcctca attgctctga atgcttccag agacacctta tgttctatac  49260
atgcaattac aacatcaggg taactcatag aaatggtgct attaagcata tttttacac  49320
gaatcagatc cacggaggga tcatcagcag attgttcttt attcattttg tcgctccatg  49380
cgcttgctct tcatctagcg gttaaaatat tacttcaaat ctttctgtat gaagatttga  49440
gcacgttggc cttacataca tctgtcggtt gtatttccct ccagaatgcc agcaggaccg  49500
cactttgtta cgcaaccaat actattaagt gaaaacattc ctaatatttg acataaatca  49560
tcaacaaaac acaaggaggt cagaccagat tgaaacgata aaaacgataa tgcaaactac  49620
gcgccctcgt atcacatgga aggttttacc aatggctcag gttgccattt ttaaagaaat  49680
attcgatcaa gtgcgaaaag atttagactg tgaattgttt tattctgaac taaaacgtca  49740
caacgtctca cattatattt actatctagc cacagataat attcacatcg tgttagaaaa  49800
cgataacacc gtgttaataa aaggacttaa aaaggttgta aatgttaaat tctcaagaaa  49860
cacgcatctt atagaaacgt cctatgatag gttgaaatca agagaaatca catttcagca  49920
atacagggaa aatcttgcta aagcaggagt tttccgatgg gttacaaata tccatgaaca  49980
taaaagatat tactatacct ttgataattc attactattt actgagagca ttcagaacac  50040
tacacaaatc tttccacgct aaatcataac gtccggtttc ttccgtgtca gcaccggggc  50100
gttggcataa tgcaatacgt gtacgcgcta aaccctgtgt gcatcgtttt aattattccc  50160
ggacactccc gcagagaagt tccccgtcag ggctgtggac atagttaatc cgggaataca  50220
atgacgattc atcgcacctg acatacatta ataaatatta acaatatgaa atttcaactc  50280
attgtttagg gtttgtttaa ttttctacac atacgattct gcgaacttca aaaagcatcg  50340
ggaataacac catgaaaaaa atgctactcg ctactgcgct ggccctgctt attacaggat  50400
gtgctcaaca gacgtttact gttcaaaaca aaccggcagc agtagcacca aaggaaacca  50460
tcacccatca tttcttcgtt tctggaattg ggcagaagaa aactgtcgat gcagccaaaa  50520
tttgtggcgg cgcagaaaat gttgttaaaa cagaaaccca gcaaacattc gtaaatggat  50580
```

tgctcggttt tattacttta ggcatttata ctccgctgga agcgcgtgtg tattgctcac 50640
aataattgca tgagttgccc atcgatatgg gcaactctat ctgcactgct cattaatata 50700
cttctgggtt ccttccagtt gtttttgcat agtgatcagc ctctctctga gggtgaaata 50760
atcccgttca gcggtgtctg ccagtcgggg ggaggctgca ttatccacgc cggaggcggt 50820
ggtggcttca cgcactgact gacagactgc tttgatgtgc aaccgacgac gaccagcggc 50880
aacatcatca cgcagagcat cattttcagc tttagcatca gctaactcct tcgtgtattt 50940
tgcatcgagc gcagcaacat cacgctgacg catctgcatg tcagtaattg ccgcgttcgc 51000
cagcttcagt tctctggcat ttttgtcgcg ctgggctttg taggtaatgg cgttatcacg 51060
gtaatgatta acagcccatg acaggcagac gatgatgcag ataaccagag cggagataat 51120
cgcggtgact ctgctcatac atcaatctct ctgaccgttc cgcccgcttc tttgaatttt 51180
gcaatcaggc tgtcagcctt atgctcgaac tgaccataac cagcgcccgg cagtgaagcc 51240
cagatattgc tgcaacggtc gattgcctga cggatatcac cacgatcaat cataggtaaa 51300
gcgccacgct ccttaatctg ctgcaatgcc acagcgtcct gacttttcgg agagaagtct 51360
ttcaggccaa gctgcttgcg gtaggcatcc caccaacggg aaagaagctg gtagcgtccg 51420
gcgcctgttg atttgagttt tgggtttagc gtgacaagtt tgcgagggtg atcggagtaa 51480
tcagtaaata gctctccgcc tacaatgacg tcataaccat gatttctggt tttctgacgt 51540
ccgttatcag ttccctccga ccacgccagc atatcgagga acgccttacg ttgattattg 51600
atttctacca tcttctactc cggctttttt agcagcgaag cgtttgataa gcgaaccaat 51660
cgagtcagta ccgatgtagc cgataaacac gctcgttata taagcgagat tgctacttag 51720
tccggcgaag tcgagaaggt cacgaatgaa ctaggcgata atggcgcaca tcgttgcgtc 51780
gattactgtt tttgtaaacg caccgccatt atatctgccg cgaaggtacg ccattgcaaa 51840
cgcaaggatt gccccgatgc cttgttcctt tgccgcgaga atggcggcca acaggtcatg 51900
tttttctggc atcttcatgt cttacccccca ataaggggat ttgctctatt taattaggaa 51960
taaggtcgat tactgataga acaaatccag gctactgtgt ttagtaatca gatttgttcg 52020
tgaccgatat gcacgggcaa aacggcagga ggttgttagc gcgacctcct gccacccgct 52080
ttcacgaagg tcatgtgtaa aaggccgcag cgtaactatt actaatgaat tcaggacaga 52140
cagtggctac ggctcagttt gggttgtgct gttgctgggc ggcgatgacg cctgtacgca 52200
tttggtgatc cggttctgct tccggtattc gcttaattca gcacaacgga aagagcactg 52260
gctaaccagg ctcgccgact cttcacgatt atcgactcaa tgctcttacc tgttgtgcag 52320
atataaaaaa tcccgaaacc gttatgcagg ctctaactat tacctgcgaa ctgtttcggg 52380
attgcatttt gcagacctct ctgcctgcga tggttggagt tccagacgat acgtcgaagt 52440
gaccaactag gcggaatcgg tagtaagcgc cgcctctttt catctcacta ccacaacgag 52500
cgaattaacc catcgttgag tcaaatttac ccaattttat tcaataagtc aatatcatgc 52560
cgttaatatg ttgccatccg tggcaatcat gctgctaacg tgtgaccgca ttcaaaatgt 52620
tgtctgcgat tgactcttct ttgtggcatt gcaccaccag agcgtcatac agcggcttaa 52680
cagtgcgtga ccaggtgggt tgggtaaggt ttgggattag catcgtcaca gcgcgatatg 52740
ctgcgcttgc tggcatcctt gaatagccga cgcctttgca tcttccgcac tctttctcga 52800
caactctccc ccacagctct gttttggcaa tatcaaccgc acggcctgta ccatggcaat 52860
ctctgcatct tgcccccggc gtcgcggcac tacggcaata atccgcataa gcgaatgttg 52920
cgagcacttg cagtaccttt gccttagtat ttccttcaag ctttgccaca ccacggtatt 52980
tccccgatac cttgtgtgca aattgcatca gatagttgat agccttttgt ttgtcgttct 53040
ggctgagttc gtgcttaccg cagaatgcag ccataccgaa tccggcttgt gattgcgcca 53100
tccccatagc agccatcaca tcagtaccgg aaagagagtc agaagccgtg gcccgtggtg 53160
agtcgctcat catcgggctt tttggcgaat gaaatttagc tacgctttcg agtctcatgc 53220
gccttctccc tgtacctgaa tcaatgttag gtttccgcag aacactgcgc cggtatcgat 53280
atacatttgg ttggcaaact tgagtggttt cactgctggc gtatgaccaa agatgaacgt 53340
gtccgcgcct ttgatttctt tcacgatccc gttttgtgag ttgctgattc gttcgcggtt 53400
ccagattacc tgctgatgat caactggctt tccaaactcg tattcgtcaa agggataatc 53460
ggcgtggcag ataacatatt ttttatcttt gctcaccagt tcgatgatta acggaagttc 53520
atctgcttta tgggcaagag ctttagccag aatttctttg tcgtaatcga gattaaagaa 53580
ccagccaccg ccattaagca gccagtgatt aacgtttcca cgctctgata agccatcaat 53640
catcatttgc tcatggtttc cacgtacagc tctgaaccag gggaatgtga ttaattccag 53700
gcattcaacg ttctctgcac cacgatcaac caaatcgccc accgagataa gcaggtcttt 53760
tttgttgtcg aatccaatcg tatccagttt gttcatcagg ttcgtgtagc atccgtgcag 53820
atcgccaact acccaaatat ttcggtattt gctgccatca attttttcgt aatagcgcat 53880
ctctttcact ccatccgcga tgaaccatga gaacgtcgtt gacgatggcg tgcattttcc 53940
cgtctttatc atcaacgtat tttctgaccg taccgcgact acatttcagt ctgcgtgcta 54000
cttctgtctg atttccgtat gtttcaacga gcatgtctgg aatggttttt actgagaacg 54060
tcatgcggcc tcacttctgc tatttcgcag gtctttgagt ttctgttggt actctgcctt 54120
gatcgccttg cactcttcga tagtccagcg atggcggtta tggtttgatt cgatttcgtc 54180
tactgcttcc tgcccgatgc ggctaatcag ttcgacgcga tacggaacga gatttccgct 54240
tttgtgctgg ttgcacacca cgcattgctt gtgaatattg cgttcattaa atcggagttg 54300
aggtgccgca gcagttgtcc ggtaatgtcc ggcatcccac tgagcagacg tgagcgttcc 54360
gcacgagata catggtaagt cgcggtctct ttctctgatg aaggcgttta cggcttgttg 54420
ggcttgttta atccagtaac tgcggggctt taaggcgagt tttcgaatct taagtttatc 54480
tttctgtttc tgctcctctc gtcgtcgttt cttctctgct gctttttccg ctttttcgcg 54540
ttctttactt cgtcgttcga gtgctatctt ggttccacac tctggagagc accaccactg 54600
attagcgaat gcagggtgaa accattcccg gcattcatcg tttttacatc gtcttcgcgc 54660
tggtttagcc atcatcttct tcctcgtgca tcgagctatt cggatcgctc atcagttctg 54720
cgcagcagtg ctcacacacg tgaacttcca gcacatgcag cttctgaccg cagttagcgc 54780
acgttaaagc tcgctcgacg ctttcttgtt cgtaacttcg attttggtca atcaccttgt 54840
tttcctcgca cgacgtctta gccaccggat atcccacagg tgagccgtgt agttgaaggt 54900
ttttacgtca gattcttttg ggattggctt gggtttattt ctggtgcgtt tcgttggaag 54960
gtatttgcag ttttcgcaga ttatgtcggt gatacttcgt cgctgtctcg ccacacgtcc 55020
tccttttcct gcggtagtgg taacacccct gttggtgttc tttcacaccg gagacaccat 55080
cgattccagt aaggttgatt tggtcggaag cggttatctt ctttgcattc accgcaccga 55140
taacatcgca tcatgcagct tccctcccga agtcgaaatc aagctgccct ccaaatattt 55200
cgcatgactc agaacaagag ccggtatcga atcttttagc tcgtaccatg tcctgataca 55260
gggcttgata atcattttct gaatacattt tcgcgatacc gtccagcgac attcttcctc 55320

```
ggtacataat ctcctttggc gtttcccgat gtccgtcacg cacatgggat cccgtgatga  55380
cctcattaaa aacacgctgc aatccctcct catctttgca ggcaagtccg attttttgcg  55440
ttgatttttt aatgcagaat atgcagttac cgagatgttc cggtatttgc aaatcgaatg  55500
gttgttgctt ccaccatgcg aggatatctt ccttctcaaa gtctgacagt tcagcaagat  55560
atctgattcc aggctttggc tttagccgct tcggttcatc agctctgatg ccaatccacg  55620
tggtgtaatt ccctcgcccg aaatggtcat cacagtattt ggtgaaggga acgagtttta  55680
atctgtcagt gcagaacgcg ccgccgacgt atggagtgcc atatttcttt accatatcga  55740
taaatggctt cagaacaggc attcgcgtct gaatatcctt tggttcccat accgtataac  55800
catttggctg tccaagctcc gggttgatat caacctgcaa tacggtgagc ggtatatccc  55860
agaacttcac aacttccctg acaaaccgat atgtcattgg atgttcacaa cctgtatcca  55920
tgaaaacgta atgcacgtct ttacctgccc gtcgcttttg ctccattagc cagagcaaat  55980
atgctgacgt cctgccaccg gagaaactaa cgacatttat catgcagccc tgtctcccca  56040
tctcgctttc cactccagag ccagtctcgc ttcgtctgac cacttaacgc cacgctctgt  56100
accgaatgcc tgtataagct ctaatagctc cgcaaattcg cctacacgca tcctgctggt  56160
tgactggcct attaccacaa agccattccc ggcaaggtta ggaacaacat cctgctgctt  56220
taatgctgcg gtaaacacac acttccagct ttctgcatcc agccagcgac catgccattc  56280
aacctgacga gagacgtcac ctaagcaggc ccatagcttc ctgttttggt ctaagctgcg  56340
gttgcgttcc tgaatggtta ctacgattgg tttggttggg tctggaagga tttgctgtac  56400
tgcgtgaata gcgttttgct gatgtgctgg agatcgaatt tcaaaggtta gtttttttcat  56460
gacttccctc tcccccaaat aaaaaggcct gcgattacca gcaggcctgt tattagctca  56520
gtaatgtaga tggtcatctt ttaactccat ataccgccaa tacccgtttc atcgcggcac  56580
tctggcgaca ctccttaaaa accaggttcg tgctcatctt tccttcccgt tcttccctgg  56640
tagcaaaccg gtaatacacc gttcgccaga ccttaccttc gataaccaga agacctgccc  56700
gtgccatttt agccgcggcc tgatttatgc tggttactgt tgcgcctgtt agcgcggcaa  56760
cgtccggcgc acagaagcta ttatgcgtcc ccaggtaatg aataattgcc tctttgcccg  56820
tcatacactt gctcctttca gtccgaactt agctttgatt tctgcgatct tcgccagagc  56880
ctgtgcacga tttagaggtc taccgcccat gacaggaagt tgttttactg gttcagggat  56940
cgcctcacca cggttaattc tcgcagtcat atggacaagc tcatctgcgg ccttacggcg  57000
taattccgca tcagtaagcg cattggcccg catgttctga tacaggttgg taaccagcca  57060
gtagtgcgcg tttgatttcc acggataaga ctccgcatcc ggatacaggc ctcgcttccg  57120
gcaatactcg taaaccatat caaccagctc gctgacgttt ggcagtccgg cggtaacgga  57180
tgcttcttcc cggcaccatg caacaaactg cccgggtgat ggcagaaatg gtcgattctg  57240
ccgacgggct acgcgcattc ctgcgttaac ctgttccatc gtggtgatcc cgttttcccg  57300
aaaagccaga acccactggc gacggatttc gttcacttcg ttctggtcac ggttagccag  57360
gctcgccggg aaagttgcca gtaactggct gaacacaccg ttgatgatct gcgctacctg  57420
ctgtacctgc ggcttttcgt cgtactgttc cggcatgttg ttggcgatcc gacgcatctg  57480
ctcacggtca aagttaacca tctgtgcggc gatgtttttc atagatccac cccgtaaatc  57540
cagtctgtgt ttgtcaggtc gagttttggt ttgctggctg tcacgcctgc ctgttgcttg  57600
ttacggttga tttcgagttg ggtccactta tcgcggagtt tggccgggct cagcacgtta  57660
```

```
ccggaccaga agttgtcctg gcatgcccag cggaacagca cacacatgtc gcggtggtta  57720
cgtccgtcac gttcacgcat caggcggata tcgttagccc acccagcaaa attcggtttt  57780
ctggctgatg gtgcgatagt cttcaccatg tcaaacatcc actctgcggc ggtcaggtct  57840
tctgctgtcc cccacttgct gccgctctga attgcagcat ccggtttcac cacagaaagg  57900
tcgttttctg gctggtcaga ggattcgcca gaattctctg acgaataatc ttttcttttt  57960
tcttttgtaa tagtgtcttt tgtgtccccc tgttttgagg gatagcaatc ccccaatttg  58020
agggatgttt tatccctcgt tttaggggat tttccctcgt tttgagggat gcaccattct  58080
gagatgtttt tatttggtcc aaacatgccg ccttgctgct tgataatatt cattctgacg  58140
agttctaact tggcttcatt gcaccgtttg acaggtaact ttgtaatctc gctaagttga  58200
gaatcggtga ttctgtccat tggtttattc cacccatagg ttttacgcag aatggcaagc  58260
agcactttaa actgtcgctt ggtcagatct gcgcccgaat aagcctcaag cagcatattt  58320
gatagtctgg cgtaaccatc atcgagatct gccacattac gctcctgtcc ggcaaagtta  58380
cctctgccga agttgagtat ttttgctgta tttgtcataa tgactcctgt tgatagatcc  58440
agtaatgacc tcagaactcc atctggattt gttcagaacg ctcggttgcc gccgggcgtt  58500
ttttattggt gagaatcgca gcaacttgtc gcgccaatcg agccatgtcg tcgtcaacga  58560
ccccccattc aagaacagca agcagcattg agaactttgg aatccagtcc ctcttccacc  58620
tgctgatctg cgacttatca acgcccacag cttccgctgt cttctcagtt ccaagcattg  58680
cgattttgtt aagcaacgca ctctcgattc gtagagcctc gttgcgtttg tttgcacgaa  58740
ccatatgtaa gtatttcctt agataacaat tgattgaatg tatgcaaata aatgcataca  58800
ccataggtgt ggtttaattt gatgcccttt ttcagggctg gaatgtgtaa gagcggggtt  58860
atttatgctg ttgttttttt gttactcggg aagggcttta cctcttccgc ataaacgctt  58920
ccatcagcgt ttatagttaa aaaaatcttt cggcctgcat gaatggcctt gttgatcgcg  58980
ctttgatata cgccgagatc tttagctgtc ttggtttgcc caaagcgcat tgcataatct  59040
ttcagggtta tgcgttgttc catacaacct ccttagtaca tgcaaccatt atcaccgcca  59100
gaggtaaaat agtcaacacg cacggtgtta gatatttatc ccttgcggtg atagatttaa  59160
cgtatgagca caaaaaagaa accattaaca caagagcagc ttgaggacgc acgtcgcctt  59220
aaagcaattt atgaaaaaaa gaaaaatgaa cttggcttat cccaggaatc tgtcgcagac  59280
aagatgggga tggggcagtc aggcgttggt gctttattta atggcatcaa tgcattaaat  59340
gcttataacg ccgcattgct tacaaaaatt ctcaaagtta gcgttgaaga atttagccct  59400
tcaatcgcca gagaaatcta cgagatgtat gaagcggtta gtatgcagcc gtcacttaga  59460
agtgagtatg agtaccctgt tttttctcat gttcaggcag ggatgttctc acctaagctt  59520
agaaccttta ccaaaggtga tgcggagaga tgggtaagca caaccaaaaa agccagtgat  59580
tctgcattct ggcttgaggt tgaaggtaat tccatgaccg caccaacagg ctccaagcca  59640
agctttcctg acggaatgtt aattctcgtt gaccctgagc aggctgttga gccaggtgat  59700
ttctgcatag ccagacttgg gggtgatgag tttaccttca agaaactgat cagggatagc  59760
ggtcaggtgt ttttacaacc actaaaccca cagtacccaa tgatcccatg caatgagagt  59820
tgttccgttg tggggaaagt tatcgctagt cagtggcctg aagagacgtt tggctgatcg  59880
gcaaggtgtt ctggtcggcg catagctgat aacaattgag caagaatctt catcgaatta  59940
ggggaatttt cactcccctc agaacataac atagtaaatg gattgaatta tgaagaatgg  60000
tttttatgcg acttaccgca gcaaaaataa agggaaagat aagcgctcaa taaacctgtc  60060
```

-continued

```
tgttttcctt aattctctgc tggctgataa tcatcacctg caggttggct ccaattattt  60120
gtatattcat aaaatcgatg gaaaaacttt tctctttacc aaaacaaatg acaagagtct  60180
ggttcagaag ataaatcgct ctaaagcttc agttgaagat attaagaaca gcctcgcaga  60240
tgacgaatca ttgggattcc catctttttt gtttgttgaa ggcgacacca ttggttttgc  60300
cagaactgtt ttcgggccga ccacatccga tctgacagat tttttaatcg ggaaaggaat  60360
gtcattaagc agtggagagc gcgttcagat agagccactg atgaggggaa ccaccaaaga  60420
cgatgttatg catatgcatt tcatcggccg aacaacggtg aaggtagaag ccaagctacc  60480
tgtatttggc gatatattaa aggtcttagg ggcaacagat attgaagggg agctttttga  60540
ctcattggat atagtcatta agccaaaatt taaaagggat ataaaaaagg ttgccaagga  60600
tattattttt aacccgtcac ctcaattttc agacattagc ctgcgggcaa aagatgaggc  60660
cggagatatt ttaacagaac attatctatc agaaaaaggc catctctcag cgcctctgaa  60720
caaggtcacc aatgctgaga tagctgaaga gatggcatat tgctacgcaa gaatgaaaag  60780
tgatatactg gaatgtttta aaaggcaggt gggcaaagtt aaggattaat tatcaggagt  60840
aattatgcgg aacagaatca tgcctggtgt ttacatagta ataattcctt acgttatcgt  60900
aagcatttgc tatctccttt tccgccacta cattcctggt gtttcttttt cagctcatag  60960
agatggtctt ggggcgacat tgtcatcata tgcaggaacc atgattgcaa tcctgattgc  61020
tgccttgacg tttctaatcg gaagcagaac gcgccgactg gccaagatta gagagtatgg  61080
gtatatgaca tcggtagtta ttgtctatgc ccttagtttt gttgagcttg gagctttgtt  61140
tttctgcggg ttattgcttc tttccagcat aagcggctac atgataccca ctatcgccat  61200
cggcattgcc tctgcatcgt tcattcatat atgcatcctt gttttccaac tatataattt  61260
gaccagagaa caagaataac ccggcctcag cgccgggttt tctttgcctc acgatcgccc  61320
ccaaaacaca taaccaattg tatttattga aaaataaata gatacaactc actaaacata  61380
gcaattcaga tctctcacct accaaacaat gcccccctgc aaaaaataaa ttcatataaa  61440
aaacatacag ataaccatct gcggtgataa attatctctg gcggtgttga cataaatacc  61500
actggcggtg atactgagca catcagcagg acgcactgac caccatgaag gtgacgctct  61560
taaaaattaa gccctgaaga agggcagcat tcaaagcaga aggctttggg gtgtgtgata  61620
cgaaacgaag cattggccgt aagtgcgatt ccggattagc tgccaatgtg ccaatcgcgg  61680
ggggttttcg ttcaggacta caactgccac acaccaccaa agctaactga caggagaatc  61740
cagatggatg cacaaacacg ccgccgcgaa cgtcgcgcag agaaacaggc tcaatggaaa  61800
gcagcaaatc ccctgttggt tggggtaagc gcaaaaccag ttaaccgccc tattctctcg  61860
ctgaatcgca aaccgaaatc acgagtagaa agcgcactaa atccgataga ccttacagtg  61920
ctggctgaat accacaaaca gattgaaagc aacctgcaac gtattgagcg caagaatcag  61980
cgcacatggt acagcaagcc tggcgaacgc ggcataacat gcagtggacg ccagaaaatt  62040
aagggaaaat cgattcctct tatctagtta cttagatatt ggccttggct ttatctcaat  62100
attatatgga tcatagctgg caactaattc agtccagtaa atatcctcaa tagggaataa  62160
tatatgcttt ccattccatc gggaaaaagt tttgttcaac acaccaagct caatcaactc  62220
actaatgtat gggaattgtt ttgatgtaac cacatacttc ctgccttcat taagggctgc  62280
gcacaaaacc atagattgct cttctgtaag gttttgaatt actgatcgca ctttatcgtt  62340
ttgcatctta atgcgttttc ttagcttaaa tcgcttatat ctggcgctgg caatagctga  62400
```

-continued

```
taatcgatgc acattaattg ctagcgaaaa tgcaagagca aagacgaaaa catgccacac  62460
atgaggaata ccgattctct cattaacata ttcaggccag ttatctgggc ttaaaagcag  62520
aagtccaacc cagataacga tcatatacat ggttctctcc agaggttcat tactgaacac  62580
tcgtccgaga ataacgagtg gatccatttc tatactcatc aaactgtagg ggttgtaata  62640
gtttatccga tttctcgctg taggggtaca cgagaaccac cgagcctgat gtggttaaaa  62700
gacaggcaca atctttacta ccgcaatcca ctatttaagg tgatatatgg aagaagaatt  62760
tgaagagttc gaagagcatc ctcaggatgt gatggaacaa taccaggact atccgtatga  62820
ctacgactat tgataaaaat caatggtgtg gacaattcaa gcgatgcaat ggatgcaagc  62880
tgcaatcgga atgcatggtt aagcctgaag aaatgtttcc tgtaatggaa gatgggaaat  62940
atgtcgataa atgggcaata cgaacgacgg caatgattgc cagagaactt ggtaaacaga  63000
acaacaaagc tgcctgatag tggcctttat ttttggcata aataacagaa taaacactgc  63060
actgtgtatt cattccaacg agtgaataca cggagcaatg tcgctcgtaa ctaaacagga  63120
gccgacttgt tctgattatt ggaaatcttc tttgccctcc agtgtgaggg cgattttttta  63180
tctgtgagga tatgaacaga tgtcaaacat caaaaaatac atcattgatt acgactggaa  63240
agcatcaata gaaattgaaa tcgaccatga cgtaatgaca gaggaaaaac ttcaccagat  63300
taataatttc tggtcagact ctgaataccg actcaataaa cacggctctg tattaaatgc  63360
tgtattaatc atgctggcgc aacatgctct gcttatagca atttcaagcg acttaaatgc  63420
atatggtgtt gtgtgtgagt tcgactggaa tgatggaaat ggtcaggaag gatggcctcc  63480
aatggatggt agcgaaggaa taagaattac cgatatcgat acatcaggaa tatttgattc  63540
agatgatatg actatcaagg ccgcctgagt gcggttttac cgcataccaa taacgcttca  63600
ctcgaggcgt ttttcgttat gtataaataa ggagcacacc atgcaatatg ccattgcagg  63660
gtggcctgtt gctggctgcc cttccgaatc tttacttgaa cgaatcaccc gtaaattacg  63720
tgacggatgg aaacgcctta tcgacatact taatcagcca ggagtcccaa agaatggatc  63780
aaacacttat ggctatccag actaaattca ctatcgccac ttttattggc gatgaaaaga  63840
tgtttcgtga agccgtcgac gcttataaaa aatggatatt aatactgaaa ctgagatcaa  63900
gcaaaagcat tcactaaccc cctttcctgt tttcctaatc agcccggcat ttcgcgggcg  63960
atattttcac agctatttca ggagttcagc catgaacgct tattacattc aggatcgtct  64020
tgaggctcag agctgggcgc gtcactacca gcagctcgcc cgtgaagaga aagaggcaga  64080
actggcagac gacatggaaa aaggcctgcc ccagcacctg tttgaatcgc tatgcatcga  64140
tcatttgcaa cgccacgggg ccagcaaaaa atccattacc cgtgcgtttg atgacgatgt  64200
tgagtttcag gagcgcatgg cagaacacat ccggtacatg gttgaaacca ttgctcacca  64260
ccaggttgat attgattcag aggtataaaa cgaatgagta ctgcactcgc aacgctggct  64320
gggaagctgg ctgaacgtgt cggcatggat tctgtcgacc cacaggaact gatcaccact  64380
cttcgccaga cggcatttaa aggtgatgcc agcgatgcgc agttcatcgc attactgatc  64440
gttgccaacc agtacggcct taatccgtgg acgaaagaaa tttacgcctt tcctgataag  64500
cagaatggca tcgttccggt ggtgggcgtt gatggctggt cccgcatcat caatgaaaac  64560
cagcagtttg atggcatgga ctttgagcag gacaatgaat cctgtacatg ccggatttac  64620
cgcaaggacc gtaatcatcc gatctgcgtt accgaatgga tggatgaatg ccgccgcgaa  64680
ccattcaaaa ctcgcgaagg cagagaaatc acggggccgt ggcagtcgca tcccaaacgg  64740
atgttacgtc ataaagccat gattcagtgt gcccgtctgg ccttcggatt tgctggtatc  64800
```

tatgacaagg atgaagccga gcgcattgtc gaaaatactg catacactgc agaacgtcag 64860
ccggaacgcg acatcactcc ggttaacgat gaaaccatgc aggagattaa cactctgctg 64920
atcgccctgg ataaaacatg ggatgacgac ttattgccgc tctgttccca gatatttcgc 64980
cgcgacattc gtgcatcgtc agaactgaca caggccgaag cagtaaaagc tcttggattc 65040
ctgaaacaga aagccgcaga gcagaaggtg gcagcatgac accggacatt atcctgcagc 65100
gtaccgggat cgatgtgaga gctgtcgaac agggggatga tgcgtggcac aaattacggc 65160
tcggcgtcat caccgcttca gaagttcaca acgtgatagc aaaaccccgc tccggaaaga 65220
agtggcctga catgaaaatg tcctacttcc acaccctgct tgctgaggtt tgcaccggtg 65280
tggctccgga agttaacgct aaagcactgg cctggggaaa acagtacgag aacgacgcca 65340
gaaccctgtt tgaattcact tccggcgtga atgttactga atccccgatc atctatcgcg 65400
acgaaagtat gcgtaccgcc tgctctcccg atggtttatg cagtgacggc aacggccttg 65460
aactgaaatg cccgtttacc tcccgggatt tcatgaagtt ccggctcggt ggtttcgagg 65520
ccataaagtc agcttacatg gcccaggtgc agtacagcat gtgggtgacg cgaaaaaatg 65580
cctggtactt tgccaactat gacccgcgta tgaagcgtga aggcctgcat tatgtcgtga 65640
ttgagcggga tgaaaagtac atggcgagtt ttgacgagat cgtgccggag ttcatcgaaa 65700
aaatggacga ggcactggct gaaattggtt ttgtatttgg ggagcaatgg cgatgacgca 65760
tcctcacgat aatatccggg taggcgcaat cactttcgtc tactccgtta caaagcgagg 65820
ctgggtattt cccggccttt ctgttatccg aaatccactg aaagcacagc ggctggctga 65880
ggagataaat aataaacgag ggctgtatg cacaaagcat cttctgttga gttaagaacg 65940
agtatcgaga tggcacatag ccttgctcaa attggaatca ggtttgtgcc aataccagta 66000
gaaacagacg aagaatttca tacgttagcc gcatcccttt cacaaaagct ggaaatgatg 66060
gtggcgaaag cagaagcaga tgagagaaac caggtatgac aaccacggaa tgcatttttc 66120
tggcagcggg cttcatattc tgtgtgctta tgcttgccga catgggactt gttcaatgac 66180
acctcagcag gaaaacgccc ttcgcagcat tgcccgtcag gctaattctg aaatcaaaaa 66240
aagccagaca gcagtttccg gataaaaacg tcgatgacat ttgccgtagc gtactgaaga 66300
agcaccgcga aacggtaacg ctgatgggat tcacaccgac tcatttaagc ctggcaatcg 66360
gcatgttaaa cggcgtcttt aaggaacgat gaacatgaaa agcaaaatca tcagggagct 66420
acaggctcct tttttattat tcgcattcac cctcaagcgt attaaccaac agttcaggga 66480
ttaatgaaag atggcagaca tcattgattc agcatcagaa atagaagaat tacagcgcaa 66540
cacagcaata aaaatgcgcc gcctgaacca ccaggctata tctgccactc attgttgtga 66600
gtgtggcgat ccgatagatg aacgaagacg cctggtcgtt cagggttgtc ggacttgtgc 66660
aagttgccag gaggatctgg aacttatcag taaacagaga ggttcgaagt gagcgaaatt 66720
aactctcagg cactgcgtga agcggcagag caggcaatgc atgacgactg gggatttgac 66780
gcagaccttt tccatgaatt ggtaacacca tcgattgtgc tggaactgct ggatgaacgg 66840
gaaagaaacc agcaatacat caaacgccgc gaccaggaga acgaggatat tgcgctaaca 66900
gtagggaaac tgcgtgttga gcttgaaaca gcaaaatcaa aactcaacga gcagcgtgag 66960
tattacgaag gtgttatctc ggatgggagt aagcgtattg ctaaactgga aagcaacgaa 67020
gtccgtgaag acggaaacca gtttcttgtt gttcgccatc ctgggaagac tcctgttatc 67080
aagcactgca ctggtgacct ggaagagttt ctgcggcagt taatcgaaca agacccgtta 67140

-continued

```
gtaactatcg acatcattac gcatcgctat tacggggttg gaggtcaatg ggttcaggat  67200
gcaggtgagt atctgcatat gatgtctgac gctggcattc gcatcaaagg agagtgagat  67260
cggttttgta aaagataacg cttgtgaaaa tgctgaattt cgcgtcgtct tcacagcgat  67320
gccagagtct gtagtgtcag atgatgaccg tactcaaaca tcgggttgag tattatctta  67380
ctgtttcttt acataaacat tgctgatacc gtttagctga aacgacatac attgcaagga  67440
gtttataaat gagtatcaat gagttagagt ctgagcaaaa agattgggcg ttatcaatgt  67500
tgtgcagatc cggtgtcttg tctccatgca gacatcacga aggtgtttat gtagatgaag  67560
gtatagatat agagtcggca tacaaatatt ccatgaaggt ttataagtct aatgaagaca  67620
aatccccatt ctgcaatgtg cgagaaatga ctgataccgt gcaaaattat tatcacgagt  67680
acggtggaaa cgatacttgc cctctctgta caaaacatat agatgattaa acccaatatt  67740
acataacaat cctcgcactc gcggggattt attttatctg aactcgctac ggcgggtttt  67800
gttttatgga gatgataaat gcacttccga gtcacaggag aatggaatgg agagccattc  67860
aacagagtta tcgaagcgga gaacatcaac gactgctacg accactggat gatatgggcg  67920
cagatagcac atgcagacgt aaccaatatt cgaattgaag aactgaaaga acaccaagcc  67980
gcctgatggc ggtttttct tgcgtgtaat tgcggagact ttgcgatgta cttgacactt  68040
caggagtgga acgcacgcca gcgacgtcca agaagccttg aaacagttcg tcgatgggtt  68100
cgggaatgca ggatattccc acctccggtt aaggatggaa gagagtatct gttccacgaa  68160
tcagcggtaa aggttgactt aaatcgacca gtaacaggtg gccttttgaa gaggatcaga  68220
aatgggaaga aggcgaagtc atgagcgccg ggatttaccc cctaaccttt atataagaaa  68280
caatggatat tactgctaca gggacccaag gacgggtaaa gagtttggat taggcagaga  68340
caggcgaatc gcaatcactg aagctataca ggccaacatt gagttatttt caggacacaa  68400
acacaagcct ctgacagcga gaatcaacag tgataattcc gttacgttac attcatggct  68460
tgatcgctac gaaaaaatcc tggccagcag aggaatcaag cagaagacac tcataaatta  68520
catgagcaaa attaaagcaa taaggagggg tctgcctgat gctccacttg aagacatcac  68580
cacaaaagaa attgcggcaa tgctcaatgg atacatagac gagggcaagg cggcgtcagc  68640
caagttaatc agatcaacac tgagcgatgc attccgagag gcaatagctg aaggccatat  68700
aacaacaaac catgtcgctg ccactcgcgc agcaaaatca gaggtaagga gatcaagact  68760
tacggctgac gaatacctga aaatttatca agcagcagaa tcatcaccat gttggctcag  68820
acttgcaatg gaactggctg ttgttaccgg gcaacgagtt ggtgatttat gcgaaatgaa  68880
gtggtctgat atcgtagatg gatatcttta tgtcgagcaa agcaaaacag gcgtaaaaat  68940
tgccatccca acagcattgc atattgatgc tctcggaata tcaatgaagg aaacacttga  69000
taaatgcaaa gagattcttg gcggagaaac cataattgca tctactcgtc gcgaaccgct  69060
ttcatccggc acagtatcaa ggtattttat gcgcgcacga aaagcatcag gtctttcctt  69120
cgaaggggat ccgcctacct ttcacgagtt gcgcagtttg tctgcaagac tctatgagaa  69180
gcagataagc gataagtttg ctcaacatct tctcgggcat aagtcggaca ccatggcatc  69240
acagtatcgt gatgacagag gcagggagtg ggacaaaatt gaaatcaaat aatgatttta  69300
ttttgactga tagtgacctg ttcgttgcaa caaattgata agcaatgctt ttttataatg  69360
ccaacttagt ataaaaaagc tgaacgagaa acgtaaaatg atataaatat caatatatta  69420
aattagattt tgcataaaaa acagactaca taatactgta aaacacaaca tatgcagtca  69480
ctatgaatca actacttaga tggtattagt gacctgtaac agagcattag cgcaaggtga  69540
```

tttttgtctt cttgcgctaa ttttttgtca tcaaacctgt cgcactccag agaagcacaa 69600
agcctcgcaa tccagtgcaa agctttgtgt gccacccact acgacctgca taaccagtaa 69660
gaagatagca gtgatgtcaa acgacgcagc tgacttcttt tctttcacga cttccccaca 69720
cccagcatgc ataccttttcc gccataactg tagtgaatgt ctgttatgag cgaggagcgg 69780
aagttaacac ttatgaaaaa tggctacgaa gtccgtggct atctatcggc ttattagtac 69840
ttgaaacgct tcttcagaag cctgaagagc taatcgttcg gcgatactat atatgcatta 69900
atagactata tcgttggtat aaacagtgca ccatgcaaca tgaataacag tgggttatcc 69960
aaaaggaagc agaaagctaa atatggaaaa ctacaatacg atgccccgtt aagttcaata 70020
ctactaattt ttagatggaa aacgtatgta atagagagta acttaaaaga gagatcctgt 70080
gttgccgcca aataaattgc ggttatttta ataaaattaa gggttactat atgttggagt 70140
ttagtgttat tgaaagaggc gggtatattc ctgcagtaga aaaaaataag gcattcctac 70200
gagcagatgg ttggaatgac tattcctttg ttacaatgtt ttatcttact gtctttgatg 70260
agcatggtga aaaatgcgat atcggaaatg ttaaaattgg ttttgtaggt caaaaagaag 70320
aagtaagcac ttattcatta atagataaaa aattcagtca actccctgaa atgttttttt 70380
ccttaggtga aagcattgac tactatgtta atctcagcaa attaagcgat ggttttaaac 70440
ataaccttct taaagctatt caggatttag tagtatggcc aaatcgatta gccgacattg 70500
aaaatgaaag cgtccttaac acctcattac ttagaggggt aactctttca gaaattcatg 70560
gacagttcgc acgtgtgtta aatggtttgc cagaattgtc agatttccac ttttcattta 70620
atagaaaaag tgctcccgga ttcagtgatt taactatacc ttttgaggtg acggttaatt 70680
ctatgcccag cacgaacatt catgctttta tcgggcggaa tgggtgtggt aaaacaacaa 70740
ttttgaatgg aatgattggt gcaatcacca acccagaaaa caatgaatat tttttctctg 70800
aaaataatag acttatcgag tcaagaatcc caaagggata ttttcgatcg cttgtttcag 70860
tttcgtttag tgcatttgat ccttttactc ctcctaaaga acaacctgac ccagcaaaag 70920
gtacacaata cttttatatt ggactcaaga atgctgccag caatagttta aaatcactag 70980
gcgatctccg cttagaattc atttcagcat ttattggttg tatgagagta gatagaaaaa 71040
gacaactctg gcttgaagct atcaaaaaac taagtagtga tgaaaacttt tcaaatatgg 71100
aactcatcag cctcatttct aaatatgaag agttaagacg taatgaacca cagattcaag 71160
tggacgatga taaattcact aaattgtttt atgacaatat ccagaaatat ctgcttcgaa 71220
tgagctctgg acatgcaatt gttttattta ctatcacaag attagtagat gtcgttggcg 71280
aaaagtcatt agttttattc gatgaaccag aggttcatct gcatccacct ttgctctctg 71340 ctttttttacg aacattaagc gacttactcg atgcacgcaa tggtgtagca ataattgcaa 71400
ctcattcccc agtagtactg caagaggttc caaaatcctg catgtggaaa gtcctacggt 71460
caagagaagc aataaatatt atccgtccgg atattgagac attcggtgag aacttaggtg 71520
ttttaactcg tgaggtgttt ttacttgaag tgacaaattc tggataccac cacttattat 71580
cgcagtccgt tgattcagag ctttcttatg aaaccattct aaaaaattat aatggtcaga 71640
taggattaga aggtcgaacc gttttaaaag cgatgataat gaacagagat gaaggtaaag 71700
tacaatgaaa aaactacctc ttccagcgag aacttatagc gaaatgctta ataaatgctc 71760
ggaaggtatg atgcagataa atgttagaaa taatttcatt actcacttcc ccactttttt 71820
gcagaaagaa caacaatata gaatattaag ctcgacaggt cagttattta cctacgacag 71880

-continued

```
gacacaccct cttgagccta caaccttagt agttggtaac ctgacaaagg ttaaattaga  71940
aaagctttat gaaaataatc tccgagataa aaacaaaccc gctagaacat attacgatga  72000
catgcttgtt tcatcaggtg aaaaatgtcc attttgtggt gatataggac agacaaaaaa  72060
tatagatcat tttcttccta ttgcacatta tcctgaattt tcggtgatgc ctattaattt  72120
agttccatcg tgccgcgact gcaatatggg agagaaaggt caagttttcg cagtagatga  72180
ggtacaccaa gcgattcatc cctatatcga caaggacatt ttttttcgtg agcaatgggt  72240
atatgcaaat ttcgtttccg gaactccggg tgctatcagt ttttatgttg aatgcccggc  72300
gaactggagg caggaagaca aacacagagc tcttcatcat ttcaagctat taaatattgc  72360
taacaggtat cgtttggagg cagggaagca cttgagtgaa gtgattactc aaagaaactc  72420
tttcgtaaaa gttataagga aatatagttc aaccgcaacg tttcagcagc tacagtcaga  72480
atttattgaa gcaaatctga aacctattat agatttgaat gacttcccca attattggaa  72540
aagagttatg tatcagtgcc tagcaaactc ggaagatttt ttcagaggga tctagaatat  72600
gatgaaagat agaaaattac gacgcttatc ggaagtgaac gaatactttt tatatgagga  72660
gggctgtttt tacaaaatcc ggtagtaact tgctaaccaa ttcctaggca ggtcattggc  72720
aacagtggca tgcaccgaga aggacgtttg taatgtccgc tccggcacat agcagtccta  72780
gggacagtgg cgtacagtca tagatggtcg gtgggaggtg gtacaaattc tctcatgcaa  72840
aaaatatgta aaatcggtag caactggaaa tcattcaaca cccgcactat cggaagttca  72900
ccagccagcc gcagcacgtt cctgcatacg acgtgtctgc ggctctacca tatctcctat  72960
gagcaacgtg ttagcagagc caagccacaa ctctaatttt aatacataat gaatgataat  73020
aataatatta aaaatttcct gtgtaactaa tttactatat ggtttctgat aagaatcatt  73080
gcaaagatca aacaacttgt attacattga cagttaagca gttaatttta tcacctctaa  73140
aatatatcag catctagcat gcaacctatc aaaatggaga gttttatgac taaaaaaacca  73200
tgggaaagaa gacttaaaga tttatcgcac ttgctcaaat gctgcattga tacatatttt  73260
gaccctgaat tatttcgctt gaatttgaat caattcctcc aaaccgcaag aacagtaaca  73320
tttattattc aaaaaaacaa aaaccagatt ataggatatg acatttggta taacaataat  73380
gttattgaaa aatggaaaaa tgatccatta atggcttggg ctaaaaattc tcgcaatacg  73440
atagaaaaac aaggcgattt agaaatgtat agcgaggcaa aggctactct tatttcatct  73500
tacattgaag aaaatgacat tgagtttatt acaaatgaaa gtatgttaaa cattggtata  73560
aaaaagttag tcagacttgc acaaaagaaa ttaccttcat atttaactga atcatctatt  73620
attaaatcag aaagacgatg ggtcgctaat acgctaaaag attacgaatt attacatgcc  73680
ttagctataa tctatggcag aatgtataac tgctgtaact ctcttggcat acaaataaac  73740
aatccaatgg gtgacgatgt gatttcgcca acatcattcg actctttatt tgatgaagcc  73800
aggagaataa cttatttaaa attaaaagat tactccataa gcaaattgtc atttagcatg  73860
atacaatatg acaataaaat aattcctgaa gatattaaag agcgtctaaa actggtagat  73920
aagcctaaaa atatcacttc gacagaagag ttagttgact atacagccaa gcttgcagaa  73980
acgacttttt taaaggacgg ttatcacatt caaacattaa ttttttatga taaacaattc  74040
catccaattg atttaatcaa tacaacattt gaagatcaag cagataaata tattttttgg  74100
cgttatgcag ctgacagagc caaaataaca aatgcctatg gcttcatttg gatatcagag  74160
ctatggctca gaaaagcaag catctactcc aataaaccaa tacatacaat gccaattata  74220
gatgaaagac ttcaggtaat tggaattgat tcaaataata atcaaaaatg tatttcatgg  74280
```

```
aaaatagtta gagaaaacga agaaaaaaaa ccgactttag aaatatcaac agcagactca  74340
aaacatgacg aaaaaccata tttcatgcgt tcagtcttaa aagcaattgg cggtgatgta  74400
aacactatga acaattgagt catagaactt ccattattct cctgaagata ataatcgcca  74460
aataaaccaa tactcagctt tacaatatac taactaaccg cagaacgtta tttcatacaa  74520
cgtttctgcg gcatatcaca aaacgattac tccataacag ggacagcagg ccactcaata  74580
tcaggtgcag ttgatgtatc aacacggttc agcaacaccc gatacttctt ccaggcttcc  74640
agcaacgagg tttcttcctt cgttgcaatt tccagatctg cagcatcctg aagcggcgca  74700
atatgctcac tggctacctg catcaggctt tttttgttt cttccgcctc ccggatccgg  74760
aacagttttt ctgcttccgt atccttcacc caggctgtgc cgttccactt ctgatattcc  74820
cctcccggcg ataaccaggt aaaattttcc ggtaacggac cgagttcaga aataaataac  74880
gcgtcgccgg aagccacgtc atagacggtt ttaccccgat ggtcttcaac gagatgccac  74940
gatgcctcat cactgttgaa aacagccaca aagccagccg gaatatctgg cggtgcaata  75000
tcggtactgt ttgcaggcag accggtatga ggcggaatat atgcgtcacc ttcaccaata  75060
aattcattag ttccggccag cagattataa atttttatgg tccgtggttg ttcactcatt  75120
ctgaatgcca ttatgcaagc ctcacaatat agttaaatgc aatgtttttg acggtgtttt  75180
ccgcgttacc cgcagcgtta acggtgatgg tgtgtccgtg tgaaccaata ctgaaagaat  75240
gggcatgagc accgataaca accggatgct ggtgcgcacc aataccaact gtatgcgcat  75300
gtgcaccggc actcacggct gtaccggaca atgagtgact gtggctgccc tgactgtccg  75360
ttttcgataa ataagcaata ccctgtgtgc tggttccttt aactgtggat aaacttcctg  75420
taatggttgc tgttccatac tgactccagc cagaactgtt catccttaaa ccacttgtgt  75480
gggcatgagc acccgcggcc cctgttgaac cgctcagact gtgagcatga gcccccgtgt  75540
tattcgtcga tttggtgccg taatcgaaac tgcctgttgt tttcgtcccg taatcaaacg  75600
acgatgtggt tttcgtcccc aaatccgtac cggatgcact ggcactgtgg gtgtgcgact  75660
taattccatc ctgttcctga gacaatacag cacgaccgct ggcgggtttc cccttgattg  75720
tccagcctcg catatcagga agcacacccg atggatacgc gacagcaagt tttgggtagg  75780
ctgatttgtc aaacgcctgc ccctgcatca ggacgtagcc agacggaacg atatctgatg  75840
gccacgggat cggcgcacct gccggaaagg ccgaattctc accggcccca aggtattcaa  75900
gaacatctgc aacggaattt tttgccagaa tatccctgcc aacctgagtc agttcagtca  75960
ggctggcggc atcattttcc gcaaaatacg gtaatttatt tttcgccgtg gaaagccctg  76020
ccagcgccgt cagtgtcgca ttcttcggtt gtttacccgc aagcgcgtta gtcatggtgg  76080
tagcaaaatc tggatcattc ccgagcgctg cggccagttc attcagcgta ttcagtgcgt  76140
caggtgacgc gtcgataaca tctgcaatcg cggccagtac aaaagcggtg ttcgcaatct  76200
gggtattgtt tgttcccctg agcgcggttg gtgctgttgg cgttccggtc agtgccggac  76260
tgtccagtgg gcttttctgt tcgtttcatc cattaccacc ttaaccgcct ttggcgttgc  76320
agcaagcgtt tcagacgtgc tgttggttgc actgctgagc tgcactatcc cctttctcgt  76380
tgtgtccgca tcctcaagcg cgacagctga agctatatct tctgcacgtt ttgccgaatt  76440
ttttgcacgt attgccgccg cttctgccgc acttttgctc tgcgatgctg ataccgcact  76500
tcccgcagcc tctgtcgcct tcgtggatgc cgttgacgca ctccccgccg ccgctgtttt  76560
tgcgtctgcc gcggcagagg cgctccgttc cgctgctgtt tcagatgacc tggcattcgt  76620
```

ctcggacgtt tttgccgccc tggcagaatt ttctgccgcc gttgccgagg aagctgcacg 76680
accggcactt gatgatgcgt tcgtttctga tgattttgct gcctcttttg aggccaccgc 76740
atctcgtgct gaagtggcgg cctctgacgc tttcgtggcc gcggtggagg cagacgtggc 76800
ggctgattgt tgtgacgctg cagcattcgt ttctgacgtt ttcgccgcac cggcactggt 76860
ggccgccgcg ttttttgagg actctgcggc tgcggcactt ttttccgctt cagtggcctt 76920
tgctgatgcc gcttctgcgc cggaggacgc ttcctgagct gacgatgcag cctgtccggc 76980
ggacgtgctg gcggcgcgtg ctgagtcagt tgcatcagtc acaagggccg cgacctgagc 77040
agctgatgca ctggcatcgc cggctgattt cttcgcgtct gccgtactct gtgccaccac 77100
ggacgcgtta cgcgccacct cttccaccat cagttcaaga cgacgcagca cctccggccg 77160
ggcatcatcc tccgtcatgg cacagagaaa atcattcagc gtccccggtt gtgaatcttc 77220
atacacggtg atggtcccgg cgtgcgatgg tggaaaaccg tcaacctgca ggatgacact 77280
gtactgaccg tactccacat ccatgctgta acgcccggct tcatccggat tctctgagcc 77340
caccgtgttc accaccaccg tggtgctgtt acgtctggct ttcagctgaa tggtgcagtt 77400
ctgtaccggt tttcctgtgc cgtctttcag gactcctgaa atctttactg ccatattcac 77460
cccacaaaaa agcccaccgg ttccggcggg ctgtcataac actgtgttac ctggctaatc 77520
agaatttata accgacccca acgatgaatc cgtcagtacg ccagtcgcca ctgccggagc 77580
cttcataagc aatatcaaca acgacggacg ctgccggatt aatctgtata cctgcactcc 77640
acgccactga ggtatgccgc attgcacttt cgtccctggc agtggtcgtc tctttcatat 77700
acccgggagt gatttccgtc ttacggtaat ccattgtact gccggaccac cgactgtgag 77760
ccactccggc catggcgtac gcactgacct gcttactgat ttgtaaaacc ggtccggcca 77820
tcacgctcac ataacgtcca cgcaggctct catagtgaaa cgtatcctcc ccggtcatca 77880
ctgtgctgct ctttttcgac gcggcgaacc ccagggaagc catcaccccc acactgtccg 77940
tcagctcata acggtacttc acgttaatcc ctttcagatg actcacaccg gtatccccgc 78000
ccgacaacga cggcaatgta cccggtttca cttgaaaata gcccaccgta aacgtaccat 78060
gtccaccttc cgcacgggcc ggagtgactg tcaccgcaag tgcggcaaag acagcaacgg 78120
caatacacac attacgcatc gttcacctct cactgtttta taataaaacg cccgttcccg 78180
gacgaacctc tgtaacacac tcagaccacg ctgatgccca gcgcctgttt cttaatcacc 78240
ataacctgca catcgctggc aaacgtatac ggcggaatat ctgccgaatg ccgtgtggac 78300
gtaagcgtga acgtcaggat cacgtttccc cgacccgctg gcatgtcaac aatacgggag 78360
aacacctgta ccgcctcgtt cgccgcgcca tcataaatca ccgcaccgtt catcagtact 78420
ttcagataac acatcgaata cgttgtcctg ccgctgacag tacgcttact tccgcgaaac 78480
gtcagcggaa gcaccactat ctggcgatca aaaggatggt catcggtcac ggtgacagta 78540
cgggtacctg acggccagtc cacactgctt tcacgctggc gcggaaaagc cgcgctcgcc 78600
gcctttacaa tgtccccgac gatttttttcc gccctcagcg taccgtttat cgtacagttt 78660
tcagctatcg tcacattact gagcgtcccg gagttcgcat tcacactgcc actgatatcc 78720
gcatttttag cggtcagctt tccgtccggt gtcagggaaa aggccggagg attgccgccg 78780
ctggtaatgg tgggggccgt caggcgcttc aggaacacgt cgttcatgaa tatctggttg 78840
ccctgcgcca caaacatcgg cgtttcattc ccgtttgccg ggtcaataaa tgcgatacga 78900
ttggcggcaa ccagaaactg gctcagtttg ccttcctccg tgtcctccat gctgaggcca 78960
atacccgcga cataatgttt gccgtctttg gtctgctcaa ttttgacagc ccacatggca 79020
ttccacttat cactggcatc cttccactct ttcgaaaact cctccagtct gctggcgtta 79080
tcctccgtca gctcgacttt ttccagcagc tccttgccga gatgggattc ggttatcttg 79140
cctttgaaaa aatccaggta accttccgca tcatcgctcg cccgaccgac ggcctccacg 79200
aatgccgatt tgccaacggt gttcacactg cggatataaa agtaataatc atggcccggt 79260
ttgatattga tactggcggc tatccagtac agcgccgtac caagataacg cgtgctggtt 79320
tcaacctgtc tgatatccgc aatctgcttt tccgagaacc agaactcaaa ctgtaccgtc 79380
gggtcataaa cggcaagatg cggcgtggcg gttatctgaa aatagcccgg cgtcagctca 79440
atcctcgacg gtgctgccgg tgcggcaatc cggaacgata ccgacgccgg atcgccctgc 79500
tgcccccacg catttaccgc ccggactgtc agcctgtagt tccccagcgc cagttgcgtg 79560
aagcggtatg tggtttccgt cgtccgggcc gtgctgacca gccgctcact gccgtcgtcc 79620
gctgttacgg tcagacggag caggaaactc acgcccttca ccaccttcgg tgtgtcccat 79680
cgcgccagca cctgatattc cccgctgtct gcagtgactt ctgcggtcag gtgctgcacc 79740
gctggcggcg tgacaccatt caccgtgcca ctctgttcgc cgtcaaagtg cgccccgtta 79800
tccacgatgg cctctttttc cggcacatgc tgcacggcgg tgatggcata cgtgccgtcg 79860
tcgttctcac ggatactcac gcagcggaac agtcgctggc gcagcgtcgg cagcttcagc 79920
tcccatacgc tgtattcagc aacaccgtca ggaacacggc tcacttttac cttcacgccg 79980
tcggtgacgg actgaacctc cacgctgacc ggattgccac ttccgtcaac caggcttatc 80040
agcgcggtac cggaggatgg cagcgtgatt tcacggtcga gcgtcagcgt ccgggtctgg 80100
ctgttcaccg ccagcacacg accaccggtg ctgataccgg catagtcatc atcgcagatt 80160
tcaataacat cgcccggtac atggcgaagc ccttctgcgc cgacgctgaa atccacggtc 80220
tgcgtttcca gcagttctgt tttaatcagc cacagcccgg cgcggtgtgc ctgcccccgg 80280
ctggtacagc caaaggcatc catcttcgta acattacgac cgtaacgggc aatggcctgc 80340
gtatcttcaa caagctctgt cgccgtctcc cagccgttgt tcgggtcaat ccagttcacc 80400
tcaacggcat tatggcggtc cttcagggcg ctgaagctgt agcggaacgg cgcgccatca 80460
tccggcatca ccacattact gcggttatag gtccacgtct tatccgacgg tcggtcctgc 80520
acgaacgtca gcgtctgccc gttccatacc ggcatacagc gcatcgccga gcagaaatcg 80580
ctgagcacat cccacgcctt acgctgtgtg gtcaggtacg cattacaggt gatgcgcggc 80640
tccgtgccgc caaagccgtc cggcactgac tggtcgcagt actggccgat gacatacagc 80700
gcccatttat ccacatccgc cgcaccaaga cgtttcccca tgccgtagcg cggatgggtc 80760
agcatatccc acagacacca ggccatgttg ttgctgtatg ccggtttaaa cgttccgtcc 80820
cagataccgc tgtattgccg cgtctgcggg ttatagttcg acggcacctg cagaatacgc 80880
ccgcgcagat gataattacg gctcacctgc tggctgccga actgctccga gtccacctgc 80940
acgccgacca gtgccgtgtt cggtgtagcac tgtttcacat cgatgatttc agtgtatgac 81000
gaccagagcg ttttgttctg cagctggtct gtggtgctgt ccggcgtcat cctgcgcatc 81060
cggatattaa acgggcgcgg cggcaggtta cccatcacca ccgaggccag atactgcgag 81120
gtggttttgc ccttaatggt gatgtctttt tccgtcaccc agccaccgtt acgttgtatc 81180
tgaaccagca ggcggacttc cgacggattc ctgtcaccct ttgaggtggt ttccaccagt 81240
gcctgtacac cgaaggtaaa gcgcagacgg tcgatgtttg cagacgtaat ggtgcgggtg 81300
atcggcgtgt catatttcac ttccgtaccc agcaccgtct cggagccgga ggattcaaat 81360

-continued

```
ccctccggcg gagtctgctc ctgctcacca gcccggaaca ccaccgtgac accggatatg  81420
ttggtattcc cctcagtgtc cagcaccggc gtactgttca gcagcacgct ttttaagcca  81480
tccaccggac cttcaatcgg cccttcgctg atggcatcga tcacactcag caactgcgtg  81540
gacttcaggt tgtccttcgc ttcgcgcggg gtatgcccct tactgcttcc tttacccatt  81600
cctcacgctc cataaatgac aaaaccgccc gcaggcggtt tcacataaaa cattttgcat  81660
cagcgaccaa tcaccacaac ctgaccaccg tccccttcgt ctgccgtgct gatctcctga  81720
gaaaccacgc gtgaccccac gcgcatttcc ccgtacagaa caggcagaac attgccctgg  81780
gcaaccatgt tatccagtga ggagaaatag gtgttctgct taccgttatc cgttgtctgt  81840
atacggggag ttctggcttt cggtgccagc atctgcgcca caccaccgag caccatactg  81900
gcaccgagag aaaacaggat gccggtcata ccaccggccc caatggctgc cccccatgct  81960
gcaagggtgg ctccggcggt aaagaatgat ccggcaatgg cggcagcccc caggacaatc  82020
tggaatacgc cacctgactt ggccccggcg actctgggaa caatatgaat tacagcgcca  82080
tcaggcagag tctcatgtaa ctgcgccgtt aacccggacg tgctgacgtc ccgcccggca  82140
atccgtacct gataccagcc gtcgctcagt ttctgacgaa acgccgggag ctgtgtggcc  82200
agtgcccgga tggcttcagc ccccgttttc acacgaaggt cgatgcggcg accaaatcgt  82260
tgtaaatccc cgtaaaggca gatgcgcgcc atgcccggtg acgccagagg gagtgtgtgc  82320
gtcgctgcca tttgtcggtg tacctctctc gtttgctcag ttgttcagga atatggtgca  82380
gcagctcgcc gtcgccgcag taaattgcgg cgtgattcgg cactgatgaa ccaaaacagc  82440
acagcagcac atcgcccggc tgtgccgctg acaacggcac ctgatacagc cccgtcgcct  82500
ccagattatc cagatagaga ttctggccgt tacgccacca gtcatcctca cgatgaaagt  82560
ccggcatctc aatccccgcc agatgataag catcccggaa cagtgtgtaa cagtccgtca  82620
caccgtgctc aaagcgccgc ccggtgagat gcggcacaca gcggaactta tgaatcgtcc  82680
cccggcagac cagccaccac ggcaaatcac tctgcacctg cagccgccgg tcggcctcac  82740
tcagccaggg cagaccaccg gggtggctgt ggaccagcgc cacaatctca ccctgcattt  82800
ctgcctgcag ccagtcttcc ggcgacatac ggaaatagcc tccggctcac cggagatatt  82860
cacgcagggg aaatatcttt ccccctccgg cgtgcttacc acgaagccgc acgactccgc  82920
tggcgcacat cgccgggcgt gcgccagaat cgctgattct gtctgtgtca tgggatttac  82980
tgcgaaagtt tgttaatgga aaggaagccg ccaaagttgc cgacgttatt gcggaactta  83040
caaccgctca ggcatttgct gcatttatcc ttcgtgatat cggacgttgg ctggtcatat  83100
tcatccgcga cagccggacc gctataaccg cactcgtcac cgcgataggt ccaggtgcag  83160
gtgttggcca gcatgatacg tcccggaaaa acagcgccat ccgtttccgt cggcgtggac  83220
agtacaaagg aggcactcac cgcgctcagt tcgctgcact gctcaatgcg ccagcggctg  83280
atcacctcct gctccggatc ggcgtaactg tttccgttga cgaagttcac cgcatccaga  83340
aaacgggcgt aaaccttacg ccggaccacc gttccgccga ccagactctg catatcttcc  83400
gccatcccgg tgaccatacc gtacaggtta gaaaccgtca gcgtggggcg cgtactggtg  83460
cctttgccat tcagttcaaa accgctcccc tgaatgggat acggctgata ctgtcgcccc  83520
tgccaggtga ccggctcacc tttttcgttc tgctcattac agaaaaaata acgttctcca  83580
ccgacctctg tcaggtcgat ttcccagagc accacgctgg ccgactgctc cgcacgggtg  83640
cattcattca gtgtttcctg ccggatatcc tgcatcagtt caccacctgt tcaaactctg  83700
cgctgaactc aacacgcagc atactgaccc gcgacgacca ttttgcgcag gtcaccttta  83760
```

-continued tctgccgcca ctcataaggc ggcgtccaca gaaaggattt ccagcccccg tgctcttcca 83820
gaaacgactc cagtaccgtg gcctcctcac gggggacaga aagcgtcacg ctgtacgttt 83880
tcaggttggc attcagcccg gcaggcgctc gctgagaata gccatcacca aagcgcacct 83940
ttcttacaga agggaccgaa gccacatcca taccgggttt cactttccag cggaaggtct 84000
tcatcgtcca cctccggaga acaggccacc atcacgcatc tgtgtctgaa tttcatcacg 84060
ggcacccttg cgggccatgt catacaccgc cttcagagca gccggaccta tctgcccgtt 84120
cgtgccgtcg ttgttaatca ccacatggtt attctgctca aacgtcccgg acgcctgcga 84180
ccggctgtct gccatgctgc ccggtgtacc gacataaccg ccggtggcat agccgcgcat 84240
cagccggtaa agattcccca cgccaatccg gctggttgcc tccttcgtga agacaaactc 84300
accacggtga acaatccccg ctggctcata tttgccgccg gttcccgtaa atcctccggt 84360
tgcaaaatgg aatttcgccg cagcggcctg aatggctgta ccgcctgacg cggatgcgcc 84420
gccaccaaca gccccgccaa tggcgctgcc gatactcccg acaatcccca ccattgcctg 84480
cttaagcaga atttctgtca tcatggacag cacggaacgg gtgaagctgc gccagttctg 84540
ctcactgccg gtcagcatcg ccgccatatt ctgtgcaata ccatcaaagg tctgcgtggc 84600
tgcacttttt acctgcgaca tactgtccgt ggcgctctct tcccactcac tccagccgga 84660
cttcaggcct gccatccagt tcccgcgaag ctggtcttca gccgcccagg tctttttctg 84720
ctctgacatg acgttattca gcgccagcgg attatcgcca tactgttcct tcaggcgctg 84780
ttccgtggct tcccgttctg cctgccggtc agtcagcccc cggcttttcg catcaatggc 84840
ggcccgtttt gcccgttgct gctgtgcgaa tttatccgcc tgctgcgcca gcgcgttcag 84900
gcgctcctga tacgtaacct tgtcgccaag tgcagccagc tggcgtttgt actccagcgt 84960
ctcatcttta tgcgccagca gggatttctc ctgtgcagac agctggcgac gttgcgccgc 85020
ctcctccagt accgcgaact gactctccgc cttccacaaa tcccggcgct gctggctgat 85080
tttctcattt gctccggcat gcttctccag cgtccggagt tctgcctgaa gcgtcagcag 85140
ggcagcatga gcactgtctt cctgacgatc gcccgcagac accttcacgc tggactgttt 85200
cggctttttc agcgtcgctt cataatcctt tttcgccgcc gccatcagcg tgttgtaatc 85260
cgcctgcagg attttcccgt ctttcagtgc cttgttcagt tcttcctgac gggcggtata 85320
tttctccagc ggcgtctgca gccgttcgta agccttctgc gcctcttcgg tatatttcag 85380
ccgtgacgct tcggtatcgc tctgctgctg cgcatttttg tcctgttgag tctgctgctc 85440
agccttcttt cgggcggctt caagcgcaag acgggccttt tcacgatcat cccagtaacg 85500
cgcccgcgct tcatcgttaa caaaataatc atccttgcgc agattccaga tgtcgtctgc 85560
tttcttatac gcagcctctg ccttaatcag catctcctgc gcggtatcag gacgaccaat 85620
atccagcacc gcatcccaca tggatttgaa tgcccgcgca gtcctgtctg cccaggtctc 85680
cagcgtgccc atgttctctt tcaggcggcg ggtctggtca tcaaaccctt tcgttgcggc 85740
ctcgttcgcc gcctgcaatg ccccggcttc atcgccggaa cgctgcaact gagcaacata 85800
cgcaatctgc tccgccgaca cgttatggaa ctggcgagcc atcgccgtca gccccgacgt 85860
cgggtctgtg gtcagcttcc cgaaggcttc agcgaccttg tccacctcca cgccggatgc 85920
agaggagaaa cgcgccacac tctggctgat ggacgcaatc tgagcctcac cgcttacccc 85980
cgccttaacc agtgcgctga gtgactcgct ggtctggtta aacgtcagcc ctgccgcctg 86040
cccggctctg gacaggacca gcatacgatc tgccgtcagt cccgcctgat tgccggaaag 86100

-continued gaccagcgtt ttgttgaaat cggacagggt tgagttgccc tgataccagg catacgccag 86160
cgcaccggtc gccaccgcca gcgaggtggc ccccaccatc ggcagggtga tcgcaccggc 86220
aagccccctg aacatgggga tcatcccgcc gaaggagtcc ttcacctgcc cccccctgttg 86280
cagcaggatc agccacggac tttgcccgcc tgcaagctgc gtggccacgt cggtgaactg 86340
tgcaggcagc atacgcatgg cggctttata ctgcccgacg gaaatccccg ctttctgtgc 86400
agccagcgcc tgtcggctca gcgactgttc aacgactgcc gctgtttttt tcgcatcact 86460
ttccgtacca gaaaaatgac gcctgactct ggccatctgc tcgtcaaatc tggccgcatc 86520
cagactcaaa tcaacgacca gatcgcctac cggttcagcc ataccggact cctcctgcga 86580
tcccttctga tactgtcatc agcattacgt catcctccgt catgtccgcc acatccgggg 86640
aagcggggat aacttcattc ccgtccgggc caaagcggac acctccggca agccctgccg 86700
ctttctgcat cagcacatca tcttcaggct cttcgtcagc ctcgcgccgg ttcagcagac 86760
tgaaatccag cggatgcata tccggatcgc tgaaaaacag gctgagcacg gtgtacgtca 86820
gcccggaaaa gtgcatatcc agcagaacat catgaaaata atgggtactg taaaagcggt 86880
gccagtcggc atactccgtg gatgacatcc cggcaagcat ggcacgccag tcgggtcgcc 86940
ccatctcacg cgccagtttc agggcaaaac tcagctcacc gtcgaacact ttcccgcaga 87000
aacaggctct gcgggcccgg cgtcctctgt ctgttcaggg gcattattca ccacaaactc 87060
atacatacca gacagccggt acaccacgtt ttcagcatga gaaattgcct ccgtgggcca 87120
ggtggtaagc acttcctgct caatctgttt aacggcttca ttcatggacg gcatctgcgt 87180
cttctgcgga tggttatgcc acagggacat cgccaccaga aacgcgccgg ttctgatggc 87240
gtcttccaca gtaaacttcc ggttgctgtc tgactccgcc tgttctgcct gccgtttcat 87300
cagggcgaga tgctcaatgc gctgcagggc tgacagttca gaaagcgtga cggtcacacc 87360
gttatgttca aatgattcgg ttttcaggaa catcgctgac tctccggatt aactggcggt 87420
gacggtaatt tctgcaaccg cagcaaactc accattaccg gatacaaccg gaatgttgac 87480
cttgcctgca gcaacgccgt tcacggtgat ggtcatacca ctgaccgaca cggtggcttt 87540
tgttttatcc gcagacaccg cacgaaagct cttgtcggtt acgccctccg gctggaaggc 87600
cacggtcagc gtggtgctct gccctttcac caccgaggtg ctggcaggcg tcacggtcat 87660
gccggttgcc gctgttaccg tgctgcgatc ttctgccatc gacggacgtc ccacattggt 87720
gactttcacc gtgcgggtga tcacttcctt cgccgtcacc gccttaccga tactgctgac 87780
ccagccacgg aacacatcga ccgtgccgtt cgggaagcgg attttatagg cacgggtatc 87840
gccttcatta aaccacgcca gcagcgcctg ctgcccctgc tctccgggca tccacgccag 87900
cgtgaagctg gtatctccgg cagatttctg cccctgcccg gtcgcagtcc agtctgcatc 87960
ttcatcatcg agatagctgt cgtcatagga ctcagcggtc agttcgccgg gcgtcaggtc 88020
tttaactttt gccagacgcg accagtcaac gtctgaaagc ggattcgcgt aagggtcacc 88080
gctcccctta taaacccaca gggtggtccc ggcacctttc accggcattg taggatttgg 88140
tacaggcata gcgtcctcac atttcatagg taatgacata agtcagatcg gctgaactcc 88200
acaagcccgc atcatcgtcg cgccggtagt catagccgct ggccaccata ctggtgatca 88260
aatctgacag tgccgggata tcgctcatca ccggataaat ccgggactcc atccacgcat 88320
ccagctctga atccggcacc tgagcaggca ggaaaacttc gatatgcagc tccgcctgcc 88380
aggtatcgct gtccagctct tcgcccgtgt attcagcgcc ggtgagataa acggcaactg 88440
ccggaaaatc cgcctcatca aaaacagcgg ggcgaccatc aaaaaacgtc gccccggtgt 88500

-continued catgcttctc cagtgcatcc agtacggctg cacggagttc agtatgtttc atcgctttat 88560
taccatcctc agttgatgct gcagcgcata gcccagctct ttcggaagac gttcacgccg 88620
tatccgctca atattttgtt taaacgccgt ggtcagcggc accgccatcg ggattttcac 88680
cacatcaatg gggtaacggt tttcccagc cacacgctgc atgacatgcc accggccatt 88740
tttcagttgc tgaataaacg cgccgggaat acgacggtta cccaccacaa gcacgctgcc 88800
gccacctttc agggatgaac gctgcccctt tttacgacgc ctgcggcgcg aaaggacaac 88860
ccgcgcatta cccagcttga ttacgggcaa atccccccgg ttaactttga ttctggcctg 88920
cggatttttg accgtggccc ttttcagcct ggccctttcc tttaccagtt tccggcgtac 88980
ctttgtctca cgggcaacct gtgacgccga ctgcgatatc gcggatgaag caacgcggtt 89040
aatggccatt gcggcggcac caggcaccgc cgttttgctg atacggctga ggttttcaac 89100
ggcctgctca agacctttta tggccataca tccccctttc agcggcgacg gttaacggca 89160
ggcggtacgc cccgtccaag ccagagatga caacttccgc catcatccgg cgaaacccga 89220
tctacccaga aattttcctc accgatggtc agcgtgtctc cacgccgcag ctgccgcacc 89280
tcatcagtcc ggacaaacag ggacgggctg gagccttcaa cgcgcacgcc ctgtccggca 89340
tagctgatat tttcagggtc atcaaaaaca ccacgtatca ccgcacctga ctgctcaccg 89400
gatgtaatgg tggctgacgt tcccatgtac ccgcgtatcg tttcatcggc gcgggcaatg 89460
gcagcatcga acaggttatc gaaatcagcc acagcgcctc ccgttattgc attctggcca 89520
ggccgcgctc tgtcatttcg gctgccacac cggcagagac acgaaacgcc gttcccggca 89580
gcacaaatgc cacaggttca tcccgcgtgg cgtgaagtgc atcagtatgc agcttcacca 89640
gtgccacgac cgtgaccagt tcagacgtat ccagaatcac ggtatccggc tgcgctgatc 89700
ccacctcatt ttcatgtccg gtcagcacat tttcccggct gagaggggtg tcctgaccgg 89760
cagtttcatc cgtgtcatca agctcctctt tcagctctgc cacacggagc gccagttctt 89820
ctttcgtccc cgtcaggctg acatcacggt tcagttgttc acccagcgag cggagacggg 89880
caatcagttc atctttcgtc atggactcct ccacagagaa acaatggccc cgaagggcca 89940
tgattacgcc agttgtacgg acacgaactc atcagggtca gccagcagca tcagcggtgc 90000
tgactgaatc atggtgaact cacgcgccgg atcgccggtg gtcacccagt tttcgggta 90060
acgggcagag gcgttaatgc cttcgcgctg tgcgtccgca tcctgaatgc agccataggt 90120
gcgcagaccg cgtgcctgag tgttccccag caccatcgtg ttgtccggca ggaagttctt 90180
tttgacgccg ttttccacgt actgtccgga atacacgacg atggccacat cgccatacat 90240
ccccttatag gacaccgctt tgcccaggtc tttcaccgct gtctccagct cggaattaga 90300
gccacgacgg gtatccagct tctccttgac ggctttgaag gaacggaaca gcgcccagcc 90360
tttcggatcg aacacgatga tattcaccac accgctggcg ttcagcgcgt aggcttcgat 90420
atcgtcggtc gggtcatacg tggacttgtc acgcttgctc cactccgtgc cgccggactg 90480
cgtgatgtta ttctcctcac tgcggcccat atccacctca accggatcga aggcttcacc 90540
ggtcatggtg tatttgccct taagcacggc agaaactgcc tgcatctctt cgacctgagc 90600
aatggccagc tcttcgtcac gcatgttctg catgatgatg cgacggcggc ggtaagccgg 90660
gtccgccaga ttctgcggat cttcatccgg caggcgacgc agggtcatct gcggattcac 90720
ttcatgcttc ggcttgacat atcccggcgt aaattcagag gtggagccgc cacgggaacg 90780
gataacctca ccggaaacaa tcggcgaaac gtacagcgcc atgtttacca gtcccggaat 90840

-continued

```
ttgtgagaga tagactttct ccgtggtgaa gggatagctc tcacggaaaa agagacgcag  90900
aaacagcgga tcaaacttaa atttctgctc atttgccgcc agcagttggg cggttgtgta  90960
catcgacata aaaaaatccc gtaaaaaaag ccgcacaggc ggcctttagt gatgaagggt  91020
aaagttaaac gatgctgatt gccgttccgg caaacgcggt ccgttttttc gtctcgtcgc  91080
tggcagcctc cggccagagc acatcctcat aacggaacgt gccggacttg tagaacgtca  91140
gcgtggtgct ggtctggtca gcagcaaccg caagaatgcc aacggcagca ccgtcggtgg  91200
tgccatccca cgcaaccagc ttacggctgg aggtgtccag catcagcggg gtcattgcag  91260
gcgctttcgc actcaatccg ccgggcgcgg ttgcggtatg agccgggtca ctgttgccct  91320
gcggctggta atgggtaaag gtttctttgc tcgtcataaa catcccttac actggtgtgt  91380
tcagcaaatc gttaacggca tcagatgccg ggttacctgc agccagcggt gccggtgccc  91440
cctgcatcag acgatccagc gcagtgtcac tgcgcgcctg tgcactctgt ggtgctgcgg  91500
ccagaatgcg gcgggccgtt ttcacggtca taccgggggt ttctgccagc acgcgtgcct  91560
gttcttcgcg tccgtgagcc tcctcacagt tgaggatccc cataatgcgg ctgttttctg  91620
ccgcaaccgc tgcggtgatc tgcgcgttca cgtccggctg cgccgcgctg gcgttctcgc  91680
cctccgtcgc tggcaccacg tcagtaacgt cagcctgcga agcagtggct gaaacagttg  91740
ttgattgagt ctctttggtc attcgccctc ctgagagacg ggatttacgt gcatccagtg  91800
catcacgcat gacggtgatc gcatcggtgc tgttaacaag ttcatcagcc agtccggcat  91860
caatggcctc ctgaccgctg tacactgcag cctcggtatc cagcacaacc tgcacggaca  91920
ggccggtata tgccgacacc ttctgcgcaa acatctggcg ggttgcgtcc atccgggact  91980
gcagtgtctc ccggacgtca tccggaagat ggctgtaggg gttgccatcc accttatggc  92040
tgccgctgta aatcagcgtg atttccacac cctgtttctc cagcgcagca ccgtaattac  92100
tgtgagccat catgacgccg atggagcctg tccgggcggt ctgcgtgacc agacgccggg  92160
aggcggcact ggcaagcaac tgacctgcac tgcagttcat gtcgttggca agcgcccata  92220
ccggttttat gtcacgcaca cgggcgatga tgtcagcgca gtcaaatgcc cccgccacca  92280
tcccgccggg cgtgtccata tcgagcagaa tgccgtccac catcggatcg ctggcagcct  92340
gttgcagacg ggcgataatg ccgttgtaac cggtcatccc cgagtacggc tgcagcgccc  92400
gcgtccggct gaccagcgtg ccggacaccg gcagcacggc gatgccgttc atgacctgat  92460
aactgcgggc ctgtcgtggt ccgtcatcat caccggataa tgccagcgtc gcgagtgcct  92520
cctgggcagt caggctgtcg ccggacaccg catccgtcag gctgctgatc ccaagctggc  92580
ctgcaagcgc acaaaagaaa acccgcgcat aggcgggttc aagcatcagc ggctcattaa  92640
aggccatgct ggcaatatgc gggagattac gcagctctgc tgtcactctt ctcctcctct  92700
gttgattgtc gcagcccgga ttcaaatgct gcagccgccc aggcgggcgg tttaagaccg  92760
gctgcacggc gctccatcgt ttcacggacc tgctgggcaa aaatttcctg atagtcgtca  92820
ccgcgttttg cgcactcttt ctcgtaggta ctcagtccgg cttctatcag catcaccgct  92880
tcctgaactt ctttcagacc atcgatggcc atacgaccgg agcctatcca gtcgcagttc  92940
ccccaggcac tgcgggcttc ctgaaaactg aagcgcgctt ttgaaggtaa cgtcaccacg  93000
cggcgaacga tggcctcttc cagccagcac agaaacatct ggctcgcctg acgggatgcg  93060
acgaattttc gccgccccat aaagtacgcc cacgactcgt tcgcactggc ccgtgccgtg  93120
gagtagctca tctgggcgta attccgggaa agctgctcat acgagacacc cagcccggca  93180
gcgatatacc gcagcagtga ctgctcaaac acggagtagc cgttatccgt atcctgagcc  93240
```

-continued gtctgcaggt tcagtgagtc acccggcatc aggtgcggta cttttgcgcc tcccagccgg 93300
accggcgctg cggcgtaata cgcggcaatt tcaccaatcc agccggtcag cctttcccgc 93360
tgctcctgac tgttcgcgcc cagaataaaa tccatcgctg actgcgtatc cagctcactc 93420
tcaatggtgg cggcatacat cgccttcaca atggcgctct gcagctgcgt gttctgcagc 93480
gtgtcgagca tcttcatctg ctccatcacg ctgtaaaaca catttgcacc gcgagtctgc 93540
ccgtcctcca cgggttcaaa aacgtgaatg aacgaggcgc gcccgccggg taactcacgg 93600
ggtatccatg tccatttctg cggcatccag ccaggatacc cgtcctcgct gacgtaatat 93660
cccagcgccg caccgctgtc attaatctgc acaccggcac ggcagttccg gctgtcgccg 93720
gtattgttcg ggttgctgat gcgcttcggg ctgaccatcc ggaactgtgt ccggaaaagc 93780
cgcgacgaac tggtatccca ggtggcctga acgaacagtt caccgttaaa ggcgtgcatg 93840
gccacacctt cccgaatcat catggtaaac gtgcgttttc gctcaacgtc aatgcagcag 93900
cagtcatcct cggcaaactc tttccatgcc gcttcaacct cgcgggaaaa ggcacgggct 93960
tcttcctccc cgatgcccag atagcgccag cttgggcgat gactgagccg gaaaaaagac 94020
ccgacgatat gatcctgatg cagctggatg gcgttggcgg catagccgtt attgcgtacc 94080
agatcgtctg cgcgggcatt gccacgggta aagttgggca acagggctgc atccacactt 94140
tcactcggtg ggttccacga ccgcaactgc cctccaaatc cgctgccacc gccgtgataa 94200
ccggcatatt cgcgcagcga tgtcatgccg tccggcccca gaagggtggg aatggtgggc 94260
gttttcatac ataaaatcct gcaggtcccc tgcgtcgctg tgtcatgccg gtctgcactt 94320
ccagctctgc aatatatttt ttcaggtcag acacggaagt ggccgtaaac tccacccttc 94380
gtccgtcttt ctgtactgtt gccacccgtt tacctgtcat caggtcatgc agtgccgcac 94440
gggcagcggc aagttcttcc tgtcgcgtca ttcatcctct ccggataagg cacgggcgta 94500
atctgccagt gttttcttgt tggttgctgc accatcctct tcctgcaggc tcgccagcag 94560
cgcactgaga tccagctgcc agcgggaaat actgatgcgc agcgccgcca gcgcataaac 94620
gaagcagtcg agtgcctcat tgcgtcgctt tttgctgtcc cacagtattt ttttcctgcc 94680
atccacccat ttttcgacct gctcttcagc agtcagctgc tgcgcttcgg tcagatcaaa 94740
aatatccggg ttattcggga agtgaacggc accgggaagc ggttcatccc cttccggcgt 94800
cagtgtgaag cggttataaa tctgctcttt cgcggtatcc gtaccgattt cggtaaggta 94860
aaccccgttt ttgtttcgct tacgtggcat gctggccacc ggctttccgt agacggatgc 94920
ccctttaatg gggatcaccc ggaacagccc atgtttttc gagcgttcat acacaatggt 94980
cgggtcaatc ccgccagtat cccagcagat acgggatatc gacatttctg caccattccg 95040
gcgggtatag gttttattga tggcctcatc cacacgcagc agcgtctgtt catcgtcgtg 95100
gcggcccata ataatctgcc ggtcaatcag ccagctttcc tcacccggcc cccatcccca 95160
tacgcgcatt tcgtagcggt ccagctggga gtcgataccg gcggtcaggt aagccacacg 95220
gtcaggaacg ggcgctgaat aatgctcttt ccgctctgcc atcacttcag catccggacg 95280
ttcgccaatt ttcgcctccc acgtctcacc gagcgtggtg tttacgaagg ttttacgttt 95340
tcccgtatcc cctttcgttt tcatccagtc tttgacaatc tgcacccagg tggtgaacgg 95400
gctgtacgct gtccagatgt gaaaggtcac actgtcaggt ggctcaatct cttcaccgga 95460
tgacgaaaac cagagaatgc catcacgggt ccagatcccg gtcttttcgc agatataacg 95520
ggcatcagta aagtccagct cctgctggcg gatgacgcag gcattatgct cgcagagata 95580

-continued

```
aaacacgctg gaggggtcat ccggcgtcca tttgaggcca aacggcgtct ctttgtcgcc  95640

aaatttaaga tactgctcct ccccgcaatg cgggcaggca acatgaaaac gcataaaatg  95700

cggggattca ctggctgcac gctcaatctg acaggtgcct ctcacttttg gcgtggagcc  95760

acggatggac tttggccaga ccgagccttc aatacgcttg tcacccagga acgtcggaga  95820

gccttcctgt tcaatatcat catcaaaagc agcaagttca tcataacccg ccacatccac  95880

cgacttttca cggtagtttt ttgccgcttt accgcccagg caccagaagc cacgcccatt  95940

agtgaaacgc ttcatggtga gcgtgttatc ccggtgcttt ttgccatacc acggggccag  96000

cgccagcagc gacggaatat cacgaatagt cggctcaacg tgggttttca taaagttctc  96060

ggcatcacca tccgtcggca accagataag ggtgttgcgc tgcttatgct ctataaagta  96120

ggcataaaca cccagcagca ttttggaata accgacacgg gcagacttca ccacattcac  96180

ctcacggatg tagtcgctgc ccatcgcatt catgatggcc cgctgaaagg gcagtgtttc  96240

ccagcgccct tcctggtatg cggattcttt cgggagatag taattagcat ccgcccattc  96300

aacggcggtc tgtggctccg gcctgaacag tgagcgaagc ccggcgcgga caaaatgccg  96360

cagcctgtta acctgactgt tcgatatatt cactcagcaa ccccggtatc agttcatcca  96420

gcgcggctgc tttgttcatg gctttgatga tatcccgttt caggaaatca acatgtcggt  96480

tttccagttc cggaaaacgc cgctgcaccg acagggggag cccgtcgaga atactggcaa  96540

tttcacctgc gatccgcgac agcacgaaag tacagaatgc ggtttccacc acttcagcgg  96600

agtctctggc attcttcagt tcctgtgcgt cggcctgcgc acgcgtaagt cgatggcgtt  96660

cgtactcaat agttcctggc tggagatctg cctcgctggc ctgccgcagt tcttcaacct  96720

cccggcgcag cttttcgttc tcaatttcag catccctttc ggcataccat tttatgacgg  96780

cggcagagtc ataaagcacc tcattaccct tgccaccgcc tcgcagaacg ggcattccct  96840

gttcctgcca gttctgaatg gtacggatac tcgcaccgaa aatgtcagcc agctgctttt  96900

tgttgacttc cattgttcat tccacggaca aaaacagaga aaggaaacga cagaggccaa  96960

aaagcctcgc tttcagcacc tgtcgtttcc tttcttttca gagggtattt taaataaaaa  97020

cattaagtta tgacgaagaa gaacggaaac gccttaaacc ggaaaatttt cataaatagc  97080

gaaaacccgc gaggtcgccg cccaggtcgc cgcccgtcaa tcggcccttt agtggagc    97138
```

```
<210> SEQ ID NO 12
<211> LENGTH: 28
<212> TYPE: DNA
<213> ORGANISM: Artificial Sequence
<220> FEATURE:
<223> OTHER INFORMATION: Polynucleotide sequence used in Examples 1 and
      9

<400> SEQUENCE: 12

gcaatatcag caccaacaga aacaacct                                      28


<210> SEQ ID NO 13
<211> LENGTH: 48502
<212> TYPE: DNA
<213> ORGANISM: Enterobacteria phage lambda

<400> SEQUENCE: 13

gggcggcgac ctcgcgggtt ttcgctattt atgaaaattt tccggtttaa ggcgtttccg     60

ttcttcttcg tcataactta atgtttttat ttaaaatacc ctctgaaaag aaaggaaacg    120

acaggtgctg aaagcgaggc tttttggcct ctgtcgtttc ctttctctgt ttttgtccgt    180
```

-continued

```
ggaatgaaca atggaagtca acaaaaagca gctggctgac attttcggtg cgagtatccg    240
taccattcag aactggcagg aacagggaat gcccgttctg cgaggcggtg gcaagggtaa    300
tgaggtgctt tatgactctg ccgccgtcat aaaatggtat gccgaaaggg atgctgaaat    360
tgagaacgaa aagctgcgcc gggaggttga agaactgcgg caggccagcg aggcagatct    420
ccagccagga actattgagt acgaacgcca tcgacttacg cgtgcgcagg ccgacgcaca    480
ggaactgaag aatgccagag actccgctga agtggtggaa accgcattct gtactttcgt    540
gctgtcgcgg atcgcaggtg aaattgccag tattctcgac gggctccccc tgtcggtgca    600
gcggcgtttt ccggaactgg aaaaccgaca tgttgatttc ctgaaacggg atatcatcaa    660
agccatgaac aaagcagccg cgctggatga actgataccg gggttgctga gtgaatatat    720
cgaacagtca ggttaacagg ctgcggcatt ttgtccgcgc cgggcttcgc tcactgttca    780
ggccggagcc acagaccgcc gttgaatggg cggatgctaa ttactatctc ccgaaagaat    840
ccgcatacca ggaagggcgc tgggaaacac tgccctttca gcgggccatc atgaatgcga    900
tgggcagcga ctacatccgt gaggtgaatg tggtgaagtc tgcccgtgtc ggttattcca    960
aaatgctgct gggtgtttat gcctacttta tagagcataa gcagcgcaac acccttatct   1020
ggttgccgac ggatggtgat gccgagaact ttatgaaaac ccacgttgag ccgactattc   1080
gtgatattcc gtcgctgctg gcgctggccc cgtggtatgg caaaaagcac cgggataaca   1140
cgctcaccat gaagcgtttc actaatgggc gtggcttctg gtgcctgggc ggtaaagcgg   1200
caaaaaacta ccgtgaaaag tcggtggatg tggcgggtta tgatgaactt gctgcttttg   1260
atgatgatat tgaacaggaa ggctctccga cgttcctggg tgacaagcgt attgaaggct   1320
cggtctggcc aaagtccatc cgtggctcca cgccaaaagt gagaggcacc tgtcagattg   1380
agcgtgcagc cagtgaatcc ccgcatttta tgcgttttca tgttgcctgc ccgcattgcg   1440
gggaggagca gtatcttaaa tttggcgaca aagagacgcc gtttggcctc aaatggacgc   1500
cggatgaccc ctccagcgtg ttttatctct gcgagcataa tgcctgcgtc atccgccagc   1560
aggagctgga ctttactgat gcccgttata tctgcgaaaa gaccgggatc tggacccgtg   1620
atggcattct ctggttttcg tcatccggtg aagagattga gccacctgac agtgtgacct   1680
ttcacatctg gacagcgtac agcccgttca ccacctgggt gcagattgtc aaagactgga   1740
tgaaaacgaa aggggatacg ggaaaacgta aaaccttcgt aaacaccacg ctcggtgaga   1800
cgtgggaggc gaaaattggc gaacgtccgg atgctgaagt gatggcagag cggaaagagc   1860
attattcagc gcccgttcct gaccgtgtgg cttacctgac cgccggtatc gactcccagc   1920
tggaccgcta cgaaatgcgc gtatggggat gggggccggg tgaggaaagc tggctgattg   1980
accggcagat tattatgggc cgccacgacg atgaacagac gctgctgcgt gtggatgagg   2040
ccatcaataa aacctatacc cgccggaatg gtgcagaaat gtcgatatcc cgtatctgct   2100
gggatactgg cgggattgac ccgaccattg tgtatgaacg ctcgaaaaaa catgggctgt   2160
tccgggtgat ccccattaaa ggggcatccg tctacggaaa gccggtggcc agcatgccac   2220
gtaagcgaaa caaaaacggg gtttacctta ccgaaatcgg tacggatacc gcgaaagagc   2280
agatttataa ccgcttcaca ctgacgccgg aaggggatga accgcttccc ggtgccgttc   2340
acttcccgaa taacccggat atttttgatc tgaccgaagc gcagcagctg actgctgaag   2400
agcaggtcga aaaatgggtg gatggcagga aaaaaatact gtgggacagc aaaaagcgac   2460
gcaatgaggc actcgactgc ttcgtttatg cgctggcggc gctgcgcatc agtatttccc   2520
gctggcagct ggatctcagt gcgctgctgg cgagcctgca ggaagaggat ggtgcagcaa   2580
```

-continued

```
ccaacaagaa aacactggca gattacgccc gtgccttatc cggagaggat gaatgacgcg   2640
acaggaagaa cttgccgctg cccgtgcggc actgcatgac ctgatgacag gtaaacgggt   2700
ggcaacagta cagaaagacg gacgaagggt ggagtttacg gccacttccg tgtctgacct   2760
gaaaaaatat attgcagagc tggaagtgca gaccggcatg acacagcgac gcaggggacc   2820
tgcaggattt tatgtatgaa aacgcccacc attcccaccc ttctggggcc ggacggcatg   2880
acatcgctgc gcgaatatgc cggttatcac ggcggtggca gcggatttgg agggcagttg   2940
cggtcgtgga acccaccgag tgaaagtgtg gatgcagccc tgttgcccaa ctttacccgt   3000
ggcaatgccc gcgcagacga tctggtacgc aataacggct atgccgccaa cgccatccag   3060
ctgcatcagg atcatatcgt cgggtctttt ttccggctca gtcatcgccc aagctggcgc   3120
tatctgggca tcggggagga agaagcccgt gccttttccc gcgaggttga agcggcatgg   3180
aaagagtttg ccgaggatga ctgctgctgc attgacgttg agcgaaaacg cacgtttacc   3240
atgatgattc gggaaggtgt ggccatgcac gcctttaacg gtgaactgtt cgttcaggcc   3300
acctgggata ccagttcgtc gcggcttttc cggacacagt tccggatggt cagcccgaag   3360
cgcatcagca acccgaacaa taccggcgac agccggaact gccgtgccgg tgtgcagatt   3420
aatgacagcg gtgcggcgct gggatattac gtcagcgagg acgggtatcc tggctggatg   3480
ccgcagaaat ggacatggat accccgtgag ttacccggcg ggcgcgcctc gttcattcac   3540
gtttttgaac ccgtggagga cgggcagact cgcggtgcaa atgtgtttta cagcgtgatg   3600
gagcagatga agatgctcga cacgctgcag aacacgcagc tgcagagcgc cattgtgaag   3660
gcgatgtatg ccgccaccat tgagagtgag ctggatacgc agtcagcgat ggattttatt   3720
ctgggcgcga acagtcagga gcagcgggaa aggctgaccg gctggattgg tgaaattgcc   3780
gcgtattacg ccgcagcgcc ggtccggctg ggaggcgcaa aagtaccgca cctgatgccg   3840
ggtgactcac tgaacctgca gacggctcag gatacggata acggctactc cgtgtttgag   3900
cagtcactgc tgcggtatat cgctgccggg ctgggtgtct cgtatgagca gctttcccgg   3960
aattacgccc agatgagcta ctccacggca cgggccagtg cgaacgagtc gtgggcgtac   4020
tttatggggc ggcgaaaatt cgtcgcatcc cgtcaggcga gccagatgtt tctgtgctgg   4080
ctggaagagg ccatcgttcg ccgcgtggtg acgttacctt caaaagcgcg cttcagtttt   4140
caggaagccc gcagtgcctg gggaactgc gactggatag gctccggtcg tatggccatc   4200
gatggtctga aagaagttca ggaagcggtg atgctgatag aagccggact gagtacctac   4260
gagaaagagt gcgcaaaacg cggtgacgac tatcaggaaa tttttgccca gcaggtccgt   4320
gaaacgatgg agcgccgtgc agccggtctt aaaccgcccg cctgggcggc tgcagcattt   4380
gaatccgggc tgcgacaatc aacagaggag gagaagagtg acagcagagc tgcgtaatct   4440
cccgcatatt gccagcatgg cctttaatga gccgctgatg cttgaacccg cctatgcgcg   4500
ggttttcttt tgtgcgcttg caggccagct tgggatcagc agcctgacgg atgcggtgtc   4560
cggcgacagc ctgactgccc aggaggcact cgcgacgctg gcattatccg gtgatgatga   4620
cggaccacga caggcccgca gttatcaggt catgaacggc atcgccgtgc tgccggtgtc   4680
cggcacgctg gtcagccgga cgcgggcgct gcagccgtac tcggggatga ccggttacaa   4740
cggcattatc gcccgtctgc aacaggctgc cagcgatccg atggtggacg gcattctgct   4800
cgatatggac acgcccggcg ggatggtggc gggggcattt gactgcgctg acatcatcgc   4860
ccgtgtgcgt gacataaaac cggtatgggc gcttgccaac gacatgaact gcagtgcagg   4920
```

-continued

```
tcagttgctt gccagtgccg cctcccggcg tctggtcacg cagaccgccc ggacaggctc   4980
catcggcgtc atgatggctc acagtaatta cggtgctgcg ctggagaaac agggtgtgga   5040
aatcacgctg atttacagcg gcagccataa ggtggatggc aacccctaca gccatcttcc   5100
ggatgacgtc cgggagacac tgcagtcccg gatggacgca acccgccaga tgtttgcgca   5160
gaaggtgtcg gcatataccg gcctgtccgt gcaggttgtg ctggataccg aggctgcagt   5220
gtacagcggt caggaggcca ttgatgccgg actggctgat gaacttgtta acagcaccga   5280
tgcgatcacc gtcatgcgtg atgcactgga tgcacgtaaa tcccgtctct caggagggcg   5340
aatgaccaaa gagactcaat caacaactgt ttcagccact gcttcgcagg ctgacgttac   5400
tgacgtggtg ccagcgacgg agggcgagaa cgccagcgcg gcgcagccgg acgtgaacgc   5460
gcagatcacc gcagcggttg cggcagaaaa cagccgcatt atggggatcc tcaactgtga   5520
ggaggctcac ggacgcgaag aacaggcacg cgtgctggca gaaacccccg gtatgaccgt   5580
gaaaacggcc cgccgcattc tggccgcagc accacagagt gcacaggcgc gcagtgacac   5640
tgcgctggat cgtctgatgc agggggcacc ggcaccgctg gctgcaggta acccggcatc   5700
tgatgccgtt aacgatttgc tgaacacacc agtgtaaggg atgtttatga cgagcaaaga   5760
aacctttacc cattaccagc cgcagggcaa cagtgacccg gctcataccg caaccgcgcc   5820
cggcggattg agtgcgaaag cgcctgcaat gaccccgctg atgctggaca cctccagccg   5880
taagctggtt gcgtgggatg gcaccaccga cggtgctgcc gttggcattc ttgcggttgc   5940
tgctgaccag accagcacca cgctgacgtt ctacaagtcc ggcacgttcc gttatgagga   6000
tgtgctctgg ccggaggctg ccagcgacga gacgaaaaaa cggaccgcgt ttgccggaac   6060
ggcaatcagc atcgtttaac tttacccttc atcactaaag gccgcctgtg cggctttttt   6120
tacgggattt ttttatgtcg atgtacacaa ccgcccaact gctggcggca aatgagcaga   6180
aatttaagtt tgatccgctg tttctgcgtc tctttttccg tgagagctat cccttcacca   6240
cggagaaagt ctatctctca caaattccgg gactggtaaa catggcgctg tacgtttcgc   6300
cgattgtttc cggtgaggtt atccgttccc gtggcggctc cacctctgaa tttacgccgg   6360
gatatgtcaa gccgaagcat gaagtgaatc cgcagatgac cctgcgtcgc ctgccggatg   6420
aagatccgca gaatctggcg gacccggctt accgccgccg tcgcatcatc atgcagaaca   6480
tgcgtgacga agagctggcc attgctcagg tcgaagagat gcaggcagtt tctgccgtgc   6540
ttaagggcaa atacaccatg accggtgaag ccttcgatcc ggttgaggtg gatatgggcc   6600
gcagtgagga gaataacatc acgcagtccg gcggcacgga gtggagcaag cgtgacaagt   6660
ccacgtatga cccgaccgac gatatcgaag cctacgcgct gaacgccagc ggtgtggtga   6720
atatcatcgt gttcgatccg aaaggctggg cgctgttccg ttccttcaaa gccgtcaagg   6780
agaagctgga tacccgtcgt ggctctaatt ccgagctgga gacagcggtg aaagacctgg   6840
gcaaagcggt gtcctataag gggatgtatg gcgatgtggc catcgtcgtg tattccggac   6900
agtacgtgga aaacggcgtc aaaaagaact tcctgccgga caacacgatg gtgctgggga   6960
acactcaggc acgcggtctg cgcacctatg gctgcattca ggatgcggac gcacagcgcg   7020
aaggcattaa cgcctctgcc cgttacccga aaaactgggt gaccaccggc gatccggcgc   7080
gtgagttcac catgattcag tcagcaccgc tgatgctgct ggctgaccct gatgagttcg   7140
tgtccgtaca actggcgtaa tcatggccct tcggggccat tgtttctctg tggaggagtc   7200
catgacgaaa gatgaactga ttgcccgtct ccgctcgctg ggtgaacaac tgaaccgtga   7260
tgtcagcctg acggggacga aagaagaact ggcgctccgt gtggcagagc tgaaagagga   7320
```

-continued gcttgatgac acggatgaaa ctgccggtca ggacacccct ctcagccggg aaaatgtgct 7380
gaccggacat gaaaatgagg tgggatcagc gcagccggat accgtgattc tggatacgtc 7440
tgaactggtc acggtcgtgg cactggtgaa gctgcatact gatgcacttc acgccacgcg 7500
ggatgaacct gtggcatttg tgctgccggg aacggcgttt cgtgtctctg ccggtgtggc 7560
agccgaaatg acagagcgcg gcctggccag aatgcaataa cgggaggcgc tgtggctgat 7620
ttcgataacc tgttcgatgc tgccattgcc cgcgccgatg aaacgatacg cgggtacatg 7680
ggaacgtcag ccaccattac atccggtgag cagtcaggtg cggtgatacg tggtgttttt 7740
gatgaccctg aaaatatcag ctatgccgga cagggcgtgc gcgttgaagg ctccagcccg 7800
tccctgtttg tccggactga tgaggtgcgg cagctgcggc gtggagacac gctgaccatc 7860
ggtgaggaaa atttctgggt agatcgggtt tcgccggatg atggcggaag ttgtcatctc 7920
tggcttggac ggggcgtacc gcctgccgtt aaccgtcgcc gctgaaaggg ggatgtatgg 7980
ccataaaagg tcttgagcag gccgttgaaa acctcagccg tatcagcaaa acggcggtgc 8040
ctggtgccgc cgcaatggcc attaaccgcg ttgcttcatc cgcgatatcg cagtcggcgt 8100
cacaggttgc ccgtgagaca aaggtacgcc ggaaactggt aaaggaaagg gccaggctga 8160
aaagggccac ggtcaaaaat ccgcaggcca gaatcaaagt taaccggggg gatttgcccg 8220
taatcaagct gggtaatgcg cgggttgtcc tttcgcgccg caggcgtcgt aaaaaggggc 8280
agcgttcatc cctgaaaggt ggcggcagcg tgcttgtggt gggtaaccgt cgtattcccg 8340
gcgcgtttat tcagcaactg aaaaatggcc ggtggcatgt catgcagcgt gtggctggga 8400
aaaaccgtta ccccattgat gtggtgaaaa tcccgatggc ggtgccgctg accacggcgt 8460
ttaaacaaaa tattgagcgg atacggcgtg aacgtcttcc gaaagagctg ggctatgcgc 8520
tgcagcatca actgaggatg gtaataaagc gatgaaacat actgaactcc gtgcagccgt 8580
actggatgca ctggagaagc atgacaccgg ggcgacgttt tttgatggtc gccccgctgt 8640
ttttgatgag gcggattttc cggcagttgc cgtttatctc accggcgctg aatacacggg 8700
cgaagagctg gacagcgata cctggcaggc ggagctgcat atcgaagttt tcctgcctgc 8760
tcaggtgccg gattcagagc tggatgcgtg gatggagtcc cggatttatc cggtgatgag 8820
cgatatcccg gcactgtcag atttgatcac cagtatggtg gccagcggct atgactaccg 8880
gcgcgacgat gatgcgggct tgtggagttc agccgatctg acttatgtca ttacctatga 8940
aatgtgagga cgctatgcct gtaccaaatc ctacaatgcc ggtgaaaggt gccgggacca 9000
ccctgtgggt ttataagggg agcggtgacc cttacgcgaa tccgctttca gacgttgact 9060
ggtcgcgtct ggcaaaagtt aaagacctga cgcccggcga actgaccgct gagtcctatg 9120
acgacagcta tctcgatgat gaagatgcag actggactgc gaccgggcag ggcagaaat 9180
ctgccggaga taccagcttc acgctggcgt ggatgcccgg agagcagggg cagcaggcgc 9240
tgctggcgtg gtttaatgaa ggcgataccc gtgcctataa aatccgcttc ccgaacggca 9300
cggtcgatgt gttccgtggc tgggtcagca gtatcggtaa ggcggtgacg gcgaaggaag 9360
tgatcacccg cacggtgaaa gtcaccaatg tgggacgtcc gtcgatggca gaagatcgca 9420
gcacggtaac agcggcaacc ggcatgaccg tgacgcctgc cagcacctcg gtggtgaaag 9480
ggcagagcac cacgctgacc gtggccttcc agccggaggg cgtaaccgac aagagctttc 9540
gtgcggtgtc tgcggataaa acaaaagcca ccgtgtcggt cagtggtatg accatcaccg 9600
tgaacggcgt tgctgcaggc aaggtcaaca ttccggttgt atccggtaat ggtgagtttg 9660

-continued

```
ctgcggttgc agaaattacc gtcaccgcca gttaatccgg agagtcagcg atgttcctga   9720
aaaccgaatc atttgaacat aacggtgtga ccgtcacgct ttctgaactg tcagccctgc   9780
agcgcattga gcatctcgcc ctgatgaaac ggcaggcaga acaggcggag tcagacagca   9840
accggaagtt tactgtggaa gacgccatca gaaccggcgc gtttctggtg gcgatgtccc   9900
tgtggcataa ccatccgcag aagacgcaga tgccgtccat gaatgaagcc gttaaacaga   9960
ttgagcagga agtgcttacc acctggccca cggaggcaat ttctcatgct gaaaacgtgg  10020
tgtaccggct gtctggtatg tatgagtttg tggtgaataa tgcccctgaa cagacagagg  10080
acgccgggcc cgcagagcct gtttctgcgg gaaagtgttc gacggtgagc tgagttttgc  10140
cctgaaactg gcgcgtgaga tggggcgacc cgactggcgt gccatgcttg ccgggatgtc  10200
atccacggag tatgccgact ggcaccgctt ttacagtacc cattattttc atgatgttct  10260
gctggatatg cacttttccg ggctgacgta caccgtgctc agcctgtttt tcagcgatcc  10320
ggatatgcat ccgctggatt tcagtctgct gaaccggcgc gaggctgacg aagagcctga  10380
agatgatgtg ctgatgcaga aagcggcagg gcttgccgga ggtgtccgct ttggcccgga  10440
cgggaatgaa gttatccccg cttccccgga tgtggcggac atgacggagg atgacgtaat  10500
gctgatgaca gtatcagaag ggatcgcagg aggagtccgg tatggctgaa ccggtaggcg  10560
atctggtcgt tgatttgagt ctggatgcgg ccagatttga cgagcagatg gccagagtca  10620
ggcgtcattt ttctggtacg gaaagtgatg cgaaaaaaac agcggcagtc gttgaacagt  10680
cgctgagccg acaggcgctg gctgcacaga aagcggggat ttccgtcggg cagtataaag  10740
ccgccatgcg tatgctgcct gcacagttca ccgacgtggc cacgcagctt gcaggcgggc  10800
aaagtccgtg gctgatcctg ctgcaacagg gggggcaggt gaaggactcc ttcggcggga  10860
tgatccccat gttcaggggg cttgccggtg cgatcaccct gccgatggtg ggggccacct  10920
cgctggcggt ggcgaccggt gcgctggcgt atgcctggta tcagggcaac tcaaccctgt  10980
ccgatttcaa caaaacgctg gtcctttccg gcaatcaggc gggactgacg gcagatcgta  11040
tgctggtcct gtccagagcc gggcaggcgg cagggctgac gtttaaccag accagcgagt  11100
cactcagcgc actggttaag gcgggggtaa gcggtgaggc tcagattgcg tccatcagcc  11160
agagtgtggc gcgtttctcc tctgcatccg gcgtggaggt ggacaaggtc gctgaagcct  11220
tcgggaagct gaccacagac ccgacgtcgg ggctgacggc gatggctcgc cagttccata  11280
acgtgtcggc ggagcagatt gcgtatgttg ctcagttgca gcgttccggc gatgaagccg  11340
gggcattgca ggcggcgaac gaggccgcaa cgaaagggtt tgatgaccag acccgccgcc  11400
tgaaagagaa catgggcacg ctggagacct gggcagacag gactgcgcgg gcattcaaat  11460
ccatgtggga tgcggtgctg gatattggtc gtcctgatac cgcgcaggag atgctgatta  11520
aggcagaggc tgcgtataag aaagcagacg acatctggaa tctgcgcaag gatgattatt  11580
ttgttaacga tgaagcgcgg gcgcgttact gggatgatcg tgaaaaggcc cgtcttgcgc  11640
ttgaagccgc ccgaaagaag gctgagcagc agactcaaca ggacaaaaat gcgcagcagc  11700
agagcgatac cgaagcgtca cggctgaaat ataccgaaga ggcgcagaag gcttacgaac  11760
ggctgcagac gccgctggag aaatataccg cccgtcagga agaactgaac aaggcactga  11820
aagacgggaa aatcctgcag gcggattaca acacgctgat ggcggcggcg aaaaaggatt  11880
atgaagcgac gctgaaaaag ccgaaacagt ccagcgtgaa ggtgtctgcg ggcgatcgtc  11940
aggaagacag tgctcatgct gccctgctga cgcttcaggc agaactccgg acgctggaga  12000
agcatgccgg agcaaatgag aaaatcagcc agcagcgccg ggatttgtgg aaggcggaga  12060
```

```
gtcagttcgc ggtactggag gaggcggcgc aacgtcgcca gctgtctgca caggagaaat  12120
ccctgctggc gcataaagat gagacgctgg agtacaaacg ccagctggct gcacttggcg  12180
acaaggttac gtatcaggag cgcctgaacg cgctggcgca gcaggcggat aaattcgcac  12240
agcagcaacg ggcaaaacgg gccgccattg atgcgaaaag ccgggggctg actgaccggc  12300
aggcagaacg ggaagccacg gaacagcgcc tgaaggaaca gtatggcgat aatccgctgg  12360
cgctgaataa cgtcatgtca gagcagaaaa agacctgggc ggctgaagac cagcttcgcg  12420
ggaactggat ggcaggcctg aagtccggct ggagtgagtg ggaagagagc gccacggaca  12480
gtatgtcgca ggtaaaaagt gcagccacgc agacctttga tggtattgca cagaatatgg  12540
cggcgatgct gaccggcagt gagcagaact ggcgcagctt cacccgttcc gtgctgtcca  12600
tgatgacaga aattctgctt aagcaggcaa tggtggggat tgtcgggagt atcggcagcg  12660
ccattggcgg ggctgttggt ggcggcgcat ccgcgtcagg cggtacagcc attcaggccg  12720
ctgcggcgaa attccatttt gcaaccggag gatttacggg aaccggcggc aaatatgagc  12780
cagcggggat tgttcaccgt ggtgagtttg tcttcacgaa ggaggcaacc agccggattg  12840
gcgtggggaa tctttaccgg ctgatgcgcg gctatgccac cggcggttat gtcggtacac  12900
cgggcagcat ggcagacagc cggtcgcagg cgtccgggac gtttgagcag aataaccatg  12960
tggtgattaa caacgacggc acgaacgggc agataggtcc ggctgctctg aaggcggtgt  13020
atgacatggc ccgcaagggt gcccgtgatg aaattcagac acagatgcgt gatggtggcc  13080
tgttctccgg aggtggacga tgaagacctt ccgctggaaa gtgaaacccg gtatggatgt  13140
ggcttcggtc ccttctgtaa gaaaggtgcg ctttggtgat ggctattctc agcgagcgcc  13200
tgccgggctg aatgccaacc tgaaaacgta cagcgtgacg ctttctgtcc cccgtgagga  13260
ggccacggta ctggagtcgt ttctggaaga gcacgggggc tggaaatcct ttctgtggac  13320
gccgccttat gagtggcggc agataaaggt gacctgcgca aaatggtcgt cgcgggtcag  13380
tatgctgcgt gttgagttca gcgcagagtt tgaacaggtg gtgaactgat gcaggatatc  13440
cggcaggaaa cactgaatga atgcacccgt gcggagcagt cggccagcgt ggtgctctgg  13500
gaaatcgacc tgacagaggt cggtggagaa cgttattttt tctgtaatga gcagaacgaa  13560
aaaggtgagc cggtcacctg gcaggggcga cagtatcagc cgtatcccat tcaggggagc  13620
ggttttgaac tgaatggcaa aggcaccagt acgcgcccca cgctgacggt ttctaacctg  13680
tacggtatgg tcaccgggat ggcggaagat atgcagagtc tggtcggcgg aacggtggtc  13740
cggcgtaagg tttacgcccg ttttctggat gcggtgaact tcgtcaacgg aaacagttac  13800
gccgatccgg agcaggaggt gatcagccgc tggcgcattg agcagtgcag cgaactgagc  13860
gcggtgagtg cctcctttgt actgtccacg ccgacggaaa cggatggcgc tgtttttccg  13920
ggacgtatca tgctggccaa cacctgcacc tggacctatc gcggtgacga gtgcggttat  13980
agcggtccgg ctgtcgcgga tgaatatgac cagccaacgt ccgatatcac gaaggataaa  14040
tgcagcaaat gcctgagcgg ttgtaagttc cgcaataacg tcggcaactt tggcggcttc  14100
ctttccatta acaaactttc gcagtaaatc ccatgacaca gacagaatca gcgattctgg  14160
cgcacgcccg gcgatgtgcg ccagcggagt cgtgcggctt cgtggtaagc acgccggagg  14220
gggaaagata tttcccctgc gtgaatatct ccggtgagcc ggaggctatt tccgtatgtc  14280
gccggaagac tggctgcagg cagaaatgca gggtgagatt gtggcgctgg tccacagcca  14340
ccccggtggt ctgccctggc tgagtgaggc cgaccggcgg ctgcaggtgc agagtgattt  14400
```

-continued

```
gccgtggtgg ctggtctgcc gggggacgat tcataagttc cgctgtgtgc cgcatctcac  14460
cgggcggcgc tttgagcacg gtgtgacgga ctgttacaca ctgttccggg atgcttatca  14520
tctggcgggg attgagatgc cggactttca tcgtgaggat gactggtggc gtaacggcca  14580
gaatctctat ctggataatc tggaggcgac ggggctgtat caggtgccgt tgtcagcggc  14640
acagccgggc gatgtgctgc tgtgctgttt tggttcatca gtgccgaatc acgccgcaat  14700
ttactgcggc gacggcgagc tgctgcacca tattcctgaa caactgagca aacgagagag  14760
gtacaccgac aaatggcagc gacgcacaca ctccctctgg cgtcaccggg catggcgcgc  14820
atctgccttt acggggattt acaacgattt ggtcgccgca tcgaccttcg tgtgaaaacg  14880
ggggctgaag ccatccgggc actggccaca cagctcccgg cgtttcgtca gaaactgagc  14940
gacggctggt atcaggtacg gattgccggg cgggacgtca gcacgtccgg gttaacggcg  15000
cagttacatg agactctgcc tgatggcgct gtaattcata ttgttcccag agtcgccggg  15060
gccaagtcag gtggcgtatt ccagattgtc ctgggggctg ccgccattgc cggatcattc  15120
tttaccgccg gagccaccct tgcagcatgg ggggcagcca ttggggccgg tggtatgacc  15180
ggcatcctgt tttctctcgg tgccagtatg gtgctcggtg gtgtggcgca gatgctggca  15240
ccgaaagcca gaactccccg tatacagaca acggataacg gtaagcagaa cacctatttc  15300
tcctcactgg ataacatggt tgcccagggc aatgttctgc ctgttctgta cggggaaatg  15360
cgcgtggggt cacgcgtggt ttctcaggag atcagcacgg cagacgaagg ggacggtggt  15420
caggttgtgg tgattggtcg ctgatgcaaa atgttttatg tgaaaccgcc tgcgggcggt  15480
tttgtcattt atggagcgtg aggaatgggt aaaggaagca gtaaggggca taccccgcgc  15540
gaagcgaagg acaacctgaa gtccacgcag ttgctgagtg tgatcgatgc catcagcgaa  15600
gggccgattg aaggtccggt ggatggctta aaaagcgtgc tgctgaacag tacgccggtg  15660
ctggacactg aggggaatac caacatatcc ggtgtcacgg tggtgttccg ggctggtgag  15720
caggagcaga ctccgccgga gggatttgaa tcctccggct ccgagacggt gctgggtacg  15780
gaagtgaaat atgacacgcc gatcacccgc accattacgt ctgcaaacat cgaccgtctg  15840
cgctttacct tcggtgtaca ggcactggtg gaaaccacct caaagggtga caggaatccg  15900
tcggaagtcc gcctgctggt tcagatacaa cgtaacggtg gctgggtgac ggaaaaagac  15960
atcaccatta agggcaaaac cacctcgcag tatctggcct cggtggtgat gggtaacctg  16020
ccgccgcgcc cgtttaatat ccggatgcgc aggatgacgc cggacagcac cacagaccag  16080
ctgcagaaca aaacgctctg gtcgtcatac actgaaatca tcgatgtgaa acagtgctac  16140
ccgaacacgg cactggtcgg cgtgcaggtg gactcggagc agttcggcag ccagcaggtg  16200
agccgtaatt atcatctgcg cgggcgtatt ctgcaggtgc cgtcgaacta taacccgcag  16260
acgcggcaat acagcggtat ctgggacgga acgtttaaac cggcatacag caacaacatg  16320
gcctggtgtc tgtgggatat gctgacccat ccgcgctacg gcatggggaa acgtcttggt  16380
gcggcggatg tggataaatg ggcgctgtat gtcatcggcc agtactgcga ccagtcagtg  16440
ccggacggct ttggcggcac ggagccgcgc atcacctgta atgcgtacct gaccacacag  16500
cgtaaggcgt gggatgtgct cagcgatttc tgctcggcga tgcgctgtat gccggtatgg  16560
aacgggcaga cgctgacgtt cgtgcaggac cgaccgtcgg ataagacgtg gacctataac  16620
cgcagtaatg tggtgatgcc ggatgatggc gcgccgttcc gctacagctt cagcgccctg  16680
aaggaccgcc ataatgccgt tgaggtgaac tggattgacc cgaacaacgg ctgggagacg  16740
gcgacagagc ttgttgaaga tacgcaggcc attgcccgtt acggtcgtaa tgttacgaag  16800
```

-continued

```
atggatgcct ttggctgtac cagccggggg caggcacacc gcgccgggct gtggctgatt  16860
aaaacagaac tgctggaaac gcagaccgtg gatttcagcg tcggcgcaga agggcttcgc  16920
catgtaccgg gcgatgttat tgaaatctgc gatgatgact atgccggtat cagcaccggt  16980
ggtcgtgtgc tggcggtgaa cagccagacc cggacgctga cgctcgaccg tgaaatcacg  17040
ctgccatcct ccggtaccgc gctgataagc ctggttgacg gaagtggcaa tccggtcagc  17100
gtggaggttc agtccgtcac cgacggcgtg aaggtaaaag tgagccgtgt tcctgacggt  17160
gttgctgaat acagcgtatg ggagctgaag ctgccgacgc tgcgccagcg actgttccgc  17220
tgcgtgagta tccgtgagaa cgacgacggc acgtatgcca tcaccgccgt gcagcatgtg  17280
ccggaaaaag aggccatcgt ggataacggg gcgcactttg acggcgaaca gagtggcacg  17340
gtgaatggtg tcacgccgcc agcggtgcag cacctgaccg cagaagtcac tgcagacagc  17400
ggggaatatc aggtgctggc gcgatgggac acaccgaagg tggtgaaggg cgtgagtttc  17460
ctgctccgtc tgaccgtaac agcggacgac ggcagtgagc ggctggtcag cacggcccgg  17520
acgacggaaa ccacataccg cttcacgcaa ctggcgctgg ggaactacag gctgacagtc  17580
cgggcggtaa atgcgtgggg gcagcagggc gatccggcgt cggtatcgtt ccggattgcc  17640
gcaccggcag caccgtcgag gattgagctg acgccgggct attttcagat aaccgccacg  17700
ccgcatcttg ccgtttatga cccgacggta cagtttgagt tctggttctc ggaaaagcag  17760
attgcggata tcagacaggt tgaaaccagc acgcgttatc ttggtacggc gctgtactgg  17820
atagccgcca gtatcaatat caaaccgggc catgattatt acttttatat ccgcagtgtg  17880
aacaccgttg gcaaatcggc attcgtggag gccgtcggtc gggcgagcga tgatgcggaa  17940
ggttacctgg attttttcaa aggcaagata accgaatccc atctcggcaa ggagctgctg  18000
gaaaaagtcg agctgacgga ggataacgcc agcagactgg aggagttttc gaaagagtgg  18060
aaggatgcca gtgataagtg gaatgccatg tgggctgtca aaattgagca gaccaaagac  18120
ggcaaacatt atgtcgcggg tattggcctc agcatggagg acacggagga aggcaaactg  18180
agccagtttc tggttgccgc caatcgtatc gcatttattg acccggcaaa cgggaatgaa  18240
acgccgatgt ttgtggcgca gggcaaccag atattcatga acgacgtgtt cctgaagcgc  18300
ctgacggccc ccaccattac cagcggcggc aatcctccgg ccttttccct gacaccggac  18360
ggaaagctga ccgctaaaaa tgcggatatc agtggcagtg tgaatgcgaa ctccgggacg  18420
ctcagtaatg tgacgatagc tgaaaactgt acgataaacg gtacgctgag ggcggaaaaa  18480
atcgtcgggg acattgtaaa ggcggcgagc gcggcttttc cgcgccagcg tgaaagcagt  18540
gtggactggc cgtcaggtac ccgtactgtc accgtgaccg atgaccatcc ttttgatcgc  18600
cagatagtgg tgcttccgct gacgtttcgc ggaagtaagc gtactgtcag cggcaggaca  18660
acgtattcga tgtgttatct gaaagtactg atgaacggtg cggtgattta tgatggcgcg  18720
gcgaacgagg cggtacaggt gttctcccgt attgttgaca tgccagcggg tcggggaaac  18780
gtgatcctga cgttcacgct tacgtccaca cggcattcgg cagatattcc gccgtatacg  18840
tttgccagcg atgtgcaggt tatggtgatt aagaaacagg cgctgggcat cagcgtggtc  18900
tgagtgtgtt acagaggttc gtccgggaac gggcgtttta ttataaaaca gtgagaggtg  18960
aacgatgcgt aatgtgtgta ttgccgttgc tgtctttgcc gcacttgcgg tgacagtcac  19020
tccggcccgt gcggaaggtg gacatggtac gtttacggtg ggctattttc aagtgaaacc  19080
gggtacattg ccgtcgttgt cgggcgggga taccggtgtg agtcatctga aaggattaa  19140
```

-continued

```
cgtgaagtac cgttatgagc tgacggacag tgtgggggtg atggcttccc tggggttcgc  19200
cgcgtcgaaa aagagcagca cagtgatgac cggggaggat acgtttcact atgagagcct  19260
gcgtggacgt tatgtgagcg tgatggccgg accggtttta caaatcagta agcaggtcag  19320
tgcgtacgcc atggccggag tggctcacag tcggtggtcc ggcagtacaa tggattaccg  19380
taagacggaa atcactcccg ggtatatgaa agagacgacc actgccaggg acgaaagtgc  19440
aatgcggcat acctcagtgg cgtggagtgc aggtatacag attaatccgg cagcgtccgt  19500
cgttgttgat attgcttatg aaggctccgg cagtggcgac tggcgtactg acggattcat  19560
cgttggggtc ggttataaat tctgattagc caggtaacac agtgttatga cagcccgccg  19620
gaaccggtgg gctttttgt ggggtgaata tggcagtaaa gatttcagga gtcctgaaag  19680
acggcacagg aaaaccggta cagaactgca ccattcagct gaaagccaga cgtaacagca  19740
ccacggtggt ggtgaacacg gtgggctcag agaatccgga tgaagccggg cgttacagca  19800
tggatgtgga gtacggtcag tacagtgtca tcctgcaggt tgacggtttt ccaccatcgc  19860
acgccgggac catcaccgtg tatgaagatt cacaaccggg gacgctgaat gatttctct  19920
gtgccatgac ggaggatgat gcccggccgg aggtgctgcg tcgtcttgaa ctgatggtgg  19980
aagaggtggc gcgtaacgcg tccgtggtgg cacagagtac ggcagacgcg aagaaatcag  20040
ccggcgatgc cagtgcatca gctgctcagg tcgcggccct tgtgactgat gcaactgact  20100
cagcacgcgc cgccagcacg tccgccggac aggctgcatc gtcagctcag gaagcgtcct  20160
ccggcgcaga agcggcatca gcaaaggcca ctgaagcgga aaaaagtgcc gcagccgcag  20220
agtcctcaaa aaacgcggcg gccaccagtg ccggtgcggc gaaaacgtca gaaacgaatg  20280
ctgcagcgtc acaacaatca gccgccacgt ctgcctccac cgcggccacg aaagcgtcag  20340
aggccgccac ttcagcacga gatgcggtgg cctcaaaaga ggcagcaaaa tcatcagaaa  20400
cgaacgcatc atcaagtgcc ggtcgtgcag cttcctcggc aacggcggca gaaaattctg  20460
ccagggcggc aaaaacgtcc gagacgaatg ccaggtcatc tgaaacagca gcggaacgga  20520
gcgcctctgc cgcggcagac gcaaaaacag cggcggcggg gagtgcgtca acggcatcca  20580
cgaaggcgac agaggctgcg ggaagtgcgg tatcagcatc gcagagcaaa agtgcggcag  20640
aagcggcggc aatacgtgca aaaaattcgg caaaacgtgc agaagatata gcttcagctg  20700
tcgcgcttga ggatgcggac acaacgagaa aggggatagt gcagctcagc agtgcaacca  20760
acagcacgtc tgaaacgctt gctgcaacgc caaaggcggt taaggtggta atggatgaaa  20820
cgaacagaaa agcccactgg acagtccggc actgaccgga acgccaacag caccaaccgc  20880
gctcagggga acaaacaata cccagattgc gaacaccgct tttgtactgg ccgcgattgc  20940
agatgttatc gacgcgtcac ctgacgcact gaatacgctg aatgaactgg ccgcagcgct  21000
cgggaatgat ccagattttg ctaccaccat gactaacgcg cttgcgggta aacaaccgaa  21060
gaatgcgaca ctgacggcgc tggcagggct ttccacggcg aaaaataaat taccgtattt  21120
tgcggaaaat gatgccgcca gcctgactga actgactcag gttggcaggg atattctggc  21180
aaaaaattcc gttgcagatg ttcttgaata ccttggggcc ggtgagaatt cggcctttcc  21240
ggcaggtgcg ccgatcccgt ggccatcaga tatcgttccg tctggctacg tcctgatgca  21300
ggggcaggcg tttgacaaat cagcctaccc aaaacttgct gtcgcgtatc catcgggtgt  21360
gcttcctgat atgcgaggct ggacaatcaa ggggaaaccc gccagcggtc gtgctgtatt  21420
gtctcaggaa caggatggaa ttaagtcgca cacccacagt gccagtgcat ccggtacgga  21480
tttggggacg aaaaccacat cgtcgtttga ttacgggacg aaaacaacag gcagtttcga  21540
```

ttacggcacc aaatcgacga ataacacggg ggctcatgct cacagtctga gcggttcaac 21600
aggggccgcg ggtgctcatg cccacacaag tggtttaagg atgaacagtt ctggctggag 21660
tcagtatgga acagcaacca ttacaggaag tttatccaca gttaaaggaa ccagcacaca 21720
gggtattgct tatttatcga aaacggacag tcagggcagc cacagtcact cattgtccgg 21780
tacagccgtg agtgccggtg cacatgcgca tacagttggt attggtgcgc accagcatcc 21840
ggttgttatc ggtgctcatg cccattcttt cagtattggt tcacacggac acaccatcac 21900
cgttaacgct gcgggtaacg cggaaaacac cgtcaaaaac attgcattta actatattgt 21960
gaggcttgca taatggcatt cagaatgagt gaacaaccac ggaccataaa aatttataat 22020
ctgctggccg gaactaatga atttattggt gaaggtgacg catatattcc gcctcatacc 22080
ggtctgcctg caaacagtac cgatattgca ccgccagata ttccggctgg ctttgtggct 22140
gttttcaaca gtgatgaggc atcgtggcat ctcgttgaag accatcgggg taaaaccgtc 22200
tatgacgtgg cttccggcga cgcgttattt atttctgaac tcggtccgtt accggaaaat 22260
tttacctggt tatcgccggg aggggaatat cagaagtgga acggcacagc ctgggtgaag 22320
gatacggaag cagaaaaact gttccggatc cgggaggcgg aagaaacaaa aaaaagcctg 22380
atgcaggtag ccagtgagca tattgcgccg cttcaggatg ctgcagatct ggaaattgca 22440
acgaaggaag aaacctcgtt gctggaagcc tggaagaagt atcgggtgtt gctgaaccgt 22500
gttgatacat caactgcacc tgatattgag tggcctgctg tccctgttat ggagtaatcg 22560
ttttgtgata tgccgcagaa acgttgtatg aaataacgtt ctgcggttag ttagtatatt 22620
gtaaagctga gtattggttt atttggcgat tattatcttc aggagaataa tggaagttct 22680
atgactcaat tgttcatagt gtttacatca ccgccaattg cttttaagac tgaacgcatg 22740
aaatatggtt tttcgtcatg ttttgagtct gctgttgata tttctaaagt cggttttttt 22800
tcttcgtttt ctctaactat tttccatgaa atacattttt gattattatt tgaatcaatt 22860
ccaattacct gaagtctttc atctataatt ggcattgtat gtattggttt attggagtag 22920
atgcttgctt ttctgagcca tagctctgat atccaaatga agccataggc atttgttatt 22980
ttggctctgt cagctgcata acgccaaaaa atatatttat ctgcttgatc ttcaaatgtt 23040
gtattgatta aatcaattgg atggaattgt ttatcataaa aaattaatgt ttgaatgtga 23100
taaccgtcct ttaaaaaagt cgtttctgca agcttggctg tatagtcaac taactcttct 23160
gtcgaagtga tatttttagg cttatctacc agttttagac gctctttaat atcttcagga 23220
attattttat tgtcatattg tatcatgcta aatgacaatt tgcttatgga gtaatctttt 23280
aattttaaat aagttattct cctggcttca tcaaataaag agtcgaatga tgttggcgaa 23340
atcacatcgt cacccattgg attgtttatt tgtatgccaa gagagttaca gcagttatac 23400
attctgccat agattatagc taaggcatgt aataattcgt aatcttttag cgtattagcg 23460
acccatcgtc tttctgattt aataatagat gattcagtta aatatgaagg taatttcttt 23520
tgtgcaagtc tgactaactt ttttatacca atgtttaaca tactttcatt tgtaataaac 23580
tcaatgtcat tttcttcaat gtaagatgaa ataagagtag cctttgcctc gctatacatt 23640
tctaaatcgc cttgtttttc tatcgtattg cgagaatttt tagcccaagc cattaatgga 23700
tcatttttcc atttttcaat aacattattg ttataccaaa tgtcatatcc tataatctgg 23760
tttttgtttt tttgaataat aaatgttact gttcttgcgg tttggaggaa ttgattcaaa 23820
ttcaagcgaa ataattcagg gtcaaaatat gtatcaatgc agcatttgag caagtgcgat 23880

-continued

```
aaatctttaa gtcttctttc ccatggtttt ttagtcataa aactctccat tttgataggt  23940
tgcatgctag atgctgatat attttagagg tgataaaatt aactgcttaa ctgtcaatgt  24000
aatacaagtt gtttgatctt tgcaatgatt cttatcagaa accatatagt aaattagtta  24060
cacaggaaat ttttaatatt attattatca ttcattatgt attaaaatta gagttgtggc  24120
ttggctctgc taacacgttg ctcataggag atatggtaga gccgcagaca cgtcgtatgc  24180
aggaacgtgc tgcggctggc tggtgaactt ccgatagtgc gggtgttgaa tgatttccag  24240
ttgctaccga ttttacatat tttttgcatg agagaatttg taccacctcc caccgaccat  24300
ctatgactgt acgccactgt ccctaggact gctatgtgcc ggagcggaca ttacaaacgt  24360
ccttctcggt gcatgccact gttgccaatg acctgcctag gaattggtta gcaagttact  24420
accggatttt gtaaaaacag ccctcctcat ataaaaagta ttcgttcact tccgataagc  24480
gtcgtaattt tctatctttc atcatattct agatccctct gaaaaaatct tccgagtttg  24540
ctaggcactg atacataact cttttccaat aattggggaa gtcattcaaa tctataatag  24600
gtttcagatt tgcttcaata aattctgact gtagctgctg aaacgttgcg gttgaactat  24660
atttccttat aacttttacg aaagagtttc tttgagtaat cacttcactc aagtgcttcc  24720
ctgcctccaa acgatacctg ttagcaatat ttaatagctt gaaatgatga agagctctgt  24780
gtttgtcttc ctgcctccag ttcgccgggc attcaacata aaaactgata gcacccggag  24840
ttccggaaac gaaatttgca tatacccatt gctcacgaaa aaaaatgtcc ttgtcgatat  24900
agggatgaat cgcttggtgt acctcatcta ctgcgaaaac ttgacctttc tctcccatat  24960
tgcagtcgcg gcacgatgga actaaattaa taggcatcac cgaaaattca ggataatgtg  25020
caataggaag aaaatgatct atattttttg tctgtcctat atcaccacaa aatggacatt  25080
tttcacctga tgaaacaagc atgtcatcgt aatatgttct agcgggtttg tttttatctc  25140
ggagattatt ttcataaagc ttttctaatt taacctttgt caggttacca actactaagg  25200
ttgtaggctc aagagggtgt gtcctgtcgt aggtaaataa ctgacctgtc gagcttaata  25260
ttctatattg ttgttctttc tgcaaaaaag tggggaagtg agtaatgaaa ttatttctaa  25320
catttatctg catcatacct tccgagcatt tattaagcat ttcgctataa gttctcgctg  25380
gaagaggtag ttttttcatt gtactttacc ttcatctctg ttcattatca tcgcttttaa  25440
aacggttcga ccttctaatc ctatctgacc attataattt tttagaatgg tttcataaga  25500
aagctctgaa tcaacggact gcgataataa gtggtggtat ccagaatttg tcacttcaag  25560
taaaaacacc tcacgagtta aaacacctaa gttctcaccg aatgtctcaa tatccggacg  25620
gataatattt attgcttctc ttgaccgtag gactttccac atgcaggatt ttggaacctc  25680
ttgcagtact actggggaat gagttgcaat tattgctaca ccattgcgtg catcgagtaa  25740
gtcgcttaat gttcgtaaaa aagcagagag caaaggtgga tgcagatgaa cctctggttc  25800
atcgaataaa actaatgact tttcgccaac gacatctact aatcttgtga tagtaaataa  25860
aacaattgca tgtccagagc tcattcgaag cagatatttc tggatattgt cataaaacaa  25920
tttagtgaat ttatcatcgt ccacttgaat ctgtggttca ttacgtctta actcttcata  25980
tttagaaatg aggctgatga gttccatatt tgaaaagttt tcatcactac ttagtttttt  26040
gatagcttca agccagagtt gtctttttct atctactctc atacaaccaa taaatgctga  26100
aatgaattct aagcggagat cgcctagtga ttttaaacta ttgctggcag cattcttgag  26160
tccaatataa aagtattgtg taccttttgc tgggtcaggt tgttctttag gaggagtaaa  26220
aggatcaaat gcactaaacg aaactgaaac aagcgatcga aaatatccct ttgggattct  26280
```

tgactcgata agtctattat tttcagagaa aaaatattca ttgttttctg ggttggtgat 26340
tgcaccaatc attccattca aaattgttgt tttaccacac ccattccgcc cgataaaagc 26400
atgaatgttc gtgctgggca tagaattaac cgtcacctca aaaggtatag ttaaatcact 26460
gaatccggga gcactttttc tattaaatga aaagtggaaa tctgacaatt ctggcaaacc 26520
atttaacaca cgtgcgaact gtccatgaat ttctgaaaga gttacccctc taagtaatga 26580
ggtgttaagg acgctttcat tttcaatgtc ggctaatcga tttggccata ctactaaatc 26640
ctgaatagct ttaagaaggt tatgtttaaa accatcgctt aatttgctga gattaacata 26700
gtagtcaatg ctttcaccta aggaaaaaaa catttcaggg agttgactga attttttatc 26760
tattaatgaa taagtgctta cttcttcttt ttgacctaca aaaccaattt taacatttcc 26820
gatatcgcat ttttcaccat gctcatcaaa gacagtaaga taaaacattg taacaaagga 26880
atagtcattc caaccatctg ctcgtaggaa tgccttattt ttttctactg caggaatata 26940
cccgcctctt tcaataacac taaactccaa catatagtaa cccttaattt tattaaaata 27000
accgcaattt atttggcggc aacacaggat ctctctttta agttactctc tattacatac 27060
gttttccatc taaaaattag tagtattgaa cttaacgggg catcgtattg tagttttcca 27120
tatttagctt tctgcttcct tttggataac ccactgttat tcatgttgca tggtgcactg 27180
tttataccaa cgatatagtc tattaatgca tatatagtat cgccgaacga ttagctcttc 27240
aggcttctga agaagcgttt caagtactaa taagccgata gatagccacg gacttcgtag 27300
ccatttttca taagtgttaa cttccgctcc tcgctcataa cagacattca ctacagttat 27360
ggcggaaagg tatgcatgct gggtgtgggg aagtcgtgaa agaaaagaag tcagctgcgt 27420
cgtttgacat cactgctatc ttcttactgg ttatgcaggt cgtagtgggt ggcacacaaa 27480
gctttgcact ggattgcgag gctttgtgct tctctggagt gcgacaggtt tgatgacaaa 27540
aaattagcgc aagaagacaa aaatcacctt gcgctaatgc tctgttacag gtcactaata 27600
ccatctaagt agttgattca tagtgactgc atatgttgtg ttttacagta ttatgtagtc 27660
tgttttttat gcaaaatcta atttaatata ttgatattta tatcatttta cgtttctcgt 27720
tcagcttttt tatactaagt tggcattata aaaaagcatt gcttatcaat ttgttgcaac 27780
gaacaggtca ctatcagtca aaataaaatc attatttgat ttcaattttg tcccactccc 27840
tgcctctgtc atcacgatac tgtgatgcca tggtgtccga cttatgcccg agaagatgtt 27900
gagcaaactt atcgcttatc tgcttctcat agagtcttgc agacaaactg cgcaactcgt 27960
gaaaggtagg cggatcccct tcgaaggaaa gacctgatgc ttttcgtgcg cgcataaaat 28020
accttgatac tgtgccggat gaaagcggtt cgcgacgagt agatgcaatt atggtttctc 28080
cgccaagaat ctctttgcat ttatcaagtg tttccttcat tgatattccg agagcatcaa 28140
tatgcaatgc tgttgggatg gcaattttta cgcctgtttt gctttgctcg acataaagat 28200
atccatctac gatatcagac cacttcattt cgcataaatc accaactcgt tgcccggtaa 28260
caacagccag ttccattgca agtctgagcc aacatggtga tgattctgct gcttgataaa 28320
ttttcaggta ttcgtcagcc gtaagtcttg atctccttac ctctgatttt gctgcgcgag 28380
tggcagcgac atggtttgtt gttatatggc cttcagctat tgcctctcgg aatgcatcgc 28440
tcagtgttga tctgattaac ttggctgacg ccgccttgcc ctcgtctatg tatccattga 28500
gcattgccgc aatttctttt gtggtgatgt cttcaagtgg agcatcaggc agacccctcc 28560
ttattgcttt aattttgctc atgtaattta tgagtgtctt ctgcttgatt cctctgctgg 28620
ccaggatttt ttcgtagcga tcaagccatg aatgtaacgt aacggaatta tcactgttga 28680
ttctcgctgt cagaggcttg tgtttgtgtc ctgaaaataa ctcaatgttg gcctgtatag 28740
cttcagtgat tgcgattcgc ctgtctctgc ctaatccaaa ctctttaccc gtccttgggt 28800
ccctgtagca gtaatatcca ttgtttctta tataaaggtt agggggtaaa tcccggcgct 28860
catgacttcg ccttcttccc atttctgatc ctcttcaaaa ggccacctgt tactggtcga 28920
tttaagtcaa cctttaccgc tgattcgtgg aacagatact ctcttccatc cttaaccgga 28980
ggtgggaata tcctgcattc ccgaacccat cgacgaactg tttcaaggct tcttggacgt 29040
cgctggcgtg cgttccactc ctgaagtgtc aagtacatcg caaagtctcc gcaattacac 29100
gcaagaaaaa accgccatca ggcggcttgg tgttctttca gttcttcaat tcgaatattg 29160
gttacgtctg catgtgctat ctgcgcccat atcatccagt ggtcgtagca gtcgttgatg 29220
ttctccgctt cgataactct gttgaatggc tctccattcc attctcctgt gactcggaag 29280
tgcatttatc atctccataa aacaaaaccc gccgtagcga gttcagataa aataaatccc 29340
cgcgagtgcg aggattgtta tgtaatattg ggtttaatca tctatatgtt ttgtacagag 29400
agggcaagta tcgtttccac cgtactcgtg ataataattt tgcacggtat cagtcatttc 29460
tcgcacattg cagaatgggg atttgtcttc attagactta taaaccttca tggaatattt 29520
gtatgccgac tctatatcta taccttcatc tacataaaca ccttcgtgat gtctgcatgg 29580
agacaagaca ccggatctgc acaacattga taacgcccaa tctttttgct cagactctaa 29640
ctcattgata ctcatttata aactccttgc aatgtatgtc gtttcagcta aacggtatca 29700
gcaatgttta tgtaaagaaa cagtaagata atactcaacc cgatgtttga gtacggtcat 29760
catctgacac tacagactct ggcatcgctg tgaagacgac gcgaaattca gcattttcac 29820
aagcgttatc ttttacaaaa ccgatctcac tctcctttga tgcgaatgcc agcgtcagac 29880
atcatatgca gatactcacc tgcatcctga acccattgac ctccaacccc gtaatagcga 29940
tgcgtaatga tgtcgatagt tactaacggg tcttgttcga ttaactgccg cagaaactct 30000
tccaggtcac cagtgcagtg cttgataaca ggagtcttcc caggatggcg aacaacaaga 30060
aactggtttc cgtcttcacg gacttcgttg ctttccagtt tagcaatacg cttactccca 30120
tccgagataa caccttcgta atactcacgc tgctcgttga gttttgattt tgctgtttca 30180
agctcaacac gcagtttccc tactgttagc gcaatatcct cgttctcctg gtcgcggcgt 30240
ttgatgtatt gctggtttct ttcccgttca tccagcagtt ccagcacaat cgatggtgtt 30300
accaattcat ggaaaaggtc tgcgtcaaat ccccagtcgt catgcattgc ctgctctgcc 30360
gcttcacgca gtgcctgaga gttaatttcg ctcacttcga acctctctgt ttactgataa 30420
gttccagatc ctcctggcaa cttgcacaag tccgacaacc ctgaacgacc aggcgtcttc 30480
gttcatctat cggatcgcca cactcacaac aatgagtggc agatatagcc tggtggttca 30540
ggcggcgcat ttttattgct gtgttgcgct gtaattcttc tatttctgat gctgaatcaa 30600
tgatgtctgc catctttcat taatccctga actgttggtt aatacgcttg agggtgaatg 30660
cgaataataa aaaaggagcc tgtagctccc tgatgatttt gcttttcatg ttcatcgttc 30720
cttaaagacg ccgtttaaca tgccgattgc caggcttaaa tgagtcggtg tgaatcccat 30780
cagcgttacc gtttcgcggt gcttcttcag tacgctacgg caaatgtcat cgacgttttt 30840
atccggaaac tgctgtctgg ctttttttga tttcagaatt agcctgacgg gcaatgctgc 30900
gaagggcgtt ttcctgctga ggtgtcattg aacaagtccc atgtcggcaa gcataagcac 30960
acagaatatg aagcccgctg ccagaaaaat gcattccgtg gttgtcatac ctggtttctc 31020

```
tcatctgctt ctgctttcgc caccatcatt tccagctttt gtgaaaggga tgcggctaac  31080
gtatgaaatt cttcgtctgt ttctactggt attggcacaa acctgattcc aatttgagca  31140
aggctatgtg ccatctcgat actcgttctt aactcaacag aagatgcttt gtgcatacag  31200
cccctcgttt attatttatc tcctcagcca gccgctgtgc tttcagtgga tttcggataa  31260
cagaaaggcc gggaaatacc cagcctcgct ttgtaacgga gtagacgaaa gtgattgcgc  31320
ctacccggat attatcgtga ggatgcgtca tcgccattgc tccccaaata caaaaccaat  31380
ttcagccagt gcctcgtcca ttttttcgat gaactccggc acgatctcgt caaaactcgc  31440
catgtacttt tcatcccgct caatcacgac ataatgcagg ccttcacgct tcatacgcgg  31500
gtcatagttg gcaaagtacc aggcattttt tcgcgtcacc cacatgctgt actgcacctg  31560
ggccatgtaa gctgacttta tggcctcgaa accaccgagc cggaacttca tgaaatcccg  31620
ggaggtaaac gggcatttca gttcaaggcc gttgccgtca ctgcataaac catcgggaga  31680
gcaggcggta cgcatacttt cgtcgcgata gatgatcggg gattcagtaa cattcacgcc  31740
ggaagtgaat tcaaacaggg ttctggcgtc gttctcgtac tgttttcccc aggccagtgc  31800
tttagcgtta acttccggag ccacaccggt gcaaacctca gcaagcaggg tgtggaagta  31860
ggacattttc atgtcaggcc acttctttcc ggagcggggt tttgctatca cgttgtgaac  31920
ttctgaagcg gtgatgacgc cgagccgtaa tttgtgccac gcatcatccc cctgttcgac  31980
agctctcaca tcgatcccgg tacgctgcag gataatgtcc ggtgtcatgc tgccaccttc  32040
tgctctgcgg ctttctgttt caggaatcca agagctttta ctgcttcggc ctgtgtcagt  32100
tctgacgatg cacgaatgtc gcggcgaaat atctgggaac agagcggcaa taagtcgtca  32160
tcccatgttt tatccagggc gatcagcaga gtgttaatct cctgcatggt ttcatcgtta  32220
accggagtga tgtcgcgttc cggctgacgt tctgcagtgt atgcagtatt ttcgacaatg  32280
cgctcggctt catccttgtc atagatacca gcaaatccga aggccagacg ggcacactga  32340
atcatggctt tatgacgtaa catccgtttg ggatgcgact gccacggccc cgtgatttct  32400
ctgccttcgc gagttttgaa tggttcgcgg cggcattcat ccatccattc ggtaacgcag  32460
atcggatgat tacggtcctt gcggtaaatc cggcatgtac aggattcatt gtcctgctca  32520
aagtccatgc catcaaactg ctggttttca ttgatgatgc gggaccagcc atcaacgccc  32580
accaccggaa cgatgccatt ctgcttatca ggaaaggcgt aaatttcttt cgtccacgga  32640
ttaaggccgt actggttggc aacgatcagt aatgcgatga actgcgcatc gctggcatca  32700
cctttaaatg ccgtctggcg aagagtggtg atcagttcct gtgggtcgac agaatccatg  32760
ccgacacgtt cagccagctt cccagccagc gttgcgagtg cagtactcat tcgttttata  32820
cctctgaatc aatatcaacc tggtggtgag caatggtttc aaccatgtac cggatgtgtt  32880
ctgccatgcg ctcctgaaac tcaacatcgt catcaaacgc acgggtaatg gatttttttgc  32940
tggccccgtg gcgttgcaaa tgatcgatgc atagcgattc aaacaggtgc tggggcaggc  33000
ctttttccat gtcgtctgcc agttctgcct ctttctcttc acgggcgagc tgctggtagt  33060
gacgcgccca gctctgagcc tcaagacgat cctgaatgta ataagcgttc atggctgaac  33120
tcctgaaata gctgtgaaaa tatcgcccgc gaaatgccgg gctgattagg aaaacaggaa  33180
agggggttag tgaatgcttt tgcttgatct cagtttcagt attaatatcc atttttttata  33240
agcgtcgacg gcttcacgaa acatcttttc atcgccaata aaagtggcga tagtgaattt  33300
agtctggata gccataagtg tttgatccat tctttgggac tcctggctga ttaagtatgt  33360
```

-continued

```
cgataaggcg tttccatccg tcacgtaatt tacgggtgat tcgttcaagt aaagattcgg  33420
aagggcagcc agcaacaggc caccctgcaa tggcatattg catggtgtgc tccttattta  33480
tacataacga aaaacgcctc gagtgaagcg ttattggtat gcggtaaaac cgcactcagg  33540
cggccttgat agtcatatca tctgaatcaa atattcctga tgtatcgata tcggtaattc  33600
ttattccttc gctaccatcc attggaggcc atccttcctg accatttcca tcattccagt  33660
cgaactcaca cacaacacca tatgcattta agtcgcttga aattgctata agcagagcat  33720
gttgcgccag catgattaat acagcattta atacagagcc gtgtttattg agtcggtatt  33780
cagagtctga ccagaaatta ttaatctggt gaagtttttc ctctgtcatt acgtcatggt  33840
cgatttcaat ttctattgat gctttccagt cgtaatcaat gatgtatttt ttgatgtttg  33900
acatctgttc atatcctcac agataaaaaa tcgccctcac actggagggc aaagaagatt  33960
tccaataatc agaacaagtc ggctcctgtt tagttacgag cgacattgct ccgtgtattc  34020
actcgttgga atgaatacac agtgcagtgt ttattctgtt atttatgcca aaaataaagg  34080
ccactatcag gcagctttgt tgttctgttt accaagttct ctggcaatca ttgccgtcgt  34140
tcgtattgcc catttatcga catatttccc atcttccatt acaggaaaca tttcttcagg  34200
cttaaccatg cattccgatt gcagcttgca tccattgcat cgcttgaatt gtccacacca  34260
ttgattttta tcaatagtcg tagtcatacg gatagtcctg gtattgttcc atcacatcct  34320
gaggatgctc ttcgaactct tcaaattctt cttccatata tcaccttaaa tagtggattg  34380
cggtagtaaa gattgtgcct gtcttttaac cacatcaggc tcggtggttc tcgtgtaccc  34440
ctacagcgag aaatcggata aactattaca acccctacag tttgatgagt atagaaatgg  34500
atccactcgt tattctcgga cgagtgttca gtaatgaacc tctggagaga accatgtata  34560
tgatcgttat ctgggttgga cttctgcttt taagcccaga taactggcct gaatatgtta  34620
atgagagaat cggtattcct catgtgtggc atgttttcgt ctttgctctt gcattttcgc  34680
tagcaattaa tgtgcatcga ttatcagcta ttgccagcgc cagatataag cgatttaagc  34740
taagaaaacg cattaagatg caaaacgata aagtgcgatc agtaattcaa aaccttacag  34800
aagagcaatc tatggttttg tgcgcagccc ttaatgaagg caggaagtat gtggttacat  34860
caaaacaatt cccatacatt agtgagttga ttgagcttgg tgtgttgaac aaaacttttt  34920
cccgatggaa tggaaagcat atattattcc ctattgagga tatttactgg actgaattag  34980
ttgccagcta tgatccatat aatattgaga taaagccaag gccaatatct aagtaactag  35040
ataagaggaa tcgattttcc cttaattttc tggcgtccac tgcatgttat gccgcgttcg  35100
ccaggcttgc tgtaccatgt gcgctgattc ttgcgctcaa tacgttgcag gttgctttca  35160
atctgtttgt ggtattcagc cagcactgta aggtctatcg gatttagtgc gctttctact  35220
cgtgatttcg gtttgcgatt cagcgagaga atagggcggt taactggttt tgcgcttacc  35280
ccaaccaaca ggggatttgc tgctttccat tgagcctgtt tctctgcgcg acgttcgcgg  35340
cggcgtgttt gtgcatccat ctggattctc ctgtcagtta gctttggtgg tgtgtggcag  35400
ttgtagtcct gaacgaaaac cccccgcgat tggcacattg gcagctaatc cggaatcgca  35460
cttacggcca atgcttcgtt tcgtatcaca caccccaaag ccttctgctt tgaatgctgc  35520
ccttcttcag ggcttaattt ttaagagcgt caccttcatg gtggtcagtg cgtcctgctg  35580
atgtgctcag tatcaccgcc agtggtattt atgtcaacac cgccagagat aatttatcac  35640
cgcagatggt tatctgtatg tttttttatat gaatttattt tttgcagggg ggcattgttt  35700
ggtaggtgag agatctgaat tgctatgttt agtgagttgt atctatttat ttttcaataa  35760
```

atacaattgg ttatgtgttt tgggggcgat cgtgaggcaa agaaaacccg gcgctgaggc 35820
cgggttattc ttgttctctg gtcaaattat atagttggaa aacaaggatg catatatgaa 35880
tgaacgatgc agaggcaatg ccgatggcga tagtgggtat catgtagccg cttatgctgg 35940
aaagaagcaa taacccgcag aaaaacaaag ctccaagctc aacaaaacta agggcataga 36000
caataactac cgatgtcata tacccatact ctctaatctt ggccagtcgg cgcgttctgc 36060
ttccgattag aaacgtcaag gcagcaatca ggattgcaat catggttcct gcatatgatg 36120
acaatgtcgc cccaagacca tctctatgag ctgaaaaaga aacaccagga atgtagtggc 36180
ggaaaaggag atagcaaatg cttacgataa cgtaaggaat tattactatg taaacaccag 36240
gcatgattct gttccgcata attactcctg ataattaatc cttaactttg cccacctgcc 36300
ttttaaaaca ttccagtata tcacttttca ttcttgcgta gcaatatgcc atctcttcag 36360
ctatctcagc attggtgacc ttgttcagag gcgctgagag atggcctttt tctgatagat 36420
aatgttctgt taaaatatct ccggcctcat cttttgcccg caggctaatg tctgaaaatt 36480
gaggtgacgg gttaaaaata atatccttgg caaccttttt tatatccctt ttaaattttg 36540
gcttaatgac tatatccaat gagtcaaaaa gctccccttc aatatctgtt gcccctaaga 36600
cctttaatat atcgccaaat acaggtagct tggcttctac cttcaccgtt gttcggccga 36660
tgaaatgcat atgcataaca tcgtctttgg tggttcccct catcagtggc tctatctgaa 36720
cgcgctctcc actgcttaat gacattcctt tcccgattaa aaaatctgtc agatcggatg 36780
tggtcggccc gaaaacagtt ctggcaaaac caatggtgtc gccttcaaca aacaaaaaag 36840
atgggaatcc caatgattcg tcatctgcga ggctgttctt aatatcttca actgaagctt 36900
tagagcgatt tatcttctga accagactct tgtcatttgt tttggtaaag agaaaagttt 36960
ttccatcgat tttatgaata tacaaataat tggagccaac ctgcaggtga tgattatcag 37020
ccagcagaga attaaggaaa acagacaggt ttattgagcg cttatctttc cctttatttt 37080
tgctgcggta agtcgcataa aaaccattct tcataattca atccatttac tatgttatgt 37140
tctgagggga gtgaaaattc ccctaattcg atgaagattc ttgctcaatt gttatcagct 37200
atgcgccgac cagaacacct tgccgatcag ccaaacgtct cttcaggcca ctgactagcg 37260
ataactttcc ccacaacgga acaactctca ttgcatggga tcattgggta ctgtgggttt 37320
agtggttgta aaaacacctg accgctatcc ctgatcagtt tcttgaaggt aaactcatca 37380
cccccaagtc tggctatgca gaaatcacct ggctcaacag cctgctcagg gtcaacgaga 37440
attaacattc cgtcaggaaa gcttggcttg gagcctgttg gtgcggtcat ggaattacct 37500
tcaacctcaa gccagaatgc agaatcactg gctttttttgg ttgtgcttac ccatctctcc 37560
gcatcacctt tggtaaaggt tctaagctta ggtgagaaca tccctgcctg aacatgagaa 37620
aaaacagggt actcatactc acttctaagt gacggctgca tactaaccgc ttcatacatc 37680
tcgtagattt ctctggcgat tgaagggcta aattcttcaa cgctaacttt gagaattttt 37740
gtaagcaatg cggcgttata agcatttaat gcattgatgc cattaaataa agcaccaacg 37800
cctgactgcc ccatccccat cttgtctgcg acagattcct gggataagcc aagttcattt 37860
ttcttttttt cataaattgc tttaaggcga cgtgcgtcct caagctgctc ttgtgttaat 37920
ggtttctttt ttgtgctcat acgttaaatc tatcaccgca agggataaat atctaacacc 37980
gtgcgtgttg actattttac ctctggcggt gataatggtt gcatgtacta aggaggttgt 38040
atggaacaac gcataaccct gaaagattat gcaatgcgct ttgggcaaac caagacagct 38100

-continued

```
aaagatctcg gcgtatatca aagcgcgatc aacaaggcca ttcatgcagg ccgaaagatt  38160
tttttaacta taaacgctga tggaagcgtt tatgcggaag aggtaaagcc cttcccgagt  38220
aacaaaaaaa caacagcata aataaccccg ctcttacaca ttccagccct gaaaaagggc  38280
atcaaattaa accacaccta tggtgtatgc atttatttgc atacattcaa tcaattgtta  38340
tctaaggaaa tacttacata tggttcgtgc aaacaaacgc aacgaggctc tacgaatcga  38400
gagtgcgttg cttaacaaaa tcgcaatgct tggaactgag aagacagcgg aagctgtggg  38460
cgttgataag tcgcagatca gcaggtggaa gagggactgg attccaaagt tctcaatgct  38520
gcttgctgtt cttgaatggg gggtcgttga cgacgacatg gctcgattgg cgcgacaagt  38580
tgctgcgatt ctcaccaata aaaaacgccc ggcggcaacc gagcgttctg aacaaatcca  38640
gatggagttc tgaggtcatt actggatcta tcaacaggag tcattatgac aaatacagca  38700
aaaatactca acttcggcag aggtaacttt gccggacagg agcgtaatgt ggcagatctc  38760
gatgatggtt acgccagact atcaaatatg ctgcttgagg cttattcggg cgcagatctg  38820
accaagcgac agtttaaagt gctgcttgcc attctgcgta aaacctatgg gtggaataaa  38880
ccaatggaca gaatcaccga ttctcaactt agcgagatta caaagttacc tgtcaaacgg  38940
tgcaatgaag ccaagttaga actcgtcaga atgaatatta tcaagcagca aggcggcatg  39000
tttggaccaa ataaaaacat ctcagaatgg tgcatccctc aaaacgaggg aaaatcccct  39060
aaaacgaggg ataaaacatc cctcaaattg gggattgct atccctcaaa acagggggac  39120
acaaaagaca ctattacaaa agaaaaaaga aaagattatt cgtcagagaa ttctggcgaa  39180
tcctctgacc agccagaaaa cgacctttct gtggtgaaac cggatgctgc aattcagagc  39240
ggcagcaagt gggggacagc agaagacctg accgccgcag agtggatgtt tgacatggtg  39300
aagactatcg caccatcagc cagaaaaccg aattttgctg ggtgggctaa cgatatccgc  39360
ctgatgcgtg aacgtgacgg acgtaaccac cgcgacatgt gtgtgctgtt ccgctgggca  39420
tgccaggaca acttctggtc cggtaacgtg ctgagcccgg ccaaactccg cgataagtgg  39480
acccaactcg aaatcaaccg taacaagcaa caggcaggcg tgacagccag caaaccaaaa  39540
ctcgacctga caaacacaga ctggatttac ggggtggatc tatgaaaaac atcgccgcac  39600
agatggttaa ctttgaccgt gagcagatgc gtcggatcgc caacaacatg ccggaacagt  39660
acgacgaaaa gccgcaggta cagcaggtag cgcagatcat caacggtgtg ttcagccagt  39720
tactggcaac tttcccggcg agcctggcta accgtgacca gaacgaagtg aacgaaatcc  39780
gtcgccagtg ggttctggct tttcgggaaa acgggatcac cacgatggaa caggttaacg  39840
caggaatgcg cgtagcccgt cggcagaatc gaccatttct gccatcaccc gggcagtttg  39900
ttgcatggtg ccgggaagaa gcatccgtta ccgccggact gccaaacgtc agcgagctgg  39960
ttgatatggt ttacgagtat tgccggaagc gaggcctgta tccggatgcg gagtcttatc  40020
cgtggaaatc aaacgcgcac tactggctgg ttaccaacct gtatcagaac atgcgggcca  40080
atgcgcttac tgatgcggaa ttacgccgta aggccgcaga tgagcttgtc catatgactg  40140
cgagaattaa ccgtggtgag gcgatccctg aaccagtaaa acaacttcct gtcatgggcg  40200
gtagacctct aaatcgtgca caggctctgg cgaagatcgc agaaatcaaa gctaagttcg  40260
gactgaaagg agcaagtgta tgacgggcaa agaggcaatt attcattacc tggggacgca  40320
taatagcttc tgtgcgccgg acgttgccgc gctaacaggc gcaacagtaa ccagcataaa  40380
tcaggccgcg gctaaaatgg cacgggcagg tcttctggtt atcgaaggta aggtctggcg  40440
aacggtgtat taccggtttg ctaccaggga agaacgggaa ggaaagatga gcacgaacct  40500
```

ggtttttaag gagtgtcgcc agagtgccgc gatgaaacgg gtattggcgg tatatggagt 40560
taaaagatga ccatctacat tactgagcta ataacaggcc tgctggtaat cgcaggcctt 40620
tttatttggg ggagagggaa gtcatgaaaa aactaacctt tgaaattcga tctccagcac 40680
atcagcaaaa cgctattcac gcagtacagc aaatccttcc agacccaacc aaaccaatcg 40740
tagtaaccat tcaggaacgc aaccgcagct tagaccaaaa caggaagcta tgggcctgct 40800
taggtgacgt ctctcgtcag gttgaatggc atggtcgctg gctggatgca gaaagctgga 40860
agtgtgtgtt taccgcagca ttaaagcagc aggatgttgt tcctaacctt gccgggaatg 40920
gctttgtggt aataggccag tcaaccagca ggatgcgtgt aggcgaattt gcggagctat 40980
tagagcttat acaggcattc ggtacagagc gtggcgttaa gtggtcagac gaagcgagac 41040
tggctctgga gtggaaagcg agatggggag acagggctgc atgataaatg tcgttagttt 41100
ctccggtggc aggacgtcag catatttgct ctggctaatg gagcaaaagc gacgggcagg 41160
taaagacgtg cattacgttt tcatggatac aggttgtgaa catccaatga catatcggtt 41220
tgtcagggaa gttgtgaagt tctgggatat accgctcacc gtattgcagg ttgatatcaa 41280
cccggagctt ggacagccaa atggttatac ggtatgggaa ccaaaggata ttcagacgcg 41340
aatgcctgtt ctgaagccat ttatcgatat ggtaaagaaa tatggcactc catacgtcgg 41400
cggcgcgttc tgcactgaca gattaaaact cgttcccttc accaaatact gtgatgacca 41460
tttcgggcga gggaattaca ccacgtggat tggcatcaga gctgatgaac cgaagcggct 41520
aaagccaaag cctggaatca gatatcttgc tgaactgtca gactttgaga aggaagatat 41580
cctcgcatgg tggaagcaac aaccattcga tttgcaaata ccggaacatc tcggtaactg 41640
catattctgc attaaaaaat caacgcaaaa aatcggactt gcctgcaaag atgaggaggg 41700
attgcagcgt gtttttaatg aggtcatcac gggatcccat gtgcgtgacg gacatcggga 41760
aacgccaaag gagattatgt accgaggaag aatgtcgctg gacggtatcg cgaaaatgta 41820
ttcagaaaat gattatcaag ccctgtatca ggacatggta cgagctaaaa gattcgatac 41880
cggctcttgt tctgagtcat gcgaaatatt tggagggcag cttgatttcg acttcgggag 41940
ggaagctgca tgatgcgatg ttatcggtgc ggtgaatgca aagaagataa ccgcttccga 42000
ccaaatcaac cttactggaa tcgatggtgt ctccggtgtg aaagaacacc aacaggggtg 42060
ttaccactac cgcaggaaaa ggaggacgtg tggcgagaca gcgacgaagt atcaccgaca 42120
taatctgcga aaactgcaaa taccttccaa cgaaacgcac cagaaataaa cccaagccaa 42180
tcccaaaaga atctgacgta aaaaccttca actacacggc tcacctgtgg gatatccggt 42240
ggctaagacg tcgtgcgagg aaaacaaggt gattgaccaa aatcgaagtt acgaacaaga 42300
aagcgtcgag cgagctttaa cgtgcgctaa ctgcggtcag aagctgcatg tgctggaagt 42360
tcacgtgtgt gagcactgct gcgcagaact gatgagcgat ccgaatagct cgatgcacga 42420
ggaagaagat gatggctaaa ccagcgcgaa gacgatgtaa aaacgatgaa tgccgggaat 42480
ggtttcaccc tgcattcgct aatcagtggt ggtgctctcc agagtgtgga accaagatag 42540
cactcgaacg acgaagtaaa gaacgcgaaa aagcggaaaa agcagcagag aagaaacgac 42600
gacgagagga gcagaaacag aaagataaac ttaagattcg aaaactcgcc ttaaagcccc 42660
gcagttactg gattaaacaa gcccaacaag ccgtaaacgc cttcatcaga gaaagagacc 42720
gcgacttacc atgtatctcg tgcggaacgc tcacgtctgc tcagtgggat gccggacatt 42780
accggacaac tgctgcggca cctcaactcc gatttaatga acgcaatatt cacaagcaat 42840
gcgtggtgtg caaccagcac aaaagcggaa atctcgttcc gtatcgcgtc gaactgatta 42900
gccgcatcgg gcaggaagca gtagacgaaa tcgaatcaaa ccataaccgc catcgctgga 42960
ctatcgaaga gtgcaaggcg atcaaggcag agtaccaaca gaaactcaaa gacctgcgaa 43020
atagcagaag tgaggccgca tgacgttctc agtaaaaacc attccagaca tgctcgttga 43080
aacatacgga aatcagacag aagtagcacg cagactgaaa tgtagtcgcg gtacggtcag 43140
aaaatacgtt gatgataaag acgggaaaat gcacgccatc gtcaacgacg ttctcatggt 43200
tcatcgcgga tggagtgaaa gagatgcgct attacgaaaa aattgatggc agcaaatacc 43260
gaaatatttg ggtagttggc gatctgcacg gatgctacac gaacctgatg aacaaactgg 43320
atacgattgg attcgacaac aaaaaagacc tgcttatctc ggtgggcgat ttggttgatc 43380
gtggtgcaga gaacgttgaa tgcctggaat taatcacatt cccctggttc agagctgtac 43440
gtggaaacca tgagcaaatg atgattgatg gcttatcaga gcgtggaaac gttaatcact 43500
ggctgcttaa tggcggtggc tggttcttta atctcgatta cgacaaagaa attctggcta 43560
aagctcttgc ccataaagca gatgaacttc cgttaatcat cgaactggtg agcaaagata 43620
aaaaatatgt tatctgccac gccgattatc cctttgacga atacgagttt ggaaagccag 43680
ttgatcatca gcaggtaatc tggaaccgcg aacgaatcag caactcacaa aacgggatcg 43740
tgaaagaaat caaaggcgcg gacacgttca tctttggtca tacgccagca gtgaaaccac 43800
tcaagtttgc caaccaaatg tatatcgata ccggcgcagt gttctgcgga aacctaacat 43860
tgattcaggt acagggagaa ggcgcatgag actcgaaagc gtagctaaat ttcattcgcc 43920
aaaaagcccg atgatgagcg actcaccacg ggccacggct tctgactctc tttccggtac 43980
tgatgtgatg gctgctatgg ggatggcgca atcacaagcc ggattcggta tggctgcatt 44040
ctgcggtaag cacgaactca gccagaacga caaacaaaag gctatcaact atctgatgca 44100
atttgcacac aaggtatcgg ggaaataccg tggtgtggca aagcttgaag gaaatactaa 44160
ggcaaaggta ctgcaagtgc tcgcaacatt cgcttatgcg gattattgcc gtagtgccgc 44220
gacgccgggg gcaagatgca gagattgcca tggtacaggc cgtgcggttg atattgccaa 44280
aacagagctg tgggggagag ttgtcgagaa agagtgcgga agatgcaaag gcgtcggcta 44340
ttcaaggatg ccagcaagcg cagcatatcg cgctgtgacg atgctaatcc caaaccttac 44400
ccaacccacc tggtcacgca ctgttaagcc gctgtatgac gctctggtgg tgcaatgcca 44460
caaagaagag tcaatcgcag acaacatttt gaatgcggtc acacgttagc agcatgattg 44520
ccacggatgg caacatatta acggcatgat attgacttat tgaataaaat tgggtaaatt 44580
tgactcaacg atgggttaat tcgctcgttg tggtagtgag atgaaaagag gcggcgctta 44640
ctaccgattc cgcctagttg gtcacttcga cgtatcgtct ggaactccaa ccatcgcagg 44700
cagagaggtc tgcaaaatgc aatcccgaaa cagttcgcag gtaatagtta gagcctgcat 44760
aacggtttcg ggattttta tatctgcaca acaggtaaga gcattgagtc gataatcgtg 44820
aagagtcggc gagcctggtt agccagtgct ctttccgttg tgctgaatta agcgaatacc 44880
ggaagcagaa ccggatcacc aaatgcgtac aggcgtcatc gccgcccagc aacagcacaa 44940
cccaaactga gccgtagcca ctgtctgtcc tgaattcatt agtaatagtt acgctgcggc 45000
cttttacaca tgaccttcgt gaaagcgggt ggcaggaggt cgcgctaaca acctcctgcc 45060
gttttgcccg tgcatatcgg tcacgaacaa atctgattac taaacacagt agcctggatt 45120
tgttctatca gtaatcgacc ttattcctaa ttaaatagag caaatcccct tattgggggt 45180
aagacatgaa gatgccagaa aaacatgacc tgttggccgc cattctcgcg gcaaaggaac 45240

```
aaggcatcgg ggcaatcctt gcgtttgcaa tggcgtacct tcgcggcaga tataatggcg  45300
gtgcgtttac aaaaacagta atcgacgcaa cgatgtgcgc cattatcgcc tagttcattc  45360
gtgaccttct cgacttcgcc ggactaagta gcaatctcgc ttatataacg agcgtgttta  45420
tcggctacat cggtactgac tcgattggtt cgcttatcaa acgcttcgct gctaaaaaag  45480
ccggagtaga agatggtaga aatcaataat caacgtaagg cgttcctcga tatgctggcg  45540
tggtcggagg gaactgataa cggacgtcag aaaaccagaa atcatggtta tgacgtcatt  45600
gtaggcggag agctatttac tgattactcc gatcaccctc gcaaacttgt cacgctaaac  45660
ccaaaactca aatcaacagg cgccggacgc taccagcttc tttcccgttg gtgggatgcc  45720
taccgcaagc agcttggcct gaaagacttc tctccgaaaa gtcaggacgc tgtggcattg  45780
cagcagatta aggagcgtgg cgctttacct atgattgatc gtggtgatat ccgtcaggca  45840
atcgaccgtt gcagcaatat ctgggcttca ctgccgggcg ctggttatgg tcagttcgag  45900
cataaggctg acagcctgat tgcaaaattc aaagaagcgg gcggaacggt cagagagatt  45960
gatgtatgag cagagtcacc gcgattatct ccgctctggt tatctgcatc atcgtctgcc  46020
tgtcatgggc tgttaatcat taccgtgata acgccattac ctacaaagcc cagcgcgaca  46080
aaaatgccag agaactgaag ctggcgaacg cggcaattac tgacatgcag atgcgtcagc  46140
gtgatgttgc tgcgctcgat gcaaaataca cgaaggagtt agctgatgct aaagctgaaa  46200
atgatgctct gcgtgatgat gttgccgctg gtcgtcgtcg gttgcacatc aaagcagtct  46260
gtcagtcagt gcgtgaagcc accaccgcct ccggcgtgga taatgcagcc tccccccgac  46320
tggcagacac cgctgaacgg gattatttca ccctcagaga gaggctgatc actatgcaaa  46380
aacaactgga aggaacccag aagtatatta atgagcagtg cagatagagt tgcccatatc  46440
gatgggcaac tcatgcaatt attgtgagca atacacacgc gcttccagcg gagtataaat  46500
gcctaaagta ataaaaccga gcaatccatt tacgaatgtt tgctgggttt ctgttttaac  46560
aacattttct gcgccgccac aaattttggc tgcatcgaca gttttcttct gcccaattcc  46620
agaaacgaag aaatgatggg tgatggtttc ctttggtgct actgctgccg gtttgttttg  46680
aacagtaaac gtctgttgag cacatcctgt aataagcagg gccagcgcag tagcgagtag  46740
cattttttc atggtgttat tcccgatgct ttttgaagtt cgcagaatcg tatgtgtaga  46800
aaattaaaca aaccctaaac aatgagttga aatttcatat tgttaatatt tattaatgta  46860
tgtcaggtgc gatgaatcgt cattgtattc ccggattaac tatgtccaca gccctgacgg  46920
ggaacttctc tgcgggagtg tccgggaata attaaaacga tgcacacagg gtttagcgcg  46980
tacacgtatt gcattatgcc aacgccccgg tgctgacacg gaagaaaccg gacgttatga  47040
tttagcgtgg aaagatttgt gtagtgttct gaatgctctc agtaaatagt aatgaattat  47100
caaaggtata gtaatatctt ttatgttcat ggatatttgt aacccatcgg aaaactcctg  47160
ctttagcaag attttccctg tattgctgaa atgtgatttc tcttgatttc aacctatcat  47220
aggacgtttc tataagatgc gtgtttcttg agaatttaac atttacaacc tttttaagtc  47280
cttttattaa cacggtgtta tcgttttcta acacgatgtg aatattatct gtggctagat  47340
agtaaatata atgtgagacg ttgtgacgtt ttagttcaga ataaaacaat tcacagtcta  47400
aatcttttcg cacttgatcg aatatttctt taaaaatggc aacctgagcc attggtaaaa  47460
ccttccatgt gatacgaggg cgcgtagttt gcattatcgt ttttatcgtt tcaatctggt  47520
ctgacctcct tgtgttttgt tgatgattta tgtcaaatat taggaatgtt ttcacttaat  47580
```

-continued agtattggtt gcgtaacaaa gtgcggtcct gctggcattc tggagggaaa tacaaccgac 47640
agatgtatgt aaggccaacg tgctcaaatc ttcatacaga aagatttgaa gtaatatttt 47700
aaccgctaga tgaagagcaa gcgcatggag cgacaaaatg aataaagaac aatctgctga 47760
tgatccctcc gtggatctga ttcgtgtaaa aaatatgctt aatagcacca tttctatgag 47820
ttaccctgat gttgtaattg catgtataga acataaggtg tctctggaag cattcagagc 47880
aattgaggca gcgttggtga agcacgataa taatatgaag gattattccc tggtggttga 47940
ctgatcacca taactgctaa tcattcaaac tatttagtct gtgacagagc caacacgcag 48000
tctgtcactg tcaggaaagt ggtaaaactg caactcaatt actgcaatgc cctcgtaatt 48060
aagtgaattt acaatatcgt cctgttcgga gggaagaacg cgggatgttc attcttcatc 48120
acttttaatt gatgtatatg ctctcttttc tgacgttagt ctccgacggc aggcttcaat 48180
gacccaggct gagaaattcc cggacccttt ttgctcaaga gcgatgttaa tttgttcaat 48240
catttggtta ggaaagcgga tgttgcgggt tgttgttctg cgggttctgt tcttcgttga 48300
catgaggttg ccccgtattc agtgtcgctg atttgtattg tctgaagttg tttttacgtt 48360
aagttgatgc agatcaatta atacgatacc tgcgtcataa ttgattattt gacgtggttt 48420
gatggcctcc acgcacgttg tgatatgtag atgataatca ttatcacttt acgggtcctt 48480
tccggtgatc cgacaggtta cg 48502

<210> SEQ ID NO 14
<211> LENGTH: 77
<212> TYPE: DNA
<213> ORGANISM: Artificial Sequence
<220> FEATURE:
<223> OTHER INFORMATION: Polynucleotide sequence used in Examples 2 and 3

<400> SEQUENCE: 14
tttttttttt tttttttttt tttttttttt tttttttttt tttttttttt ggttgtttct 60
gttggtgctg atattgc 77

<210> SEQ ID NO 15
<211> LENGTH: 50
<212> TYPE: DNA
<213> ORGANISM: Artificial Sequence
<220> FEATURE:
<223> OTHER INFORMATION: Polynucleotide sequence used in Examples 2 and 3

<400> SEQUENCE: 15
gttttcgcat ttatcgtgaa acgctttcgc gtttttcgtg cgccgcttca 50

<210> SEQ ID NO 16
<211> LENGTH: 29
<212> TYPE: DNA
<213> ORGANISM: Artificial Sequence
<220> FEATURE:
<223> OTHER INFORMATION: Polynucleotide sequence used in Examples 2 and 3

<400> SEQUENCE: 16
gcaatatcag caccaacaga aacaacctt 29

<210> SEQ ID NO 17
<211> LENGTH: 970
<212> TYPE: PRT
<213> ORGANISM: Citromicrobium bathyomarinum -continued

<400> SEQUENCE: 17

```
Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415
```

-continued

```
Gln Arg Ile Leu Ser Glu Val Ala Ala Gly Lys Gly Asp Ser Ser Pro
            420                 425                 430

Ala Ile Thr Pro Gln Lys Ala Ala Ala Ser Val Gln Ala Ala Ala Leu
        435                 440                 445

Thr Gly Gln Gly Phe Arg Leu Asn Glu Gly Gln Leu Ala Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
            660                 665                 670

Thr Arg Ala Arg Thr Ser Ile Tyr Ala Ser Gly Arg Ala Ile Arg Ser
        675                 680                 685

Ala Val Asn Ala Ala Val Gln Gln Gly Leu Leu Ala Ser Arg Glu Ile
    690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
        755                 760                 765

Lys Arg Gly Lys Arg Phe Arg Phe Asp Pro Ala Arg Ile Arg Ala Gly
    770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830
```

```
Val Thr Phe Glu Thr Ser Lys Gly Asp Leu Val Glu Leu Lys Lys Asp
        835                 840                 845

Asp Pro Met Leu Lys Arg Ile Asp Leu Ala Tyr Ala Leu Asn Val His
    850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
        915                 920                 925

Val Thr Gly Ser Val Lys Pro Thr Ala Thr Lys Gly Ser Gly Val Asp
    930                 935                 940

Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970


<210> SEQ ID NO 18
<211> LENGTH: 55
<212> TYPE: DNA
<213> ORGANISM: Artificial Sequence
<220> FEATURE:
<223> OTHER INFORMATION: Polynucleotide sequence used in Example 3
<220> FEATURE:
<221> NAME/KEY: modified_base
<222> LOCATION: (1)..(5)
<223> OTHER INFORMATION: n is I
<220> FEATURE:
<221> NAME/KEY: misc_feature
<222> LOCATION: (1)..(5)
<223> OTHER INFORMATION: n is a, c, g, or t

<400> SEQUENCE: 18

nnnnntgaag cggcgcacga aaaacgcgaa agcgtttcac gataaatgcg aaaac          55


<210> SEQ ID NO 19
<211> LENGTH: 54
<212> TYPE: DNA
<213> ORGANISM: Artificial Sequence
<220> FEATURE:
<223> OTHER INFORMATION: Polynucleotide sequence used in Example 2

<400> SEQUENCE: 19

gatcugaagc ggcgcacgaa aaacgcgaaa gcgtttcacg ataaatgcga aaac           54


<210> SEQ ID NO 20
<211> LENGTH: 49
<212> TYPE: DNA
<213> ORGANISM: Artificial Sequence
<220> FEATURE:
<223> OTHER INFORMATION: Polynucleotide sequence used in Example 2

<400> SEQUENCE: 20

gaagcggcgc acgaaaaacg cgaaagcgtt tcacgataaa tgcgaaaac                 49


<210> SEQ ID NO 21

<400> SEQUENCE: 21

000
```

<210> SEQ ID NO 22

<400> SEQUENCE: 22

000

<210> SEQ ID NO 23
<211> LENGTH: 73
<212> TYPE: DNA
<213> ORGANISM: Artificial Sequence
<220> FEATURE:
<223> OTHER INFORMATION: Polynucleotide sequence used in Example 4

<400> SEQUENCE: 23
tttttttttt tttttttttt tttttttttt tttttttttt ttttttggtt gtttctgttg 60
gtgctgatat tgc 73

<210> SEQ ID NO 24
<211> LENGTH: 606
<212> TYPE: DNA
<213> ORGANISM: Artificial Sequence
<220> FEATURE:
<223> OTHER INFORMATION: Polynucelotide sequence used in Example 9

<400> SEQUENCE: 24
gccatcagat tgtgtttgtt agtcgctttt tttttttgga attttttttt tggaattttt 60
tttttgacgc tcagtaatgt gacgatagct gaaaactgta cgataaacgg tacgctgagg 120
gcggaaaaaa tcgtcgggga cattgtaaag gcggcgagcg cggcttttcc gcgccagcgt 180
gaaagcagtg tggactggcc gtcaggtacc cgtactgtca ccgtgaccga tgaccatcct 240
tttgatcgcc agatagtggt gcttccgctg acgtttcgcg gaagtaagcg tactgtcagc 300
ggcaggacaa cgtattcgat gtgttatctg aaagtactga tgaacggtgc ggtgatttat 360
gatggcgcgg cgaacgaggc ggtacaggtg ttctcccgta ttgttgacat gccagcgggt 420
cggggaaacg tgatcctgac gttcacgctt acgtccacac ggcattcggc agatattccg 480
ccgtatacgt ttgccagcga tgtgcaggtt atggtgatta agaaacaggc gctgggcatc 540
agcgtggtct gagtgtgaaa aaaaaggtac caaaaaaaac atcgtcgtga gtagtgaacc 600
gtaagc 606

<210> SEQ ID NO 25
<211> LENGTH: 60
<212> TYPE: DNA
<213> ORGANISM: Artificial Sequence
<220> FEATURE:
<223> OTHER INFORMATION: Polynucleotide sequence used in Example 5

<400> SEQUENCE: 25
ctattctgtt tatgtttctt gtttgttagc cctattctgt cccccccccc accccccccc 60

<210> SEQ ID NO 26
<211> LENGTH: 40
<212> TYPE: DNA
<213> ORGANISM: Artificial Sequence
<220> FEATURE:
<223> OTHER INFORMATION: Polynucleotide sequence used in Examples 5 and
6

<400> SEQUENCE: 26
acagaatagg gctaacaaac aagaaacata aacagaatag 40

<210> SEQ ID NO 27

<211> LENGTH: 40
<212> TYPE: DNA
<213> ORGANISM: Artificial Sequence
<220> FEATURE:
<223> OTHER INFORMATION: Polynucleotide sequence used in Examples 5 and
      6

<400> SEQUENCE: 27
ctattctgtt tatgtttctt gtttgttagc cctattctgt                    40

<210> SEQ ID NO 28
<211> LENGTH: 760
<212> TYPE: PRT
<213> ORGANISM: Methanococcoides burtonii

<400> SEQUENCE: 28

```
Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320
```

-continued

```
Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
        595                 600                 605

Glu Trp Val Thr Glu Val Ser Ala Glu Asp Ile Thr Arg His Phe Asn
    610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
        675                 680                 685

Arg Lys Leu Tyr Asn Ala Gly Phe Val Ser Val Ala Lys Leu Lys Gly
    690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
```

```
        740                 745                 750

Gln Lys Thr Phe Asn Asp Phe Gln
        755                 760


<210> SEQ ID NO 29
<211> LENGTH: 20
<212> TYPE: DNA
<213> ORGANISM: Artificial Sequence
<220> FEATURE:
<223> OTHER INFORMATION: Polynucleotide sequence used in Example 5

<400> SEQUENCE: 29

cccccccccc accccccccc                                                  20


<210> SEQ ID NO 30
<211> LENGTH: 19
<212> TYPE: DNA
<213> ORGANISM: Artificial Sequence
<220> FEATURE:
<223> OTHER INFORMATION: Polynucleotide sequence used in Example 6

<400> SEQUENCE: 30

ccccccccca ccccccccc                                                   19


<210> SEQ ID NO 31
<211> LENGTH: 16
<212> TYPE: DNA
<213> ORGANISM: Artificial Sequence
<220> FEATURE:
<223> OTHER INFORMATION: Polynucleotide sequence used in Example 6

<400> SEQUENCE: 31

ccccccaccc cccccc                                                      16


<210> SEQ ID NO 32
<211> LENGTH: 80
<212> TYPE: DNA
<213> ORGANISM: Artificial Sequence
<220> FEATURE:
<223> OTHER INFORMATION: Polynucleotide sequence used in Example 6

<400> SEQUENCE: 32

ctattctgtt tatgtttctt gtttgttagc cctattctgt cccccccccc accccccccc      60

accccccccc accccccccc                                                  80


<210> SEQ ID NO 33
<211> LENGTH: 50
<212> TYPE: DNA
<213> ORGANISM: Artificial Sequence
<220> FEATURE:
<223> OTHER INFORMATION: Polynucleotide sequence used in Example 6

<400> SEQUENCE: 33

ctattctgtt tatgtttctt gtttgttagc cctattctgt cccccccccc                 50


<210> SEQ ID NO 34
<211> LENGTH: 83
<212> TYPE: DNA
<213> ORGANISM: Artificial Sequence
<220> FEATURE:
<223> OTHER INFORMATION: Polynucleotide sequence used in Example 7

<400> SEQUENCE: 34

tttttttttt tttttttttt tttttttttt tttttttttt tttttttttt tcgctgctcc      60
```

acaggtctca gcttgagcag cga 83

<210> SEQ ID NO 35
<211> LENGTH: 33
<212> TYPE: DNA
<213> ORGANISM: Artificial Sequence
<220> FEATURE:
<223> OTHER INFORMATION: Polynucleotide sequence used in Examples 7 and 8

<400> SEQUENCE: 35
tcgctgctca agctgagacc tgtggagcag cga 33

<210> SEQ ID NO 36
<211> LENGTH: 33
<212> TYPE: DNA
<213> ORGANISM: Artificial Sequence
<220> FEATURE:
<223> OTHER INFORMATION: Polynucleotide sequence used in Examples 7 and 8

<400> SEQUENCE: 36
tcgctgctcc acaggtctca gcttgagcag cga 33

<210> SEQ ID NO 37
<211> LENGTH: 10
<212> TYPE: DNA
<213> ORGANISM: Artificial Sequence
<220> FEATURE:
<223> OTHER INFORMATION: Polynucleotide sequence used in Examples 7, 8 and 9

<400> SEQUENCE: 37
tttttttttt 10

<210> SEQ ID NO 38
<211> LENGTH: 20
<212> TYPE: DNA
<213> ORGANISM: Artificial Sequence
<220> FEATURE:
<223> OTHER INFORMATION: Polynucleotide sequence used in Examples 8 and 10

<400> SEQUENCE: 38
tttttttttt tttttttttt 20

<210> SEQ ID NO 39
<211> LENGTH: 16
<212> TYPE: DNA
<213> ORGANISM: Artificial Sequence
<220> FEATURE:
<223> OTHER INFORMATION: Polynucleotide sequence used in Example 8

<400> SEQUENCE: 39
tttttttttt tttttt 16

<210> SEQ ID NO 40
<211> LENGTH: 18
<212> TYPE: DNA
<213> ORGANISM: Artificial Sequence
<220> FEATURE:
<223> OTHER INFORMATION: Polynucleotide sequence used in Example 8

<400> SEQUENCE: 40
tttttttttt tttttttt 18

-continued

```
<210> SEQ ID NO 41
<211> LENGTH: 27
<212> TYPE: DNA
<213> ORGANISM: Artificial Sequence
<220> FEATURE:
<223> OTHER INFORMATION: Polynucleotide sequence used in Example 9

<400> SEQUENCE: 41

gccatcagat tgtgtttgtt agtcgct                                    27


<210> SEQ ID NO 42
<211> LENGTH: 27
<212> TYPE: DNA
<213> ORGANISM: Artificial Sequence
<220> FEATURE:
<223> OTHER INFORMATION: Polynucleotide sequence used in Example 9

<400> SEQUENCE: 42

gcaatatcag caccaacaga aacaacc                                    27


<210> SEQ ID NO 43
<211> LENGTH: 27
<212> TYPE: DNA
<213> ORGANISM: Artificial Sequence
<220> FEATURE:
<223> OTHER INFORMATION: Polynucleotide sequence used in Example 9

<400> SEQUENCE: 43

agcgactaac aaacacaatc tgatggc                                    27
```